(12) United States Patent
Jones et al.

(10) Patent No.: US 11,730,427 B2
(45) Date of Patent: Aug. 22, 2023

(54) SYSTEMS AND METHODS FOR AUTOCORRELATION BASED ASSESSMENT OF PPG SIGNAL QUALITY

(71) Applicant: BIOSPECTAL SA, Lausanne (CH)

(72) Inventors: Eliott Jones, Truckee, CA (US); Jean-Francois Knebel, Montricher (CH); Urvan Christen, Pully (CH); Frederic Frappereau, Menlo Park, CA (US); Patrick Schoettker, Menlo Park, CA (US)

(73) Assignee: BIOSPECTAL SA, Lausanne (CH)

( * ) Notice: Subject to any disclaimer, the term of this patent is extended or adjusted under 35 U.S.C. 154(b) by 0 days.

(21) Appl. No.: 17/511,550

(22) Filed: Oct. 27, 2021

(65) Prior Publication Data
US 2022/0133241 A1   May 5, 2022

Related U.S. Application Data

(60) Provisional application No. 63/220,369, filed on Jul. 9, 2021, provisional application No. 63/107,927, filed on Oct. 30, 2020.

(51) Int. Cl.
*A61B 5/00*        (2006.01)
*G06V 10/56*       (2022.01)
(Continued)

(52) U.S. Cl.
CPC .......... *A61B 5/7221* (2013.01); *A61B 5/0004* (2013.01); *A61B 5/0013* (2013.01);
(Continued)

(58) Field of Classification Search
CPC . A61B 5/7221; A61B 5/0077; A61B 5/02255; A61B 5/743; A61B 5/02416; A61B 5/02455; G06V 10/56
See application file for complete search history.

(56) References Cited

U.S. PATENT DOCUMENTS 10,772,394 B1   9/2020   Michalske
11,188,730 B1*  11/2021  Kwon ................... G06F 3/0421
(Continued)

FOREIGN PATENT DOCUMENTS

EP       3 501 388       6/2019
WO   WO-2019/122260 A1  6/2019

OTHER PUBLICATIONS

Elgendi, (Optimal Signal Quality Index for Photoplethysmogram Signals, Bioengineering 3(4), 2016, pp. 1-15 (Year: 2016).*
(Continued)

*Primary Examiner* — Jacqueline Cheng
*Assistant Examiner* — Tho Q Tran
(74) *Attorney, Agent, or Firm* — Foley & Lardner LLP

(57) ABSTRACT

Systems and methods for assessing PPG signals generated based on transdermal optical data can include a computing device generating a color intensity signal using an acquired sequence of transdermal images of a subject. The computing device can compute a signal quality metric of the color intensity signal. The computing device can provide an indication of a quality of the color intensity signal for display on a display device associated with the computing device. The indication of the quality of the color intensity signal can be determined based on the signal quality metric.

10 Claims, 83 Drawing Sheets

(51) Int. Cl.

| | |
|---|---|
| *A61B 5/024* | (2006.01) |
| *A61B 5/103* | (2006.01) |
| *G06T 7/90* | (2017.01) |
| *G06V 10/40* | (2022.01) |
| *A61B 5/021* | (2006.01) |
| *A61B 5/026* | (2006.01) |
| *A61B 5/1455* | (2006.01) |
| *A61B 5/0225* | (2006.01) |
| *G06V 40/12* | (2022.01) |

(52) U.S. Cl.
CPC .......... *A61B 5/0077* (2013.01); *A61B 5/0261* (2013.01); *A61B 5/02108* (2013.01); *A61B 5/02141* (2013.01); *A61B 5/02255* (2013.01); *A61B 5/02416* (2013.01); *A61B 5/1032* (2013.01); *A61B 5/6826* (2013.01); *A61B 5/6898* (2013.01); *A61B 5/7225* (2013.01); *A61B 5/7264* (2013.01); *A61B 5/742* (2013.01); *A61B 5/743* (2013.01); *G06T 7/90* (2017.01); *G06V 10/40* (2022.01); *G06V 10/56* (2022.01); *G06V 40/1382* (2022.01); *A61B 5/14551* (2013.01); *A61B 2560/0223* (2013.01); *A61B 2562/0247* (2013.01); *A61B 2562/0271* (2013.01)

(56) References Cited

U.S. PATENT DOCUMENTS

| | | | |
|---|---|---|---|
| 2003/0118219 | A1 | 6/2003 | Higuchi et al. |
| 2006/0009698 | A1 | 1/2006 | Banet et al. |
| 2006/0084878 | A1 | 4/2006 | Banet et al. |
| 2010/0194572 | A1 | 8/2010 | Chan et al. |
| 2011/0077531 | A1 | 3/2011 | Watson et al. |
| 2014/0066785 | A1 | 3/2014 | Watson et al. |
| 2014/0303454 | A1* | 10/2014 | Clifton ................. A61B 5/0816 600/479 |
| 2015/0083590 | A1 | 3/2015 | Rajala et al. |
| 2015/0141774 | A1 | 5/2015 | Ogawa et al. |
| 2015/0230759 | A1* | 8/2015 | Ochs .................. A61B 5/14551 600/476 |
| 2015/0302158 | A1* | 10/2015 | Morris ............... G06K 9/00563 702/19 |
| 2016/0235312 | A1 | 8/2016 | Jeanne et al. |
| 2016/0253820 | A1* | 9/2016 | Jeanne ..................... G06T 7/90 382/107 |
| 2016/0353998 | A1* | 12/2016 | Lee .................... A61B 5/02125 |
| 2016/0367138 | A1* | 12/2016 | Kim ...................... A61B 5/6898 |
| 2017/0014038 | A1 | 1/2017 | Futatsuyama et al. |
| 2017/0014040 | A1* | 1/2017 | Shim .................. A61B 5/02427 |
| 2017/0188864 | A1 | 7/2017 | Drury |
| 2017/0258340 | A1 | 9/2017 | Przybyszewski et al. |
| 2018/0235468 | A1 | 8/2018 | Khachaturian et al. |
| 2018/0368707 | A1* | 12/2018 | De Haan ............... G06T 7/0016 |
| 2019/0008399 | A1 | 1/2019 | Mukkamala et al. |
| 2019/0209029 | A1 | 7/2019 | Shimuta |
| 2019/0223737 | A1 | 7/2019 | Tzvieli et al. |
| 2020/0196881 | A1 | 6/2020 | Zemel |
| 2020/0367773 | A1 | 11/2020 | Wang et al. |
| 2021/0000429 | A1 | 1/2021 | Yoon et al. |
| 2021/0007615 | A1 | 1/2021 | Jang et al. |
| 2021/0038085 | A1 | 2/2021 | Liao |
| 2021/0345892 | A1 | 11/2021 | Han et al. |
| 2021/0369234 | A1 | 12/2021 | Bremer |
| 2021/0393214 | A1 | 12/2021 | Jang et al. |

OTHER PUBLICATIONS

Selvaraj et al. (Statistical Approach for the Detection of Motion/Noise Artifacts in Photoplethysmogram, 33rd Annual International Conference of the IEEE EMBS, Aug. 30-Sep. 3, 2011, pp. 4972-4975 (Year: 2011).*

Foreign Action other than Search Report on PCT PCT/IB2021/059906 dated Feb. 2, 2022.

International Search Report and Written Opinion on PCT PCT/IB2021/059906 dated Mar. 23, 2022.

Nemcova Andrea et al: "Monitoring of heart rate, blood oxygen saturation, and blood pressure using a smartphone", Biomedical Signal Processing and Control, Elsevier, Amsterdam, NL, vol. 59, Mar. 6, 2020 (Mar. 6, 2020).

Final Office Action on U.S. Appl. No. 17/511,548 dated Jul. 27, 2022.

Final Office Action on U.S. Appl. No. 17/511,553 dated May 20, 2022.

Non-Final Office Action on U.S. Appl. No. 17/511,548 dated Apr. 11, 2022.

Non-Final Office Action on U.S. Appl. No. 17/511,553 dated Dec. 8, 2022.

Notice of Allowance on U.S. Appl. No. 17/511,549 dated Sep. 21, 2022.

Notice of Allowance on U.S. Appl. No. 17/511,551 dated Apr. 20, 2022.

Notice of Allowance on U.S. Appl. No. 17/511,551 dated Oct. 13, 2022.

* cited by examiner

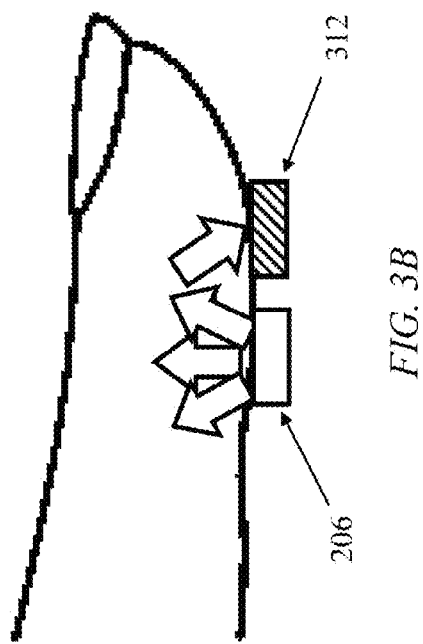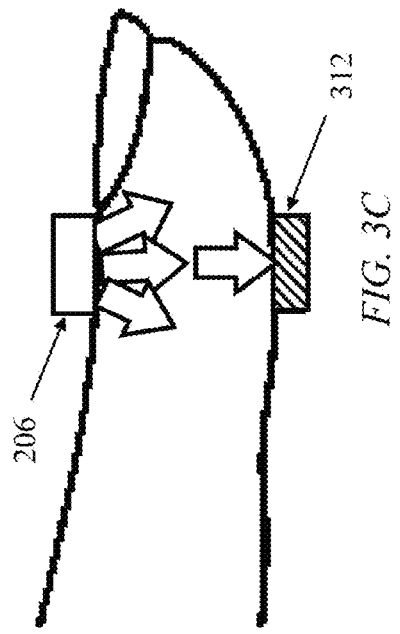

SYSTEMS AND METHODS FOR AUTOCORRELATION BASED ASSESSMENT OF PPG SIGNAL QUALITY

CROSS REFERENCE TO RELATED APPLICATIONS

This application claims priority to, and the benefit of, U.S. Provisional Application No. 63/107,927 filed on Oct. 30, 2020, and entitled "DEVICES AND METHODS FOR BLOOD PRESSURE ESTIMATION USING TRANSDERMAL OPTICAL RECORDING," and U.S. Provisional Application No. 63/220,369 filed on Jul. 9, 2021, and entitled "DEVICES AND METHODS FOR BLOOD PRESSURE ESTIMATION USING TRANSDERMAL OPTICAL RECORDING," both applications are incorporated herein by reference in their entirety.

FIELD OF THE DISCLOSURE

The present application relates generally to devices and methods for blood pressure estimation using transdermal optical recordings. Specifically, the present application relates to novel techniques of measuring blood pressure using computing devices equipped with a camera.

BACKGROUND

Hypertension is a major challenge in nowadays world. This silent disease belongs to the non-communicable diseases class (NCD) that are the cause of more than 50% total annual deaths. It alone is the cause of around 7.5 million deaths world-wide. The most dangerous aspect of this disease is its high prevalence in population. That is, about 1.13 billion people suffer from hypertension, and it spreads all around the world.

A too high blood pressure is known to be an important risk factor of a huge amount of cardiovascular diseases such as stroke or coronary heart disease. However hypertension is a disease without any apparent symptom before a crisis occur which make of it a very dangerous and treacherous disease. According to World Health Organization (WHO) less than one people out of five that have hypertension has it under control.

Since no apparent symptom is visible before an accident occur, the only way of being aware someone suffers from hypertension is to measure it. Blood pressure (BP) is measured thanks to two numbers: systolic blood pressure (SBP) which is the rise of pressure caused by a heartbeat and diastolic blood pressure (DBP) corresponding to the following decrease in BP caused by the ventricles loading blood in order to prepare the next beat. They are measured in mmHg and often transcribed by SBP/DBP. A normal blood pressure lies between 110/70 mmHg and 120/80 mmHg. Above 115/75 mmHg, cardiovascular risk double at each increment of 20/10 mmHg.

SUMMARY

According to one aspect, a method can include acquiring, by a photodetector of a computing device, a sequence of images representing transdermal optical data of a subject. The method can include generating, by the computing device, a sequence of downsampled color frames corresponding to the sequence of images by downsampling a respective color frame for each image of the sequence of images. The method can include identifying, by the computing device, in each downsampled color frame of the sequence of downsampled color frames, a respective image block representing a central image region of the downsampled color frame and having a first size smaller than a second size of the downsampled color frame. The method can include generating, by the computing device, for each downsampled color frame of the sequence of downsampled color frames, a corresponding color intensity value based on the respective image block representing a central image region of the downsampled color frame. The method can include generating, by the computing device, using color intensity values corresponding to the sequence of downsampled color frames, a photoplethysmographic (PPG) signal of the subject to determine a blood pressure value of the subject.

In some implementations, the method can further include the computing device determining a blood pressure value of the subject using the PPG signal, and displaying the blood pressure value of the user on a display device. Determining the blood pressure value of the subject can include using an optical blood pressure monitoring (OBPM) algorithm. In some implementations, the respective color frame can be a green color frame or a red color frame. In some implementations, each downsampled color frame can have an n by n size and the respective image block representing the central image region of the downsampled color frame can have an m by m size where n and m are integers and m is smaller than n. The integer n can be equal to 5 and m can be equal to 3.

In some implementations, the PPG signal can be a color intensity signal representing average color intensity values of image blocks of the sequence of downsampled color frames. The method can further include filtering the PPG signal using a high-pass filter, and determining the blood pressure measurement of the subject using a high-pass filtered version of the PPG signal. The high-pass filter can have a cut-off frequency between 0.4 Hz and 4 Hz. The method can further include determining a measurement of a pulse of the subject using the PPG signal.

According to one other aspect, a computing device can include a photodetector, a processor and a memory storing computer code instructions. The computer code instructions when executed by the processor can cause the photodetector to acquire a sequence of images representing transdermal optical data of a subject. The processor can generate a sequence of downsampled color frames corresponding to the sequence of images by downsampling a respective color frame for each image of the sequence of images. The processor can identify, in each downsampled color frame of the sequence of downsampled color frames, a respective image block representing a central image region of the downsampled color frame and having a first size smaller than a second size of the downsampled color frame. The processor can generate, for each downsampled color frame of the sequence of downsampled color frames, a corresponding color intensity value based on the respective image block representing a central image region of the downsampled color frame. The processor can generate, using color intensity values corresponding to the sequence of downsampled color frames, a photoplethysmographic (PPG) signal of the subject to determine a blood pressure value of the subject.

In some implementations, the computing device can include a smartphone, tablet, or laptop. In some implementations, the processor can further determine a blood pressure value of the subject using the PPG signal, and cause display of the blood pressure value of the user on a display device. In determining the blood pressure value of the subject, the processor can use an optical blood pressure monitoring (OBPM) algorithm. In some implementations, the respective color frame can be a green color frame or a red color frame. In some implementations, each downsampled color frame can have an n by n size and the respective image block representing the central image region of the downsampled color frame can have an m by m size where n and m are integers and m is smaller than n. The integer n can be equal to 5 and m can be equal to 3.

In some implementations, the PPG signal can be a color intensity signal representing average color intensity values of image blocks of the sequence of downsampled color frames. The processor can further filter the PPG signal using a high-pass filter, and determine the blood pressure measurement of the subject using a high-pass filtered version of the PPG signal. The high-pass filter can have a cut-off frequency between 0.4 Hz and 4 Hz. The processor can further determine a measurement of a pulse of the subject using the PPG signal.

According to yet one other aspect, a computer readable medium can include computer code instructions stored thereon. The computer code instructions when executed by one or more processors can cause a photodetector to acquire a sequence of images representing transdermal optical data of a subject. The one or more processors can generate a sequence of downsampled color frames corresponding to the sequence of images by downsampling a respective color frame for each image of the sequence of images. The one or more processors can identify, in each downsampled color frame of the sequence of downsampled color frames, a respective image block representing a central image region of the downsampled color frame and having a first size smaller than a second size of the downsampled color frame. The one or more processors can generate, for each downsampled color frame of the sequence of downsampled color frames, a corresponding color intensity value based on the respective image block representing a central image region of the downsampled color frame. The one or more processors can generate, using color intensity values corresponding to the sequence of downsampled color frames, a photoplethysmographic (PPG) signal of the subject to determine a blood pressure value of the subject.

According to one aspect, a method can include (a) configuring, according to one or more predefined data acquisition requirements, one or more operational settings of a photodetector of a computing device, and (b) adjusting, by the computing device, a gain of the photodetector. The method can include (c) acquiring, by the photodetector after updating the gain, a sequence of images, and (d) generating, using the sequence of images, a photoplethysmographic (PPG) signal, by determining for each image of the sequence of images a corresponding signal value. The method can include (e) determining a sequence of local quality values of the PPG signal, where each local quality value is indicative of a local quality of a respective portion of a plurality of portions of the PPG signal. The method can include (f) determining, by the computing device, a calibration of the photodetector to be successful upon detecting a first predefined number of consecutive local quality values, among the sequence of local quality values, exceeding a threshold quality.

In some implementations, the method can further include repeating steps (b)-(e) upon detecting a second predefined number of local quality values, among the sequence of local quality values, below the threshold quality without detecting the first predefined number of consecutive local quality values exceeding the threshold quality. In some implementations, the method can further include repeating steps (b)-(e) for a number of iterations until detecting the first predefined number of consecutive local quality values exceeding a threshold quality, or until the number of iterations reaches a predefined number of iterations. In some implementations, the method can include providing, by the computing device, an alert message indicative of calibration timeout upon the number of iterations reaches the predefined number of iterations without detecting the first predefined number of consecutive local quality values exceeding the threshold quality.

Determining the sequence of local quality values can include determining a sequence of autocorrelation values. Each autocorrelation value of the sequence of autocorrelation values can be associated with a respective signal value of the PPG signal. Configuring the one or more operational settings of the photodetector can include disabling a color correction setting of the photodetector. Configuring the one or more operational settings of the photodetector can include disabling an autocorrection setting of the photodetector. Configuring the one or more operational settings of the photodetector can include enabling a light source associated with the photodetector. Configuring the one or more operational settings of the photodetector can include setting a frame rate of the photodetector to at least 25 frames per second.

According to one other aspect, a computing device can include a photodetector, a processor and a memory storing computer code instructions. The computer code instructions when executed by the processor can cause the processor to (a) configure, according to one or more predefined data acquisition requirements, one or more operational settings of a photodetector of a computing device, and (b) adjust a gain of the photodetector. The processor can (c) cause the photodetector to acquire, after updating the gain, a sequence of images, and (d) generate, using the sequence of images, a photoplethysmographic (PPG) signal, by determining for each image of the sequence of images a corresponding signal value. The processor can (e) determine a sequence of local quality values of the PPG signal, where each local quality value is indicative of a local quality of a respective portion of a plurality of portions of the PPG signal. The processor can (f) determine a calibration of the photodetector to be successful upon detecting a first predefined number of consecutive local quality values, among the sequence of local quality values, exceeding a threshold quality.

In some implementations, the processor can further repeat steps (b)-(e) upon detecting a second predefined number of local quality values, among the sequence of local quality values, below the threshold quality without detecting the first predefined number of consecutive local quality values exceeding the threshold quality. In some implementations, the processor can repeat steps (b)-(e) for a number of iterations until detecting the first predefined number of consecutive local quality values exceeding a threshold quality, or until the number of iterations reaches a predefined number of iterations. In some implementations, the processor can provide, by the computing device, an alert message indicative of calibration timeout upon the number of iterations reaches the predefined number of iterations without detecting the first predefined number of consecutive local quality values exceeding the threshold quality.

In determining the sequence of local quality values, the processor can determine a sequence of autocorrelation values. Each autocorrelation value of the sequence of autocorrelation values can be associated with a respective signal value of the PPG signal. In configuring the one or more operational settings of the photodetector, the processor can disable a color correction setting of the photodetector. In configuring the one or more operational settings of the photodetector, the processor can disable an autocorrection setting of the photodetector. In configuring the one or more operational settings of the photodetector, the processor can enable a light source associated with the photodetector. In configuring the one or more operational settings of the photodetector, the processor can set a frame rate of the photodetector to at least 25 frames per second.

According to yet one other aspect, a computer readable medium can include computer code instructions stored thereon. The computer code instructions when executed by one or more processors can cause the one or more processors to (a) configure, according to one or more predefined data acquisition requirements, one or more operational settings of a photodetector of a computing device, and (b) adjust a gain of the photodetector. The one or more processors can (c) cause the photodetector to acquire, after updating the gain, a sequence of images, and (d) generate, using the sequence of images, a photoplethysmographic (PPG) signal, by determining for each image of the sequence of images a corresponding signal value. The one or more processors can (e) determine a sequence of local quality values of the PPG signal, where each local quality value is indicative of a local quality of a respective portion of a plurality of portions of the PPG signal. The one or more processors can (f) determine a calibration of the photodetector to be successful upon detecting a first predefined number of consecutive local quality values, among the sequence of local quality values, exceeding a threshold quality. According to one aspect, a method can include acquiring, by a photodetector of a computing device, a sequence of images, and generating, by the computing device, a sequence of downsampled images by downsampling each image of the sequence of images. The method can include, for each downsampled image of the sequence of downsampled images, the computing device (i) determining, for each pixel of a plurality of pixels in the downsampled image, a respective local variation value based on a color value of the pixel and one or more color values of adjacent pixels, (ii) determining a metric using the respective local variation value of each pixel of the plurality of pixels of the downsampled image, and (iii) classifying, using the metric, the downsampled image as usable or unusable for measuring blood pressure.

In some implementations, determining the respective local variation value can include determining, by the computing device, a Laplacian value for each pixel of the plurality of pixels. Determining the metric can include determining an average Laplacian value using the respective Laplacian value for each pixel. The method may further include normalizing, by the computing device, the metric by an average color intensity of the downsampled image. In some implementations, classifying the downsampled image can include comparing the metric of the downsampled image to a threshold. The threshold can be determined using a machine learning model trained using a plurality of image frames. The method can further include generating an alert responsive to determining that a predetermined number of downsampled images are classified as unusable. The method can further include computing a blood pressure value using a plurality of downsampled images classified as usable.

According to one other aspect, a computing device can include a photodetector, a processor and a memory storing computer code instructions. The computer code instructions when executed by the processor can cause the photodetector to acquire a sequence of images, and cause the processor to generate a sequence of downsampled images by downsampling each image of the sequence of images. The processor can, for each downsampled image of the sequence of downsampled images, (i) determine, for each pixel of a plurality of pixels in the downsampled image, a respective local variation value based on a color value of the pixel and one or more color values of adjacent pixels, (ii) determine a metric using the respective local variation value of each pixel of the plurality of pixels of the downsampled image, and (iii) classify, using the metric, the downsampled image as usable or unusable for measuring blood pressure.

In some implementations, in determining the respective local variation value, the processor can determine a Laplacian value for each pixel of the plurality of pixels. In determining the metric, the processor can determine an average Laplacian value using the respective Laplacian value for each pixel. The processor may further normalize the metric by an average color intensity of the downsampled image. In some implementations, in classifying the downsampled image, the processor can compare the metric of the downsampled image to a threshold. The threshold can be determined using a machine learning model trained using a plurality of image frames. The processor may further generate an alert responsive to determining that a predetermined number of downsampled images are classified as unusable. The processor may further compute a blood pressure value using a plurality of downsampled images classified as usable.

According to yet one other aspect, a computer readable medium can include computer code instructions stored thereon. The computer code instructions when executed by one or more processors can cause the photodetector to acquire a sequence of images, and cause the one or more processors to generate a sequence of downsampled images by downsampling each image of the sequence of images. The one or more processors can, for each downsampled image of the sequence of downsampled images, (i) determine, for each pixel of a plurality of pixels in the downsampled image, a respective local variation value based on a color value of the pixel and one or more color values of adjacent pixels, (ii) determine a metric using the respective local variation value of each pixel of the plurality of pixels of the downsampled image, and (iii) classify, using the metric, the downsampled image as usable or unusable for measuring blood pressure.

According to one aspect, a method can include acquiring, by a photodetector of a computing device, a sequence of images, and generating, by the computing device, a sequence of downsampled images by downsampling each image of the sequence of images. The method can include determining, by the computing device, for each pixel position of a plurality of pixel positions of the sequence of downsampled images, a respective aggregate pixel similarity score indicative of a similarity of a pixel of the pixel position to pixels of other pixel positions over a time window. The method can include determining, by the computing device, using aggregate pixel similarity scores of the plurality of pixel positions of the sequence of downsampled images, a vector indicative of a position of a body part of a user.

In some implementations, the method can include determining, for each pixel position of the plurality of pixel positions of the sequence of downsampled images, a respective sequence of pixel intensity values representing pixel intensities of the pixel position over the time window, and determining, for each pair of pixel positions, a cross correlation value representing a cross correlation between a pair of sequences of pixel intensity values representing pixel intensities of the pair of pixel positions over the time window. The method can include determining, for each pixel position, the respective aggregate pixel similarity score using cross correlation values associated with the pixel position. Determining the respective aggregate pixel similarity score using cross correlation values associated with the pixel position can include (i) determining, for each pair of pixel positions, a respective distance score using the cross correlation value representing the cross correlation between the pair of sequences of pixel intensity values representing pixel intensities of the pair of pixel positions over the time window, and (ii) determining, for each pixel position, the respective aggregate pixel similarity score as an aggregation of respective distance scores associated with the pixel position.

In some implementations, determining the vector can include determining a center of mass of the aggregate pixel similarity scores of the plurality of pixel positions of the downsampled images. The method may further include determining an angle of the vector indicative of a direction along which to move the body part of the user. The method may further include determining a magnitude of the vector indicative of a distance along which to move the body part of the user. The method may further include providing a visual output generated using the vector to guide the user to move the body part relative to the photodetector. The body part can be a finger.

According to one other aspect, a computing device can include a photodetector, a processor and a memory storing computer code instructions. The computer code instructions when executed by the processor can cause the photodetector to acquire a sequence of images, and cause the processor to generate a sequence of downsampled images by downsampling each image of the sequence of images. The processor can determine, for each pixel position of a plurality of pixel positions of the sequence of downsampled images, a respective aggregate pixel similarity score indicative of a similarity of a pixel of the pixel position to pixels of other pixel positions over a time window. The processor can determine, using aggregate pixel similarity scores of the plurality of pixel positions of the sequence of downsampled images, a vector indicative of a position of a body part of a user.

In some implementations, the processor can determine, for each pixel position of the plurality of pixel positions of the sequence of downsampled images, a respective sequence of pixel intensity values representing pixel intensities of the pixel position over the time window, and determine, for each pair of pixel positions, a cross correlation value representing a cross correlation between a pair of sequences of pixel intensity values representing pixel intensities of the pair of pixel positions over the time window. The processor can determine, for each pixel position, the respective aggregate pixel similarity score using cross correlation values associated with the pixel position. In determining the respective aggregate pixel similarity score using cross correlation values associated with the pixel position, the processor can (i) determine, for each pair of pixel positions, a respective distance score using the cross correlation value representing the cross correlation between the pair of sequences of pixel intensity values representing pixel intensities of the pair of pixel positions over the time window, and (ii) determine, for each pixel position, the respective aggregate pixel similarity score as an aggregation of respective distance scores associated with the pixel position.

In some implementations, in determining the vector the processor can determine a center of mass of the aggregate pixel similarity scores of the plurality of pixel positions of the downsampled images. The processor may further determine an angle of the vector indicative of a direction along which to move the body part of the user. The processor may further determine a magnitude of the vector indicative of a distance along which to move the body part of the user. The processor may further provide a visual output generated using the vector to guide the user to move the body part relative to the photodetector. The body part can be a finger.

According to yet one other aspect, a computer readable medium can include computer code instructions stored thereon. The computer code instructions when executed by one or more processors can cause the photodetector to acquire a sequence of images, and cause the one or more processors to generate a sequence of downsampled images by downsampling each image of the sequence of images. The one or more processors can determine, for each pixel position of a plurality of pixel positions of the sequence of downsampled images, a respective aggregate pixel similarity score indicative of a similarity of a pixel of the pixel position to pixels of other pixel positions over a time window. The one or more processors can determine, using aggregate pixel similarity scores of the plurality of pixel positions of the sequence of downsampled images, a vector indicative of a position of a body part of a user.

According to one aspect, a method can include obtaining, by a computing device, a photoplethysmographic (PPG) signal generated from a sequence of images acquired using a photodetector, and detecting, by the computing device, a plurality of signal features of different signal feature types of the PPG signal. The method can include determining, by the computing device, using the detected plurality of signal features, a predefined sequence of signal feature types included in a portion of the PPG signal. The predefined sequence of signal feature types can be used to define PPG pulse segments. The method can include classifying, by the computing device, the portion of the PPG signal as a PPG pulse segment.

In some implementations, the plurality of signal feature types can include a peak, a trough, a zero-crossing up and a zero-crossing down. The predefined sequence of signal feature types can include an ordered sequence of a first peak, a zero-crossing down, a trough, a zero-crossing up and a second peak. The portion of the PPG signal can start at the first peak and can end at the second peak and the method can further include determining, by the computing device, a duration of the PPG pulse segment based on a length of time between the first peak and the second peak.

In some implementations, the predefined sequence of signal feature types can include an ordered sequence of a first trough, a zero-crossing up, a peak, a zero-crossing down and a second trough. The portion of the PPG signal can start at the first trough and can end at the second trough, and the method can further include determining, by the computing device, a duration of the PPG pulse segment based on a length of time between the first trough and the second trough. In some implementations, the portion of the PPG signal can be a first portion and can end at a first signal feature. The method can further include determining, using the detected plurality of signal features, the predefined sequence of signal feature types in a second portion of the PPG signal, and classifying the second portion of the PPG signal as a second PPG pulse segment. The second portion of the PPG signal can start at the first signal feature.

The method can further include generating, from the PPG signal, a plurality of PPG pulse segments. Each PPG segment can include signal features that include the predefined sequence of signal feature types. The method can include the computing device determining a time difference between a first signal feature of a first signal feature type and a second signal feature of a second signal feature type within the PPG pulse segment, comparing the time difference between the first signal feature and the second signal feature to a time duration threshold, and setting a flag to the PPG pulse segment responsive to determining that time difference between the first signal feature and the second signal feature exceeds the time duration threshold.

In some implementations, the method can further include the computing device (i) generating a sequence of downsampled color frames corresponding to the sequence of images by downsampling a respective color frame for each image of the sequence of images, (ii) identifying in each downsampled color frame of the sequence of downsampled color frames, a respective image block representing a central image region of the downsampled color frame and having a first size smaller than a second size of the downsampled color frame, and (iii) generating the PPG signal using the respective image blocks of the sequence of downsampled color frames. The PPG signal can be for use to determine a blood pressure value. In some implementations, the method can further include the computing device determining a duration of the PPG pulse segment based on a length of time between a first signal feature and a last signal feature of the predefined sequence, and determining a type of the PPG pulse segment based on the duration of the PPG pulse segment.

According to one other aspect, a computing device can include a processor and a memory storing computer code instructions. The computer code instructions when executed can cause the processor to obtain a photoplethysmographic (PPG) signal generated from a sequence of images acquired using a photodetector, and detect a plurality of signal features of different signal feature types of the PPG signal. The processor can determine, using the detected plurality of signal features, a predefined sequence of signal feature types included in a portion of the PPG signal. The predefined sequence of signal feature types can be used to define PPG pulse segments. The processor can classify the portion of the PPG signal as a PPG pulse segment.

In some implementations, the plurality of signal feature types can include a peak, a trough, a zero-crossing up and a zero-crossing down. The predefined sequence of signal feature types can include an ordered sequence of a first peak, a zero-crossing down, a trough, a zero-crossing up and a second peak. The portion of the PPG signal can start at the first peak and can end at the second peak, and the processor can further determine a duration of the PPG pulse segment based on a length of time between the first peak and the second peak.

In some implementations, the predefined sequence of signal feature types can include an ordered sequence of a first trough, a zero-crossing up, a peak, a zero-crossing down and a second trough. The portion of the PPG signal can start at the first trough and can end at the second trough, and the processor can further determine a duration of the PPG pulse segment based on a length of time between the first trough and the second trough. In some implementations, the portion of the PPG signal can be a first portion and can end at a first signal feature. The processor can further determine, using the detected plurality of signal features, the predefined sequence of signal feature types in a second portion of the PPG signal, and classify the second portion of the PPG signal as a second PPG pulse segment. The second portion of the PPG signal can start at the first signal feature.

The processor can further generate, from the PPG signal, a plurality of PPG pulse segments. Each PPG segment can include signal features that include the predefined sequence of signal feature types. The processor can (i) determine a time difference between a first signal feature of a first signal feature type and a second signal feature of a second signal feature type within the PPG pulse segment, (ii) compare the time difference between the first signal feature and the second signal feature to a time duration threshold, and (iii) set a flag to the PPG pulse segment responsive to determining that time difference between the first signal feature and the second signal feature exceeds the time duration threshold.

In some implementations, the processor can (i) generate a sequence of downsampled color frames corresponding to the sequence of images by downsampling a respective color frame for each image of the sequence of images, (ii) identify in each downsampled color frame of the sequence of downsampled color frames, a respective image block representing a central image region of the downsampled color frame and having a first size smaller than a second size of the downsampled color frame, and (iii) generate the PPG signal using the respective image blocks of the sequence of downsampled color frames. The PPG signal can be for use to determine a blood pressure value. In some implementations, the processor can further determine a duration of the PPG pulse segment based on a length of time between a first signal feature and a last signal feature of the predefined sequence, and determine a type of the PPG pulse segment based on the duration of the PPG pulse segment.

According to yet one other aspect, a computer readable medium can include computer code instructions stored thereon. The computer code instructions when executed by one or more processors can cause the one or more processors to obtain a photoplethysmographic (PPG) signal generated from a sequence of images acquired using a photodetector, and detect a plurality of signal features of different signal feature types of the PPG signal. The one or more processors can determine, using the detected plurality of signal features, a predefined sequence of signal feature types included in a portion of the PPG signal. The predefined sequence of signal feature types can be used to define PPG pulse segments. The one or more processors can classify the portion of the PPG signal as a PPG pulse segment.

According to one aspect, a method can include identifying, by a computing device, from a photoplethysmographic (PPG) signal generated from a sequence of images acquired using a photodetector, a plurality of PPG pulse segments. Each PPG pulse segment of the plurality of PPG pulse segments can be identified using a predefined sequence of signal feature types. The method can include determining, by the computing device, for each PPG pulse segment, one or more respective pulse features determined from the PPG pulse segment, and detecting, by the computing device, one or more conditions based on the one or more respective pulse features of the plurality of PPG pulse segments.

In some implementations, the one or more respective pulse features for each PPG pulse segment can include the respective pulse duration for each PPG pulse segment. The one or more conditions can include an arrhythmia condition. The method can include determining, for each pair of consecutive PPG pulse segments of a plurality of pairs of consecutive PPG pulse segments, a respective duration ratio of the durations representing a quantitative relation between durations of the pair of consecutive PPG pulse segments, and detecting the arrhythmia condition using respective duration ratios for the plurality of pairs of consecutive PPG pulse segments. Detecting the arrhythmia condition using respective duration ratios for the plurality of pairs of consecutive PPG pulse segments can include (i) determining, by the computing device, a reference duration ratio using the respective duration ratios for the plurality of pairs of consecutive PPG pulse segments, (ii) comparing, by the computing device, the reference duration ratio to a threshold value, and (iii) detecting, by the computing device, the arrhythmia condition based on the comparison of the reference duration ratio to the threshold value.

In some implementations, the reference duration ratio can include at least one of a maximum of the respective duration ratios for the plurality of pairs of consecutive pulse segments, or a quantile of the respective duration ratios for the plurality of pairs of consecutive pulse segments.

In some implementations, the one or more conditions can include an irregular heartbeat condition. The method can include determining, for each PPG pulse segments of the plurality of PPG pulse segments, a respective pulse duration, determining a first pulse duration of a first PPG pulse segment and a second pulse duration of a second PPG pulse segment, and detecting the irregular heartbeat condition based on a relative variation between the first and second pulse durations. The first pulse duration can be a minimum pulse duration of respective pulse durations of the plurality of PPG pulse segments, and the second pulse duration can be a maximum pulse duration of respective pulse durations of the plurality of PPG pulse segments. The first pulse duration can be a first quantile of respective pulse durations of the plurality of PPG pulse segments and the second pulse duration can be a second quantile of respective pulse durations of the plurality of PPG pulse segments. The relative variation between the first and second pulse durations can include at least one of a ratio of the second pulse duration over the first pulse duration, a difference between the first pulse duration and the second pulse duration or a normalized difference between the first pulse duration and the second pulse duration.

According to one other aspect, a computing device can include a processor and a memory storing computer code instructions. The computer code instructions when executed can cause the processor to identify, from a photoplethysmographic (PPG) signal generated from a sequence of images acquired using a photodetector, a plurality of PPG pulse segments. Each PPG pulse segment of the plurality of PPG pulse segments can be identified using a predefined sequence of signal feature types. The processor can determine, for each PPG pulse segment, one or more respective pulse features determined from the PPG pulse segment, and detect one or more conditions based on the one or more respective pulse features of the plurality of PPG pulse segments.

In some implementations, the one or more respective pulse features for each PPG pulse segment can include the respective pulse duration for each PPG pulse segment. The one or more conditions can include an arrhythmia condition. The processor can determine, for each pair of consecutive PPG pulse segments of a plurality of pairs of consecutive PPG pulse segments, a respective duration ratio of the durations representing a quantitative relation between durations of the pair of consecutive PPG pulse segments, and detect the arrhythmia condition using respective duration ratios for the plurality of pairs of consecutive PPG pulse segments. In detecting the arrhythmia condition using respective duration ratios for the plurality of pairs of consecutive PPG pulse segments, the processor can (i) determine a reference duration ratio using the respective duration ratios for the plurality of pairs of consecutive PPG pulse segments, (ii) compare the reference duration ratio to a threshold value, and (iii) detect the arrhythmia condition based on the comparison of the reference duration ratio to the threshold value.

In some implementations, the reference duration ratio can include at least one of a maximum of the respective duration ratios for the plurality of pairs of consecutive pulse segments, or a quantile of the respective duration ratios for the plurality of pairs of consecutive pulse segments.

In some implementations, the one or more conditions can include an irregular heartbeat condition. The processor can determine, for each PPG pulse segments of the plurality of PPG pulse segments, a respective pulse duration, determining a first pulse duration of a first PPG pulse segment and a second pulse duration of a second PPG pulse segment, and detect the irregular heartbeat condition based on a relative variation between the first and second pulse durations. The first pulse duration can be a minimum pulse duration of respective pulse durations of the plurality of PPG pulse segments, and the second pulse duration can be a maximum pulse duration of respective pulse durations of the plurality of PPG pulse segments. The first pulse duration can be a first quantile of respective pulse durations of the plurality of PPG pulse segments and the second pulse duration can be a second quantile of respective pulse durations of the plurality of PPG pulse segments. The relative variation between the first and second pulse durations can include at least one of a ratio of the second pulse duration over the first pulse duration, a difference between the first pulse duration and the second pulse duration or a normalized difference between the first pulse duration and the second pulse duration.

According to yet one other aspect, a computer readable medium can include computer code instructions stored thereon. The computer code instructions when executed by one or more processors can cause the one or more processors to identify, from a photoplethysmographic (PPG) signal generated from a sequence of images acquired using a photodetector, a plurality of PPG pulse segments. Each PPG pulse segment of the plurality of PPG pulse segments can be identified using a predefined sequence of signal feature types. The one or more processors can determine, for each PPG pulse segment, one or more respective pulse features determined from the PPG pulse segment, and detect one or more conditions based on the one or more respective pulse features of the plurality of PPG pulse segments.

According to one aspect, a method can include obtaining, by a computing device, a photoplethysmographic (PPG) signal generated from a sequence of images acquired using a photodetector while a body part is placed in proximity of the photodetector. The method can include determining, by the computing device, a logarithmic PPG signal by computing a logarithm of the PPG signal. The logarithmic PPG signal can be indicative of blood absorbance of light. The method can include the computing device determining an envelope of the logarithmic PPG signal, and determining a blood perfusion condition of the body part based on the envelope of the logarithmic PPG signal.

In some implementations, the blood perfusion condition can include a low blood perfusion condition indicative of a cold body part. The method can further include providing an alert indicative of the cold body part. The alert can include one or more instructions for warming up the body part. Determining the envelope of the logarithmic PPG signal can include applying a low-pass filter to the logarithmic PPG signal.

In some implementations, determining the envelope of the logarithmic PPG signal can include determining for each time interval of a plurality of time intervals a respective maximum and a respective minimum of the logarithmic PPG signal. The method can further include determining, for each time interval of the plurality of time intervals, a respective local variation of the envelope of the logarithmic PPG signal. The respective local variation can be equal to a difference between the respective maximum and the respective minimum of the logarithmic PPG signal within the time interval. The method can determine an estimate of an amplitude of the logarithmic PPG signal based using respective local variations of the envelope of the logarithmic PPG signal within the plurality of time intervals. The blood perfusion condition of the body part can be determined based on the estimate of the amplitude of the logarithmic PPG signal.

Determining the blood perfusion condition of the body part can include the computing device comparing the estimate of the amplitude of the logarithmic PPG signal to a threshold value, and determining the blood perfusion condition of the body part based on the comparison of the estimate of the amplitude of the logarithmic PPG signal to the threshold value. Determining the estimate of the amplitude of the logarithmic PPG signal can include at least one of (i) determining the estimate of the amplitude of the logarithmic PPG signal as a predefined quantile of the respective local variations of the envelope of the logarithmic PPG signal within the plurality of time intervals, (ii) determining the estimate of the amplitude of the logarithmic PPG signal as a median of the respective local variations of the envelope of the logarithmic PPG signal within the plurality of time intervals (iii) determining the estimate of the amplitude of the logarithmic PPG signal as an average of the respective local variations of the envelope of the logarithmic PPG signal within the plurality of time intervals (iv) determining the estimate of the amplitude of the logarithmic PPG signal as a maximum of the respective local variations of the envelope of the logarithmic PPG signal within the plurality of time intervals, or (v) determining the estimate of the amplitude of the logarithmic PPG signal as a minimum of the respective local variations of the envelope of the logarithmic PPG signal within the plurality of time intervals.

In some implementations, the method can include the computing device generating a sequence of downsampled color frames corresponding to the sequence of images by downsampling a respective color frame for each image of the sequence of images, identifying, in each downsampled color frame of the sequence of downsampled color frames, a respective image block representing a central image region of the downsampled color frame and having a first size smaller than a second size of the downsampled color frame, and generating the PPG signal using the respective image blocks of the sequence of downsampled color frames. The PPG signal can be used to determine a blood pressure value.

According to one other aspect, a computing device can include a processor and a memory storing computer code instructions. The computer code instructions when executed can cause the processor to obtain a photoplethysmographic (PPG) signal generated from a sequence of images acquired using a photodetector while a body part is placed in proximity of the photodetector. The processor can determine a logarithmic PPG signal by computing a logarithm of the PPG signal. The logarithmic PPG signal can be indicative of blood absorbance of light. The processor can determine an envelope of the logarithmic PPG signal, and determine a blood perfusion condition of the body part based on the envelope of the logarithmic PPG signal.

In some implementations, the blood perfusion condition can include a low blood perfusion condition indicative of a cold body part. The processor can further provide an alert indicative of the cold body part. The alert can include one or more instructions for warming up the body part. In determining the envelope of the logarithmic PPG signal, the processor can apply a low-pass filter to the logarithmic PPG signal.

In some implementations, in determining the envelope of the logarithmic PPG signal, the processor can determine for each time interval of a plurality of time intervals a respective maximum and a respective minimum of the logarithmic PPG signal. The processor can further determine, for each time interval of the plurality of time intervals, a respective local variation of the envelope of the logarithmic PPG signal. The respective local variation can be equal to a difference between the respective maximum and the respective minimum of the logarithmic PPG signal within the time interval. The processor can determine an estimate of an amplitude of the logarithmic PPG signal using respective local variations of the envelope of the logarithmic PPG signal within the plurality of time intervals. The blood perfusion condition of the body part can be determined based on the estimate of the amplitude of the logarithmic PPG signal.

In determining the blood perfusion condition of the body part, the processor can compare the estimate of the amplitude of the logarithmic PPG signal to a threshold value, and determine the blood perfusion condition of the body part based on the comparison of the estimate of the amplitude of the logarithmic PPG signal to the threshold value. In determining the estimate of the amplitude of the logarithmic PPG signal, the processor can perform at least one of (i) determine the estimate of the amplitude of the logarithmic PPG signal as a predefined quantile of the respective local variations of the envelope of the logarithmic PPG signal within the plurality of time intervals, (ii) determine the estimate of the amplitude of the logarithmic PPG signal as a median of the respective local variations of the envelope of the logarithmic PPG signal within the plurality of time intervals (iii) determine the estimate of the amplitude of the logarithmic PPG signal as an average of the respective local variations of the envelope of the logarithmic PPG signal within the plurality of time intervals (iv) determine the estimate of the amplitude of the logarithmic PPG signal as a maximum of the respective local variations of the envelope of the logarithmic PPG signal within the plurality of time intervals, or (v) determine the estimate of the amplitude of the logarithmic PPG signal as a minimum of the respective local variations of the envelope of the logarithmic PPG signal within the plurality of time intervals.

In some implementations, the processor can generate a sequence of downsampled color frames corresponding to the sequence of images by downsampling a respective color frame for each image of the sequence of images. The processor can identify, in each downsampled color frame of the sequence of downsampled color frames, a respective image block representing a central image region of the downsampled color frame and having a first size smaller than a second size of the downsampled color frame. The processor can generate the PPG signal using the respective image blocks of the sequence of downsampled color frames. The PPG signal can be used to determine a blood pressure value.

According to yet one other aspect, a computer readable medium can include computer code instructions stored thereon. The computer code instructions when executed by one or more processors can cause the one or more processors to obtain a photoplethysmographic (PPG) signal generated from a sequence of images acquired using a photodetector while a body part is placed in proximity of the photodetector. The one or more processors can determine a logarithmic PPG signal by computing a logarithm of the PPG signal. The logarithmic PPG signal can be indicative of blood absorbance of light. The one or more processors can determine an envelope of the logarithmic PPG signal, and determine a blood perfusion condition of the body part based on the envelope of the logarithmic PPG signal.

According to one aspect, a method can include obtaining, by a computing device, a sequence of images acquired by a photodetector. The method can include determining, by the computing device, for each pixel position of a plurality of pixel positions associated with the sequence of images, a respective penalty score indicative of a similarity between a color value of a pixel of the pixel position and a desired color value. The desired color value can represent a color property of light emitted from body parts of users when placed opposite to the photodetector. The method can include determining, by the computing device, using penalty scores of the plurality of pixel positions, a relative position of a body part of a user with respect to a desired position.

In some implementations, the method can include generating, by the computing device, a sequence of downsampled images by downsampling each image of the sequence of images. The plurality of pixel positions can represent pixel positions of the sequence of downsampled images. In some implementations, the method can include transforming, by the computing device, the sequence of images to a hue, saturation, luminance (HSL) color space. The color value can represent a hue color value of the pixel of the pixel position and the desired color value representing a desired hue color value. The penalty score can be defined as a function of $\min(|H-T_H|, 360-|H-T_H|)$, where H represents the hue color value and $T_H$ represents the desired hue color value. In some implementations, the penalty score can be defined in terms of a difference between the color value and the desired color value.

In some implementations, determining the relative position can include determining a center of mass of the penalty scores of the plurality of pixel positions. Determining the relative position can include determining a magnitude and a direction of a position vector. The position vector can represent the relative position with respect to the desired position. The method can include providing a visual output indicative of the relative position for display on a display device. The visual output can include an indication of a classification of the relative position of the body part. The body part can be a finger of the user.

According to one other aspect, a computing device can include a processor and a memory storing computer code instructions. The computer code instructions when executed can cause the processor to obtain a sequence of images acquired by a photodetector. The processor can determine, for each pixel position of a plurality of pixel positions associated with the sequence of images, a respective penalty score indicative of a similarity between a color value of a pixel of the pixel position and a desired color value. The desired color value can represent a color property of light emitted from body parts of users when placed opposite to the photodetector. The processor can determine, using penalty scores of the plurality of pixel positions, a relative position of a body part of a user with respect to a desired position.

In some implementations, the processor can generate a sequence of downsampled images by downsampling each image of the sequence of images. The plurality of pixel positions can represent pixel positions of the sequence of downsampled images. In some implementations, the processor can transform the sequence of images to a hue, saturation, luminance (HSL) color space. The color value can represent a hue color value of the pixel of the pixel position and the desired color value representing a desired hue color value. The penalty score can be defined as a function of $\min(|H-T_H|, 360-|H-T_H|)$, where H represents the hue color value and $T_H$ represents the desired hue color value. In some implementations, the penalty score can be defined in terms of a difference between the color value and the desired color value.

In some implementations, in determining the relative position, the processor can determine a center of mass of the penalty scores of the plurality of pixel positions. Determining the relative position can include determining a magnitude and a direction of a position vector. The position vector can represent the relative position with respect to the desired position. The processor can provide a visual output indicative of the relative position for display on a display device. The visual output can include an indication of a classification of the relative position of the body part. The body part can be a finger of the user.

According to yet one other aspect, a computer readable medium can include computer code instructions stored thereon. The computer code instructions when executed by one or more processors can cause the one or more processors to obtain a sequence of images acquired by a photodetector. The one or more processors can determine, for each pixel position of a plurality of pixel positions associated with the sequence of images, a respective penalty score indicative of a similarity between a color value of a pixel of the pixel position and a desired color value. The desired color value can represent a color property of light emitted from body parts of users when placed opposite to the photodetector. The one or more processors can determine, using penalty scores of the plurality of pixel positions, a relative position of a body part of a user with respect to a desired position.

According to one aspect, a method can include obtaining, by a computing device, a sequence of images representing transdermal optical data of a subject. The sequence of images can be acquired by a photodetector. The method can include identifying, by the computing device, a plurality of image regions across the sequence of images. The method can include generating, by the computing device, a plurality of color intensity signals associated with the plurality of image regions across the sequence of images. The method can include determining, by the computing device, using a machine learning model and the plurality of color intensity signals associated with the plurality of image regions, a condition associated with acquisition of the sequence of images. The machine learning model can receive the plurality color intensity signals as input and provide an indication of the condition as output. The method can include providing, by the computing device, feedback for presentation to a user based on the condition associated with the acquisition of the sequence of images.

In some implementations, identifying the image regions across the sequence of images can include downsampling, for each image of the sequence of images, corresponding red and green color frames, and identifying, for each image of the sequence of images, the plurality of image regions across downsampled green color image frames and across downsampled red color frames. In some implementations, generating the plurality of color intensity signals can include at least one of generating one or more green color intensity signals associated with one or more image regions across the downsampled green color frames, or generating one or more red color intensity signals associated with one or more image regions across the downsampled red color frames.

In some implementations, the plurality of image regions can include a central image region and one or more side image regions. In some implementations, generating a color intensity signal associated with an image region across the sequence of images can include averaging pixel color values of the image region for each image of the sequence of images. The condition can include at least one of a condition related to placement of a body part of the subject relative to the photodetector or a blood perfusion condition of the subject. The condition can include a color intensity saturation condition of the sequence of images. The method can further include training the machine learning model using a second plurality of color intensity signals from one or more second image sequences. The second plurality of color intensity signals can be associated with the plurality of image regions across the one or more second image sequences.

According to one other aspect, a computing device can include a processor and a memory storing computer code instructions. The computer code instructions when executed can cause the processor to obtain a sequence of images representing transdermal optical data of a subject. The sequence of images can be acquired by a photodetector. The processor can identify a plurality of image regions across the sequence of images. The processor can generate a plurality of color intensity signals associated with the plurality of image regions across the sequence of images. The processor can determine, using a machine learning model and the plurality of color intensity signals associated with the plurality of image regions, a condition associated with acquisition of the sequence of images. The machine learning model can receive the plurality color intensity signals as input and provide an indication of the condition as output. The processor can provide feedback for presentation to a user based on the condition associated with the acquisition of the sequence of images.

In some implementations, in identifying the image regions across the sequence of images, the processor can downsample, for each image of the sequence of images, corresponding red and green color frames, and identify, for each image of the sequence of images, the plurality of image regions across downsampled green color image frames and across downsampled red color frames. In some implementations, in generating the plurality of color intensity signals, the processor can generate one or more green color intensity signals associated with one or more image regions across the downsampled green color frames, or generate one or more red color intensity signals associated with one or more image regions across the downsampled red color frames.

In some implementations, the plurality of image regions can include a central image region and one or more side image regions. In some implementations, in generating a color intensity signal associated with an image region across the sequence of images, the processor can average pixel color values of the image region for each image of the sequence of images. The condition can include at least one of a condition related to placement of a body part of the subject relative to the photodetector or a blood perfusion condition of the subject. The condition can include a color intensity saturation condition of the sequence of images. The processor can further train the machine learning model using a second plurality of color intensity signals from one or more second image sequences. The second plurality of color intensity signals can be associated with the plurality of image regions across the one or more second image sequences.

According to yet one other aspect, a computer readable medium can include computer code instructions stored thereon. The computer code instructions when executed by one or more processors can cause the one or more processors to obtain a sequence of images representing transdermal optical data of a subject. The sequence of images can be acquired by a photodetector. The one or more processors can identify a plurality of image regions across the sequence of images. The processor can generate a plurality of color intensity signals associated with the plurality of image regions across the sequence of images. The one or more processors can determine, using a machine learning model and the plurality of color intensity signals associated with the plurality of image regions, a condition associated with acquisition of the sequence of images. The machine learning model can receive the plurality color intensity signals as input and provide an indication of the condition as output. The one or more processors can provide feedback for presentation to a user based on the condition associated with the acquisition of the sequence of images.

According to one aspect, a method of assessing PPG signals generated based on transdermal optical data can include generating, by a computing device, a color intensity signal using an acquired sequence of transdermal images of a subject. The method can include computing, by the computing device, a signal quality metric of the color intensity signal. The method can include providing, by the computing device, an indication of a quality of the color intensity signal for display on a display device associated with the computing device. The indication of the quality of the color intensity signal can be determined based on the signal quality metric.

The signal quality metric can include a normalized autocorrelation score. The signal quality metric can include a spectrum entropy based signal quality metric. The spectrum entropy based signal quality metric can be defined based on a normalized power spectrum of the color intensity signal. The method can further include comparing, by the computing device, the signal quality metric to a corresponding threshold value, and determining, by the computing device, the indication of the quality of the color intensity signal based on comparing the signal quality metric to the corresponding threshold value. Computing the signal quality metric can include computing a plurality of values of the signal quality metric based on a sliding window. The method can further include determining, by the computing device, a local period of the color intensity signal using the plurality of values of the signal quality metric. Determining the local period of the color intensity signal can include determining a maximum of normalized autocorrelation parameters computed based on a sliding window.

The method can further include comparing, by the computing device, each value of the plurality of values of the signal quality metric to a corresponding threshold value, and determining, by the computing device, for each value of the plurality of values of the signal quality metric, a corresponding indication of the quality of the color intensity signal based on comparing the value of signal quality metric to the corresponding threshold value. The method can include aborting, by the computing device, the recording if the multiple indications of the quality of the color intensity signal corresponding to a predefined cumulative time period are below the corresponding threshold value. The method can include at least one of displaying a graph of at least a portion of the color intensity signal, displaying a signal quality bar depicting a visual representation of the indication of the quality of the color intensity signal or displaying a timer indicative of time left for acquiring the sequence of transdermal images of the subject.

According to one other aspect, a computing device can include a processor and a memory storing computer code instructions. The computer code instructions when executed can cause the processor to generate a color intensity signal using an acquired sequence of transdermal images of a subject, and compute a signal quality metric of the color intensity signal. The processor can provide an indication of a quality of the color intensity signal for display on a display device associated with the computing device. The indication of the quality of the color intensity signal can be determined based on the signal quality metric.

The signal quality metric can include a normalized autocorrelation score. The signal quality metric can include a spectrum entropy based signal quality metric. The spectrum entropy based signal quality metric can be defined based on a normalized power spectrum of the color intensity signal. The processor can compare the signal quality metric to a corresponding threshold value, and determine the indication of the quality of the color intensity signal based on comparing the signal quality metric to the corresponding threshold value. In computing the signal quality metric, the processor can compute a plurality of values of the signal quality metric based on a sliding window. The processor can determine a local period of the color intensity signal using the plurality of values of the signal quality metric. In determining the local period of the color intensity signal, the processor can determine a maximum of normalized autocorrelation parameters computed based on a sliding window.

The processor can further compare each value of the plurality of values of the signal quality metric to a corresponding threshold value, and determine for each value of the plurality of values of the signal quality metric, a corresponding indication of the quality of the color intensity signal based on comparing the value of signal quality metric to the corresponding threshold value. The processor can abort the recording if the multiple indications of the quality of the color intensity signal corresponding to a predefined cumulative time period are below the corresponding threshold value. The processor can perform at least one of display a graph of at least a portion of the color intensity signal, display a signal quality bar depicting a visual representation of the indication of the quality of the color intensity signal or display a timer indicative of time left for acquiring the sequence of transdermal images of the subject.

According to yet one other aspect, a computer readable medium can include computer code instructions stored thereon. The computer code instructions when executed by one or more processors can cause the one or more processors to generate a color intensity signal using an acquired sequence of transdermal images of a subject, and compute a signal quality metric of the color intensity signal. The one or more processors can provide an indication of a quality of the color intensity signal for display on a display device associated with the computing device. The indication of the quality of the color intensity signal can be determined based on the signal quality metric.

According to one aspect, a method can include associating, by a computing device, a calibration photoplethysmographic (PPG) signal generated from a first sequence of image frames obtained from a photodetector of the computing device with one or more measurement values generated by a blood pressure measurement device different from the computing device. The method can include obtaining, by the computing device, a recording PPG signal generated from a second sequence of image frames obtained from the photodetector, and identifying, by the computing device, a calibration model from a plurality of blood pressure calibration models based on the calibration PPG signal and the recording PPG signal. The method can include generating, by the computing device, a calibrated blood pressure value using the recording PPG signal, features associated with the calibration PPG signal and the identified calibration model.

In some implementations, the method can further include the computing device generating, from the recording PPG signal, a logarithmic recording PPG signal, and generating, from the calibration PPG signal, a logarithmic calibration PPG signal. In some implementations, the method can include the computing device determining whether the recording PPG signal generates a first blood pressure estimate, determining whether the logarithmic recording PPG signal generates a second blood pressure estimate, determining whether the calibration PPG signal generates a third blood pressure estimate, and determining whether the logarithmic calibration PPG signal generates a fourth blood pressure estimate. Identifying the calibration model can include selecting the calibration model from a plurality of calibration models based on (i) whether the recording PPG signal generates the first blood pressure estimate, (ii) whether the logarithmic recording PPG signal generates the second blood pressure estimate, (iii) whether the calibration PPG signal generates the third blood pressure estimate, and (iv) whether the logarithmic calibration PPG signal generates the fourth blood pressure estimate.

In some implementations, each blood pressure calibration model of the plurality of blood pressure calibration models can be associated with a corresponding set of parameter variables used to determine calibrated blood pressure values. The corresponding set of parameter variables can includes at least one of (i) one or more parameter variables indicative of one or more recording signal features extracted from a logarithmic recording PPG signal where the logarithmic recording PPG signal can be generated from the recording PPG signal, or (ii) one or more parameter variables indicative of one or more calibration signal features extracted from a logarithmic calibration PPG signal where the logarithmic calibration PPG signal can be generated from the calibration PPG signal. The corresponding set of parameter variables can include at least one of (i) one or more parameter variables indicative of one or more first pulse related features extracted from pulses of the recording PPG signal, or (ii) one or more parameter variables indicative of one or more second pulse related features extracted from pulses of the calibration PPG signal.

In some implementations, the corresponding set of parameter variables can include one or more parameter variables indicative of one or more calibration features of the calibration PPG signal. The one or more calibration features can include at least one of (i) a first systolic blood pressure estimate generated using the calibration PPG signal as an input signal, (ii) a first diastolic blood pressure estimate generated using the calibration PPG signal as an input signal, (iii) a second systolic blood pressure estimate generated using a logarithmic calibration PPG signal as input signal where the logarithmic calibration PPG signal can be generated from the calibration PPG signal, or (iv) a second diastolic blood pressure estimate generated using the logarithmic calibration PPG signal as input signal.

In some implementations, the corresponding set of parameter variables can include one or more parameter variables indicative of one or more features of the recording PPG signal. The one or more features of the recording PPG signal can include at least one of (i) a first systolic blood pressure estimate generated using the recording PPG signal as an input signal, (ii) a first diastolic blood pressure estimate generated using the recording PPG signal as an input signal, (iii) a second systolic blood pressure estimate generated using a logarithmic recording PPG signal as input signal where the logarithmic recording PPG signal can be generated from the recording PPG signal, or (iv) a second diastolic blood pressure estimate generated using the logarithmic recording PPG signal as input signal. The corresponding set of parameter variables can include one or more parameter variables indicative of one or more demographic features of a user of the computing device. The plurality of blood pressure calibration models can include one or more machine learning models and the method can further include training each machine learning model of the one or more machine learning models using labeled data to determine the corresponding set of parameter variables. According to one other aspect, a computing device can include a processor and a memory storing computer code instructions. The computer code instructions when executed can cause the processor to associate a calibration photoplethysmographic (PPG) signal generated from a first sequence of image frames obtained from a photodetector of the computing device with one or more measurement values generated by a blood pressure measurement device different from the computing device. The processor can obtain a recording PPG signal generated from a second sequence of image frames obtained from the photodetector, and identify a calibration model from a plurality of blood pressure calibration models based on the calibration PPG signal and the recording PPG signal. The processor can generate a calibrated blood pressure value using the recording PPG signal, features associated with the calibration PPG signal and the identified calibration model.

In some implementations, the processor can further generate, from the recording PPG signal, a logarithmic recording PPG signal, and generate, from the calibration PPG signal, a logarithmic calibration PPG signal. In some implementations, the processor can determine whether the recording PPG signal generates a first blood pressure estimate, determine whether the logarithmic recording PPG signal generates a second blood pressure estimate, determine whether the calibration PPG signal generates a third blood pressure estimate, and determine whether the logarithmic calibration PPG signal generates a fourth blood pressure estimate. In identifying the calibration model, the processor can select the calibration model from a plurality of calibration models based on (i) whether the recording PPG signal generates the first blood pressure estimate, (ii) whether the logarithmic recording PPG signal generates the second blood pressure estimate, (iii) whether the calibration PPG signal generates the third blood pressure estimate, and (iv) whether the logarithmic calibration PPG signal generates the fourth blood pressure estimate.

In some implementations, each blood pressure calibration model of the plurality of blood pressure calibration models can be associated with a corresponding set of parameter variables used to determine calibrated blood pressure values. The corresponding set of parameter variables can include at least one of (i) one or more parameter variables indicative of one or more recording signal features extracted from a logarithmic recording PPG signal where the logarithmic recording PPG signal can be generated from the recording PPG signal, or (ii) one or more parameter variables indicative of one or more calibration signal features extracted from a logarithmic calibration PPG signal where the logarithmic calibration PPG signal can be generated from the calibration PPG signal. The corresponding set of parameter variables can include at least one of (i) one or more parameter variables indicative of one or more first pulse related features extracted from pulses of the recording PPG signal, or (ii) one or more parameter variables indicative of one or more second pulse related features extracted from pulses of the calibration PPG signal.

In some implementations, the corresponding set of parameter variables can include one or more parameter variables indicative of one or more calibration features of the calibration PPG signal. The one or more calibration features can include at least one of (i) a first systolic blood pressure estimate generated using the calibration PPG signal as an input signal, (ii) a first diastolic blood pressure estimate generated using the calibration PPG signal as an input signal, (iii) a second systolic blood pressure estimate generated using a logarithmic calibration PPG signal as input signal where the logarithmic calibration PPG signal can be generated from the calibration PPG signal, or (iv) a second diastolic blood pressure estimate generated using the logarithmic calibration PPG signal as input signal.

In some implementations, the corresponding set of parameter variables can include one or more parameter variables indicative of one or more features of the recording PPG signal. The one or more features of the recording PPG signal can include at least one of (i) a first systolic blood pressure estimate generated using the recording PPG signal as an input signal, (ii) a first diastolic blood pressure estimate generated using the recording PPG signal as an input signal, (iii) a second systolic blood pressure estimate generated using a logarithmic recording PPG signal as input signal where the logarithmic recording PPG signal can be generated from the recording PPG signal, or (iv) a second diastolic blood pressure estimate generated using the logarithmic recording PPG signal as input signal. The corresponding set of parameter variables can include one or more parameter variables indicative of one or more demographic features of a user of the computing device. The plurality of blood pressure calibration models can include one or more machine learning models and the processor can further train each machine learning model of the one or more machine learning models using labeled data to determine the corresponding set of parameter variables.

According to yet one other aspect, a computer readable medium can include computer code instructions stored thereon. The computer code instructions when executed by one or more processors can cause the one or more processors to associate a calibration photoplethysmographic (PPG) signal generated from a first sequence of image frames obtained from a photodetector of a computing device with one or more measurement values generated by a blood pressure measurement device different from the computing device. The one or more processors can obtain a recording PPG signal generated from a second sequence of image frames obtained from the photodetector, and identify a calibration model from a plurality of blood pressure calibration models based on the calibration PPG signal and the recording PPG signal. The one or more processors can generate a calibrated blood pressure value using the recording PPG signal, features associated with the calibration PPG signal and the identified calibration model.

According to one aspect, a method can include a computing device obtaining a photoplethysmographic (PPG)

generated from a sequence of images obtained from a photodetector, and identifying a blood pressure estimation model from a plurality of machine learning blood pressure estimation models based on the PPG signal. The method can include the computing device generating a blood pressure value using the PPG signal and the identified blood pressure estimation model.

The method can further include the computing device generating, from the PPG signal, a logarithmic PPG signal. The method can further include determining whether the PPG signal generates a first blood pressure estimate, and determining whether the logarithmic PPG signal generates a second blood pressure estimate. Identifying the blood pressure estimation model can include selecting the blood pressure estimation model from a plurality of blood pressure estimation models based on (i) whether the PPG signal generates the first blood pressure estimate and (ii) whether the logarithmic PPG signal generates the second blood pressure estimate.

In some implementations, the blood pressure estimation model can be selected from a plurality of machine learning models. Each machine learning model of the plurality of machine learning models can be associated with a corresponding set of parameter variables used to determine calibrated blood pressure values. The corresponding set of parameter variables can include one or more parameter variables indicative of one or more signal features extracted from a logarithmic PPG signal, the logarithmic PPG signal generated from the PPG signal. The corresponding set of parameter variables can include one or more parameter variables indicative of one or more pulse related features extracted from pulses of the PPG signal.

In some implementations, the corresponding set of parameter variables can include one or more parameter variables indicative of one or more features of the PPG signal. The one or more features of the PPG signal can include at least one of (i) a first systolic blood pressure estimate generated using the PPG signal as an input signal, (ii) a first diastolic blood pressure estimate generated using the PPG signal as an input signal, (iii) a second systolic blood pressure estimate generated using a logarithmic PPG signal as an input signal, the logarithmic PPG signal generated from the PPG signal, or (iv) a second diastolic blood pressure estimate generated using the logarithmic PPG signal as an input signal. The corresponding set of parameter variables can include one or more parameter variables indicative of one or more demographic features of a user of the computing device. The method can further include training each machine learning model of the plurality of machine learning models using labeled data to determine the corresponding set of parameter variables. The blood pressure estimation model can include a linear regression model or a nonlinear regression model.

According to one other aspect, a computing device can include a processor and a memory storing computer code instructions. The computer code instructions when executed can cause the processor to obtain a photoplethysmographic (PPG) generated from a sequence of images obtained from a photodetector of the computing device, and identify a blood pressure estimation model from a plurality of machine learning blood pressure estimation models based on the PPG signal. The processor can generate a blood pressure value using the PPG signal and the identified blood pressure estimation model.

The processor can generate, from the PPG signal, a logarithmic PPG signal. The processor can determine whether the PPG signal generates a first blood pressure estimate, and determine whether the logarithmic PPG signal generates a second blood pressure estimate. In identifying the blood pressure estimation model, the processor can select the blood pressure estimation model from a plurality of blood pressure estimation models based on (i) whether the PPG signal generates the first blood pressure estimate and (ii) whether the logarithmic PPG signal generates the second blood pressure estimate.

In some implementations, the blood pressure estimation model can be selected from a plurality of machine learning models. Each machine learning model of the plurality of machine learning models can be associated with a corresponding set of parameter variables used to determine calibrated blood pressure values. The corresponding set of parameter variables can include one or more parameter variables indicative of one or more signal features extracted from a logarithmic PPG signal, the logarithmic PPG signal generated from the PPG signal. The corresponding set of parameter variables can include one or more parameter variables indicative of one or more pulse related features extracted from pulses of the PPG signal.

In some implementations, the corresponding set of parameter variables can include one or more parameter variables indicative of one or more features of the PPG signal. The one or more features of the PPG signal can include at least one of (i) a first systolic blood pressure estimate generated using the PPG signal as an input signal, (ii) a first diastolic blood pressure estimate generated using the PPG signal as an input signal, (iii) a second systolic blood pressure estimate generated using a logarithmic PPG signal as an input signal, the logarithmic PPG signal generated from the PPG signal, or (iv) a second diastolic blood pressure estimate generated using the logarithmic PPG signal as an input signal. The corresponding set of parameter variables can include one or more parameter variables indicative of one or more demographic features of a user of the computing device. The method can further include training each machine learning model of the plurality of machine learning models using labeled data to determine the corresponding set of parameter variables. The blood pressure estimation model can include a linear regression model or a nonlinear regression model.

According to yet one other aspect, a computer readable medium can include computer code instructions stored thereon. The computer code instructions when executed by one or more processors can cause the one or more processors to obtain a photoplethysmographic (PPG) generated from a sequence of images obtained from a photodetector of the computing device, and identify a blood pressure estimation model from a plurality of machine learning blood pressure estimation models based on the PPG signal. The one or more processors can generate a blood pressure value using the PPG signal and the identified blood pressure estimation model.

According to one aspect, a method can include obtaining, by a computing device, one or more photoplethysmographic (PPG) signals generated from a sequence of images obtained from a photodetector of the computing device. The method can include extracting, by the computing device, a plurality of features of the PPG signal. The method can include generating, by the computing device, a blood pressure classification using the plurality of features of the PPG signal and a blood pressure classification model.

In some implementations, the blood pressure classification model can be a machine learning model associated with a corresponding set of parameter variables used to determine the blood pressure classification. The method can further include training the machine learning model using labeled data to determine the corresponding set of parameter variables. The plurality of features of the PPG signal can include one or more signal features extracted from a logarithmic PPG signal generated from the PPG signal. The plurality of features of the PPG signal can include one or more pulse related features extracted from pulses of the PPG signal.

The plurality of features of the PPG signal can include at least one of (i) a first systolic blood pressure estimate generated using the PPG signal as an input signal, (ii) a first diastolic blood pressure estimate generated using the PPG signal as an input signal, (iii) a second systolic blood pressure estimate generated using a logarithmic PPG signal as an input signal where the logarithmic PPG signal can be generated from the PPG signal, or (iv) a second diastolic blood pressure estimate generated using the logarithmic PPG signal as an input signal. The blood pressure classification can be generated using one or more demographic features of a user of the computing device.

According to one other aspect, a computing device can include a processor and a memory storing computer code instructions. The computer code instructions when executed can cause the processor to obtain one or more photoplethysmographic (PPG) signals generated from a sequence of images obtained from a photodetector of the computing device. The processor can extract a plurality of features of the PPG signal. The processor can generate a blood pressure classification using the plurality of features of the PPG signal and a blood pressure classification model.

In some implementations, the blood pressure classification model can be a machine learning model associated with a corresponding set of parameter variables used to determine the blood pressure classification. The processor can further train the machine learning model using labeled data to determine the corresponding set of parameter variables. The plurality of features of the PPG signal can include one or more signal features extracted from a logarithmic PPG signal generated from the PPG signal. The plurality of features of the PPG signal can include one or more pulse related features extracted from pulses of the PPG signal.

The plurality of features of the PPG signal can include at least one of (i) a first systolic blood pressure estimate generated using the PPG signal as an input signal, (ii) a first diastolic blood pressure estimate generated using the PPG signal as an input signal, (iii) a second systolic blood pressure estimate generated using a logarithmic PPG signal as an input signal where the logarithmic PPG signal can be generated from the PPG signal, or (iv) a second diastolic blood pressure estimate generated using the logarithmic PPG signal as an input signal. The blood pressure classification can be generated using one or more demographic features of a user of the computing device.

According to yet one other aspect, a computer readable medium can include computer code instructions stored thereon. The computer code instructions when executed by one or more processors can cause the one or more processors to obtain one or more photoplethysmographic (PPG) signals generated from a sequence of images obtained from a photodetector of the computing device. The one or more processors can extract a plurality of features of the PPG signal. The one or more processors can generate a blood pressure classification using the plurality of features of the PPG signal and a blood pressure classification model.

According to one aspect, a method of measuring vital signs of a user can include receiving a finger within a groove of a housing of a device. The device can include a processor, a light source disposed within the housing and positioned at a bottom region of the groove, and a photodetector disposed within the housing and positioned at the bottom region of the groove. The method can include emitting, by the light source, light in the groove and capturing, by the photodetector, a sequence of images of the finger while the light is emitted. The method can include generating, by the processors, a photoplethysmographic (PPG) signal using the sequence of images to determine one or more vital signs of the user.

The method can further include determining a measurement of the one or more vital signs using the PPG signal, and displaying the measurement of the one or more vital signs on a display device. The method can further include transmitting the PPG signal to a remote device. The remote device can determine a measurement of the one or more vital signs using the PPG signal and display the measurement of the one or more vital signs on a display device. The method can further include assessing, by the processor, a quality of the sequence of image frames or a quality of the PPG signal, and providing a light signal indicative of the quality of the sequence of image frames or the quality of the PPG signal.

The method can further include instructing the user to adjust placement of the finger within the groove, responsive to determining a poor quality of the sequence of image frames or a poor quality of the PPG signal. The method can further include providing, via a finger groove light pipe located at an upper edge of the groove, a light signal to prompt the user to take a measurement of the one or more vital signs.

According to one other aspect, a device for measuring blood pressure can include a housing including a groove to receive a finger of a user. The groove can have a curved end towards a center of the housing and can have a first dimension between 20 mm and 70 mm, a second dimension between 20 mm and 35 mm and a third dimension between 3 mm and 10 mm. The device can include a light source disposed within the housing and positioned at a bottom region of the groove and configured to emit light in the groove. The device can include a photodetector disposed within the housing and positioned at the bottom region of the groove and configured to capture a sequence of image frames while the light is emitted. The device can include a processor configured to generate a photoplethysmographic (PPG) signal of a user using the sequence of image frames to determine a blood pressure of the user.

The groove can extend from an edge of the housing towards a center of the device. The device can further include one or more tactile surface features at a first portion of the bottom region of the groove to aid the user to position the finger such that a pulp region of the finger is positioned above the photodetector. The photodetector can be positioned within the first portion and configured to capture images of the pulp region of the finger of the user. The one or more surface features can include a protrusion at the bottom region and forming a closed loop to accommodate the pulp region of the finger of the user. The first portion of the bottom region can have a first dimension between 2 mm and 10 mm and a second dimension between 5 mm and 20 mm. The thickness of the protrusion can be less than 1 mm. The first portion of the bottom region can be less than 15 mm and greater than 2 mm from a center of the curved end.

The photodetector can include at least one of a red-green-blue (RGB) photodetector, a full light spectrum photodetector, or a combination of a RGB photodetector and an infrared photodetector. The device can further include a communications interface configured to communicate with a remote device. The processor can be configured to cause the communication interface to transmit the PPG signal to the remote device. The remote device can be configured to determine a blood pressure measurement of the user using the PPG signal, and display the blood pressure measurement on a display device.

The device can further include a display device disposed within the housing. The processor can determine a blood pressure measurement of the user using the PPG signal, and display the blood pressure measurement on a display device. The device can further include at least one of a pressure sensor to measure pressure applied by the finger to a first portion of the bottom region of the groove, a thermometer to measure a temperature of the finger, or an oximeter to measure oxygen level in blood flowing through the finger.

The device can further include a visual output device. The processor can be configured to assess a quality of the sequence of image frames or a quality of the PPG signal, select, based on the quality of the sequence of image frames or the quality of the PPG signal, from a plurality of light outputs, a light output, and cause the visual output device to emit the light output. The device can further include a light pipe disposed within the housing at an upper edge of the groove. The processor can cause the light pipe to be illuminated to prompt the user to take a measurement of the one or more vital signs.

BRIEF DESCRIPTION OF THE DRAWINGS

FIGS. 3A-3D show diagrams illustrating the physics behind the use of transdermal image data to measure blood pressure of the corresponding subject.

DETAILED DESCRIPTION

For purposes of reading the description of the various embodiments below, the following descriptions of the sections of the specification and their respective contents may be helpful:

Section A describes an example architecture of devices and systems configured to implement embodiments described in this disclosure.

Section B describes systems and methods for estimation of blood pressure using transdermal optical recordings.

Section C describes systems and methods for calibrating a photodetector for measuring blood pressure.

Section D describes systems and methods for enhancing acquisition of transdermal optical recordings for use to estimate blood pressure.

Section E describes systems and methods for assessment of photoplethysmographic (PPG) signal quality for initiating blood pressure measurement.

Section F describes systems and methods for improving an accuracy of a blood pressure measurement using offsets based on reference signals generated using a measurement device.

Section G describes systems and methods for improving an accuracy of a blood pressure measurement using offsets generated without reference signals.

Section H describes systems and methods for classifying blood pressure measurements instead of estimating actual blood pressure values.

Section I describes a standalone blood pressure measurement device.

Section J describes various design aspects of the standalone blood pressure measurement device.

A. Device Architecture

Figure 1:
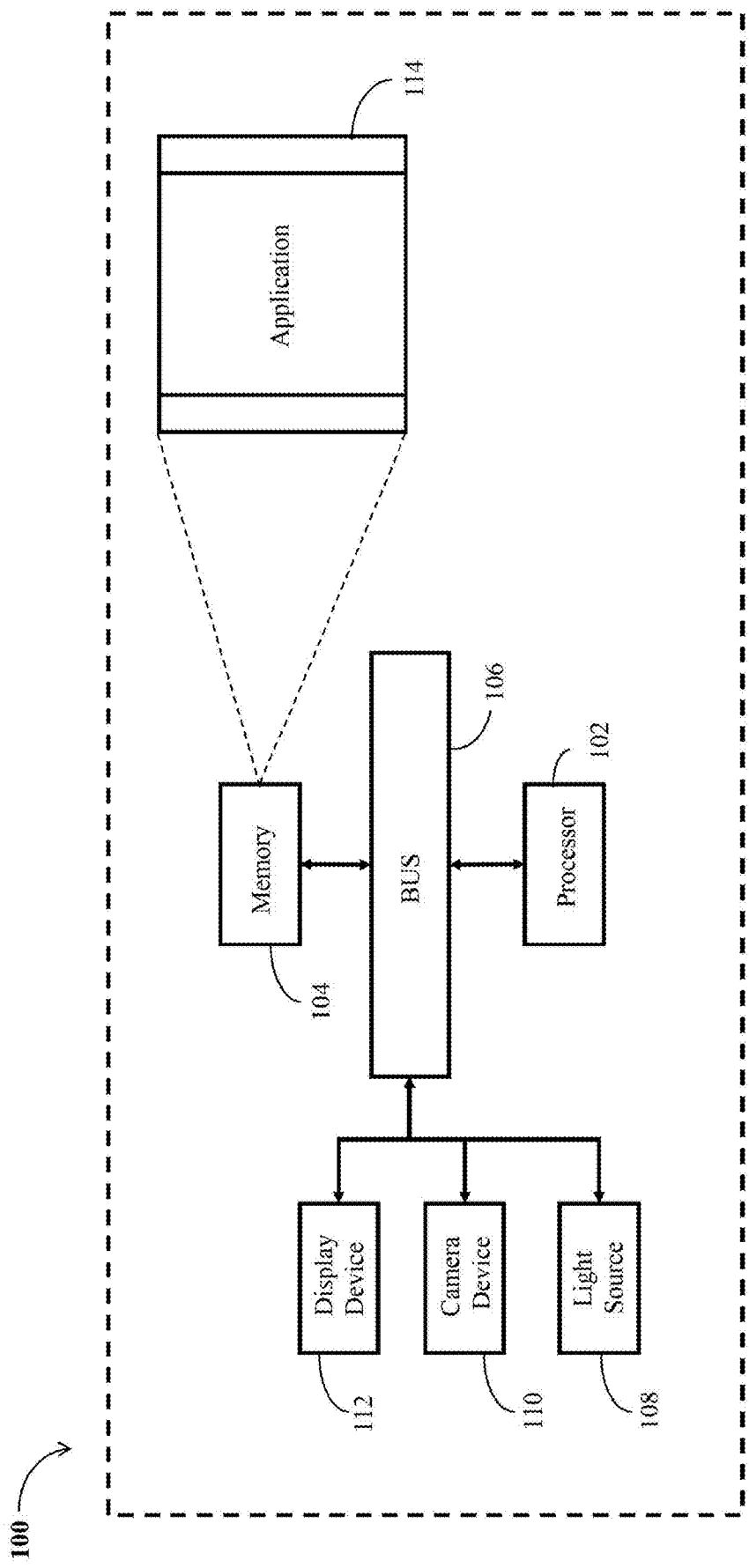
FIG. 1 is a block diagram of an example architecture of a computing device for implementing methods and processes described herein.

FIG. 1 shows a block diagram depicting one implementation of a system architecture for a computer system 100 that may be employed to implement methods described herein, according to inventive concepts of the current disclosure. In general, the embodiments described in this disclosure can be implemented by the computer system 100. The computer system 100 can include a single computing device including, but is not limited to, a smartphone, a tablet device, a handheld device, a smart watch, a personal digital assistant, a mobile computing device, a laptop, a desktop, a hardware computer server, a standalone blood pressure measurement device, a workstation, or other type of computing device. The single computing device can be a standalone device designated for measuring various vital signs, e.g., blood pressure, pulse rate, respiratory rate, oxygen saturation and/or body temperature, such as the device described in Section I. In some implementations, the computer system 100 can include multiple computing devices that are communicatively connected to each other and configured to perform methods or processes described herein. For instance, the computer system 100 can include a first device (e.g., a standalone device) for acquiring photoplethysmographic (PPG) signals, and a second device (e.g., one or more remote servers or one or more other computing devices) communicatively coupled to the first device and configured to process the PPG signals acquired by the first device or other related signals.

In brief overview, the computer system 100 can include one or more processors 102 to execute computer code instructions, a memory 104 to store the computer code instructions and/or other data, a bus 106 communicatively coupling various components of the computer system 100, a light source 108, a camera device (or a photodetector) 110 and a display device 112.

The one or more processors 102 can include a microprocessor, a general purpose processor, a multi-core processor, a digital signal processor (DSP) or a field programmable gate array (FPGA), an application-specific integrated circuit (ASIC) or other type of processor. The one or more processors 102 can be communicatively coupled to the bus 106 for processing information. The memory 104 can include a main memory device, such as a random-access memory (RAM) or other dynamic storage device, coupled to the bus 106 for storing information and instructions to be executed by the processor 102. The main memory device can be used for storing temporary variables or other intermediate information during execution of instructions (e.g., related to methods described herein or operations thereof) by the processor 102. The computer system 100 can include a read-only memory (ROM) or other static storage device coupled to the bus 106 for storing static information and instructions for the processor 102. The ROM can store computer code instructions related to, or representing an implementation of, methods described herein, such as application 114. A storage device, such as a solid state device, magnetic disk or optical disk, can be coupled to the bus 106 for storing (or providing as input) information and/or instructions.

The computer system 100 can include, or can be communicatively coupled to, the light source 108, the camera device 110 and the display device 112. The one or more processors 102 and memory 104 can be communicatively coupled to the light source 108, the camera device 110 and the display device 112 via the bus 106. The light source 108 and camera device 110 can be positioned on a front side of the computer system 100 or on back side of the computer system 100. The light source 108 can be a flash device associated with the camera device 110. In some implementations, the computer system 100 can include multiple camera devices 110, such as one or more front cameras and one or more back cameras. In some embodiments, the camera device 110 may be a separate device that can be communicatively coupled to the computer system 100. The one or more processors 102 can control the light source and the camera device 110. For instance, the one or more processors 102 can automatically or upon user input, trigger the light source 108 to emit light and trigger the camera device 110 to capture images or a sequence of image frames. The one or more processors 102 can control settings of the light source 108 and the camera device 110. For instance, the one or more processors 102 can adjust one or more settings of the camera device 110 prior to or while capturing image frames.

The computer system 100 can include other input devices (e.g., other than the camera device 110), such as a keyboard including alphanumeric and other keys, a touch screen, or a communication interface for receiving input data. The input devices can be communicatively coupled to the bus 106 for communicating information and command selections to the one or more processors 102, the memory 104 and/or the camera device 110. The input devices can include a cursor control, such as a mouse, a trackball, or cursor direction keys, for communicating information and command selections to the one or more processors 102, the memory 104 and/or the camera device 110.

The display device 112 can include a Liquid Crystal Display (LCD), Thin-Film-Transistor LCD (TFT), an Organic Light Emitting Diode (OLED) display, LED display, Electronic Paper display, Plasma Display Panel (PDP), or other display, for displaying information to a user of the computer system 100. The display device 112 can include a touch screen capable of acting as an input/output (I/O) device. The computer system 100 can include other output devices (e.g., other than the display device 112) such as a communication interface (not shown in FIG. 1) for communicating information to other external devices. The communication interface can include a wired communication interface, a wireless communication interface, BLUETOOTH, near field communication (NFC) interface, other communication interface or a combination thereof.

According to various implementations, the methods described herein or respective operations can be implemented as an arrangement of computer code instructions that are executed by the one or more processors 102 of the computer system 100. The arrangement of computer code instructions can be implemented as client application 114. The client application 114 can be installed on, and executed by, the computer system 100 to perform embodiments described herein. The client application 114 can include modules, instructions and/or application programming interfaces (APIs) for executing various operations related to embodiments described herein, such as triggering the light source 108 to emit light, triggering the camera device 110 to capture images, controlling settings of the camera device 110, displaying user interfaces (UIs) on the display device 112, processing image data, generating photoplethysmographic (PPG) signals based on image data, processing and/or assessing the quality of PPG signals, computing blood pressure and/or pulse measurements or a combination thereof. The computer code instructions and/or data associated with the application 114 can be stored in ROM or the storage device of the computer system 100, and read into a main memory device (e.g., RAM) of the computing device, for example, when the application is initiated.

In some implementations, the application 114 can include a client application to run on the computer system 100 and a server application to run on a cloud server or other remote computer server. The server application can be a web application. The remote server and the server application running thereon can be configured to serve a plurality of computing devices 100 that can connect to the server via a communication network. In some implementations, the client application and the computer system 100 can perform some of the operations associated with embodiments described herein, while the server and the server application can execute other operations of the embodiments. For instance, the computer system 100 and the client application 114 can perform image data acquisition, PPG signal generation and/or display of output results, while the server and the server application can compute blood pressure and/or pulse measurements based on PPG signals received from the computer system 100.

In some other implementations, hard-wired circuitry may be used in place of or in combination with software instructions to effect illustrative implementation of the methods described herein or operations thereof. In general, implementations are not limited to any specific combination of hardware circuitry and software. The functional operations described in the following sections can be implemented in other types of digital electronic circuitry, in computer software, firmware, hardware or a combination thereof.

B. Estimation of Blood Pressure Using Transdermal Optical Recordings

The most common non-invasive approach for measuring blood pressure makes use of the sphygmomanometer; a device that includes an inflatable cuff and a configured to surround the arm of a patient or subject and a stethoscope. A user inflates the cuff above an expected systolic blood pressure (SBP) level and then releases the pressure inside the cuff. The stethoscope is used to listen to the blood circulating in the arteries. When the blood pressure decreases below the SBP level, blood flow turbulence generates noise known as Korotkoff noise that is audible until the blood pressure gets below the diastolic blood pressure (DBP) level. As such, the SBP is determined as the recorded pressure at the start of the Korotkoff noise, and the DBP is determined as the recorded pressure at the end of the Korotkoff noise. While it provides accurate blood pressure measurements, the sphygmomanometer may not be easy and comfortable to use. For instance, many patients need the help of another person to place the cuff on the patient's arm and operate the sphygmomanometer. Also, the sphygmomanometer provides single measurements at specific time instances, but does not allow for continuous monitoring of blood pressure or for analyzing blood pressure waveforms over time.

A more advanced noninvasive approach for measuring blood pressure includes the use of oscillometric cuffs, which operate in a similar way as sphygmomanometers except for the use of the stethoscope to listen to the blood circulating in the arteries. Instead, the oscillometric cuff includes an auto-inflatable cuff that is linked to a microphone for monitoring the Korotkoff noise and deducing the SBP and DBP levels based on the Korotkoff noise. Oscillometric cuffs are easier and more convenient to use to monitor blood pressure on a regular basis, especially for hypertensive patients. However, the oscillometric cuffs still need to be placed around the patient's arm to apply a pressure thereon, and are usually less accurate than sphygmomanometers. Furthermore, the oscillometric cuffs are not so cheap and are not convenient to carry around.

Another approach is to measure intra-arterial blood pressure using a catheter. This approach allows for continuous recording and monitoring of blood pressure over time, and provides other indicators such as gas concentration in the blood, which is useful to measure blood oxygenation. However, this is an invasive approach that requires a heavy equipment to prevent the patient from moving. Also, the procedure is significantly uncomfortable for patients, and is usually available for patient in relatively sever conditions.

In the current disclosure, a simpler and easier to use noninvasive approach for measuring blood pressure makes use of transdermal optical data recorded by a camera 110 of a computer system 100, such as a smart phone, tablet, Internet-of-things (IoT) device, or other device configured or structured to measure blood pressure. The computer system 100 can leverage the non-invasive technique of photo plethysmography (PPG) to estimate the blood pressure of a user or subject. Specifically, upon the user placing his fingertip (or other surface of the body) to face the lens of the camera, the camera 110 can capture a sequence of images of the fingertip. The computer system 100 can generate a color signal representing a PPG signal using the sequence of images, and use the generated PPG signal to determine blood pressure measurements and/or pulse measurements.

Figure 2B:
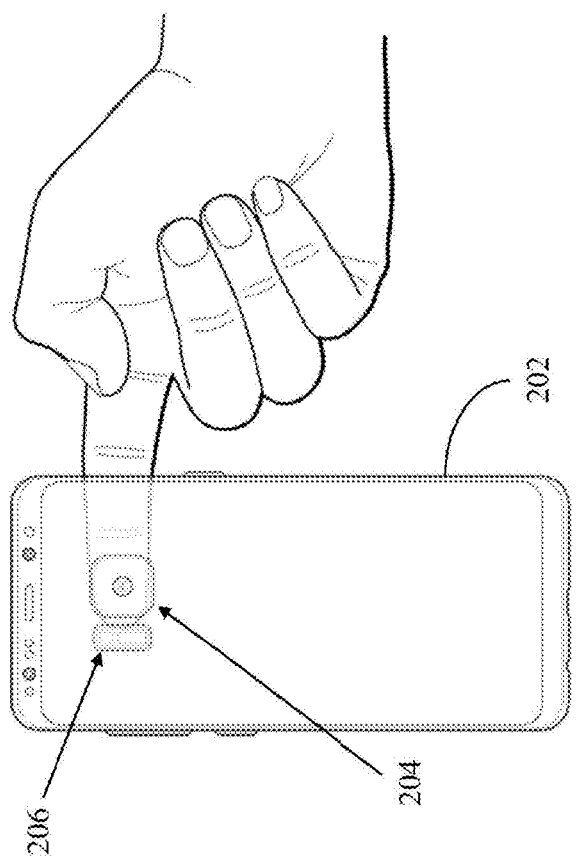
FIGS. 2A and 2B show diagrams illustrating placement of a fingertip against a camera of a mobile device, according to example embodiments.
Figure 2A:
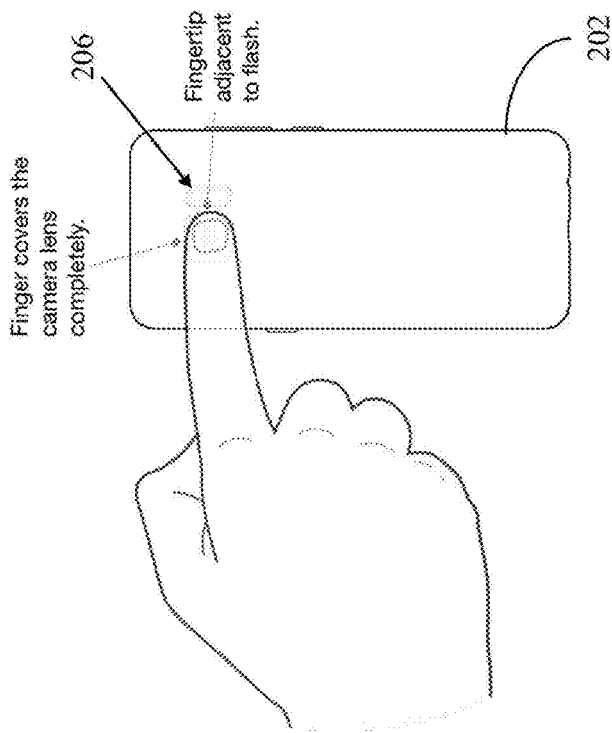

FIGS. 2A and 2B show diagrams illustrating the placement of a subject's finger to a camera 204 of a mobile phone 202, according to inventive concepts of the current disclosure. FIG. 2A shows a rear side of the mobile phone 202 with a rear-facing camera 204. The rear-facing camera 202 can include a lens (not shown in FIGS. 2A and 2B) and an optical (or light) waveguide to channel light towards the camera lens. The optical waveguide can include a recess or groove in the rear side or surface of the mobile phone 202. The mobile phone 202 can include a transparent glass (or other material) arranged at the upper end of the optical waveguide, e.g., aligned with the rear surface of the mobile phone 202. The mobile phone 202 can include a flash device (or light source) 206 arranged adjacent to the camera 204 or the glass at the upper end of the optical waveguide. The flash device 206 can automatically produce artificial light to help illuminate a scene at the time of capturing images or image frames by the camera 204. In some implementations, the flash device 206 can be positioned adjacent to the camera 204, e.g., within or at the bottom of the optical waveguide. FIG. 2B shows the front side of the mobile phone 202 with the camera 202 facing downward. The smartphone 202 represents an example implementation of the computer system 100, and the camera 204 represents an example implementation of the camera device 110. Other devices can be used, instead of the mobile phone 202, to capture image frames and use the captured image frames to measure blood pressure and/or other vital signs. Also, while FIGS. 2A and 2B show a finger is being used, in general other body parts can be placed in front of the camera lens to capture image frames for the purpose of measuring blood pressure or other vital signs.

The user can place or apply their fingertip, or other body part, against the camera lens, the optical waveguide of the camera 204 or against the transparent glass arranged at the upper end of the optical waveguide. In some implementations, the user can place their fingertip or other body part to face, or in front of, the lens of the camera. The fingertip or the other body part can be placed to be exposed (e.g., adjacent) to the flash device 206. Considering FIG. 2B, the user can place their fingertip or other body part against the camera lens, the optical waveguide or the transparent glass covering the optical waveguide while the screen of the mobile device 202 is facing the user. Accordingly, the user can activate the application 114 to trigger the camera 204 to capture a sequence of image frames, and use the image data to estimate blood pressure of the user. From the user's perspective, the procedure is simple, easy, and can be carried out anywhere as long as the user is equipped with the smartphone 202 or other computer system 100 having a respective light source 108, a camera (or photodetector) 110 and installing the application 114.

Figure 3A:
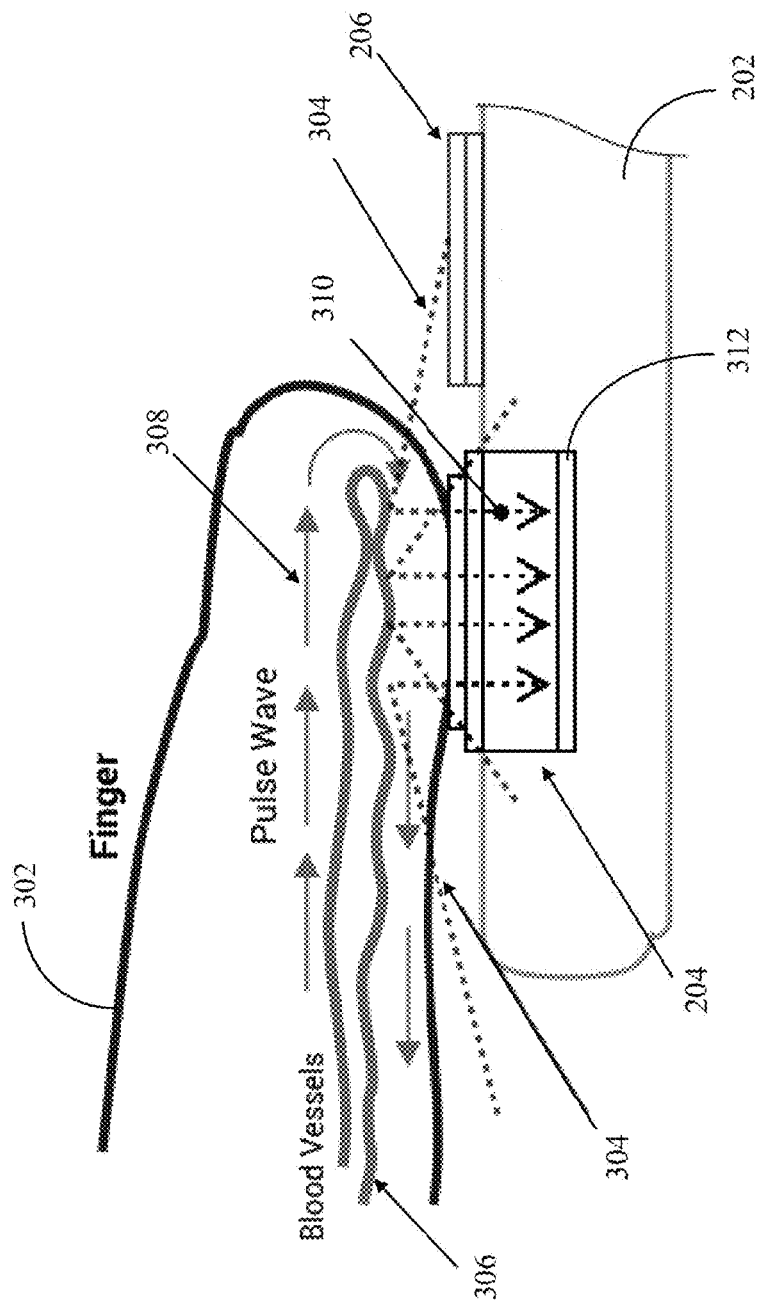

FIGS. 3A-3D are diagrams illustrating the physics behind the use of transdermal image data to measure blood pressure of the corresponding subject. The diagrams in FIGS. 3A-3C illustrates propagation of light when a finger 302 or other body part is applied to a camera 204 of smartphone 202 (or other device). Light rays 304 emitted by the flash device (or light source) 206 penetrate the finger 302. Specifically, incident light 304 penetrates the tissue as well as the blood vessels 306 of the finger 302 or other body part. The blood circulating in the blood vessels 306 includes arterial blood and venous blood, and the light rays 304 penetrates both the arterial blood and the venous blood. The flow of arterial blood is pulsatile, or following a pulse wave 308 caused by extension of the intramural coronary vessels due to additional pressure consequent to contraction of the cardiac muscle.

A first portion of the incident light 304 gets absorbed by the blood while a second portion 310 gets reflected back from the finger 302, and is received by the red-green-blue (RGB) sensor 312 of the camera 204. The light intensity received by the RGB sensor 312 can be described as:

$$I = I_0 \cdot 10^{-A} = I_0 \cdot 10^{-\Sigma_i \varepsilon_i d_i}, \qquad (1)$$

where $I_0$ represents the light intensity 304 produced by the light source 206, I represents the light intensity 310 received by the RGB sensor (or photodetector) 312, A represents light absorbance by the finger 302 (or other body part) applied to the camera 204, the coefficient $a_i$ represents a linear absorption coefficient of tissue i and $l_i$ represents the thickness of tissue i. The reflected light intensity I represents a transdermal optical signal of the subject or user. The camera 204 can use the reflected light intensity I 310 received at each time instance by the RGB sensor 312 to generate a corresponding image. Specifically, the camera 204 can generate a sequence of image frames representing the light intensity I 310 received at a plurality of time instances. For instance, the camera 204 can generate the image frames at a frame rate of 25 frames per second, at 30 frames per second or at other frame rate.

Figure 3D:
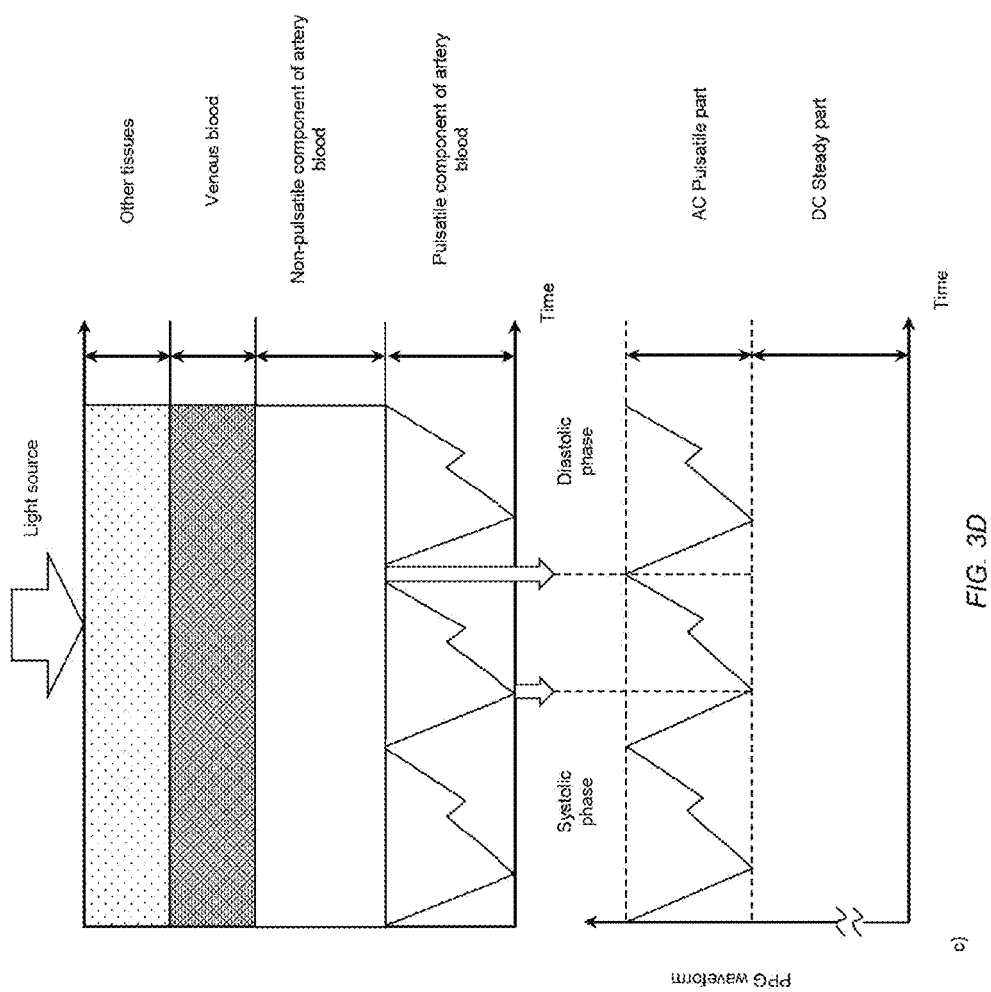

FIG. 3D shows a diagram illustrating various light absorption components associated with the finger 302 or other body parts. Light for a given wavelength is absorbed by the different layers of flesh of the finger. Tissue and venous blood absorb a constant proportion of light through time while pulsatile arterial blood has a varying volume and thus has a varying absorption through time. Specifically the light absorbance A can be described as:

$$A = a_{flesh} \cdot l_{flesh} + \ldots + a_{veinous} \cdot l_{veinous} + a_{arterial} \cdot l_{arterial}(t) = A_0 + a_{arterial} \cdot l_{arterial}(t). \quad (2)$$

The term $a_{flesh} \cdot l_{flesh}$ represents the light absorbance of flesh, $a_{veinous} \cdot l_{veinous}$ represent the light absorbance by the veins, and $a_{arterial} \cdot l_{arterial}(t)$ represents the light absorbance by pulsatile arterial blood. The term $A_0$ represents the aggregate non-pulsatile light absorbance by the finger (or body part) 302. For the purpose of measuring blood pressure and/or pulse of the subject, the focus is on the component of the reflected light intensity I 304 defined in terms of $a_{arterial} \cdot l_{arterial}(t)$, e.g., as $I_0 e^{-a_{arterial} \cdot l_{arterial}(t)}$, because it is time varying (AC signal) and is expected to reflect the pulse wave 308. Other useful metrics that are defined herein to estimate the proportion of light absorbed by a system, include the transmittance T that measures the proportion (or ratio) of light transmitted or reflected by a system (e.g., finger 302) relative to incident light $I_0$ or light $I_0$ produced by light source 108 or 206. That is, $$T = \frac{I}{I_0}. \quad (3)$$

Another metric is opacity which measures the proportion (or ratio) of light that is absorbed:

$$O = \frac{1}{T}. \quad (4)$$

Figure 4:
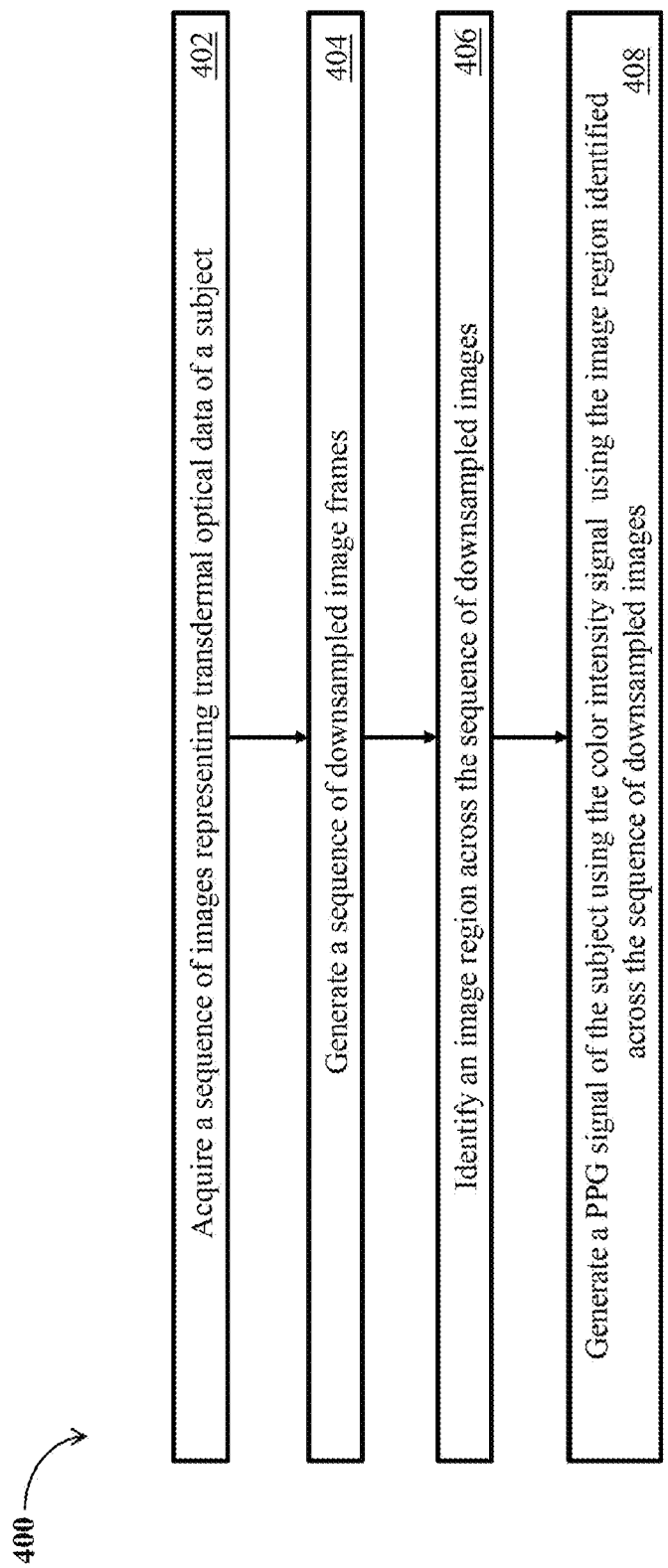
FIG. 4 shows a flowchart illustrating a method of generating a photoplethysmographic (PPG) signal using transdermal image data, according to example embodiments.

Referring to FIG. 4, a flowchart illustrating a method 400 of generating a PPG signal, for measuring blood pressure, using transdermal image data is shown, according to inventive concepts of this disclosure. The method 400 can include acquiring a sequence of images representing transdermal optical data of a subject (STEP 402), and generating a sequence of downsampled image frames using the acquired sequence of images (STEP 404). The method 400 can include identifying an image region across the sequence of downsampled image frames (STEP 406), and generating a PPG signal associated with the image region across the sequence of downsampled images (STEP 408). The method 400 can be performed by the computer system 100 or the corresponding processor 102, for example, upon executing the application 114.

Figure 5:
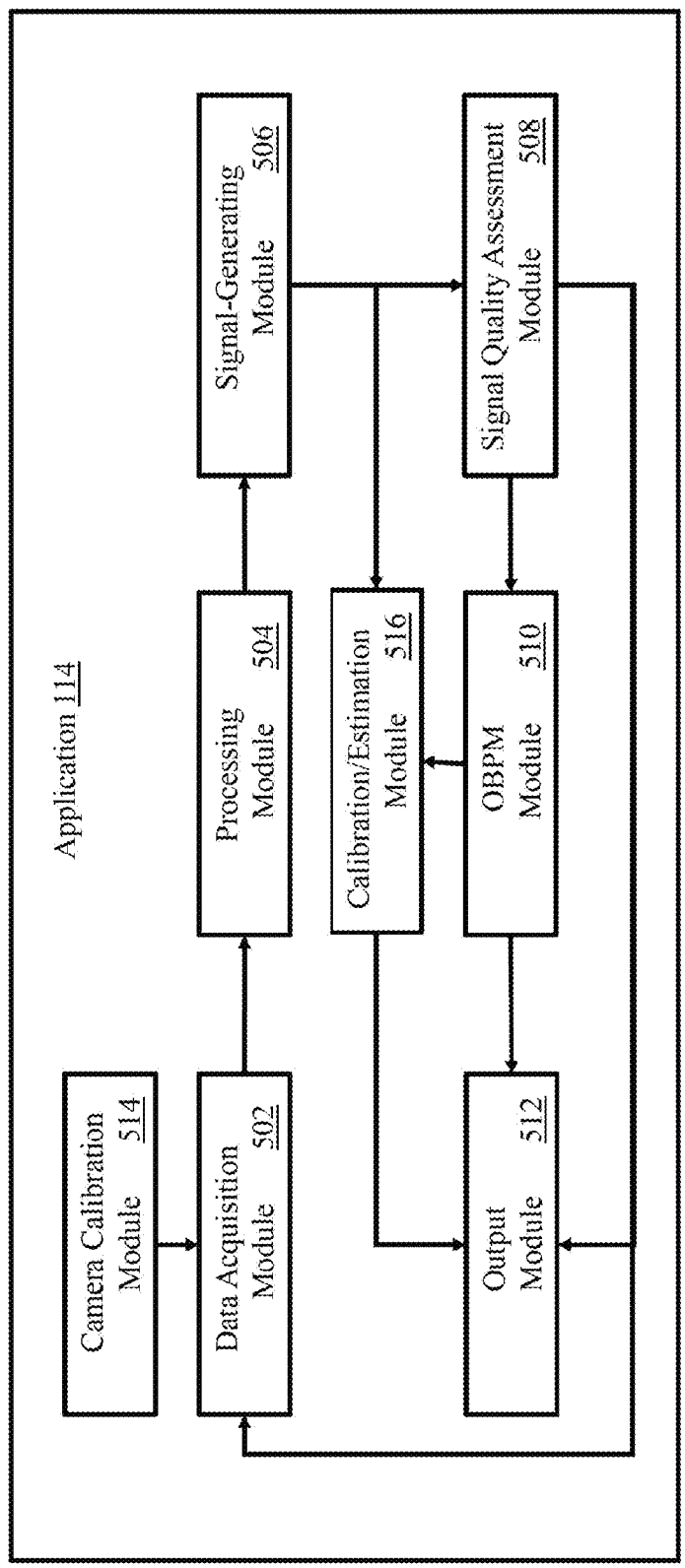
FIG. 5 shows a block diagram depicting components of a computer application for measuring blood pressure using transdermal image data, according to example embodiments of the current disclosure.

Referring to FIG. 5, a block diagram describing components of the application 114 is shown, according to example embodiments of the current disclosure. The application 114 can include a data acquisition module 502 to acquire image data, and a processing module 504 to process the image data. The application 114 can include a signal-generating module 506 to generate a PPG signal using the image data, and a signal quality assessment module 508 to assess the quality or validity of the PPG signal. The application 114 can include an optical blood pressure monitoring (OBPM) module 510 to estimate blood pressure measurements using the PPG signal, and an output module 512 to output or display blood pressure measurements. The application 114 can include a camera calibration module 514 for calibrating the camera or photodetector 110, and a calibration/estimation module 516 for enhancing the accuracy of blood pressure measurements. The functions associated with these modules or components are discussed in further detail below.

Referring back to FIGS. 1-5, the method 400 can include the computer system 100 acquiring a sequence of images representing transdermal optical data of a subject (STEP 402). A user can actuate the application 114 on the computer system 100, and apply their finger pulp or other body part to the camera 110 or photodetector 312, for example, as illustrated in FIGS. 2A, 2B and 3A-3C. Upon initiation, the application 114 can cause the computer system 100 to display a user interface (UI) on the display device 112. The UI can provide instructions to the user to apply their finger pulp against the camera 110 or photodetector 312 (or against a light/optical waveguide of the camera) for a given period of time, e.g., 30 seconds. The UI can provide an option, e.g., upon user selection, to present further instructions, images or a demo explaining how the finger pulp (or other body part) is to be applied to the camera 110.

The application 114 or the data acquisition module 502 can automatically trigger the camera 110 to acquire a sequence of image frames. In some implementations, the application 114 or the data acquisition module 502 can cause the computer system 100 to display an interactive item as part of the UI. The application 114 or the data acquisition module 502 can automatically trigger the camera device 110 to acquire the sequence of images, upon the user interacting with the interactive item. Triggering the camera device 110 can include actuating the flash device 206 to emit artificial light either continuously or periodically according to a given frequency.

The camera device 110 can acquire the sequence of image frames while the user's finger pulp (or other body part) is applied against the optical waveguide of the camera or the corresponding transparent glass. Specifically, the RGB sensor 312 can acquire the sequence of image frames according to a specific or predefined frame rate based on the light intensity $I_r$ reflected from the user's finger. The frame rate can be equal to 25 frames/second (fps), 30 fps, 50 fps or other frame rate supported by the camera device 110. The data acquisition module 502 can receive image data corresponding to image frames from the camera device 110. In some implementations, the data acquisition module 502 can receive image data for each frame immediately after the image frame is captured or recorded by the RGB sensor 312 or the camera device 110.

In some implementations, the computer system 100 can include a plurality of cameras (or photodetectors) 110. The computer system 100 can automatically select one of the cameras (or photodetectors) 110 to acquire the sequence of image frames, and display (e.g., via a user interface of the application 114) a notification to the user of the computer system 100 of the selected camera 110. The user can place his/her finger against the selected camera. The selection can be based on features or characteristics of the various cameras. In some implementations, the user can select the camera to be used to acquire the sequence of image frames. The computer system 100 can receive or obtain the user selection via an input device, e.g., a keyboard, a mouse or a touch screen, among others, of the computer system 100. The computer system 100 may confirm the user selection via, for example, the display device 112. The computer application 114 may include different settings for distinct cameras 110. The computer system 100 can maintain camera ID/phone model matrix in the memory 104. Besides the camera ID, the computer system 100 can store the preferred camera settings in the matrix, such as ISO, exposure time, tonemap, RGB gain or a combination thereof, among other settings.

The method 400 can include the computer system 100 generating a sequence of downsampled image frames (STEP 404), and identifying an image region or an image block across the sequence of downsampled image frames (STEP 406). The camera device 110 can generate, for each frame, an image having several thousands of pixels. This information is often noisy and redundant. The pixels provide essentially the same information about blood flow in finger arteries since they capture light transmitted by very close regions of finger flesh. In other words, the image frames captured by the camera 110 are not expected to have much contrast, edges or other visual details of interest. The relevant data here is the variation in cumulative color intensity of the captured image frames.

Figure 6:
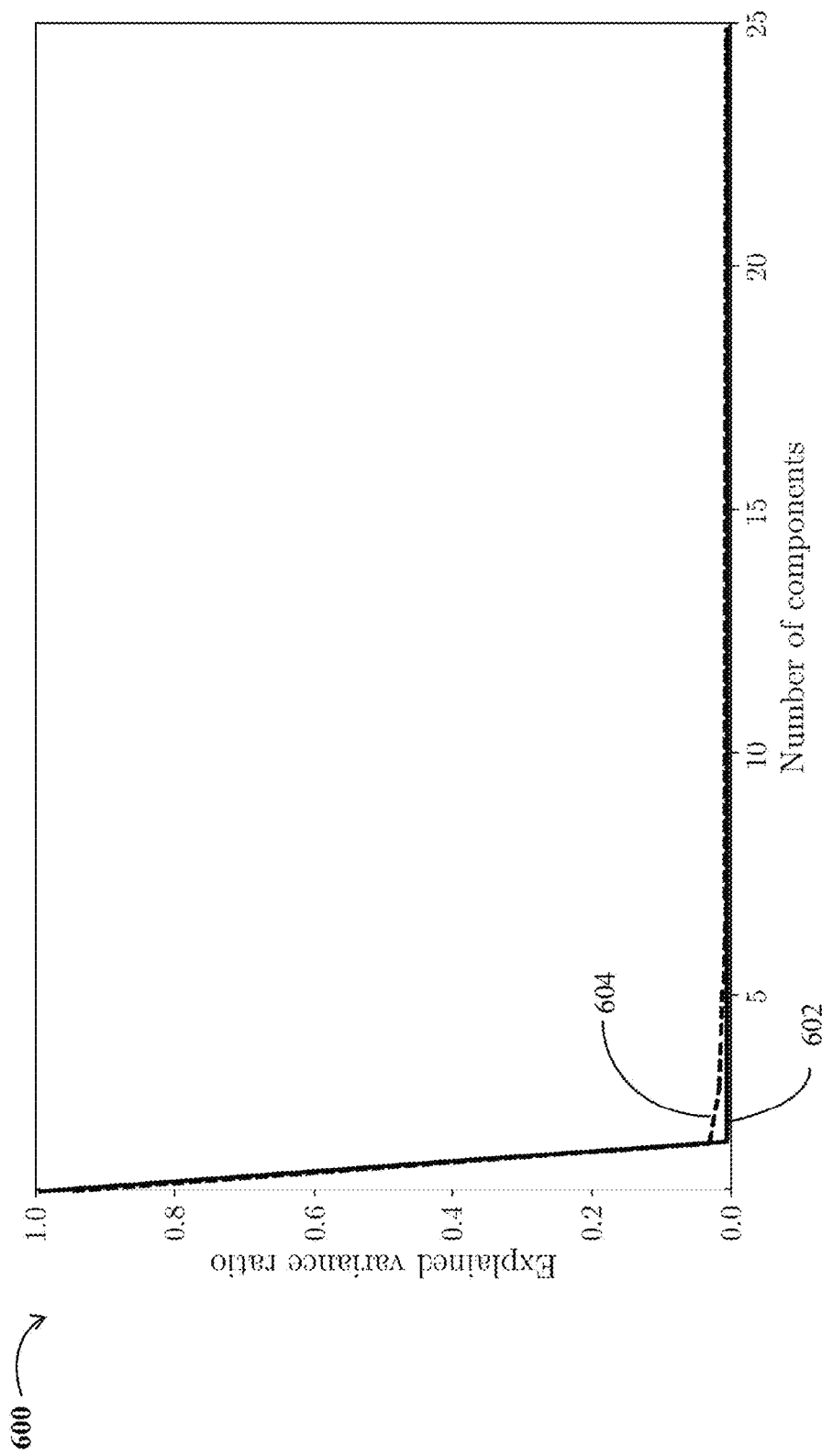
FIG. 6 shows plots of explained variance ratio for red (R) and green (G) frames of an image frame of a user finger.

Principal component analysis (PCA) for an image frame reveals how to reduce the dimensionality of the data samples and find out which aggregation function best captures all information in the sequence of captured image frames or signals. FIG. 6 shows a graph 600 illustrating plots 602 and 604 of the explained variance ratio for the red (R) and green (G) frames of an image frame of a user finger, respectively. The x-axis represents the component number or index, and the y-axis represents the explained variance ratio. For each component, the corresponding variance ratio represents the variance of the component divided by the total variance of the color frame. Both the red plot 602 and the green plot 602 in FIG. 6 show that almost all the variance of the signal is contained in a single component, i.e., the first component. The first component captures more than 99% of the color (e.g., R or G) frame variance. This decomposition is strikingly close to a simple averaging —give or take a multiplicative factor—of the pixels in each color (e.g., R or G) frame of the sequence of image frames.

The data acquisition module 502 or the processing module 504 can decompose each image frame into R, G and blue (B) frames. For the purpose of estimating blood pressure and/or pulse of the user, the application 114 or the computer system 100 can use the R frames or the G frames. In some implementation, the application 114 or the computer system 100 may use the B frames for estimating blood pressure or pulse. In some implementations, the application 114 or the computer system 100 may use a combination of R, G and/or B frames. In some implementations, the application 114 or the computer system 100 may use image frames associated with another color space (or color model), e.g., other than the RGB color space (or RGB color model), such as the YUV color space or the cyan, magenta, yellow (CMY) color space.

Figure 7:
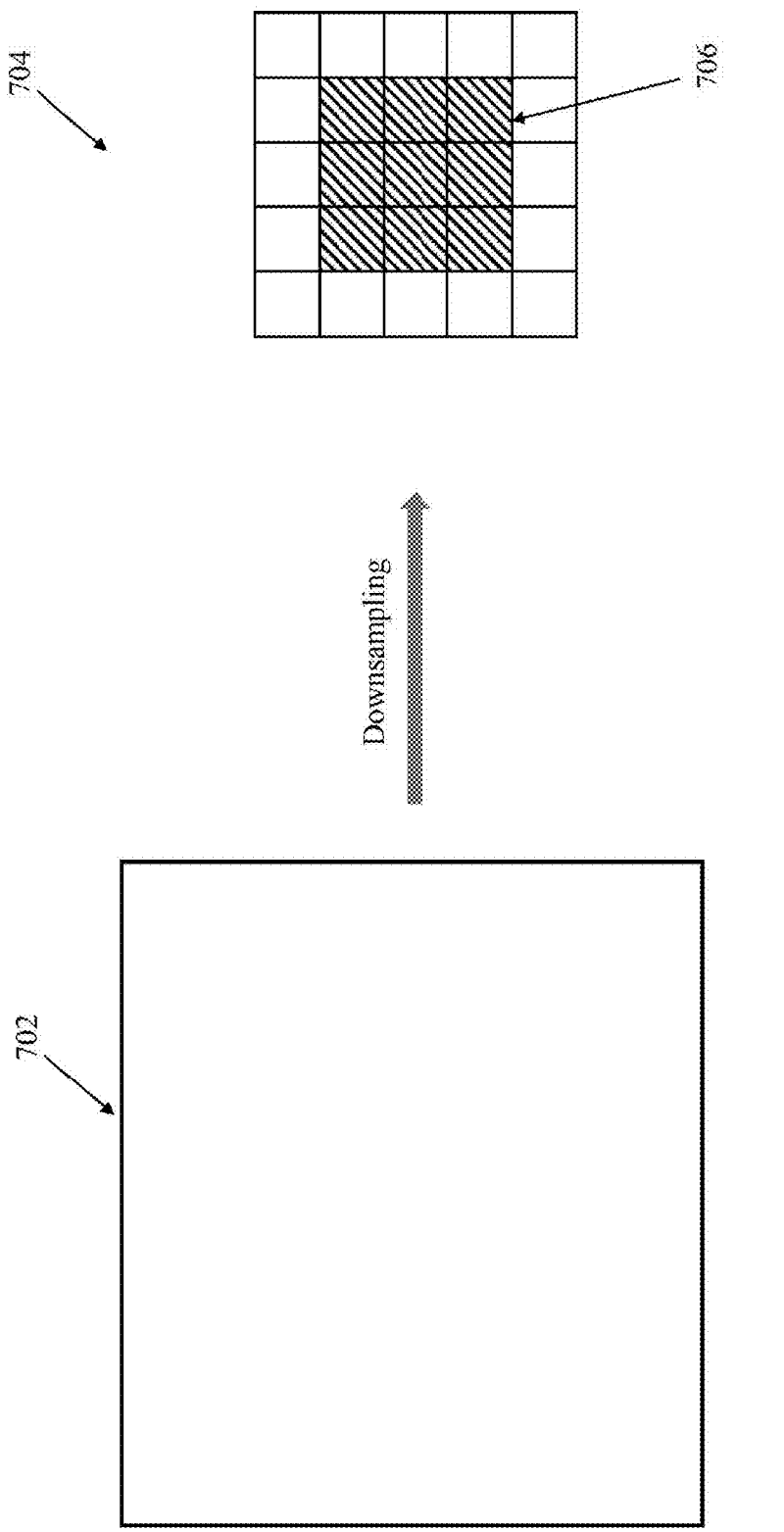
FIG. 7 shows a diagram illustrating an example embodiment of identifying an image region or block associated with a color frame for use in generating a PPG signal, according to example embodiments.

FIG. 7 shows a diagram illustrating an example embodiment of downsampling the sequence of image frames and identifying an image region or block associated with a color (e.g. G or R) frame 702. The processing module 504 can downsample each color (e.g. G or R) frame 702 of the sequence of image frames to a corresponding downsampled image frame 704. The processing module 504 can downsample the color (e.g. G or R) frame 702 to a 5×5 image (or data) block, a 9×9 image (or data) block, or an image block 704 of a different size. In downsampling the color frame 702, the processing module 504 can apply low-pass filtering or averaging to the pixel values of the original color frame 702. The processing module 504 can downsample the color frame 702 using known downsampling techniques.

The processing module 504 can identify a sub-block 706 of the image block 704 for use to generate a color signal. The processing module 504 can identify a central zone or sub-block of the image block 704 as sub-block 706. Depending on the size and the placement of the user finger against the camera, the color intensities of a central zone of the image block 704 (or the color frame 702) are more likely to reflect the pulsatile nature of arterial blood in the finger than outer regions of the image block 704 (or the color frame 702). In some cases, the user finger may not be placed right at the center of the camera device 110, but rather shifted towards one direction over another. In such cases, at least one outer region of the image frame may not adequately reflect the light (or optical signal reflected from the user finger. In general, the downsampled image block 704 can have an n×n size while the sub-block 706 can have an m×m size, where n and m are integers and n is greater than m. In some implementations, n=5 and m=3, or n=9 and m=5. In some implementations, the downsampled image block 704 and/or the sub-block 706 can have rectangular shape.

Referring back to FIG. 4, the method 400 can include the computer system 100 generating a PPG signal, for use to determine a blood pressure of the subject, using the image region or image block identified across the sequence of downsampled image frames (STEP 408). For each color (e.g., R or G) frame of the sequence of image frames, the signal-generating module 506 can average the pixel intensities of the corresponding sub-block 706 to generate a single value for the corresponding image frame. Repeating the averaging process for each image frame leads to a one dimensional color intensity signal representing the PPG signal. Considering, the nature of the information in the image frames and the PCA results discussed above with regard to FIG. 6, the averaging of the pixel intensities of the each sub-block 706 is a good way to capture essentially the variation in light intensity I over time. In some implementations, the signal-generating module 506 may apply a weighted averaging to the pixel intensities of each sub-block 706.

The signal-generating module 506 can filter the color or PPG signal using a high-pass filter to remove DC or non-pulsatile components of the signal. Specifically, referring back to FIG. 3B, the high-pass filtering can remove components of the color or PPG signal representing light reflections from the finger tissue, venous and capillary blood and non-pulsatile arterial blood. The high-pass filtered signal can represent essentially the light reflected from pulsatile arterial blood. In some implementations, the signal-generating module 506 can apply a high-pass filter with cut-off frequency between 0.4 Hz and 4 Hz to the generated color or PPG signal. For instance, the cut-off frequency can be equal to, but not limited to, 0.4 Hz, 0.5 Hz, 0.6 Hz, 0.7 Hz, 0.8 Hz, 0.9 Hz, 1 Hz, 1.1 Hz, 1.2 Hz, 1.3 Hz, 1.4 Hz, 1.5 Hz, 1.6 Hz, 1.7 Hz, 1.8 Hz, 1.9 Hz, 2 Hz, 2.1 Hz, 2.2 Hz, 2.3 Hz, 2.4 Hz, 2.5 Hz, 2.6 Hz, 2.7 Hz, 2.8 Hz, 2.9 Hz, 3 Hz, 3.1 Hz, 3.2 Hz, 3.3 Hz, 3.4 Hz, 3.5 Hz, 3.6 Hz, 3.7 Hz, 3.8 Hz, 3.9 Hz or 4 Hz, among others. In some implementations, the cut-off frequency can be determined based on training PPG data.

Figure 8:
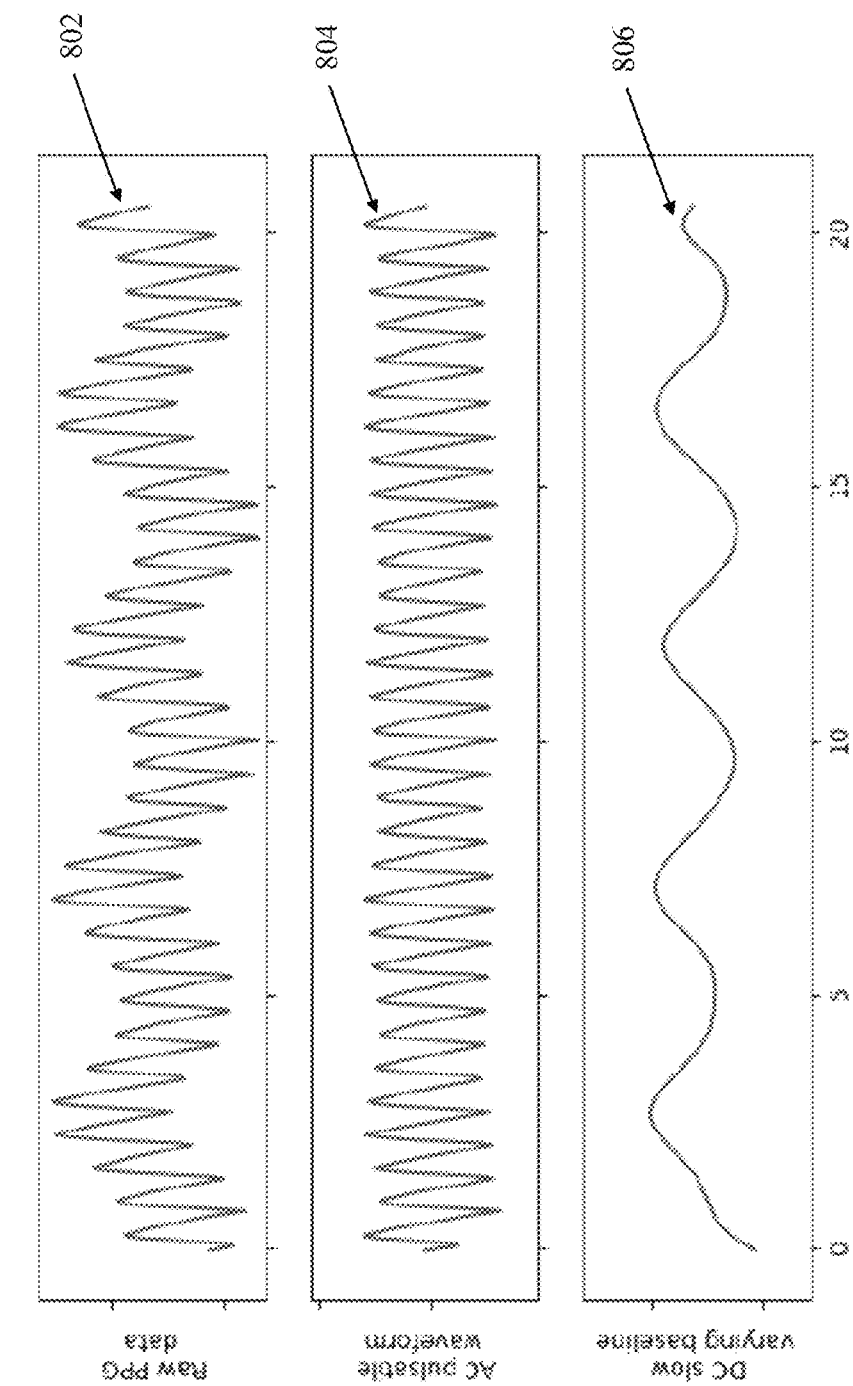
FIG. 8 shows plots of raw and filtered PPG signals, according to example embodiments.

FIG. 8 shows a graph 800 illustrating plots of raw and filtered PPG signals, according to inventive concepts of the current disclosure. The plot 802 represents a raw color or PPG signal generated by averaging pixel values for each sub-block 706. The plot 804 represents the high-pass filtered PPG signal corresponding to the raw PPG signal 802. The plot 806 represents the low-pass component of the PPG signal 802 (or color intensity signal) removed by the high-pass filter. The high-pass filtered signal 804 shows a pulse waveform that reflects better (e.g., compared to the raw PPG signal 802) the pulse of the user.

In a way, the computer system 100 or application 114 can reduce each image frame captured by the camera device 110 to a single numerical value equal to the sum (or weighted sum) of the pixel values of the corresponding sub-block 706. Such single numerical value can be viewed as representing an estimate of the intensity of the light reflected from the finger (or other body part) at the time the image frame was captured. The signal-generating module 506 can stack the numerical values for a given color channel (e.g., R or G) to generate the PPG signal, and filter the PPG signal using the high-pass filter to eliminate DC or non-pulsatile signal components. The PPG signal 802 can be viewed as a sequence of color intensity values each of which generated from a corresponding image frame or a corresponding color frame of the acquired sequence of images.

The method 400 can further include determining a blood pressure measurement of the subject using the PPG signal. The optical blood pressure monitoring (OBPM) module 510 can implement an OBPM algorithm to estimate or compute systolic and diastolic blood pressure measurements of the subject, using the PPG signal. The OBPM module 510 can receive the PPG signal or the corresponding logarithmic PPG signal to estimate or compute the systolic and diastolic blood pressure measurements of the user. The OBPM module 510 can estimate or compute the heart rate or pulse rate of the user, using the PPG signal. The pulse rate can be estimated by identifying pulses of the PPG signal and computing the inverse of pulse duration or counting the number of pulses per second. The OBPM module 510 can estimate or compute the mean blood pressure or other blood pressure features of the user, using the PPG signal.

The OBPM algorithm is based on pulse wave analysis (PWA), for example, as discussed in Chapter 8 of the book entitled "The Handbook of Cuffless Blood Pressure Monitoring A Practical Guide For Clinicians, Researchers and Engineers" by Josep Solà and Ricard Delgado-Gonzalo, Springer Nature Switzerland AG 2019. The OBPM module 510 can employ the oBPM™ approach/technology described in the International Patent Publication No. WO2016138965A1 and in "Measuring Pressure: Introducing oBPM, the Optical Revolution for Blood Pressure Monitoring" IEEE Pulse (Volume: 9, Issue: 5, Sep.-Oct. 2018).

In some implementations, the computer system 100 or the calibration/estimation module 516 can use outputs of the OBPM algorithm and/or other features to determine blood pressure measurements/estimates, as discussed in further detail in sections F and G below. In some implementations, the computer system 100 or the calibration/estimation module 516 can use outputs of the OBPM algorithm as well as other features to determine a classification of the blood pressure of the subject, as discussed in further detail in section H below The output module 512 can cause the computed blood pressure measurement and/or other measurements to be presented to the user on the display device 112. The output module 512 can also manage the rendering of UI(s) of the application 114 and the rendering of data or content associated with such UI(s). For instance, while the camera device 110 is still acquiring image frames, the output module 512 can render a UI or content indicating that the blood pressure measuring process is still going on so that the user keeps his finger (or other body part) applied to the camera device 110. The output module 512 can render instructions, images or demos to explain to the user how to place the finger (or other body part) against the camera device 110 or how to access (or use) various features of the application 114. The output module 512 can cause the computer system 100 to transmit measured blood pressure values or other measurements to another device or to the cloud via a communication network.

Figure 9:
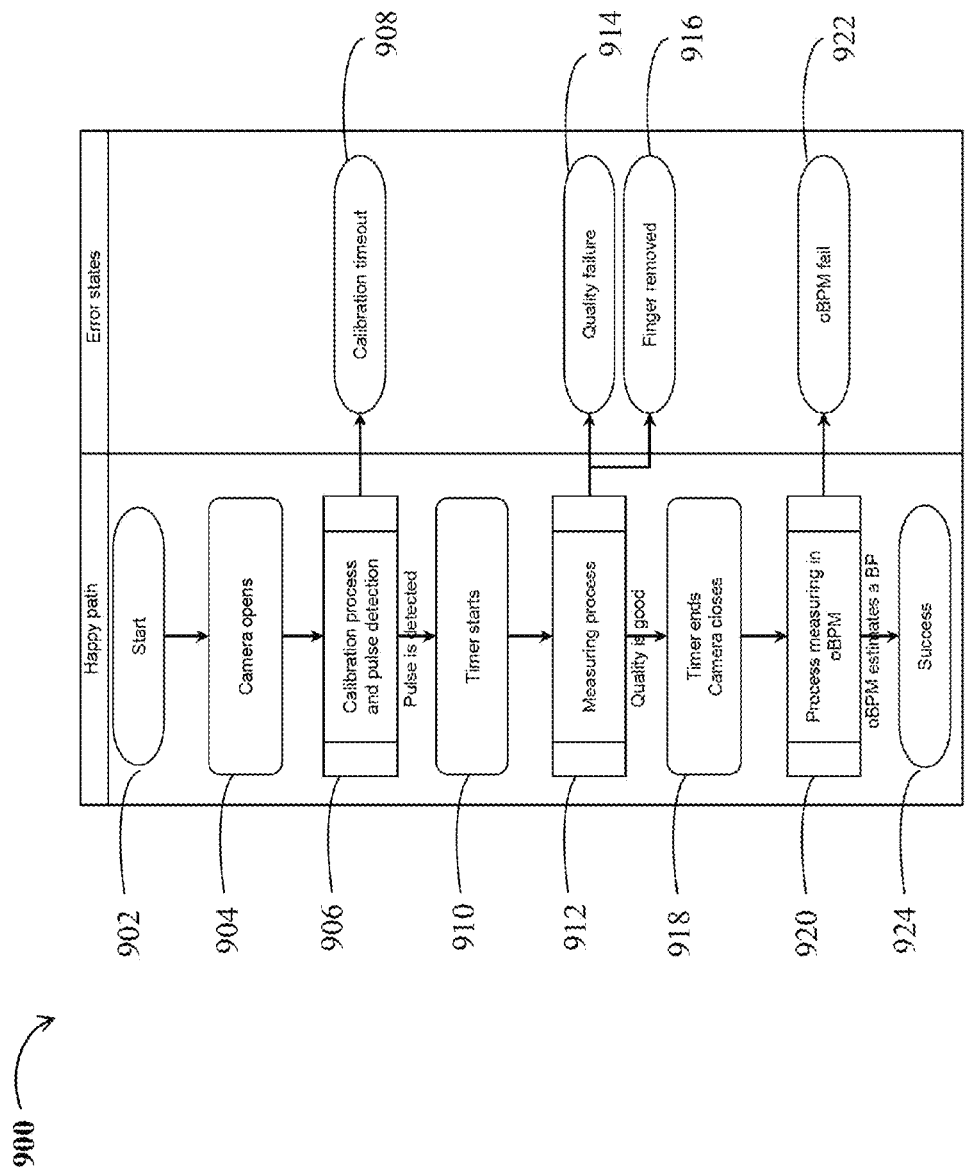
FIG. 9 shows a flowchart illustrating a method of estimating blood pressure based on a light intensity signal, according to example embodiments.

Estimating blood pressure based on a sequence of RGB images can involve more processes or steps than those described in relation to FIG. 4. Referring to FIG. 9, a flowchart illustrating a method 900 for estimating blood pressure based on RGB image data is shown, according to example embodiments. The method 900 can be implemented in the application 114, and can be executed by a single device, such as computer system 100, or by more than one device, such as a mobile device and remote server, a standalone device and a mobile device or other combinations of devices. Accordingly, the application 114 can be implemented as a single application executing on a single device or as multiple applications executing on different devices to perform different processes or steps of method 900.

The method 900 can include initiating (e.g., via application 114) the blood pressure measuring process (STEP 902), and the computer system 100 opening or activating the camera responsive to the initiation of the blood pressure measuring process (STEP 804). The computer system 100 can calibrate the camera (or photodetector) 110, 204 or 312 (STEP 906) before starting the acquisition of image frames. The camera calibration can be timed. If the camera calibration fails within a predefined maximum time duration for camera calibration, the computer system 100 can provide an alert signal (e.g., for display on display device 112) to indicate the failure of camera calibration (STEP 908). If the camera calibration process is successful within the predefined maximum time duration for camera calibration, the computer system 100 can initiate a data acquisition timer (STEP 910), and start the acquisition of image frames for use to measure blood pressure and/or other vital signs (STEP 912). During the data acquisition process, the computing device can assess the quality of the acquired data, and may provide feedback (e.g., via display device 112) regarding the quality of the acquired data. If the quality of the PPG signal or a portion thereof is determined to be poor or unsatisfactory, the computer system 100 can provide an alert signal/message regarding the quality (STEP 914). The computer system 100 can detect placement of the finger (or body part) over the camera or the corresponding lens or light waveguide, and output alert signals/messages regarding the finger or body part placement (STEP 916). If a PPG signal of a predefined duration (e.g., 30 seconds) that is generated from a sequence of image frames is determined to have a "good quality" (e.g., based on some quality assessment metrics or procedures), the computer system 100 can terminate the data acquisition timer and close/deactivate the camera 110 (STEP 918), and generate an estimate or a classification of the blood pressure and/or other vital signs based on the PPG signal (STEP 920). If the computer system 100 is unable to generate the estimate of the blood pressure, it can provide an alert or error message (STEP 922). Otherwise, the computer system 100 can determine the blood pressure estimation process to be a success (STEP 924), and can output the blood pressure estimate or classification on the display device 112.

Figure 10:
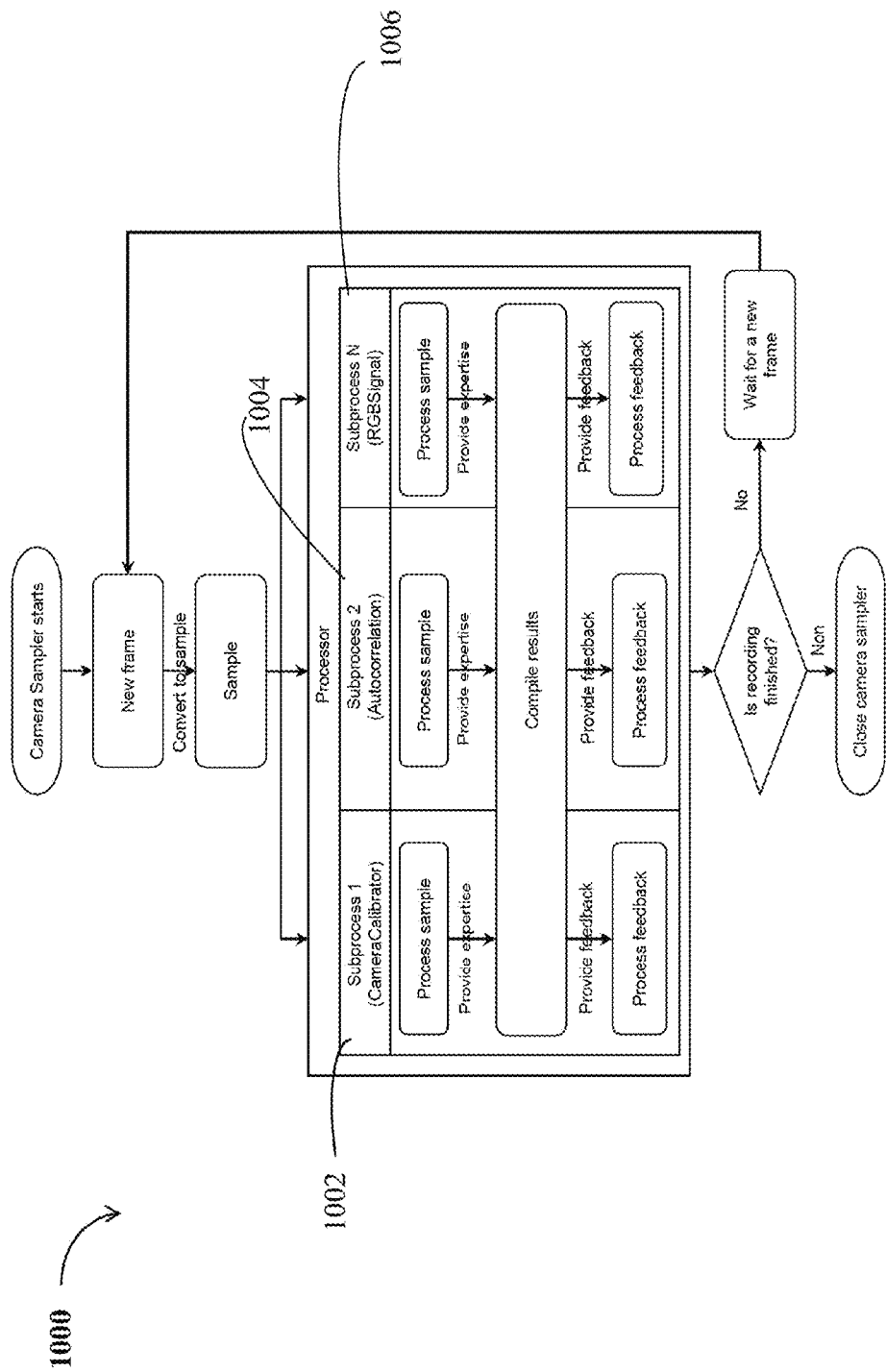
FIG. 10 shows a diagram depicting various processes that receive image frames as input, according to example embodiments.

Referring to FIG. 10, a diagram 1000 depicting various processes that involve access to the camera are shown, according to example embodiments. Processes such as the camera calibration process 1002, the signal quality assessment (autocorrelation) process 1004 and the PPG signal generation process 1006 receive image frames as input from the camera 110 and may assess signal quality on a frame by frame basis.

Processes described in FIGS. 9 and 10, and other processes implemented within application 104 or within another component of a blood pressure estimation system, are described in further detail in the following sections.

C. Camera Calibration

A photodetector, also referred to as a photosensor, is a sensor of light or other electromagnetic radiation that can transform a continuous physical value, e.g., light intensity, into a discrete numerical value, e.g., a pixel value. A photodetector has a gain that represents the relationship between the number of electrons acquired on an image sensor and the number of photoelectrons measured at the end of exposure (e.g., analog-to-digital units (ADUs)). As a result of increasing the gain, the image signal can be amplified and the apparent brightness of an image at a given exposure can be improved.

Figure 11:
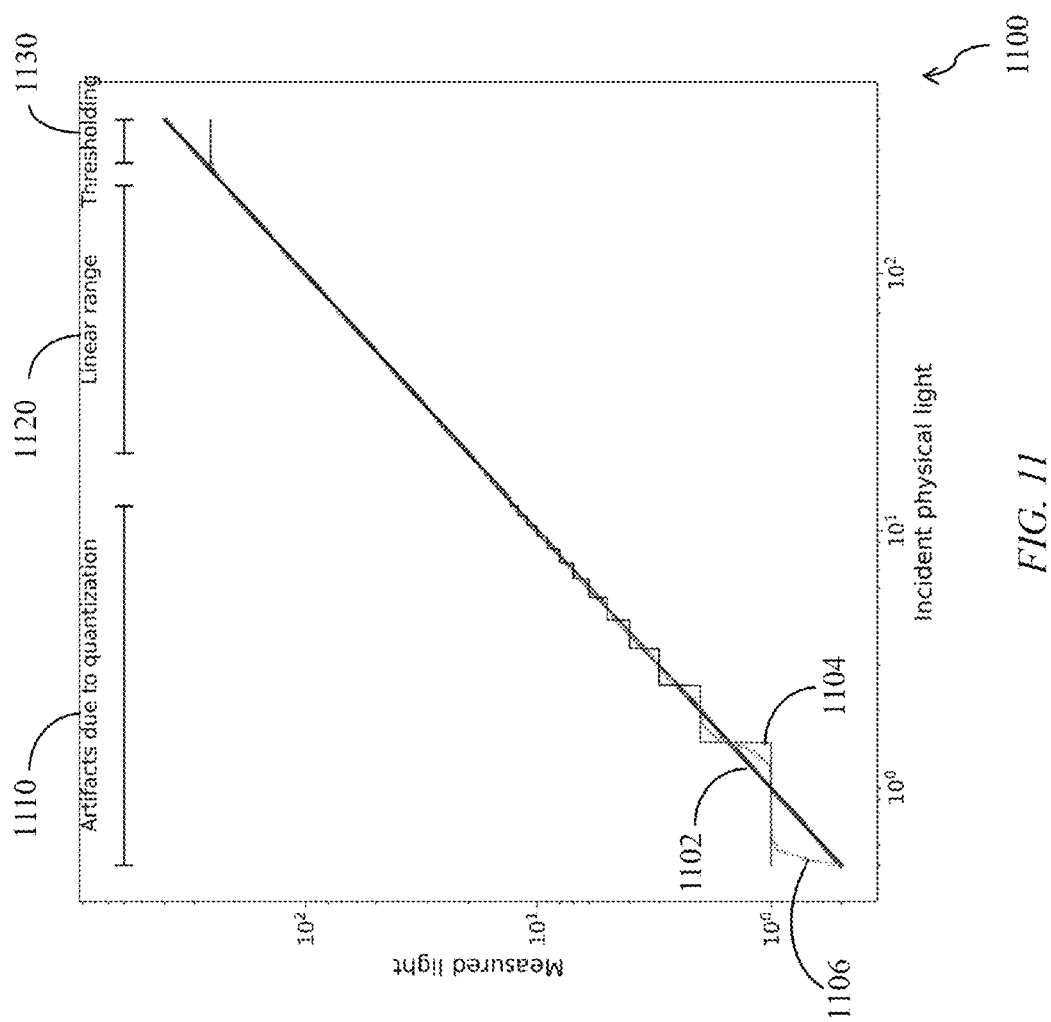
FIG. 11 is a diagram showing an example transfer function of a photodetector, according to example embodiments.

One problem relates to calibrating the photodetector (or camera) 110 is to determine an optimal or adequate light intensity range associated with an approximatively linear portion of a transfer function of the photodetector 110. FIG. 11 shows a diagram 1100 showing example transfer functions of a photodetector, representing a relationship between photon inputs (e.g., incident physical light) and electron outputs (e.g., measured light). FIG. 11 shows three different transfer functions including (1) an ideal transfer function 1102 with no quantization, (2) a transfer function 1104 depicting the effect of quantization, and (3) a transfer function 1106 depicting the effect of both quantization and noise.

If there were no quantization nor any noise, the transfer function would be perfectly linear (e.g., the identity function or a multiplicative scaling) as is the case for the transfer function 1102, which would be an ideal scenario in the context of blood pressure (or other vital signs) measurement. A linear function would simply add a constant and/or scale incident light by a multiplicative factor, but would not change the shape of the resulting or corresponding PPG signal. Quantization is a nonlinear operation or transformation, which introduces nonlinear distortions into the measured signal (e.g., pixel intensities) compared to the light intensity I reflected from the finger or body part. Even in the absence of noise, the nonlinear distortions due to quantization can be significant especially for relatively low light intensity values. As depicted in the transfer function 1104, the quantization transfer function is a stair-like function. Since the quantization error is usually constant, the lower the measured light intensity the lower is the signal-to-noise ratio (SNR) of (or the more significant is the effect of the quantization on) the recorded pixel values. Also, light intensity values that are relatively high may lead to pixel saturation, where the pixel values are capped to a predefined threshold as depicted in the upper end of transfer function 1104. These effects of quantization at the lower and upper ends of the transfer function 1104 can significantly degrade the SNR of the generated PPG signal. However, in the central or middle region of the transfer function 1104, the effect of quantization is less significant because the quantization error is significantly smaller than the measured light intensities. Also, pixel saturation is less likely to happen when the measured cumulative light intensity (e.g., color intensity values forming the PPG signal) is limited or restricted to a medium or central range.

Besides quantization, noise adds to the degradation of the SNR of pixel intensities as well as the SNR of the PPG signal as depicted in the transfer function 1106, which depicts a cumulative effect of quantization and noise. The transfer function 1106 represents a more realistic transfer function because cameras usually apply quantization and suffer from noise (e.g., additive noise). Accordingly, it is desirable to limit measured intensity values to a middle range, such as the range 1120, and avoid the lower range 1110 and the upper range 1130 so that the transfer function (e.g., transfer function 1106) of the photodetector is approximately linear. Given that the PPG signal is generated by averaging pixel intensity valued of image blocks 706 within downsampled image or color frames, limiting the measured intensity values to a middle range away from lower and upper ends of the transfer function (e.g., transfer function 1106) can reduce the likelihood of significant artifacts due to camera hardware and increase the SNR of the generated PPG signal.

To solve these problems, according to certain aspects, embodiments in the present disclosure relate to techniques for maintaining good quality PPG signals by reducing the likelihood of artifacts due to camera hardware. As described above, a PPG signal may be generated by averaging pixel values of sub-blocks of downsampled image frames (e.g., sub-block 706 of color image frame 702 in FIG. 7). Accordingly, the PPG signal values are in the range of pixel values (for example, the range of (0, 255) if a pixel value is stored in an 8-bit integer). In some embodiments, in order to maintain good quality PPG signals, a system for calibrating a camera device 110 can calibrate the camera gain to maintain PPG signal values within a middle range 1120 that corresponds to an approximately linear portion of the transfer function (e.g., transfer function 1106) of the photodetector or a camera 110. Such calibration ensures that the transformation of the incident light signal to a corresponding digital signal is as close to a linear transformation as possible. For example, the computer system 100 can calibrate the photodetector (or camera) gain so that values of the PPG signal are between 100 and 150. In some implementations, other ranges can be used such as 90 to 160, 95 to 155 or 105 to 145. In some implementations, a camera calibration process for blood pressure measurement can adjust camera gain so that at the generated PPG signal values are within a range around (or centered at) 128 or around (or centered at) a value close to 128.

According to certain aspects, embodiments in the present disclosure relate to techniques for allowing a camera calibration process to have two possible output states that are mutually incompatible and reachable in a finite time—(1) a ready-to-record state of starting a recording, and (2) an error state of calibration timeout. If the camera calibration process is successful (e.g., successful in adjusting or setting the camera gain to enforce PPG values to be within a target range and/or detecting a pulsatile of the user, etc.), the process can include outputting the ready-to-record state to start the recording. If the camera calibration process is not successful, the computer system 100 can output the error state to raise a calibration timeout.

According to certain aspects, embodiments in the present disclosure relate to techniques for configuring settings of a photodetector (or a camera) to ensure that the photodetector or camera should be compatible with predetermined requirements. For example, camera settings are configured to ensure that (1) measured numerical values are as close to underlying physical signal as possible and that (2) a user is able to take measurements in good conditions for PPG signals to be of good quality for measuring blood pressure.

In some embodiments, a camera calibration process may start with initial settings of camera parameters. For example, the gains can be set using previously saved settings (e.g., exposure time, sensitivity, etc.) and default values for others. In some embodiments, camera parameters can be set according to the following rules: (1) the camera is able to take at least a predetermined number of frames per second (e.g., 25 frames per second or more); (2) an output digital value for the pixels is as close to a linear transform of an input light intensity as possible; (3) recorded PPG input signals can evolve or vary in a range of values that is still in a linear response domain while having a wide spread, e.g., a value that is not too high nor too low; (4) flash is enabled; (5) no color correction is applied, or alternatively such transformation is applied in a respective single color channel and is linear (or close to linear), e.g., color channel by color channel, so that a transformation matrix is diagonal; and/or (6) no autocorrection is applied, or all settings are defined manually by an application (e.g., an app in a mobile device).

According to certain aspects, embodiments in the present disclosure relate to techniques for performing a process of updating an exposure value (EV) to set PPG signals to be in an appropriate range of values (e.g., between 100 and 150). For example, at the end of the EV update process, PPG signals can be in an appropriate range of values (e.g., around 128 out of the full range (0, 255)) if the calibration is successful, or close to the appropriate range even if the calibration is not successful.

In some embodiments, the camera calibration process can update the gains to set a PPG signal in an acceptable range (e.g., a linear response domain) by updating an exposure value (EV) of the camera. If the EV update is successful in setting the camera gain to set PPG values in a target range, the camera calibration process can finalize or end the EV update. If the EV update is not successful, the camera calibration process can continue the EV update until PPG values lie in the target range.

In some embodiments, for updating EV, the camera calibration process may record a color intensity (or PPG) signal for a predetermined or predefined duration (e.g., 0.5 seconds of image frames) such that an ongoing capture request can have time to be built and gains can be indeed updated. The predetermined or predefined duration allows for any EV or sensitivity update that was previously made to take effect or become effective. After the predetermined or predefined duration, the processor 102 can compute an average value of luminosity over each new acquired the image. This processor 102 may compare the average luminosity value to a target range. If the average luminosity value lies in the target range, the processor 102 can determine that the EV (or sensitivity) calibration is successfully finalized and the process can proceed to a next step, e.g., pulsatile signal detection.

If the average luminosity value lies outside the target range, the processor 102 can determine whether the value is greater than the target range (e.g., when the luminosity is too bright) or the value is smaller than the target range (e.g., when the luminosity is too dark). If luminosity is too bright, the camera calibration process may proceed to a high luminosity update process that can reduce the exposure value by a predetermined factor. On the other hand, if luminosity is too dark, the camera calibration process may proceed to a low luminosity update process that can increase the exposure value by a predetermined factor.

In some embodiments, the low luminosity update process may be performed as follows. The low luminosity update process may check whether the number of the high luminosity update processes previously performed is greater than a predetermined threshold (e.g., whether too many high luminosity update processes were previously performed to decrease EV). If it is determined that too many high luminosity update processes were previously performed to decrease EV, the low luminosity update process may (1) determine that the user is not stable yet or that the EV oscillates around a target value, (2) issue or state a not-steady warning, and (3) end or exit. If (1) it is not determined that too many high luminosity update processes were previously performed to decrease EV and (2) the current value of exposure time is not a maximum value, the low luminosity update process may increase the exposure time value by a predetermined exposure time update factor (e.g., 1.2) or a computed exposure time update factor responsive to the difference between the actual luminosity and the target luminosity. In some embodiments, the low luminosity update process may increase the exposure time value and then increase the sensitivity value. After at least one of the sensitivity or exposure time is updated, the low luminosity update process may submit the new updated gain to the camera. In some embodiments, after submission of a new gain, the low luminosity update process may wait for settings to be effectively taken into account before performing a new update process (either the high luminosity update process or the low luminosity update process).

In some embodiments, the high luminosity update process may be performed as follows. The high luminosity update process may check whether the number of the low luminosity update processes previously performed is greater than a predetermined threshold (e.g., whether too many low luminosity update processes were previously performed to increase EV). If it is determined that too many low luminosity update processes were previously performed to increase EV, the high luminosity update process may (1) determine that the user is not stable yet or that the EV oscillates around a target value, (2) issue or state a not-steady warning, and (3) abort or end the EV update. If (1) it is not determined that too many low luminosity update processes were previously performed to increase EV and (2) the current value of sensitivity is not a minimum value, the high luminosity update process may decrease the sensitivity value by a predetermined sensitivity update factor (e.g., 1.2) or a computed sensitivity update factor responsive to the difference between the actual luminosity and the target luminosity. In this manner, the high luminosity update process can maintain the sensitivity value and the exposure time value to be at least the respective minimum values. In some embodiments, the high luminosity update process may decrease the sensitivity value and then decrease the exposure time value. After at least one of the sensitivity or exposure time is updated, the high luminosity update process may submit the new updated gain to the camera. In some embodiments, after submission of a new gain, the high luminosity update process may wait for settings to be effectively taken into account before performing a new update process (either the high luminosity update process or the low luminosity update process).

According to certain aspects, embodiments in the present disclosure relate to techniques for detecting a pulsatile signal (e.g., a signal including a sequence of pulses) of a user so as to ensure that the user has its finger well positioned and/or in a good state, in order for PPG signals to be of good quality. PPG quality is not insured by the hardware alone. A good behavior or condition of the user may be mandatory for the PPG signal to be of good quality. Those cases may be caught by user conditions such as movement of a user, or cold finger conditions so that these conditions can be considered in processing pixel values captured by a photodetector.

In some embodiments, after the gains are updated to set a PPG signal in an acceptable range, the camera calibration process can proceed to a pulsatile signal detection process of detecting a pulsatile signal of a user. The pulsatile signal detection process may calculate autocorrelation of a PPG signal. In some embodiments, the pulsatile signal detection process may calculate a value of autocorrelation of a PPG signal between consecutive frames and compare the autocorrelation value with a predetermined quality threshold. If the autocorrelation value is greater than or equal to the quality threshold, the pulsatile signal detection process may determine that the PPG signal is of good quality between the consecutive frames. If the autocorrelation value is smaller than the quality threshold, the pulsatile signal detection process may determine that the PPG signal is of poor quality between the consecutive frames. The pulsatile signal detection process may count the number of consecutive frames among which the PPG signal is of good quality. If the number of consecutive frames of good quality is greater than or equal to a predetermined threshold (e.g., 30 frames), the pulsatile signal detection process may determine that a pulsatile signal is detected and the camera calibration process can output the ready-to-record state to start the recording. The pulsatile signal detection process can include the computer system 100 or the processor 102 counting the number of cumulative frames among which the PPG signal is of poor quality. If the number of cumulative frames of poor quality is greater than or equal to a predetermined threshold (e.g., 120 frames), the pulsatile signal detection process may (1) determine that a pulsatile signal is not detected and (2) abort pulsatile signal detection.

In some embodiments, the camera calibration process may include the processor 102 counting the number of pulsatile signal detection processes (or signal quality assessment processes. If the number of performed pulsatile signal detection processes is greater than or equal to a predetermined threshold (e.g., 3), the camera calibration process may include the processor 102 (1) issuing or raising an error of calibration timeout and (2) aborting or ending the calibration.

According to certain aspects, embodiments in the present disclosure relate to a method including step (a) configuring, according to one or more predefined data acquisition requirements/rules, one or more operational settings of a photodetector of a computing device. According to the method, in step (b), a gain of the photodetector may be adjusted by the computing device. In step (c), after updating the gain, a sequence of images may be acquired by the photodetector. In step (d), a photoplethysmographic (PPG) signal may be generated using the sequence of images by determining for each image of the sequence of images a corresponding signal value. In step (e), a sequence of local quality values of the PPG signal may be determined. Each local quality value may be indicative of a local quality of a respective portion of a plurality of portions of the PPG signal. In step (f), a first predefined number of consecutive local quality values exceeding a threshold quality may be detected among the sequence of local quality values. Upon detecting the first predefined number of consecutive local quality values among the sequence of local quality values, a calibration of the photodetector may be determined to be successful by the computing device.

In some embodiments, a second predefined number of local quality values below the threshold quality may be detected among the sequence of local quality values, without detecting the first predefined number of consecutive local quality values exceeding the threshold quality. Upon detecting the second predefined number of local quality values below the threshold quality, steps (b)-(e) may be repeated.

In some embodiments, steps (b)-(e) may be repeated for a number of iterations until detecting the first predefined number of consecutive local quality values exceeding a threshold quality, or until the number of iterations reaches a predefined number of iterations. Upon the number of iterations reaching the predefined number of iterations without detecting the first predefined number of consecutive local quality values exceeding the threshold quality, an alert message indicative of calibration timeout may be provided by the computing device.

In some embodiments, in determining the sequence of local quality values, a sequence of autocorrelation values may be determined. Each autocorrelation value of the sequence of autocorrelation values may be associated with a respective signal value of the PPG signal.

In some embodiments, in configuring the one or more operational settings of the photodetector, a color correction setting of the photodetector may be disabled. In configuring the one or more operational settings of the photodetector, an autocorrection setting of the photodetector may be disabled. In configuring the one or more operational settings of the photodetector, a light source associated with the photodetector may be enabled. In configuring the one or more operational settings of the photodetector, a frame rate of the photodetector may be set to at least 30 frames per second.

Embodiments in the present disclosure can have the following advantages. First, some embodiments can provide useful techniques for allowing pixel values or a PPG signal to lie in a range where linearity can be approximated, thereby reducing the likelihood of artifacts due to camera hardware. For example, a process of updating exposure value (EV) can be performed to set PPG signals to be in an appropriate range of values.

Second, some embodiments can provide useful techniques for configuring settings of a photodetector (or a camera) to ensure that the photodetector or camera should be compatible with predetermined requirements, for example, that (1) measured numerical values are as close to underlying physical signal as possible and that (2) a user is able to take measurements in good conditions for PPG signals to be of good quality.

Third, some embodiments can provide useful techniques for detecting a pulsatile signal of a user so as to ensure that the user has its finger well positioned and/or in a good state, in order for PPG signals to be of good quality.

Fourth, some embodiments can provide useful techniques for using saturation conditions to perform a transformation of a physical signal to a corresponding digitalized signal (e.g., PPG signal) such that the transformation is as close to a linear transformation as possible and the PPG signal can lie in the linear range of the camera.

Figure 12A:
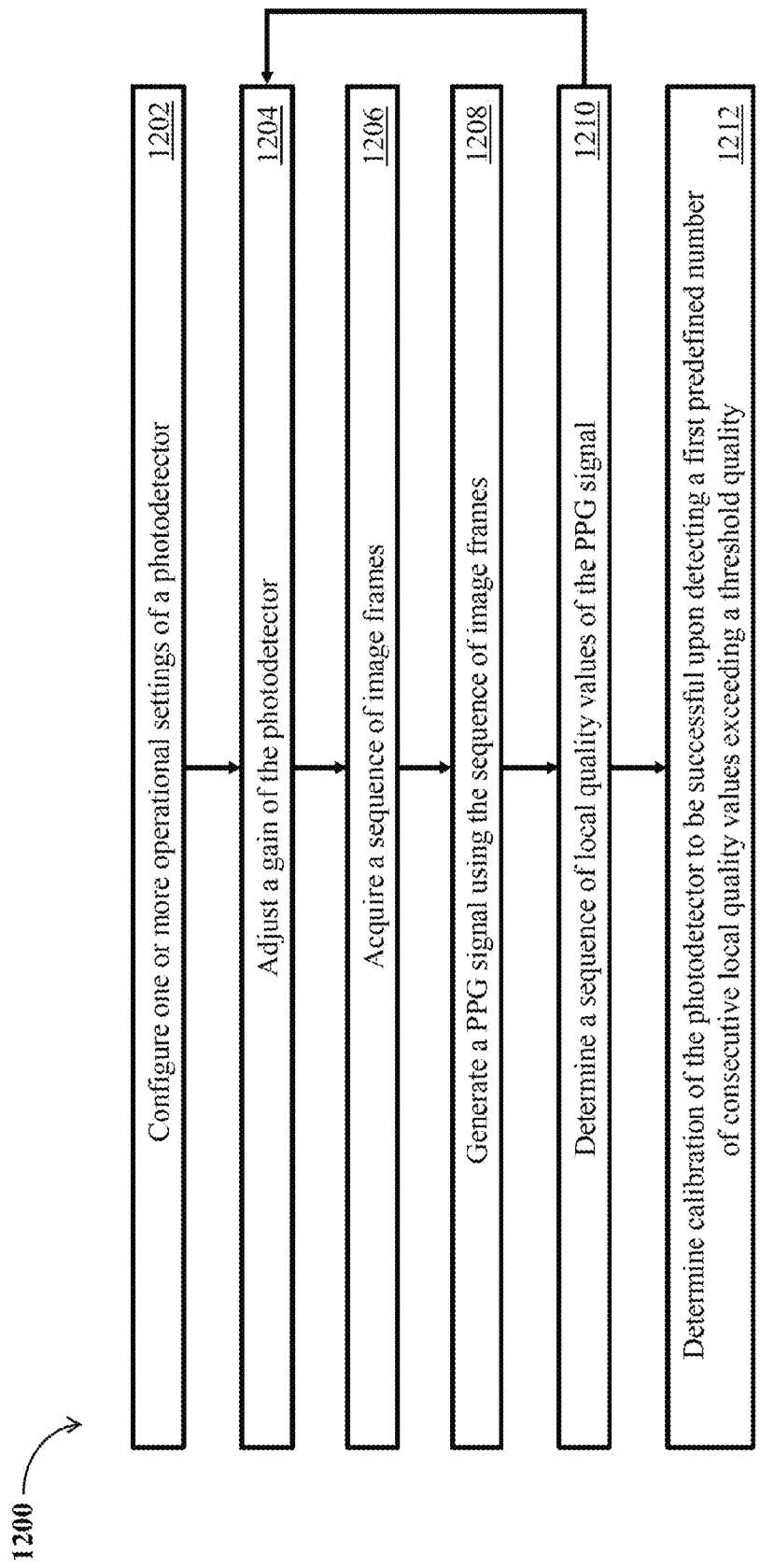
FIG. 12A is a flowchart illustrating a methodology for calibrating a photodetector, according to example embodiments.

FIG. 12A shows a flowchart illustrating a method 1200 for calibrating a photodetector of a computing device for use to estimate blood pressure, according to example embodiments. In brief overview, the method 1200 can include configuring, according to one or more predefined data acquisition requirements or rules, one or more operational settings of the photodetector (STEP 1202), and adjusting a gain of the photodetector by the computing device (STEP 1204). The method 1200 can include acquiring, by the photodetector after updating the gain, a sequence of images (STEP 1206), and generating, using the sequence of images, a PPG signal by determining for each image of the sequence of images a corresponding signal value (STEP 1208). The method 1200 can include determining a sequence of local quality values of the PPG signal, each local quality value indicative of a local quality of a respective portion of a plurality of portions of the PPG signal (STEP 1210), and determining, by the computing device, a calibration of the photodetector to be successful upon detecting a first predefined number of consecutive local quality values, among the sequence of local quality values, exceeding a threshold quality (STEP 1212).

In further detail, the method 1200 can include the computing device 100 configuring, according to one or more predefined data acquisition requirements or rules, one or more operational settings of the photodetector (or camera device) 110 (STEP 1202). In some embodiments, in configuring the one or more operational settings of the photodetector, a color correction setting of the photodetector may be disabled. In configuring the one or more operational settings of the photodetector, an autocorrection setting of the photodetector 110 may be disabled. In configuring the one or more operational settings of the photodetector, the computer system 100 can enable or activate the light source 108 associated with the photodetector (or camera device) 110. In configuring the one or more operational settings of the photodetector, the computer system 100 or the respective processor 102 can set a frame rate of the photodetector 110 to at least 30 frames per second.

In some embodiments, the one or more operational settings of the photodetector may be initial settings of camera parameters. For example, the gains of the photodetector may be set using previously saved settings (e.g., exposure time, sensitivity, etc.) and default values for others. In some embodiments, camera parameters may be set according to the following rules: (1) the camera is able to take at least a predetermined number of frames per second (e.g., 30 frames per second); (2) output digital pixel intensity values are as close to a linear transform of an input light intensity as possible; (3) generated PPG signal values can vary within a range of values (e.g., between 100 and 150) that corresponds to an approximately linear portion of the transfer function of the photodetector while having a wide spread; (4) the flash device (or light source) 108 is enabled; (5) no color correction is applied, or alternatively such transformation should be linear and is applied in a respective single color channel, e.g., color channel by color channel, so that a transformation matrix is diagonal; and/or (6) no autocorrection is applied, or all settings are defined or set by the application 114. Color correction and/or autocorrection functionalities may apply nonlinear transformations to incident light intensities or change exposure value settings during the recording, which can lead to degraded PPG signal quality. Disabling such functionalities avoids or mitigates nonlinear distortions to the PPG signal.

Table 1 below shows an example general camera setting in a camera device, according to the above-noted rules.

TABLE 1

A General Camera Setting for Camera Calibration

| Group | Setting key | Value | Description |
|---|---|---|---|
| General | CONTROL_CAPTURE_INTENT | TEMPLATE_MANUAL | This control helps the 3A algorithms to be set to OFF |
| | FLASH_MODE | TORCH | This forces the light of the flash to be always on. This way the finger can be lightened. |
| | JPEG_ORIENTATION | 0 | This forces the camera to be frozen vertically. |
| 3A Algorithms | CONTROL_MODE | OFF | This stops all auto correction algorithms from camera |
| | CONTROL_AE_MODE | OFF | This stops auto exposure algorithm, forcing the app to use the computed exposure values settings and freezing them |
| | CONTROL_AE_ANTIBANDING_MODE | OFF | Remove any processing stabilizing the video. |
| | CONTROL_AF_MODE | OFF | This stops the auto focus algorithm, forcing the zoom level to be stable. |
| | CONTROL_AWB_MODE | OFF | This stops the white level balance update processing, so that relative color ratios stay the same |
| Color Correction | COLOR_CORRECTION_ABERRATION_MODE | OFF | This stops the color correction aberration mode |
| | COLOR_CORRECTION_MODE | TRANSFORM_MATRIX | This forces the color correction algorithm to use a transform matrix |
| | COLOR_CORRECTION_GAINS | [1, 3, 3, 3] | This gives more strength to the green and blue color channels than to the red one since the blood absorbs those colors way more than red |

TABLE 1-continued

A General Camera Setting for Camera Calibration

| Group | Setting key | Value | Description |
|---|---|---|---|
| | COLOR_CORRECTION_TRANSFORM | [[1, 0, 0], [0, 1, 0], [0, 0, 1]] | This forces the color transformation matrix to be identity so that it gets as close to the sensor raw data as possible |
| | TONEMAP_MODE | CONTRAST_CURVE | This forces the mapping between the sensor values and the digitized pixel values to be linear |
| | TONEMAP_CURVE | [(0, 0), (1, 1)] | This forces the mapping between the sensor values and the digitized pixel values to be linear |
| | SHADING_MODE | OFF | This ensures that no lens shading is performed |

Figure 12B:
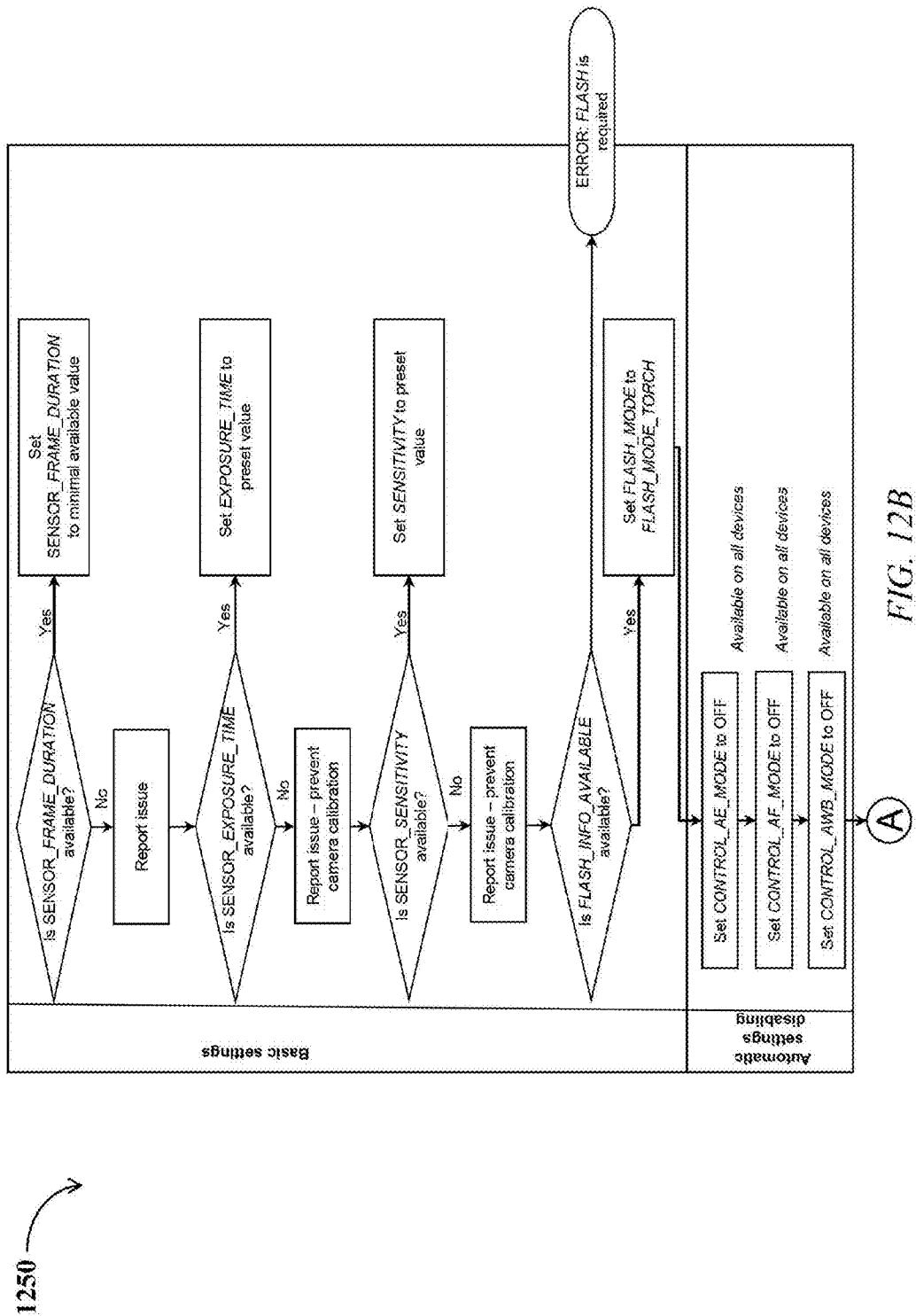
FIG. 12B shows a flowchart illustrating a process for resetting or adjusting operational settings of the photodetector or camera, according to example embodiments.
Figure 12B:
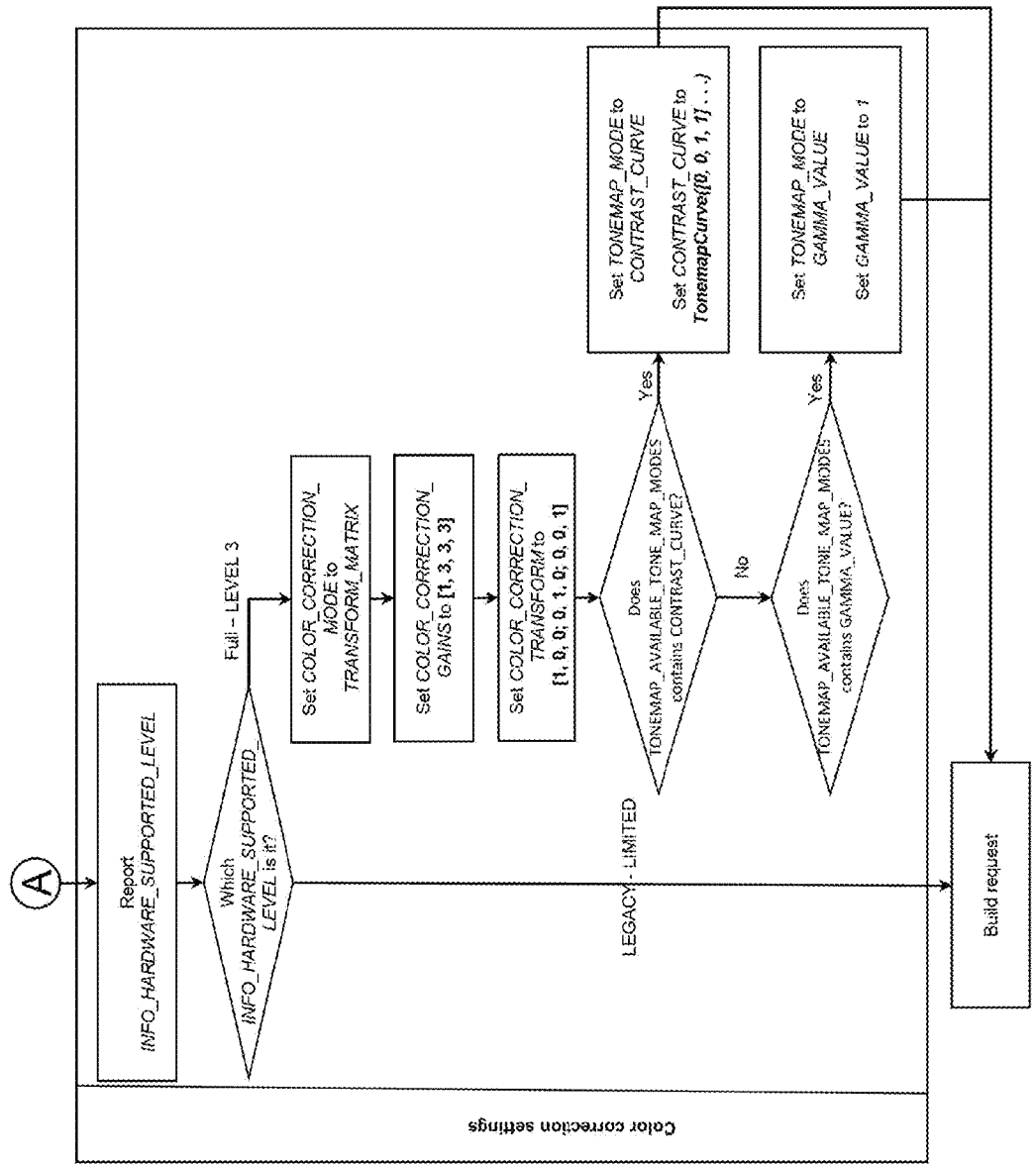

FIG. 12B shows a flowchart illustrating an example process 1250 for resetting or adjusting operational settings of the camera device 110 or 204. The data acquisition module 502 can adjust, or reset, basic settings, automatic settings and/or color correction settings of the camera device 110 or 204. Adjusting the basic settings can include adjusting, or resetting, the sensor frame duration, the sensor exposure time, the sensor sensitivity and/or the flash mode to corresponding predefined values. Adjusting the automatic settings can include disabling one or more automatic settings of the camera device 110 or 204, such as auto-white balance (AWB), auto-focus (AF) and/or auto-exposure (AE). Adjusting the color correction settings can include setting the color correction mode, the color correction gains and/or the color correction transform to corresponding predefined values. For instance, the data acquisition module 502 can set the color correction mode to color correction transform, set the color correction gains to [1, 3, 3, 3], and set the color correction transform to an identity matrix. The data acquisition module 502 can set a tone map mode, a contrast curve and/or a gamma value to corresponding predefined setting values. While most cameras usually apply a non-linear gamma correction to have a greater range of sensitivity, the data acquisition module 502 can select settings parameters that lead linear, rather than non-linear, correction.

The method 1200 can include the computer system 100 adjusting a gain of the photodetector (STEP 1204). Initially (or in a first iteration), the computing device may set the photodetector gain to previously calibrated gain value, e.g., stored in memory 104. If no previously calibrated gain value is available, the computer system 100 may set the gain to a default gain value of the photodetector 110. In adjusting the photodetector gain, the computer system 100 can adjust an exposure time and/or a sensitivity of the photodetector. In subsequent iterations, e.g., after determining a sequence of local quality values of a PPG signal (STEP 1210), the computer system 100 may adjust the gain in a way to enforce the generated PPG signal values to be within a predefined range (e.g., 100 to 150 or other range around 128 in the overall range of (0, 255)). For example, the computer system 100 may adjust the gain based on the PPG signal values by increasing an exposure time and/or sensitivity (e.g., ISO value) or decreasing an exposure time and/or sensitivity. A process of adjusting or calibrating the photodetector gain, or calibrating the photodetector exposure time and/or sensitivity, according to some embodiments is described in further detail below with reference to FIG. 15. In other words, in adjusting the gain at STEP 1204, the computer system 100 can execute the method 1500 described below in relation to FIG. 15.

The method 1200 can include the photodetector acquiring, after updating the gain, a sequence of images (STEP 1206). The computer system 100 can acquire a sequence of RGB image frames at a preset frame rate (e.g., 25 or 30 frames per second). The computer system 100 can use one color frame or channel (e.g., G or R) of each acquired image frame to generate the PPG signal. For example, referring to FIG. 7, the computing device may extract a color frame (e.g., a G frame or R frame) 702 from each acquired RGB image frame and use the sequence of color frames to generate the PPG signal.

The method 1200 can include the computing device generating, using the sequence of images, a PPG signal by determining for each image of the sequence of images a corresponding signal value (STEP 1208). As described above in relation to FIG. 7, the computer system 100 may downsample each color frame and identify an image sub-block 706 within the downsampled color frame 704. The computer system 100 can average pixel values of each sub-block 606 of the downsampled color frame 704 to generate a corresponding PPG signal value.

The method 1200 can include the computing device determining a sequence of local quality values of the PPG signal (STEP 1210). Each local quality value may be indicative of a local quality of a respective portion of a plurality of portions of the PPG signal. In some embodiments, in determining the sequence of local quality values, the computer system 100 can determine a sequence of autocorrelation values. Each autocorrelation value of the sequence of autocorrelation values may be associated with a corresponding signal value of the PPG signal. As discussed in further detail below with regard to FIG. 30, the computer system 100 can associate a given PPG signal value (e.g., last generated PPG signal value) or a corresponding image frame (e.g., last acquired image frame) with a corresponding signal window of a predefined size of the PPG signal. For example, the signal window can be formed of n consecutive PPG signal values, where n is an integer, and may end at the given PPG signal value PPG (e.g., the last acquired PPG signal value). The computer system 100 can compute local autocorrelation values of the PPG signal by incrementally sliding the signal window and computing, after each incremental slide, an autocorrelation value using the signal window and another overlapping window of the PPG signal. The computer system 100 can then determine the maximum autocorrelation value among the computed local autocorrelation values. The maximum local autocorrelation value can be viewed as, or can represent, a local quality value associated with the given PPG signal value or the corresponding image frame. Accordingly, a separate local quality value can be computed or determined for each acquired image frame or the corresponding PPG signal value.

The method 1200 can include the computer system 100 determining a calibration of the photodetector to be successful upon detecting a first predefined number of consecutive local quality values, among the sequence of local quality values, exceeding a threshold quality (STEP 1212). The computer system 100 can compare each local quality value (or maximum local autocorrelation value) associated with a corresponding image frame or corresponding PPG signal value to a predetermined/predefined quality threshold (e.g., 0.85). If the computer system 100 detects, based on the comparisons, that a first predefined number of consecutive local quality values are all greater than or equal to the predetermined/predefined quality threshold, it may determine that the generated PPG signal is pulsatile and that the calibration of the photodetector 110 is successful. An example method of determining that a PPG signal is pulsatile according to some embodiments is described in more detail below with reference to FIG. 14A. In some embodiments, the computing device can maintain a counter of consecutive frames with corresponding local quality values exceeding predetermined/predefined quality threshold. If the number of consecutive frames of good quality reaches or exceeds the first predefined number (e.g., 30 frames), the computer system 100 can determine that the calibration of the photodetector 110 is successful (e.g., PPG signal is pulsatile), and can initiate a recording of a second PPG signal for use to measure blood pressure.

In some embodiments, a second predefined number of local quality values below the threshold quality may be detected among the sequence of local quality values, without detecting the first predefined number of consecutive local quality values exceeding the threshold quality. Upon detecting the second predefined number of local quality values below the threshold quality, steps (b)-(e) may be repeated. For example, the computer system 100 or the processor 102 may count the number of cumulative frames among which the PPG signal is of poor quality. If the number of cumulative frames of poor quality is greater than or equal to a predetermined threshold (e.g., 120 frames), it may be determined that a calibration of the photodetector is not successful (or a pulsatile signal of the user is not detected), and the method may proceed to STEP 1204 so that the computing device can adjust the gain such that values of the PPG signal are in a middle range of values. A process of determining a calibration of the photodetector to be successful or not according to some embodiments will be described in more detail with reference to FIG. 14A.

The computer system 100 or the processor 102 can count all poor quality frames (not just consecutive poor quality frames) to be compared to the corresponding predetermined threshold (e.g., 120 frames). However, with regard to good quality frames, the computer system 100 or the processor 102 can count or keep track of consecutive good quality frames. For example, if a total of 120 poor quality frames (not necessarily consecutive) are detected while the total number of detected consecutive good quality frames is less than 30, the processor 102 can determine that the calibration of the photodetector is not successful (or a good quality pulsatile signal of the user is not detected), and the computer system 100 or the processor 102 may proceed to STEP 1204 so that the computer system 100 or the processor 102 can adjust the gain such that values of the PPG signal are in a middle range of values. However, if the number of detected consecutive good quality frames is greater than or equal to 30 and the total number of detected poor quality frames is less than 120, the computer system 100 or the processor 102 can determine the photodetector calibration process to be successful.

In some embodiments, the computer system 100 may repeat STEPs 1204-1210 for a number of iterations until detecting the first predefined number of consecutive local quality values exceeding a threshold quality, or until the number of iterations reaches a predefined number of iterations. Upon the number of iterations reaching the predefined number of iterations without detecting the first predefined number of consecutive local quality values exceeding the threshold quality, the computer system 100 may provide an alert message indicative of calibration timeout. The computer system 100 may maintain a counter indicative of the number of iterations that did not lead to a successful calibration of the photodetector. For example, if the number of iterations with no successful calibration is greater than or equal to a predetermined threshold (e.g., 3), the computer system 100 may display an error of calibration timeout on the display device 112, and the calibration of the photodetector may be aborted or ended. An example implementation of the method 1200, according to some embodiments, is described in more detail below with reference to FIG. 13.

Figure 13:
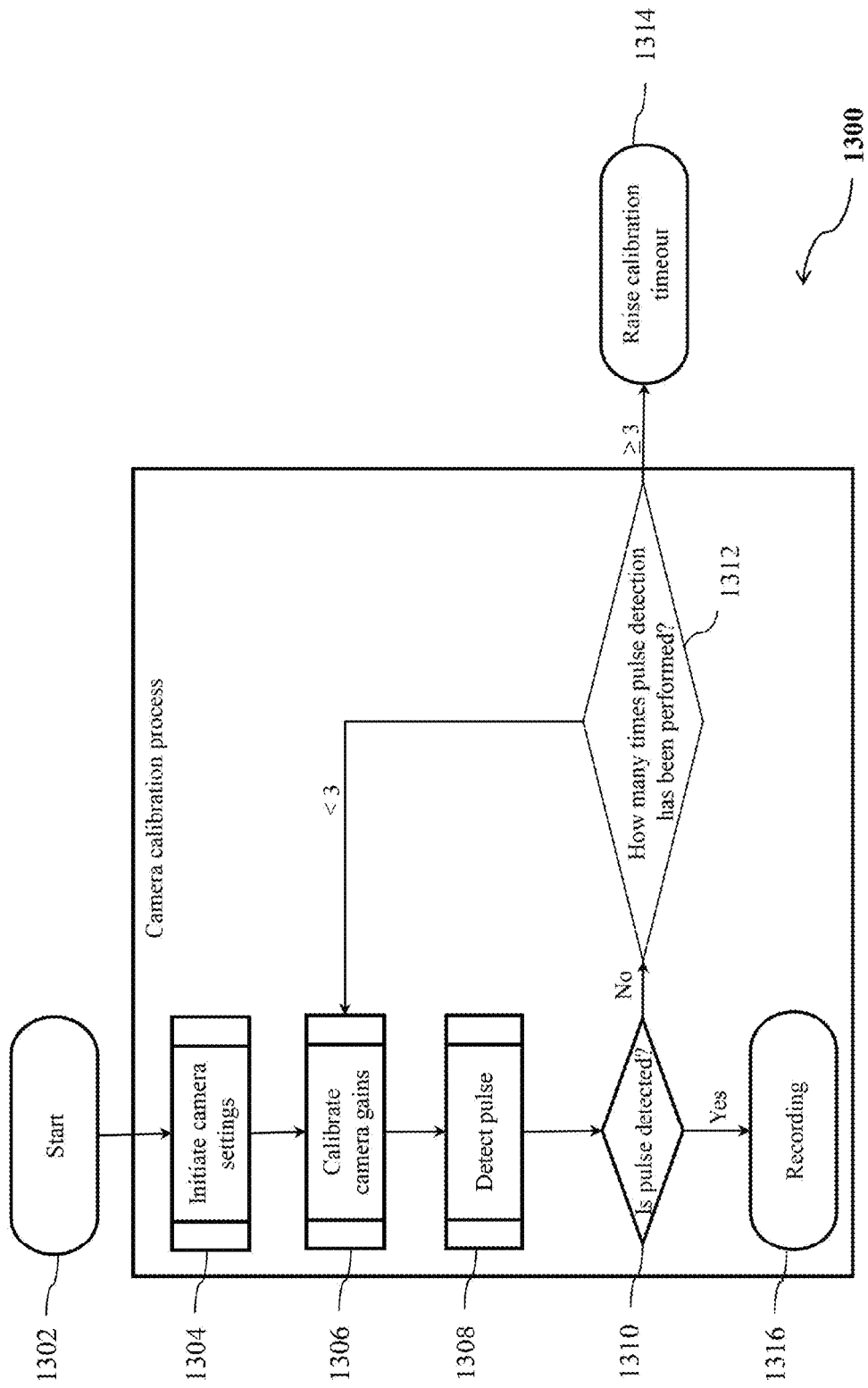
FIG. 13 is a flowchart illustrating another methodology for calibrating a photodetector, according to example embodiments.

FIG. 13 is a flowchart illustrating another method 1300 for calibrating the photodetector 110, according to some embodiments. The flowchart in FIG. 13 illustrates a method 1300 for calibrating a photodetector (e.g., camera device 110 in FIG. 1), according to inventive concepts of the current disclosure. In brief overview, the method 1300 can include starting a camera calibration process (STEP 1302), and configuring initial camera settings (STEP 1304). The method 1300 can include calibrating gains of camera or photodetector (STEP 1306), and detecting a pulsatile signal of a user to determine whether the camera calibration process is successful or not (STEP 1308). The method 1300 can include determining whether the pulsatile signal (of good quality) is detected or not (STEP 1310), and recording a PPG signal for determining a blood pressure measurement of the user (STEP 1312).

In further detail, the method 1300 can include a computing device (e.g., computer system 100) starting a camera calibration process (STEP 1302).

The method 1300 can include the computing device configuring initial camera settings (STEP 1304). In some embodiments, the computing device may configure initial camera settings by at least one of disabling a color correction setting, disabling an autocorrection setting of the camera, enabling a light source (e.g., light source 108 in FIG. 1) associated with the camera, or setting a frame rate of the photodetector to a predetermined rate, e.g., at least 30 frames per second.

The method 1300 can include the computing device calibrating gains of camera or photodetector (STEP 1306). In some embodiments, the computing device may calibrate or adjust the gain such that values of a PPG signal are in a middle range of values (e.g., around 128 in the overall range of (0, 255)). For example, the computing device may calibrate or adjust the gain by increasing an exposure time and/or sensitivity (e.g., ISO value) or decreasing an exposure time and/or sensitivity. A process of calibrating gains of camera according to some embodiments will be described in more detail with reference to FIG. 15.

The method 1300 can include the computing device detecting a pulsatile signal of a user to determine whether the camera calibration process is successful or not (STEP 1308). In some embodiments, the computing device may determine a sequence of local quality values of a PPG signal from a sequence of image frames (e.g., frame 602 in FIG. 7). The computing device may determine whether a pulsatile signal of good quality is detected or not (or whether the camera calibration process is successful or not), based on the local quality values of the PPG signal. For example, the computing device may determine that a pulsatile signal of good quality is detected, based on the number of consecutive frames of good quality (e.g., frames with quality values of the PPG signal exceeding a predetermined threshold quality). The computing device may determine that a pulsatile signal of good quality is not detected based on the number of cumulative frames of poor quality (e.g., frames with quality values of the PPG signal smaller than the predetermined threshold quality). A process of detecting a pulsatile signal (or determining whether the camera calibration process is successful or not) according to some embodiments will be described in more detail with reference to FIG. 14A.

The method 1300 can include the computing device determining whether the pulsatile signal (of good quality) is detected or not (STEP 1310). If it is determined that the pulsatile signal is detected, the method may proceed to STEP 1316. If it is not determined that the pulsatile signal is detected, the computing device may count the number of executing the pulsatile signal detection (STEP 1312). If the number of executing the pulsatile signal detection is greater than or equal to a predetermined threshold (e.g., 3), the camera calibration process may (1) issue or raise an error of calibration timeout (STEP 1314) and (2) abort or end the calibration. If the number of executing the pulsatile signal detection is smaller than the predetermined threshold (e.g., 3), the camera calibration process may proceed to STEP 1306 to adjust or calibrate the camera gains.

The method 1300 can include the computing device recording a PPG signal for determining a blood pressure measurement of the user (STEP 1316).

Figure 14A:
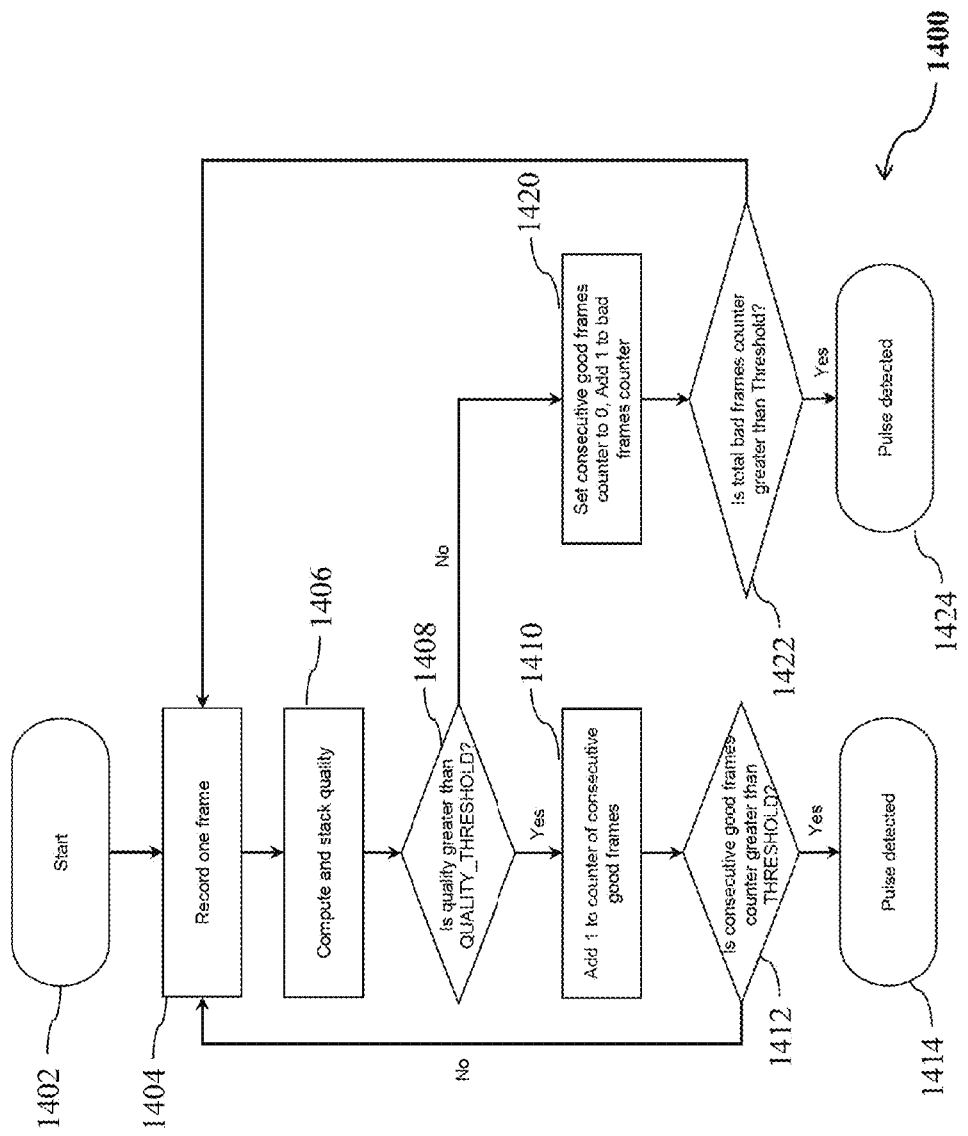
FIG. 14A is a flowchart illustrating a methodology for determining a sequence of local quality values of a PPG signal, according to some embodiments.

FIG. 14A is a flowchart illustrating a method 1400 for determining a sequence of local quality values of a PPG signal, according to some embodiments.

The flowchart in FIG. 14A illustrates a method 1400 of a pulsatile signal quality determination for determining a sequence of local quality values of a PPG signal for measurement of blood pressure or a pulse of a user, according to inventive concepts of the current disclosure. The method 1400 may correspond to STEP 1308 of the method 1300. The pulsatile signal quality determination process performed by the method 1400 can determine whether a pulsatile signal of good quality is detected or not, in other words, whether the camera calibration process is successful or not. In brief overview, the method 1400 can include starting the pulsatile signal quality determination process (STEP 1402), and recording one image frame (STEP 1404). The method 1400 can include computing and stacking quality values of a PPG signal from image frames (STEP 1406), and determining whether the PPG signal is of good quality or of poor quality (STEP 1408).

In further detail, the method 1400 can include a computing device (e.g., computer system 100 in FIG. 1) starting a pulsatile signal quality determination process (STEP 1402).

The method 1400 can include the computing device recording one image frame (STEP 1404). In some embodiments, the computing device may record a single image frame (e.g., frame 602 in FIG. 7) of a user's body part (e.g., finger). The computing device may generate or obtain a resampled (or downsampled) image of the original image frame. For example, a resampled image is a 5×5 small image with macropixels (e.g., image block 606 in FIG. 7).

The method 1400 can include the computing device computing and stacking quality values of a PPG signal from image frames (STEP 1406). In some embodiments, the computing device may stack numerical values for a given color channel (e.g., R or G) to generate a PPG signal. The computing device may compute or generate a PPG signal by averaging pixel values for each sub-block of an image frame (e.g., sub-block 606 of color image frame 602 in FIG. 7). The computing device may calculate autocorrelation of the PPG signal. In some embodiments, the computing device may calculate a value of autocorrelation of a PPG signal between consecutive frames and compare the autocorrelation value with a predetermined quality threshold (e.g., 0.85; see QUALITY_THRESHOLD in Table 2 below).

The method 1400 can include the computing device determining whether the PPG signal is of good quality or of poor quality (STEP 1408). If the autocorrelation value calculated in STEP 1406 is greater than or equal to the quality threshold, the computing device may determine that the PPG signal is of good quality between the consecutive frames and proceed STEP 1410 which adds one to a first counter of consecutive good frames. In STEP 1412, if the value of the first counter is greater than or equal to a predetermined threshold (e.g., 30 frames; see PULSE_MIN_GOOD_FRAMES in Table 2 below), the computing device may determine that a pulsatile signal of good quality is detected (STEP 1414) an proceed to starting a recording of PPG signal (e.g., STEP 1316 in FIG. 13).

If the autocorrelation value is smaller than the quality threshold, the computing device may determine that the PPG signal is of poor quality between the consecutive frames and proceed STEP 1420 which sets the first counter to 0 (zero) and adds one to a second counter of cumulative poor frames. In STEP 1422, if the value of the second counter is greater than or equal to a predetermined threshold (e.g., 120 frames; see PULSE_MAX_POOR_FRAMES in Table 2 below), the computing device may determine that a pulsatile signal of poor quality is detected (STEP 1424) an proceed to STEP 1312 which determines whether to proceed to the gain calibration (STEP 1306) or proceed to issuing or raising an error of calibration timeout (STEP 1314).

Figure 14B:
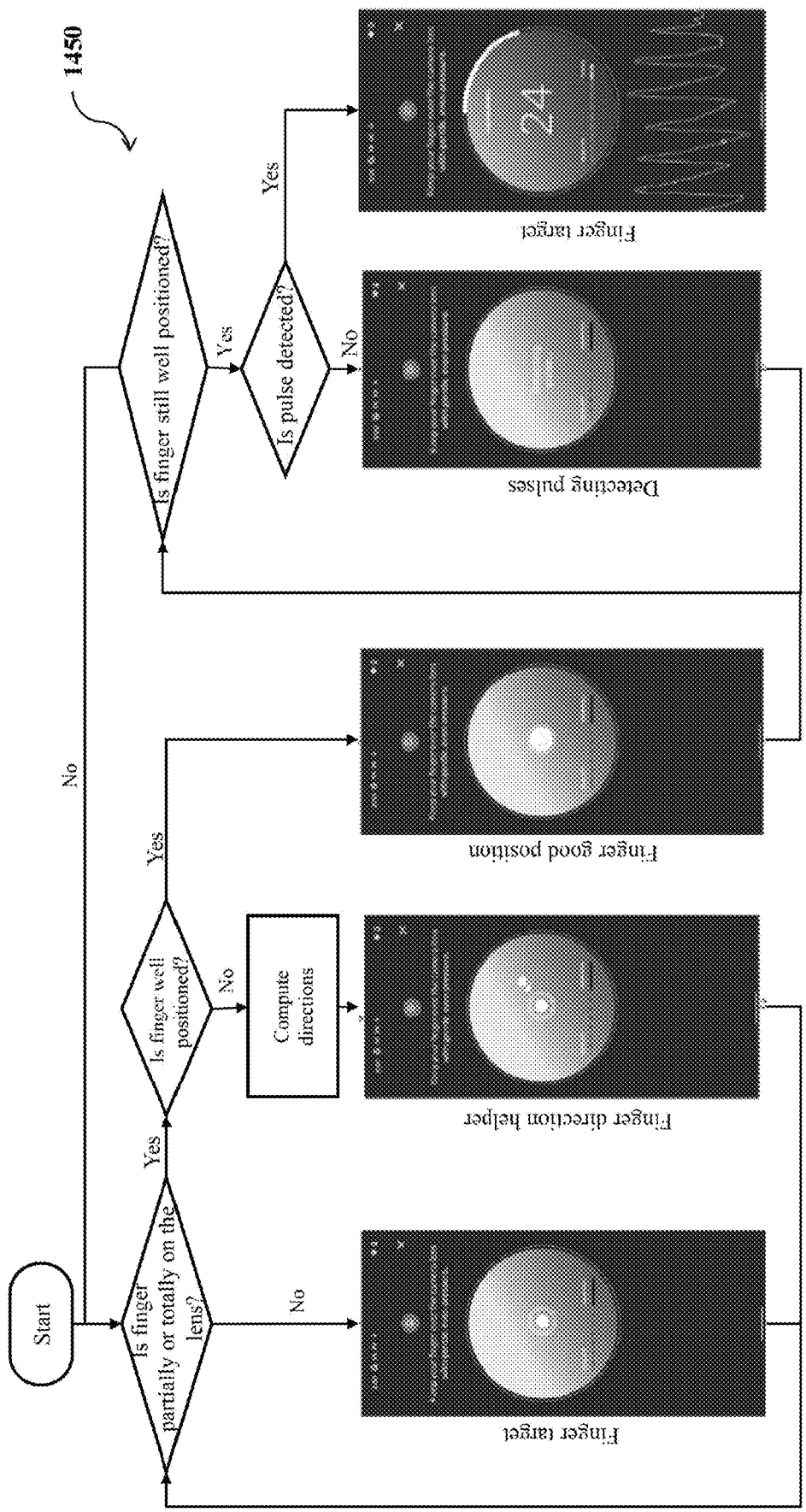
FIG. 14B is a flowchart illustrating a methodology for assisting finger placement on the lens during camera calibration, according to some embodiments.

FIG. 14B shows a flowchart illustrating a method 1450 for assisting finger placement on the lens during camera calibration, according to some embodiments. While FIGS. 12A, 13 and 14A do not invoke assessing the placement of the finger (or other body part) on the photodetector lens during acquisition of image frames during camera calibration, FIG. 14B shows an example process 1450 for detecting presence or absence of the finger as well as finger positioning, and displaying proper alert signals/messages to the user. The computer system 100 can perform the finger detection as well as the finger positioning as described in subsections D.1 and D.2 below.

Table 2 shows example threshold values used in the pulsatile signal quality determination process.

TABLE 2

Threshold Values for Pulsatile Signal Detection

| Name | Value | Description |
| --- | --- | --- |
| QUALITY_THRESHOLD | 0.85 | Minimal value of local autocorrelation for a single frame to be considered as good |
| PULSE_MIN_GOOD_FRAMES | 30 | Minimal number of consecutive frames to consider that a pulsatile signal is detected |
| PULSE_MAX_POOR_FRAMES | 120 | Maximal number of frames with poor quality before aborting pulsatile signal detection |

Figure 15:
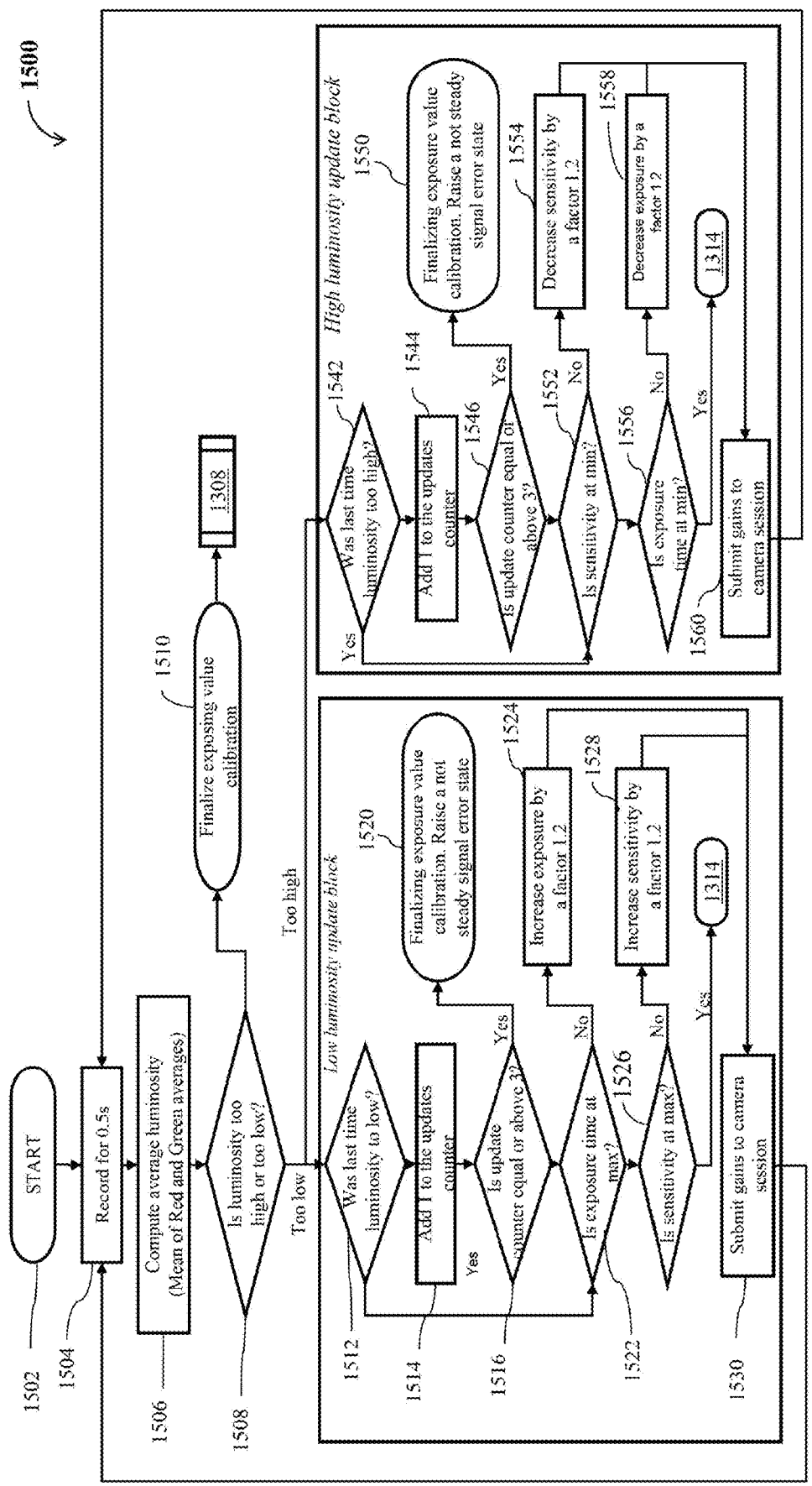
FIG. 15 shows a flowchart illustrating a method 1500 for calibrating exposure time and sensitivity of a photodetector or a camera, according to example embodiments.

FIG. 15 shows a flowchart illustrating a gain calibration method 1500 for updating exposure time and sensitivity of a photodetector or a camera, according to example embodiments. The method 1500 may correspond to STEP 1306 of the method 1300. In some embodiments, the gain calibration process can update the gains to set a PPG signal in an acceptable range (e.g., a linear response domain) by updating exposure values (EVs) of the camera. In some embodiments, the gain calibration process may calibrate or adjust the gain such that values of a PPG signal are in a middle range of values (e.g., around 128 in the overall range of (0, 255)) by increasing or decreasing EVs of the camera. For example, at the end of the EV update process, PPG signals can be in an appropriate range of values (e.g., around 128 out of 255) if the calibration is successful, or close to the appropriate range even if the calibration is not successful. The EVs may include at least one of an exposure time or sensitivity (e.g., ISO value) of the camera.

In brief overview, the method 1500 can include starting the gain calibration process (STEP 1502), and recording a predetermined duration of signal of image frames (STEP 1504). The method 1500 can include computing or obtaining a luminosity value over the image frames (STEP 1506), and determining whether the luminosity value is too high or too low (STEP 1508). The method 1500 can include performing a low luminosity update process (or block) (STEP 1512 to STEP 1530), and performing a high luminosity update process (or block) (STEP 1542 to STEP 1558).

In further detail, the method 1500 can include a computing device (e.g., computer system 100 in FIG. 1) starting the gain calibration process (STEP 1502).

The method 1500 can include the computing device recording a predetermined duration of signal of image frames (STEP 1504). In some embodiments, the computing device may record a predetermined duration (e.g., 0.5 seconds) of signal of image frames (e.g., image frame 602 in FIG. 7) such that an ongoing capture request can have time to be built and gains can be indeed updated.

The method 1500 can include the computing device computing or obtaining a luminosity value over the image frames (STEP 1506). The computing device may compute or obtain an average value of luminosity over one or more images of the image frames. The computing device may compute or obtain an average value of luminosity over an image frame (e.g., image frame 602 in FIG. 7) by averaging pixel intensities of a corresponding sub-block of the image frame (e.g., sub-block 606 in FIG. 7) for each color (e.g., R or G) frame of the image frame. In some embodiments, computing device may compute or obtain an average value of luminosity over an image frame by averaging (1) pixel intensities of a corresponding sub-block of R frame of the image frame and (2) pixel intensities of a corresponding sub-block of G frame of the image frame.

The method 1500 can include the computing device determining whether the luminosity value is too high or too low (STEP 1508). This average luminosity value may be compared to a target range. Assuming that the luminosity value range is (0, 255), the target range may be around a middle value, e.g., (128-α, 128+α), α=10%, 20%, or 30% of the middle value (13, 26, 39). In some embodiments, the target range may be determined based on a linear range of a transfer function. For example, according to the transfer function shown in FIG. 11, the target range may be (100, 150) or another range where the effect of quantization is relatively low (e.g., less than 1%) compared to the intensity values. If the average luminosity value lies in the target range, the computing device may determine that the gain calibration or EV calibration is successfully finalized (STEP 1510), end the gain calibration process, and proceed to a next step, e.g., pulse detection (STEP 1308 in FIG. 13).

On the other hand, if the average luminosity value lies outside the target range, the computing device may determine that the gain calibration or EV calibration is not successful, and continue the EV update until the average luminosity value lies in the target range. In some embodiments, the computing device may determine whether the value is greater than the target range (e.g., when the luminosity is too bright) or the value is smaller than the target range (e.g., when the luminosity is too dark). If luminosity is too dark, the computing device may proceed to a low luminosity update process that can increase EVs by a predetermined factor (STEP 1512 to STEP 1530). If luminosity is too bright, the computing device may proceed to a high luminosity update process that can reduce EVs by a predetermined factor (STEP 1542 to STEP 1558).

The method 1500 can include the computing device performing the low luminosity update process (or block) (STEP 1512 to STEP 1530). The computing device may check whether the number of the high luminosity update processes previously performed is greater than a predetermined threshold (e.g., whether too many high luminosity update processes were previously performed to decrease EVs). The computing device may determine whether the luminosity value obtained last time (e.g., the luminosity value obtained immediately before obtaining the current luminosity value) is too low (STEP 1512). Alternatively, the computing device may check whether the low luminosity update process was performed last time (e.g., immediately before the current low luminosity update process was performed).

If it is not determined that the luminosity value obtained last time is too low, the computing device may determine that the high luminosity update process was performed last time, and add one to a high luminosity update counter (STEP 1514). If it is determined that the value of the high luminosity update counter exceeds a predetermined threshold number, e.g., 3 (STEP 1516), the computing device may determine that too many high luminosity update processes were previously performed to decrease EVs (which indicates that the user is not stable yet or that the EV oscillates around a target value), and issue a not-steady warning as an error state and end or exit the gain calibration process (STEP 1520). If it is determined that the value of the high luminosity update counter is smaller than the predetermined threshold number, e.g., 3 (STEP 1516), the computing device may (1) determine that there have not been too many high luminosity update processes previously performed to decrease EVs and (2) determine whether the current value of exposure time is a maximum value (STEP 1522). If the current value of exposure time is not a maximum value, the computing device may increase the exposure time value by a predetermined exposure time update factor (e.g., 1.2) (STEP 1524). On the other hand, if the current value of exposure time is the maximum value, the computing device may determine whether the current value of sensitivity (e.g., ISO value) is a maximum value (STEP 1526). If the current value of sensitivity is not a maximum value, the computing device may increase the sensitivity value by a predetermined sensitivity update factor (e.g., 1.2) (STEP 1528). In other words, if (1) it is determined that there have not been too many high luminosity update processes previously performed to decrease EVs, (2) the current value of exposure time is the maximum value, and (3) the current value of sensitivity is not a maximum value, the computing device may increase the sensitivity value by a predetermined sensitivity update factor (e.g., 1.2). In this manner, the low luminosity update process can increase the exposure time while keeping the sensitivity value at the minimum value, which means that the low luminosity update process rather increases the exposure time then the sensitivity while the high luminosity update process (see the description below) decreases the sensitivity first and then decrease the exposure time if it is not possible. After at least one of the sensitivity or exposure time is updated, the low luminosity update process may submit the new updated gain to the camera (STEP 1530) and proceed to the recording of new image frames (STEP 1504). In some embodiments, after submission of a new gain, the low luminosity update process may wait for settings to be effectively taken into account before performing a new update process (either the high luminosity update process or the low luminosity update process). If the current value of sensitivity is a maximum value, the computing device may (1) issue or raise an error of calibration timeout (STEP 1314) and (2) abort or end the gain calibration.

The method 1500 can include the computing device performing a high luminosity update process (or block) (STEP 1542 to STEP 1558). The computing device may check whether the number of the low luminosity update processes previously performed is greater than a predetermined threshold (e.g., whether too many low luminosity update processes were previously performed to increase EVs). The computing device may determine whether the luminosity value obtained last time (e.g., the luminosity value obtained immediately before obtaining the current luminosity value) is too high (STEP 1542). Alternatively, the computing device may check whether the high luminosity update process was performed last time (e.g., immediately before the current high luminosity update process was performed).

If it is not determined that the luminosity value obtained last time is too high, the computing device may determine that the low luminosity update process was performed last time, and add one to a low luminosity update counter (STEP 1544). If it is determined that the value of the low luminosity update counter exceeds a predetermined threshold number, e.g., 3 (STEP 1546), the computing device may determine that too many low luminosity update processes were previously performed to increase EVs (which indicates that the user is not stable yet or that the EV oscillates around a target value), and issue a not-steady warning as an error state and end or exit the gain calibration process (STEP 1550). If it is determined that the value of the low luminosity update counter is smaller than the predetermined threshold number, e.g., 3 (STEP 1546), the computing device may (1) determine that there have not been too many low luminosity update processes previously performed to increase EVs and (2) determine whether the current value of sensitivity (e.g., ISO value) is a minimum value (STEP 1552). If the current value of sensitivity is not a minimum value, the computing device may decrease the sensitivity value by a predetermined sensitivity update factor (e.g., 1.2) (STEP 1554). On the other hand, if the current value of sensitivity is the minimum value, the computing device may determine whether the current value of exposure time is a minimum value (STEP 1556). If the current value of exposure time is not a minimum value, the computing device may decrease the exposure time value by a predetermined exposure time update factor (e.g., 1.2) (STEP 1558). In other words, if (1) it is determined that there have not been too many low luminosity update processes previously performed to increase EVs, (2) the current value of sensitivity is the minimum value, and (3) the current value of exposure time is not a minimum value, the computing device may decrease the exposure time value by a predetermined exposure time update factor (e.g., 1.2). In this manner, the high luminosity update process decreases the sensitivity value first and then decrease the exposure time if it is not possible. After at least one of the sensitivity or exposure time is updated, the high luminosity update process may submit the new updated gain to the camera (STEP 1560) and proceed to the recording of new image frames (STEP 1504). In some embodiments, after submission of a new gain, the high luminosity update process may wait for settings to be effectively taken into account before performing a new update process (either the high luminosity update process or the low luminosity update process). If the current value of exposure time is a minimum value, the computing device may (1) issue or raise an error of calibration timeout (STEP 1314) and (2) abort or end the gain calibration.

D. Improving Accuracy of Blood Pressure Measurements By Enhancing Acquisition of Transdermal Optical Data The accuracy of the blood pressure measurements or heart rate measurements output by method 400 depends on the quality of the generated PPG signal, which in turn depends on the acquired transdermal optical data or sequence of image frames acquired by the camera device 110. Specifically, the less noisy the image frames acquired by the camera device 110 and the more accurately they reflect the light intensity reflected from the user finger (or other body part), the more accurately the corresponding PPG signal mimics the pulse waveform of the user. A PPG signal of good quality is more likely to contain more information about blood pressure and other physiological data than one of poor quality. Feeding a "cleaner" PPG signal (e.g., with respect to how accurately it mimics the pulse waveform of the user) to the OBPM module 510 leads to more accurate blood pressure and/or pulse (or heart rate) measurements output by the OBPM module 510.

During the acquisition of optical signals (or sequence of image frames) through the camera device 110, there are several factors that can compromise the quality of the recorded image frames or optical data. Among these, there are several that involve the interaction of the user's finger (or other body part) with the camera' optical waveguide or the corresponding transparent glass. Other factors relate to noise or distortions originating at the camera device 110. For instance, many camera devices apply some image processing techniques to captured images or image frames, for example, to enhance contrast, brightness, sharpness or other visual characteristics. The image processing techniques applied by the camera device 110 can be nonlinear in nature, therefore, introducing a distortion in the in the corresponding PPG signal.

To address these problems, the computer system 100 or the application 114 can guide the user to position the finger (or other body part) properly on the camera lens or transparent glass, to apply appropriate pressure, and to maintain a stable position during recording. The computer system 100 or the application 114 can guide the user before the start of data acquisition by the camera device 110 and/or after the start of data acquisition. For instance, the computer system 100 or the signal quality assessment module 508 can assess the quality of color signals generated based on acquired image frames, and cause the output module 512 to present feedback to the user, if needed. As to the distortions originating at the camera device 110, the data acquisition module 502 can adjust one or more settings of the camera device 110.

To correct finger (or other body part) location, the computer system 100 or the application 114 can detect pre-recording and/or intra recording finger location relative to the lens and provide user feedback and guidance via the UI(s). Also, the computer system 100 or the application 114 can detect pre-recording and/or intra recording finger pressure against the optical waveguide leading to the lens, the corresponding transparent glass or the lens, and provide user feedback and guidance via the UI. In some implementations, to detect the location or pressure of the user finger (or other body part), the computer system 100 or signal quality assessment module 508 can assess color signals generated based on acquired image frames based on one or more corresponding criteria or rules.

Different finger sizes, as well as variation of finger placement/orientation over the camera lens usually results in different illumination characteristics, including partial occlusion of the image field and variation in the location of the optimal region or block of the image field for constructing or generating the PPG signal to be input to the OBPM module 510. In addition, during the acquisition of image frames, the user's finger (or other body part) can move causing the finger position, orientation or pressure to change, and therefore degrading the quality of the PPG signal. The computer system 100 or the signal quality assessment module 508 can iteratively assess the image data or the corresponding PPG signal, for example, before and during the acquisition of the image frames.

D.1. Finger Detection

The computer system 100 can capture, record, or obtain PPG signals using at least one camera device 110 and at least one light source 108 for the camera device 110 to capture the light intensity reflected from the user finger, among other body parts. The computer system 100 executing the application 114 can use the PPG signals to determine or estimate the amount of blood present in the finger of the user. The computer system 100 (or other devices processing the PPG signals) can obtain good PPG signals for accurate measurement by having the user place their finger well on a device capturing the PPG signals, such as the camera device 110. By placing the finger well on the device, the computer system 100 can obtain, output, or generate good results to accurately measure at least the amount of blood present in the finger of the user, among other health features of the user. For example, the computer system 100 can process a sequence of images to make sure that the user places their finger well on the camera device 110. The computer system 100 may determine that the user is placing their finger well on the camera device 110. In some cases, the computer system 100 may determine that the user is not placing their finger well (e.g., displacement from the center, pressure applied, or lighting reflected from a finger) or that their finger is not on the camera device 110. To detect that a finger of the user is well placed or present on the capturing device (e.g., camera device 110), the application 114 executing on the computer system 100 can use an algorithm to distinguish or discriminate frames with or without a finger.

The application 114 can use Laplacian or other derivative operators/imaging techniques for finger detection, such as to detect texture in the image frames. Laplacian can be a measure of variations of multidimensional signal, calculated by using second derivatives over x and y axes. Using Laplacian, the application 114 can highlight regions of rapid intensity changes (e.g., the intensity of the color in an image frame), which can be used for edge detection for the image. For example, the application 114 can consider image frames with little textures as being a finger and image frames with an abundance of textures as not being a finger, in some cases. The use of the Laplacian may not distinguish between texture of a finger or other objects having no or little texture. Such distinction can be made by other processes described in this disclosure, such as the signal quality assessment method of FIG. 29. The application 114 can use Laplacian to measure the uniformity and texture of each downsampled image using local variation values at each pixel position. Specifically, the application 114 can apply the Laplacian equation for individual pixels of image frames to determine characteristics of the image frame, such as whether there are various different textures or uniformed textures within an image to detect the presence of a finger on the camera device 110, for example.

By using Laplacian on downsampled images (e.g., 5×5 images or frames), the application 114 can efficiently detect whether a frame displays a finger or if no finger is present within the respective frames. For example, the computer system 100 executing the application 114 can compute the Laplacian of a sequence of images (e.g., a sequence of downsampled images) to determine how much texture is captured in individual image frames. If a finger is present (e.g., against the camera device 110, photodetector, or photodetector lens when capturing the image), the computer system 100 can compute one or more values indicating that the image has little texture. Images frames with little texture can include uniform images. Specifically, the computer system 100 can compute the Laplacian of images to determine the uniformity of individual images represented by at least one value.

For computation, the computer system 100 can provide one or more image frames or a sequence of downsampled images as input(s) for the Laplacian operator. The input can be denoted as X, at least for this section, and has shape ($d_x$, $d_y$, 3). The $d_x$ and $d_y$ can represent the height and width of an image frame used as the input, respectively. In some cases, the $d_x$ and $d_y$ of the shape can represent the x-axis pixels and y-axis pixels of an image frame, respectively. The constant 3 can represent the number of color channels (e.g., R, G, or B) for the shape. For example, the computer system 100 can provide one or more sequences of downsampled images as input for the Laplacian operator, where each sequence can include one of the color channels. The computer system 100 can compute the Laplacian of individual pixels for the respective downsampled images having a respective color channel (e.g., a sequence of G downsampled images or a sequence of R downsampled images).

The computer system 100 can output or generate a transformed image including the Laplacian of the image for each color channel. The Laplacian can refer to a normalized (e.g., denoted as $\tilde{L}$ or raw average Laplacian of an image frame. The Laplacian can be denoted as L. For example, the computer system 100 can output a first Laplacian of a sequence of downsampled images in the G color channel, a second Laplacian of a sequence of downsampled images in the R color channel, and a third Laplacian of a sequence of downsampled images in the B color channel. The Laplacian output by the computer system 100 can include a shape of $(d_x-2, d_y-2, 3)$, e.g., height and width of two less than the input height and width. Each value L[x,y,c] representing each image frame of the sequence of downsampled images can include the local Laplacian of X (or of the image) on color channel c around pixel (x+1, y+1).

Figure 16:
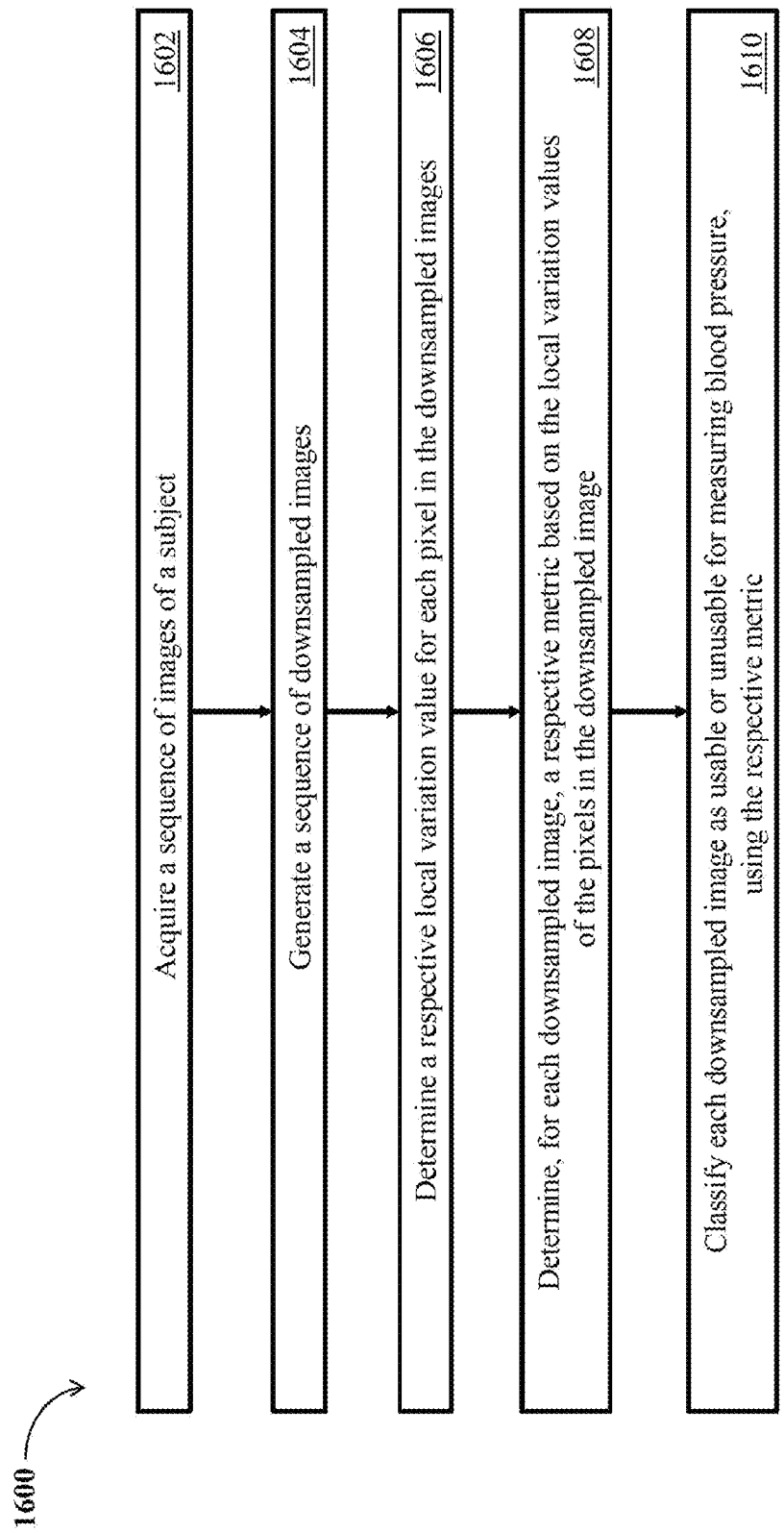
FIG. 16 shows a flowchart illustrating a method for detecting presence or absence of a finger or a body part, according to example embodiments.

Referring to FIG. 16, a flowchart illustrating a method 1600 of detecting a finger is shown, according to inventive concepts of this disclosure. The method 1500 can include acquiring a sequence of images (STEP 1602). The method 1600 can include generating a sequence of downsampled images of the sequence of images (STEP 1604). The method 1600 can include determining a respective local variation value for each pixel of various pixels in the downsampled image (STEP 1606). The method 1600 can include determining a respective metric based on the local variation values of each pixel of the various pixels of the downsampled image (STEP 1608). The method 1600 can include classifying each downsampled image as usable or unusable for measuring blood pressure using the respective metric (STEP 1610). The method 1600 can be performed by the computer system 100 or the corresponding processor 102, for example, upon executing the application 114. The method 1600 can be performed by other components (e.g., memory 104, BUS 106, light source 108, camera device 110, or display device 112) of the computer system 100, in conjunction with FIG. 1. The method 1600 can be performed by a remote device or a remote server. In some implementations, the method 1600 can be performed by a computer system 100 and a remote server. For example, the computer system 100 can establish a communication channel with the remote server to forward data to or receive processed data from the remote server. The computer system 100 can acquire the sequence of images and pass the sequence of images to a remote server. Responsive to receiving the sequence of images, the remote server can perform STEPS 1004-1010. After classifying the downsampled image, the remote server can transmit the processed data or the classification of the downsampled image to the computer system 100. Accordingly, each STEP of method 1500 can be performed by a combination of the computer system 100 and the remote server. The method 1500 can be performed by other components discussed herein and perform features and functionalities in conjunction with FIGS. 1-10, for example.

Still referring to FIG. 16, in further detail, a photodetector of the computer system 100 can acquire a sequence of images (STEP 1602). The photodetector can be referred to as a photosensor, which can include or be the light source 108. The sequence of images can represent transdermal optical data of a subject. A user can actuate the application 114 on the computer system 100, and apply their fingertip or other body parts to the camera 110 for example, as illustrated in FIGS. 2A, 2B, and 3A. Upon initiation, the application 114 can cause the computer system 100 to display a user interface (UI) on the display device 112. The UI can provide instructions to the user to apply their fingertip against the camera 110 or a corresponding transparent glass for a given period of time, e.g., 20 seconds. The UI can provide an option, e.g., upon user selection, to present further instructions, images, or a demo explaining how the fingertip (or other body parts) is to be applied to the camera 110.

The application 114 or the data acquisition module 502 can automatically trigger the camera 110 to acquire a sequence of image frames. In some implementations, the application 114 or the data acquisition module 502 can cause the computer system 100 to display an interactive item as part of the UI. The application 114 or the data acquisition module 502 can automatically trigger the camera device 110 to acquire the sequence of images, upon the user interacting with the interactive item. Triggering the camera device 110 can include actuating the flash device 206 to emit artificial light either continuously or periodically according to a given frequency.

The camera device 110 can acquire the sequence of image frames while the user's fingertip (or other body parts) is applied against the optical waveguide of the camera or the corresponding transparent glass. Specifically, the RGB sensor 312 can acquire the sequence of image frames according to a specific or predefined frame rate based on the light intensity $I_r$ reflected from the user's finger. The frame rate can be equal to 25 frames/second (fps), 30 fps, 50 fps or other frame rate supported by the camera device 110. The data acquisition module 502 can receive image data corresponding to image frames from the camera device 110. In some implementations, the data acquisition module 502 can receive image data for each frame immediately after the image frame is captured or recorded by the RGB sensor 312 or the camera device 110.

In some implementations, the computer system 100 can include a plurality of cameras 110. The computer system 100 can automatically select one of the cameras 110 to acquire the sequence of image frames, and display (e.g., via a user interface of the application 114) a notification to the user of the computer system 100 of the selected camera 110. The user can place his/her finger against the selected camera. The selection can be based on the features or characteristics of the various cameras. In some implementations, the user can select the camera to be used to acquire the sequence of image frames. The computer system 100 can receive or obtain the user selection via an input device, e.g., a keyboard, a mouse, or a touch screen, among others, of the computer system 100. The computer system 100 may confirm the user selection via, for example, the display device 112. The computer application 114 may include different settings for distinct cameras 110. The computer system 100 can maintain camera ID/phone model matrix in the memory 104. Besides the camera ID, the computer system 100 can store the preferred camera settings in the matrix, such as ISO, exposure time, tone map, RGB gain or a combination thereof, among other settings.

The computer system 100 can generate a sequence of downsampled images by downsampling each image of the sequence of images (STEP 1604). The sequence of images can include an image region or block associated with at least one color (e.g., red (R), green (G), or blue (B)) frame 702. The data acquisition module 502 of the application 114 executing on the computer system 100 can decompose each image into a respective color (e.g., R, G, or B) frame. The computer system 100 can generate the sequence of downsampled images responsive to or immediately after acquiring or obtaining the images of the subject. In some cases, the computer system 100 can delegate the generation of the sequence of downsampled images to a remote server or a remote computing device. For example, the computer system 100 can acquire and transmit the sequence of images to a remote server to process the sequence of images. Processing the sequence of images can include downsampling the sequence of images to generate a sequence of downsampled images. The sequence of downsampled images can be further analyzed or processed by the remote server or transmitted to the computer system 100.

The computer system 100 can downsample each image of the sequence of images. The computer system 100 can perform the downsampling process in conjunction with FIG. 4 and FIG. 7 or execute the features or functionalities as described in FIG. 4 and FIG. 7. For example, the processing module 504 of the application 114 executing on the computer system 100 can identify an image region or block associated with a color (e.g. G or R) frame 702. The image can be from one of the sequence of images. The processing module 504 can downsample each color (e.g. G or R) frame 702 of the sequence of image frames to smaller image block 704. The processing module 504 can downsample the color (e.g. G or R) frame 702 to a 5×5 image (or data) block, a 9×9 image (or data) block, or a data block 704 of a different size. In downsampling the color frame 702, the processing module 504 can apply low-pass filtering or averaging to the pixel values of the color frame 702. The processing module 504 can downsample the color frame 702 using known downsampling techniques.

The processing module 504 can identify a sub-block 706 of the image block 704 for use to generate a color signal. The processing module 504 can identify a central zone or sub-block of the image block 704 as sub-block 706. Depending on the size and the placement of the user finger against the camera, the color intensities of a central zone of the image block 604 (or the color frame 702) are more likely to reflect the pulsatile nature of arterial blood in the finger than outer regions of the image block 704 (or the color frame 702). In some cases, the user finger may not be placed right at the center of the camera device 110, but rather shifted towards one direction over another. In such cases, at least one outer region of the image frame may not adequately reflect the light (or optical signal reflected from the user finger. In some implementations, the identified sub-block 706 can be a 3×3 image (or data) block, a 5×5 data block, or a data block of other sizes. By downsampling individual images of the sequence of images, computational resources used to process the images, as well as resource consumption for storing the images that are not downsampled, can be reduced. For example, by downsampling images with thousands of pixels (e.g., 320×240, 720×576, 1024×768, among other image sizes) to a 3×3 image, the computer system 100 can significantly reduce computational resources used to process the downsampled images and resource consumption to store the downsampled images.

The computer system 100 can determine a respective local variation value for individual pixels in each downsampled image of the sequence of downsampled images (STEP 1606). The local variation value can include or be referred to as a Laplacian value. The computer system 100 can compute the local variation value for each pixel using a Laplacian operator or a Laplacian equation. The computer system 100 can determine the respective local variation value based on a color value of the pixel and one or more color values of adjacent pixels. In some cases, the computer system 100 can determine the respective local variation value based on a color intensity of the pixel and one or more color intensities of adjacent pixels. The adjacent pixels can be pixels above, below, or to the sides of the pixel being computed for the local variation value. In this case, the adjacent pixels can be contiguous (e.g., forming a cross ("+")) with the pixel to compute the local variation value. The computer system 100 can compute the local variable value for the inner pixels of each image frame from the sequence of downsampled images. For example, in a 5×5 image, the local variation value can be computed for the inner 3×3 pixels of the image.

For example, the computer system 100 (or a remote server) executing the application 114 can use Laplacian on individual pixels of each image frame of a sequence of downsampled images. The Laplacian can be described using the following formula/equation (e.g., sometimes referred to as a Laplacian formula or formula (7)):

$$\Delta X(x, y) = \vec{\nabla} \cdot \vec{\nabla} X(x, y) = \frac{\partial^2 X}{\partial x^2}(x, y) + \frac{\partial^2 X}{\partial y^2}(x, y). \tag{7}$$

The denoted x and y can represent the pixel location that the computer system 100 is computing the local variation value for. The denoted $\vec{\nabla} \cdot \vec{\nabla} X$ (x, y) and $$\frac{\partial^2 X}{\partial x^2}(x, y) + \frac{\partial^2 X}{\partial y^2}(x, y)$$

can represent the double derivative of the X(x, y) function. In other words, the Laplacian can be described as or calculated by taking double derivative each pixel of the image X having shape ($d_x$, $d_y$, C). The formula (7) can be used for a continuous signal. However, since the image frames or downsampled images are discrete (e.g., each pixel having a discrete value representing the color value or color intensity for a respective color channel), the computer system 100 can use an updated Laplacian for determining the local variation value of individual pixels. The updated formula can be described in formula (8) (e.g., sometimes referred to as the discrete Laplacian formula):

$$\Delta X[x, y] = \frac{\partial^2 X}{\partial x^2}[x, y] + \frac{\partial^2 X}{\partial y^2}[x, y] = X[x+1, y] - 2X[x, y] + \tag{8}$$
$$X[x-1, y] + X[x, y+1] - 2X[x, y] + X[x, y-1].$$

Specifically, $$\frac{\partial^2 X}{\partial x^2}[x, y]$$

can be equated with X[x+1, y]−2X[x, y]+X[x−1,y] and $$\frac{\partial^2 X}{\partial y^2}[x, y]$$

can be equated with X[x, y+1]−2X[x, y]+X[x, y−1] Using the discrete Laplacian formula (e.g., formula (7)), the outer pixels can be cropped (e.g., local variation values may not be calculated for the outer pixels), as denoted in equation x+1, x−1, y+1, and y−1, since the computer system 100 may not extend to a null value or a value outside the image frame to calculate the local variation values.

The computer system 100 can use the formula (8) to calculate a respective local variation value for individual pixels of an image frame. The computer system 100 can use formula (8) for interior pixels. For example, in a 5×5 image, the computer system 100 can calculate one or more local variation values for each pixel in the 3×3 inner region of the 5×5 image. In some embodiments, with x and y representing the pixel location for calculating the local variation value and the X[x, y] can represent the color value (or other values) corresponding to the pixel location. The computer system 100 can use the discrete Laplacian formula to determine the local variation value of each interior pixel. For example, X[x+1, y] can correspond to a color value of the pixel at position (x+1, y), X[x−1, y] can correspond to a color value of the pixel at position ([x−1, y), X[x, y+1] can correspond to a color value of the pixel at position (x, y+1), and X[x, y−1] can correspond to a color value of the pixel at position (x, y−1). Each of the aforementioned functions can represent the color value of the respective pixel. To simplify, the discrete Laplacian formula can be calculated by taking the sum of color values adjacent to a respective pixel (e.g., pixel at [x, y] pixel location), such as the sum of four color values of the adjacent pixels, and subtract the sum by 4 times the color values at [x, y] pixel location. The computer system 100 can perform similar procedures for other pixels. Accordingly, the computer system 100 can determine the local variation value for individual pixels for each image frame, where the local variation value can represent the magnitude of similarity, uniformity, or differences between a pixel (e.g., a first pixel) and the adjacent pixels (e.g., pixels contiguous to the first pixel).

The computer system 100 can determine a metric based on or using the respective local variation values of each of the pixels of the downsampled image (STEP 1508). The metric can be referred to as a uniformity metric or a texture metric, and can be indicative of the uniformity of (or a measure of texture in) individual downsampled images. The computer system 100 can aggregate the local variation values of the respective pixels of each downsampled image to determine a single scalar value (e.g., the metric). To aggregate, the computer system 100 can compute an average or mean of the local variation values. In some cases, the computer system 100 can determine the metric by determining the average Laplacian value using the respective Laplacian value for each pixel of individual downsampled images. Formula (9) can be used to determine the Laplacian of the image:

$$L = \frac{1}{(d_x - 2) \cdot (d_y - 2)} \Sigma_{x=1}^{d_x-2} \Sigma_{y=1}^{d_y-2} \Delta X[x, y]. \quad (9)$$

To compute L, the computer system 100 can compute a sum of all local variation values, as represented by $\Sigma_{x-1}^{d_x-2} \Sigma_{y-1}^{d_y-2} \Delta X[x, y]$. If processing a 5×5 image block, the computer system 100 or the processor 102 can sum up Laplacian or local variation values for $(d_x-2) \times (d_y-2)$ or 3×3 pixels. In this example, the computer system 100 can compute a sum of local variation values at pixel locations [1, 1], [1, 2], [1, 3], [2, 1], [2, 2], [2, 3], [3, 1], [3, 2], and [3, 3], where the indexing of pixel locations is from 0 to 4. After summing the nine values, the computing device can divide the sum by the total number of pixels the local variation values were computed from. In this case, the product of $(d_x-2)$ and $(d_y-2)$ is 9. The denominator can be $(d_x-2)$ and $(d_y-2)$, due to cropping the outer pixels of each image frame when using the discrete Laplacian formula. Accordingly, the computer system 100 can determine L or the metric based on the local variation values.

In some implementations, the computer system 100 can normalize the metric (or the Laplacian metric) into a normalized metric (or a normalized Laplacian metric). By normalizing the metric, the computer system 100 can account for the fact that high-valued images are likely to vary more than low-valued images. The computer system 100 can utilize the normalization formula (e.g., formula (10)) to compute the normalized metric denoted as $\tilde{L}$:

$$\tilde{L} = \frac{L}{\overline{X}}. \quad (10)$$

The variable $\overline{X}$ can represent the mean of the downsampled image or the mean of central block (e.g., 3×3) of the downsampled image. For example, as a first step to calculate the standard deviation, the computer system 100 can compute the mean or the average of the local variation values, which is L. Second, the computer system 100 can calculate the mean of the downsampled image. Accordingly, using L and $\overline{X}$, the computer system 100 can determine the normalized metric $\tilde{L}$.

The computer system 100 can classify each downsampled image as usable or unusable for measuring blood pressure using the respective metric (STEP 1510). For example, the computer system 100 can compare a metric of the respective downsampled image to a threshold. The threshold can include or be referred to as a quality threshold. By satisfying the threshold, the computer system 100 can classify the downsampled image as usable for measuring blood pressure, for example. Otherwise, if the metric does not satisfy the threshold, the computer system 100 can classify the downsampled image as unusable. In some implementations, the computer system 100 can classify each downsampled image as usable or unusable for measuring blood pressure using a respective normalized metric. In such implementations, the computer system 100 can compare the normalized metric of the respective downsampled image to a second threshold (e.g., a second quality threshold for normalized metric).

The computer system 100 can determine the threshold using a machine learning model trained using various image frames or at least one sequence of images. The machine learning model can operate on the computer system 100 or a remote server, where the computer system 100 can forward the image frames for processing/classification by the remote server. For example, the computer system 100 can feed or input image data of image frames captured by the camera device 110 or other cameras from other devices into a machine learning model. For each image, the computer system 100 can provide an indication of whether a user finger (e.g., or other body parts) is against the camera (e.g., should or should not be classified as detecting the finger). In some cases, the computer system 100 can provide an indication of whether the user finger covers the entire camera, cover a portion of the camera, or away from the camera. The machine learning model can process the image data to determine the metric (e.g., averaged Laplacian value or normalized Laplacian value) of one or more respective images. In some cases, the computer system 100 can also provide the machine learning model with the metrics associated with the respective image frames. The machine learning model can determine based on the metrics for input image frames corresponding to existing finger(s) and the metrics of image frames corresponding to no finger one or more thresholds for the metric. The computer system 100 can use a range (e.g., from a minimum value to a maximum value) as the threshold or a single threshold value (e.g., greater than a minimum value or less than a maximum value) to determine if the user finger is present. In some implementations, the computer system 100 can determine if the user finger is well placed (e.g., covering the entirety of the camera) based on the metric compared to the threshold obtained by the machine learning model. In some implementations, a threshold can be determined by an administrator of the computer system 100 or the application 114.

The computer system 100 can use the metric to determine the texture or uniformity of each image frame. By using Laplacian, a small amount of training is sufficient for the machine learning model to determine a threshold for the computer system 100 to accurately detect if the user finger is present. Thus, the computer system 100 can train a good threshold for Laplacian to discriminate or distinguish frames with no finger from those with a user finger with minimum false negatives. In some implementations, the computer system 100 can train a different machine learning model without Laplacian computation to obtain a threshold and a metric to detect the presence of a user finger.

In some implementations, the computer system 100 can compute a blood pressure value using various downsampled images classified as usable. For example, the computer system 100 can determine that the respective metrics of one or more image frames satisfied a threshold. The computer system 100 can classify the image frames as usable for measuring blood pressure. Responsive to the determination, the computer system 100 executing the application 114 can initiate or transmit an instruction to the OBPM module 510 to measure at least one blood pressure based on the captured sequence of images (e.g., downsampled images). In some cases, the computer system 100 can instruct the OBPM module 510 to compute or estimate the heart rate or pulse rate of the user based on the sequence of images.

In some implementations, the computer system 100 can generate an alert responsive to determine that a predetermined number of downsampled images are classified as unusable. For example, the computer system 100 can determine that the respective metrics of one or more image frames do not satisfy a threshold. In this case, the computer system 100 can classify the image frames as unusable. Responsive to classifying one or more image frames as unusable, the computer system 100 executing the application 114 can initiate an alert to be presented on the UI to display to the user. The alert can indicate that the computer system 100 is unable to detect the presence of the user finger. In some cases, the computer system 100 can transmit an alert responsive to a time threshold for capturing unusable image frames. For example, the computer system 100 can be configured to alert the user after 1 second, 2 seconds, 3 seconds, 5 seconds, etc. after not receiving one or more usable image frames. In some implementations, the computer system 100 can be configured to transmit an alert after a predetermined number of image frames classified as unusable, such as 20 frames, 40 frames, 60 frames, etc.

Figure 17:
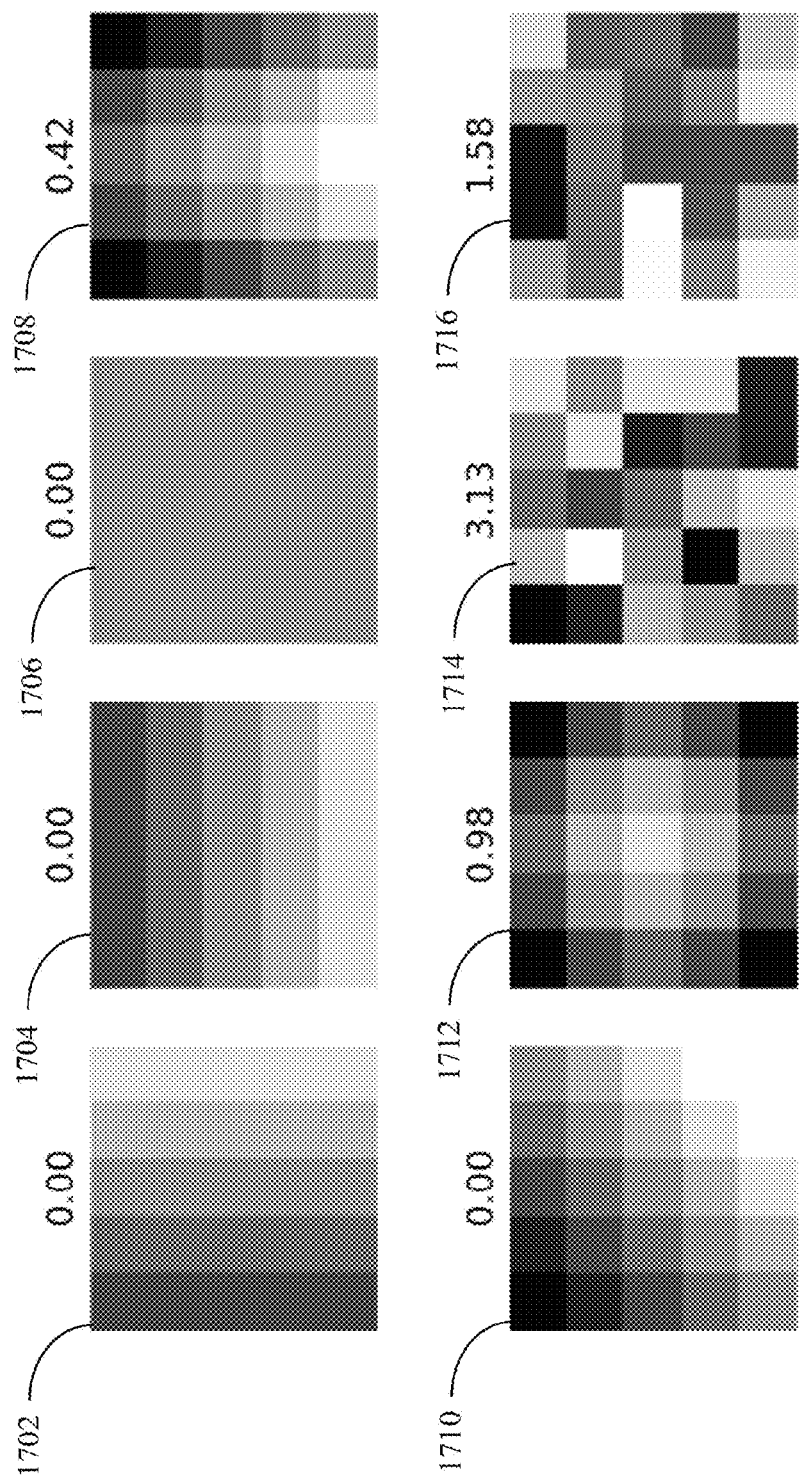
FIG. 17 shows examples of individual downsampled frames or images of the sequence of downsampled images with corresponding Laplacian scores, according to example embodiments.

FIG. 17 illustrates examples of individual downsampled frames or images 1702-1716 of the sequence of downsampled images. The downsampled image frames can be generated by the computer system 100, the application 114 executing on the computer system 100, or a remote server, such as executing STEP 1604 in conjunction with FIG. 16. In this example, the downsampled images can include 5×5 images containing at least one color value and one or more color intensities (or pixel intensities). Each image can include or correspond to a color (e.g., R or G) frame based on the configuration of the computer system 100. For example, the computer system 100 can extract individual colors (e.g., R, G, or B) from a sequence of images and output a second sequence of images with one of the colors corresponding to a color channel, such as R or G. Each region or pixel of the image can include a color (e.g., G, R, or B) having a respective color value and color intensity (e.g., averaged color intensity) of the color. In some cases, the color value can refer to the brightness of the color (e.g., ranging from 0% to 100%, where a lower percentage represents a darker color and a higher percentage represents a brighter or whiter color). The color intensity can refer to the saturation of the color (e.g., ranging from 0% to 100%, where a lower percentage indicates no color, which can be a shade of gray, and a higher percentage can represent a more intense or vibrate color). In some implementations, the color intensity may be interchanged with the color value for detecting the user finger. In some implementations, the downsampled images can be generated with different pixel densities, such as 10×10 images, 25×25 images, among others.

The computer system 100 can use the downsampled image frames of FIG. 17 to determine if a finger of the use is on the camera device 110. For example, the camera device 110 can capture, or the computer system 100 can obtain the image frames. Depending on the size and the placement of the user finger against the camera, the color intensities of a central zone of the image (or the color frame) are more likely to reflect the pulsatile nature of arterial blood in the finger than outer regions of the image (e.g., image block 704 or the color frame 702). Further, depending on if the user finger is against or away from the camera, the texture of each image frame may be more uniform (e.g., having little texture indicating that the user finger is on the camera) or less uniform (e.g., having more texture indicating that the user finger is away from the camera), for example. In some cases, having no texture or complete uniformity in color intensities (or color values) may indicate that the finger is not against the camera. In some cases, having a color intensity higher than a threshold (e.g., above 90% intensity) can indicate that at least a portion of the user finger is away from or not covering the camera, such that other lights (e.g., room lighting or non-reflective lights directed from the light source 108) is captured by the camera.

Referring to FIG. 17, the computer system 100 can compute the metric for each image frame based on the local variation values of individual pixels (e.g., inner 3×3 pixels of the 5×5 pixels). The value associated with the respective image frames (e.g., 0.00, 0.42, 0.98, 3.13, and 1.58) can represent the metric calculated for the respective image frames. In this example, with more texture or the greater the Laplacian of the image frame, the computer system 100 can compute a higher valued metric. Based on the threshold, the computer system 100 can discriminate or distinguish between image frames with a user finger or image frames without a user finger.

For example, referring to the three image frames 1702, 1704 and 1706 of the top row, the computer system 100 can compute metrics with a low value, indicating a high uniformity of the pixels or a small amount of texture. In another example, referring to the image frames 1714 and 1716, the computer system 100 can compute metrics with higher values (e.g., 3.13 and 1.58), indicating a low uniformity of the pixels or high amount of texture. If the threshold is set to 0.5, the computer system 100 can classify image frames 1702, 1704, 1706, 1708 and 1710 as usable, e.g., all of which are below the threshold. The computer system 100 may classify other image frames 1712, 1714 and 1716 as unusable due to the respective metrics surpassing the threshold, for example.

The computer system 100 can determine if the body part (e.g., a finger) of the user is present on the camera lens to measure the PPG of the user. Having the body part present on the camera is one of various conditions assessed by the computer system 100 to proceed with measuring the PPG. The computer system 100 can use a single image frame to determine, at least the likelihood of, whether the finger is on the lens of the camera or photodetector. The computer system 100 can downsample a sequence of image frames captured by the camera to generate a sequence of downsampled images. Each of the downsampled images can include a dimension of 5×5 pixels or other predetermined dimensions.

The computer system 100 can compute the Laplacian of each image frame using one or more techniques or formulas described above. Based on the Laplacian, the computer system 100 can attribute three normalized Laplacian values (e.g., denoted as $\tilde{L}^c$) for each color channel denoted as c. For example, a first normalized Laplacian value can correspond to the green color channel, a second normalized Laplacian value can correspond to the red color channel, and a third normalized Laplacian value can correspond to the blue color channel. The computer system 100 can compare the normalized Laplacian values to one or more thresholds corresponding to the respective normalized Laplacian values. The one or more thresholds can be denoted as $\theta_p$ in the finger. For example, the computer system 100 can compare the normalized Laplacian values to the threshold to determine if the Laplacian should be considered as a finger (or a body part) of the user. In some implementations, the threshold can be set to 0.8 (or other threshold value) for at least one of the color channels, such as red or green. In some cases, the threshold may not be set for one of the color channels, such as blue.

In some implementations, the computer system 100 can capture and downsample a sequence of images in a single color channel, such as green or blue. In this case, the computer system 100 can compute a single normalized Laplacian value for each of the sequence of downsampled images. The single normalized Laplacian value corresponding to the respective color channel. Accordingly, the computer system 100 can compare the normalized Laplacian value to the respective threshold corresponding to the color channel similar to the normalized Laplacian value. In some implementations, subsequent to computing the three normalized Laplacian values (e.g., for all color channels, including R, G, and B), the computer system 100 may not compare one of the normalized Laplacian values to a threshold, such as the blue color channel.

The computer system 100 can compare one or more of the normalized Laplacian values to one or more thresholds respective of the color channels of the normalized Laplacian values. Based on the comparison, the computer system 100 can provide an alert to the user if the user's finger is not on the camera. For example, the computer system 100 can determine or detect that a flesh (e.g., finger or other body parts) is present on the camera based on the following comparison:

$$\begin{cases} \tilde{L}^{red} < \theta^{red} \\ \tilde{L}^{green} < \theta^{green} \end{cases} \text{and.}$$

The computer system 100 can determine if the finger is not detected for a duration of consecutive frames. The duration of consecutive frames with no finger detected can be denoted as $T_{abs\,finger}$. The duration $T_{abs\,finger}$ can be preset or preconfigured to a time duration, such as 1 second, 0.5 seconds, 2 seconds, among others. If the finger (or other body parts) of the user is not detected for at least $T_{abs\,finger}$, the computer system 100 can flag the recording or the sequence of images of the finger as, e.g., isAbsentFinger condition (sometimes also referred to as finger abort condition, finger absent condition, or ABSENT_FINGER condition). The computer system 100 can raise the finger absent condition if the computer system 100 does not detect a finger for $T_{abs\,finger}$ duration of consecutive frames. In some implementations, the computer system 100 can raise the finger absent condition if the computer system 100 does not detect a finger for a total $T_{abs\,finger}$ duration of non-consecutive frames.

For example, if $T_{abs\,finger}$ duration is 1 second and the second duration is 2 seconds, if the computer system 100 determines that a total of 1 second out of the 2 seconds does not present the finger, the computer system 100 can raise the finger absent condition. Accordingly, the computer system 100 can output a boolean value (e.g., 1 or 0 based on the comparison between the normalized Laplacian values and the thresholds and the $T_{abs\,finger}$ duration) corresponding to the error condition (e.g., absent finger condition) to either trigger the absent finger condition or proceed with determining other conditions or measuring the user's PPG. In some implementations, the absence of finger condition may be redundant with the error state corresponding to abortion by finger removal. Thus, if the finger abort condition is raised, the condition of absorption by finger removal may also be raised. In another example, if the finger abort condition is not raised, the condition of absorption by finger removal may also not be raised.

D.2. Finger Position Helper

One key factor for obtaining a good result for measuring blood pressure, heart rate/pulse rate, or other blood measurement is to have a good placement of a user finger, or other body parts for measuring characteristic of the blood stream, at the lens of the camera or a measuring/capturing device. The lens of the camera can be in electrical communication with or a part of the computer system 100 or a mobile device 204. To assist users with the positioning of their finger to obtain good measurements, the computer system 100 executing the application 114 can process a video (e.g., one or more sequences of image frames) of the user finger captured by the camera.

An indication of whether the user finger is well positioned on the lens is to determine if all the pixels of images captured by the camera evolve in the same way (e.g., similar color values or intensities (or consistent changes in the color values or intensities) throughout the image frames of a sequence of images). To determine such indication, the computer system 100 can measure the resemblance of pixels in the images by calculating the cross-correlation for one or more sequences of images.

The computer system 100 can measure the similarity between two or more vectors of the images by computing their cross-correlation. The cross-correlation between a pixel and other pixels in an image (or between a vector and other vectors in a sequence of images) can be referred to as a correlation matrix. The computer system 100 can store intermediate sums between correlation matrices of one or more pixels, such that the intermediate sums between overlapping integrals are not computed multiple times, thereby reducing resource consumption and computation time. Further, the computer system 100 can aggregate the cross-correlation matrices (e.g., similarity matrix or distance matrix) to assess similarities (or differences) between each pixel and the rest of the pixels in the downsampled image. The computer system 100 can use the aggregate cross-correlation matrices to estimate a finger position relative to the center of the camera or photodetector lens. Accordingly, the computer system 100 can compute a gradient to assist users in orienting their fingers to cover the lens properly.

Figure 18A:
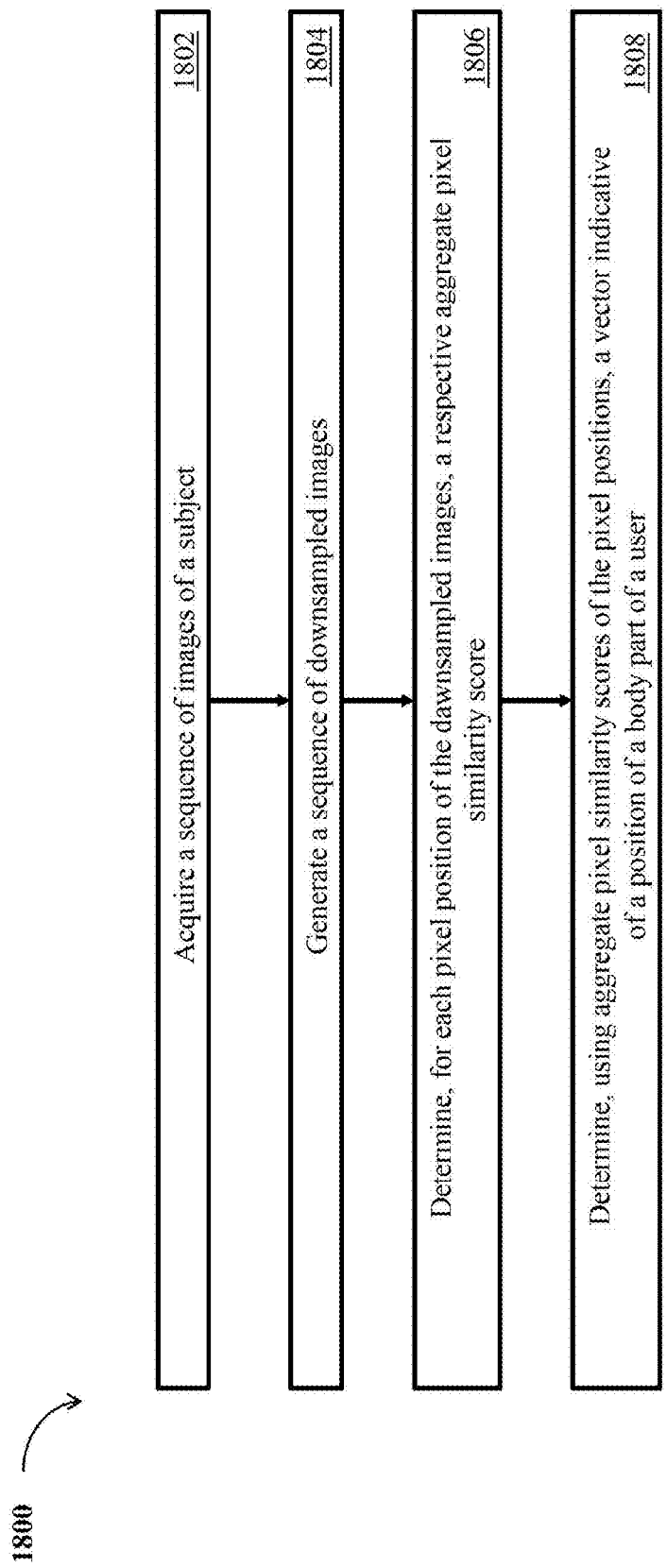
FIG. 18A shows a flowchart illustrating a method of determining a placement of a finger or body part, according to example embodiments.

Referring to FIG. 18A, a flowchart illustrating a method 1800 of determining a placement of a finger or body part is shown, according to example embodiments. The method 1800 can include acquiring a sequence of images (STEP 1802). The method 1800 can include generating a sequence of downsampled images (STEP 1804). The method 1800 can include determining, for each pixel position of the downsampled images, a respective aggregate pixel similarity score (STEP 1806). The method 1800 can include determining, using aggregate pixel similarity scores of pixel positions, a vector indicative of a position of a body part of a user (STEP 1808). The method 1800 can be performed by the computer system 100 or the corresponding processor 102, for example, upon executing the application 114. The method 1800 can be performed by other components (e.g., memory 104, BUS 106, light source 108, camera device 110, or display device 112) of the computer system 100, in conjunction with FIG. 1. The method 1800 can be performed by a remote device or a remote server. In some implementations, the method 1800 can be performed by a computer system 100 and a remote server. For example, the computer system 100 can establish a communication channel with the remote server to forward data to or receive processed data from the remote server. The computer system 100 can acquire the sequence of images and pass the sequence of images to a remote server. Responsive to receiving the sequence of images, the remote server can perform the steps 1804-1808. After determining the vector indicative of a position of a body part of the user, the remote server can transmit the processed data or the vector to the computer system 100 (e.g., for presentation to the user via a display device 112). Accordingly, each step of method 1800 can be performed by a combination of the computer system 100 and the remote server. The method 1800 can be performed by other components discussed herein and perform features and functionalities in conjunction with FIGS. 1-17, for example. The method 1800 can include one or more steps of or perform one or more similar steps to at least one of other methods discussed herein, such as methods 400, 1200 or 1500, among other methods discussed in this disclosure.

Still referring to FIG. 18A, in further detail, a photodetector of the computer system 100 can acquire a sequence of images (STEP 1802). The photodetector can be referred to as a photosensor, which can include or be the light source 108. The computer system 100 can acquire the sequence of images by performing features or functionalities similar to step 1602 discussed above in relation to FIG. 16. For example, the sequence of images can represent transdermal optical data of a subject. A user can actuate the application 114 on the computer system 100, and apply their fingertip, finger pulp or other body parts to the camera 110 for example, as illustrated in FIGS. 2A, 2B, and 3A. Upon initiation, the application 114 can cause the computer system 100 to display a user interface (UI) on the display device 112. The UI can provide instructions to the user to apply their fingertip against the camera 110 or a corresponding transparent glass for a given period of time, e.g., 30 seconds. The UI can provide an option, e.g., upon user selection, to present further instructions, images, or a demo explaining how the fingertip (or other body parts) is to be applied to the camera 110.

The application 114 or the data acquisition module 502 can automatically trigger the camera 110 to acquire a sequence of image frames. In some implementations, the application 114 or the data acquisition module 502 can cause the computer system 100 to display an interactive item as part of the UI. The application 114 or the data acquisition module 502 can automatically trigger the camera device 110 to acquire the sequence of images, upon the user interacting with the interactive item. Triggering the camera device 110 can include actuating the flash device 206 to emit artificial light either continuously or periodically according to a given frequency.

The camera device 110 can acquire the sequence of image frames while the user's fingertip (or other body parts) is applied against the optical waveguide of the camera or the corresponding transparent glass. Specifically, the RGB sensor 312 can acquire the sequence of image frames according to a specific or predefined frame rate based on the light intensity $I_r$ reflected from the user's finger. The frame rate can be equal to 25 frames/second (fps), 30 fps, 50 fps or other frame rate supported by the camera device 110. The data acquisition module 502 can receive image data corresponding to image frames from the camera device 110. In some implementations, the data acquisition module 502 can receive image data for each frame immediately after the image frame is captured or recorded by the RGB sensor 312 or the camera device 110.

In some implementations, the computer system 100 can include a plurality of cameras 110. The computer system 100 can automatically select one of the cameras 110 to acquire the sequence of image frames, and display (e.g., via a user interface of the application 114) a notification to the user of the computer system 100 of the selected camera 110. The user can place his/her finger against the selected camera. The selection can be based on the features or characteristics of the various cameras. In some implementations, the user can select the camera to be used to acquire the sequence of image frames. The computer system 100 can receive or obtain the user selection via an input device, e.g., a keyboard, a mouse, or a touch screen, among others, of the computer system 100. The computer system 100 may confirm the user selection via, for example, the display device 112. The computer application 114 may include different settings for distinct cameras 110. The computer system 100 can maintain camera ID/phone model matrix in the memory 104. Besides the camera ID, the computer system 100 can store the preferred camera settings in the matrix, such as ISO, exposure time, tone map, RGB gain or a combination thereof, among other settings The computer system 100 can generate a sequence of downsampled images by downsampling each image of the sequence of images (STEP 1804). The computer system 100 can generate a sequence of downsampled images by performing features or functionalities similar to step 1604 of FIG. 16, such as in conjunction with FIG. 9. For example, the sequence of images can include an image region or block associated with at least one color (e.g., red (R), green (G), or blue (B)) frame 702. The data acquisition module 502 of the application 114 executing on the computer system 100 can decompose each image into a respective color (e.g., R, G, or B) frame. The computer system 100 can generate the sequence of downsampled images responsive to or immediately after acquiring or obtaining the images of the subject. In some cases, the computer system 100 can delegate the generation of the sequence of downsampled images to a remote server or a remote computing device. For example, the computer system 100 can acquire and transmit the sequence of images to a remote server to process the sequence of images. Processing the sequence of images can include downsampling the sequence of images to generate a sequence of downsampled images. The sequence of downsampled images can be further analyzed or processed by the remote server or transmitted to the computer system 100.

The computer system 100 can downsample each image of the sequence of images. The computer system 100 can perform the downsampling process in conjunction with FIG. 4 and FIG. 7 or execute the features or functionalities as described in FIG. 4 and FIG. 7. For example, the processing module 504 of the application 114 executing on the computer system 100 can identify an image region or block associated with a color (e.g. G or R) frame 702. The image can be from one of the sequence of images. The processing module 504 can downsample each color (e.g. G or R) frame 702 of the sequence of image frames to smaller image block 704. The processing module 504 can downsample the color (e.g. G or R) frame 702 to a 5×5 image (or data) block, a 9×9 image (or data) block, or a data block 704 of a different size. In downsampling the color frame 702, the processing module 504 can apply low-pass filtering or averaging to the pixel values of the color frame 702. The processing module 504 can downsample the color frame 702 using known downsampling techniques.

The processing module 504 can identify a sub-block 706 of the image block 704 for use to generate a color signal. The processing module 504 can identify a central zone or sub-block of the image block 704 as sub-block 706. Depending on the size and the placement of the user finger against the camera, the color intensities of a central zone of the image block 704 (or the color frame 702) are more likely to reflect the pulsatile nature of arterial blood in the finger than outer regions of the image block 704 (or the color frame 702). In some cases, the user finger may not be placed right at the center of the camera device 110, but rather shifted towards one direction over another. In such cases, at least one outer region of the image frame may not adequately reflect the light (or optical signal reflected from the user finger. In some implementations, the identified sub-block 706 can be a 3×3 image (or data) block, a 5×5 data block, or a data block of other sizes. By downsampling individual images of the sequence of images, computational resources used to process the images, as well as resource consumption for storing the images that are not downsampled, can be reduced. For example, by downsampling images with thousands of pixels (e.g., 320×240, 720×576, 1024×768, among other image sizes) to a 3×3 image, the computer system 100 can significantly reduce computational resources used to process the downsampled images and resource consumption to store the downsampled images.

The computer system 100 can determine, for each pixel position of various pixel positions of the sequence of downsampled images, a respective aggregate pixel similarity score. The respective aggregate pixel similarity score can be indicative of a similarity of a pixel of the pixel position to pixels of other pixel positions over a time window (STEP 1806). The aggregate pixel similarity score can include or be referred to as an aggregate penalty score associated with each pixel position of the sequence of downsampled images or generally as a similarity score aggregated for a respective pixel position. The computer system 100 can compute the aggregate pixel similarity score indicating the similarity of a pixel of the pixel position to pixels of other pixel positions over a time window. For example, the computer system 100 can compare a pixel at a pixel position to other pixels for each downsampled image. The computer system 100 can repeat the process for all pixels of each downsampled image at different pixel locations. In some cases, the computer system 100 can compare a pixel at a pixel location from a downsampled image with another pixel at the same pixel location from another downsampled image at a different time, for example.

To determine or compute the aggregate pixel similarity score The computer system 100 can determine or compute a matrix containing the cross-correlation values for the reshaped input video. Subsequent to determine the matrix, the computer system 100 can determine a single score (e.g., the aggregate pixel similarity score) for each pixel by aggregating multiple score values associated with the pixel position of the sequence of images. The computer system 100 can obtain or use a video of the finger as input. The video can include or refer to a sequence of images, denoted as V. The video V can have a shape or size (T, $d_x$, $d_y$, 3). The T can represent the sequence of images in V, which can be represented as the total duration or the total image frames of V. The $d_x$ and $d_y$ can represent the height and width of V or the images of the sequence of images. For example, in downsampled images, $d_x$ can equal to $d_y$, which is equal to 5. The last variable in the shape of V can represent the total number of color channels, such as 3 in this case. In some cases, the computer system 100 may use a single channel, such as green instead of red or blue, or red instead of green or blue color channels, in which case V can have a shape or size (T, $d_x$, $d_y$).

To reduce the dimension of V, the computer system 100 can reshape V to a reshaped video, denoted as X (e.g., the reshaped version of V). The reshaped video X can include shape (T, p) corresponding to vectorization of each image from the 3-dimensional shape ($d_x$, $d_y$, 3) to a vector of length $p=d_x \times d_y \times 3$. In other words, p can represent the length of a vector representing color intensity values of an image frame having a 3-dimensional shape or size ($d_x$, $d_y$, 3) in the video (or sequence of image frames) V. In some implementations, a single color channel (instead of all color cannels) can be used, in which case $p=d_x \times d_y$. In some cases, the reshaped video X can be zero padded to have the shape (T+n−1, p). With the zero padded shape of X, the computer system 100 can calculate and output cross-correlation matrices having the same number of timestamps as input video. The n can denote a window size used to measure the cross-correlation of each pixel position. The window size can be set to 1 second, 30 frames, among other duration and number of image frames. The window size can be configured, for example, by the operator of the computer system 100, the application 114, or a remote server, if the images are being processed remotely. The window size can include or refer to a time window that the computer system 100 computes at least a sequence of pixel intensity values, color values, or aggregate pixel similarity score to determine the orientation and positioning of the user finger. Further, p can denote the number of pixels (e.g., size of each image) used for cross-correlation. If only one color channel is used for determining the finger position of the user, p can be described as $d_x \times d_y$, such as only green, only red, or only blue.

The computer system 100 can determine or output a matrix including cross-correlation values for respective pixel positions of the input video X (e.g., the reshaped video). The matrix containing the cross-correlation values can be denoted as Γ. The matrix Γ can include a shape (T−n+1, p) or (T, p) if the input is zero-padded. To perform cross-correlation between two vectors x and y, the computer system 100 can use formula (11) for computation.

$$cor(x, y) = \frac{cov(x, y)}{\sqrt{V(x) \cdot V(y)}}, \quad (11)$$

where $$cov(x, y) = \frac{1}{n}\sum_{i=0}^{n-1} x_i \cdot y_i - \left(\frac{1}{n}\sum_{i=0}^{n-1} x_i\right) \cdot \left(\frac{1}{n}\sum_{i=0}^{n-1} y_i\right)$$

is the covariance of x and y, and V(x)=cov(x, x) is the variance of x.

The computer system 100 can cross-correlate each pixel position with other pixel positions in the sequence of images. Subsequently, the computer system 100 can construct the cross-correlation matrix of the reshaped video X by leveraging formula (12).

$$\Gamma[t;i,j]=cor(X[t-n+1:t,i],X[t-n+1:t,j]) \text{ with } 0 \le t < T, 0 \le i, j < p. \quad (12)$$

As indicated above, the matrix containing the cross-correlation values can be denoted as F, which can be equated with the cor(X[t−n+1:t,i], X[t−n+1 t,j]). To further optimize the computation of the cross-correlation matrix, the computer system 100 can utilize the symmetric nature of the cross-correlation matrix Γ as depicted in equation (13), which can be formulated (or recognized) from equation (12).

$$\forall t,i,j, \Gamma[t;i,j]=\Gamma[t;j,i] \quad (13)$$

Considering the symmetric nature of the cross-correlation matrix Γ depicted in equation (13), the computer system 100 can compute half of the entries of the cross-correlation matrix and determine the second half using the symmetric nature of the cross-correlation matrix Γ to obtain cross-correlation values for all pixel locations of the sequence of images.

In some implementations, the computer system 100 can determine the respective sequence of pixel intensity values for each of various pixel positions of the sequence of downsampled images. The respective sequence of pixel intensity values can represent pixel intensities of the pixel position over the time window. Each pixel position of the sequence of downsampled images can include their respective color values, color intensities, among other features or characteristics representing the pixel. The computer system 100 can determine a cross-correlation value representing a cross-correlation between a pair of sequences of pixel intensity values representing pixel intensities of the pair of pixel positions over the time window. The computer system 100 can determine the cross-correlation value for each pair of pixel positions throughout the time window (or window size) of the video X For example, the computer system 100 can cross-correlate pixel values (e.g., pixel intensity or pixel color) between a first pixel position and a second pixel position, the first pixel position and a third pixel position, the first pixel position and a fourth pixel position, and so forth over the time window. Based on the formula discussed above, the computer system 100 may not re-compute or perform cross-correlation for pairs that have previously been cross-correlated to reduce computation resources. With the various cross-correlation values for each pixel position, the computer system 100 can aggregate the pixel similarity score using the cross-correlation values associated with each of the pixel positions. To aggregate, the computer system 100 can perform the aggregate features, functionalities, and techniques discussed herein.

For optimization purposes, the computer system 100 can use the $O(T \times n \times p^2)$ operations to compute the complete cross-correlation matrix for the sequence of images for video X The computer system 100 can use a dynamic programming paradigm for optimizing the code or operations described above, which can consume more memory. Thus, by performing this optimization the complexity for computing the cross-correlation matrix for each new frame can be reduced to $O(p^2)$.

In some implementations, the computer system 100 can store intermediate sums between the cross-correlation of vectors for each pixel of the sequence of images. For example, the cross-correlation between two vectors x and y can further be described in equation (14) for the reshaped video X as:

$$\Gamma[t; i, j] = \quad (14)$$

$$cor(X[t-n+1:t; i], X[t-n+1:t; j]) = \frac{C[t, i, j]}{\sqrt{C[t; i, i] \cdot C[t; j, j]}},$$

with C[t;i,j]=cov(X[t−n+1: t;i], X[t−n+1: t;j]) being the covariance of pixels i and j on the time window ending at t. The covariance can be rewritten or constructed as:

$$C[t; i, j] = cov(X[t-n+1:t; i], X[t-n+1:t; j]) \quad (15)$$

$$= cov(X_t^i, X_t^j)$$

$$= \frac{1}{n}\sum_{t'=t-n+1}^{t} X_{t'}^i X_{t'}^j - \left(\frac{1}{n}\sum_{t'=t-n+1}^{t} X_{t'}^i\right)\left(\frac{1}{n}\sum_{t'=t-n+1}^{t} X_{t'}^j\right)$$

$$= \frac{1}{n}(C_t^{i,j} - C_{t-n}^{i,j}) - \left(\frac{1}{n}(S_t^i - S_{t-n}^i)\right)\left(\frac{1}{n}(S_t^j - S_{t-n}^j)\right).$$

where $C_t^{i,j}=\Sigma_{t'=0}^{t} X_{t'}^i \cdot X_{t'}^j$ is the cumulated sum of the first cross products between pixels i and j, and where $S_t^i=\Sigma_{t'=0}^{t} X_{t'}^i$ is the cumulated sum of the first pixel i.

By using these equations, the computer system 100 can reduce the complexity of the process by a factor of n. Further, to reduce resource consumption (e.g., memory space for storing the cumulated sums), the computer system 100 can drop or discard the cumulative sums for one or more image frames that are outdated or beyond a predetermined duration, such as dropping cumulative sums stored before time instance t−n or associated with time indices (e.g., subscript of $S_{t-k}^i$) less than t−n. As such, the computer system can maintain only the last n cumulative sums $S_{t-1}^i$ to $S_{t-n}^i$ when moving from one image frame to the next image frame.

The computer system 100 can compute a score to obtain a single value for each pixel. The score can include or be referred to as an aggregate pixel similarity score, which aggregated the cross-correlation values determined for each of the pixel positions in the video X Using the aggregated pixel similarity score, the computer system 100 can determine or compute a gradient (e.g., a vector) for presentation in a UI to assist users with their finger positioning. For example, the computer system 100 can indicate how the user should orient or move their finger to cover the lens, such as the center of the camera lens. The computer system 100 can use at least one of V (e.g., video of the finger), X (e.g., reshaped version of V), and Γ (e.g., correlation matrix for each pixel for at least one timestamp for simplicity) as inputs to compute the score. The correlation matrix Γ can include a shape with one of the three color channels, such as only green. The shape of the correlation matrix Γ can be ($d_x \times d_y$, $d_x \times d_y$).

The computer system 100 can use an aggregate function to aggregate multiple score values for one pixel in a single value. The aggregate function can be denoted as a in this case. The computer system 100 can use a quantile, e.g., denoted q, for computing scores for individual pixels. An aggregation function can be the q-th quantile with q=0.8. With the inputs and parameters, the computer system 100 can determine the orientation and position of the finger, as well as the distance from the optimal position (e.g., center) of the lens for blood measurement. Responsive to determining the orientation and position, the computer system 100 can determine or generate a vector pointing or directing the user to move the finger to where it should be, thereby properly covering the lens to obtain good measurements and results. Further, the computer system 100 can provide a UI to guide users with their finger positioning, such as indicating where they move the finger, such that pixels with lower scores (e.g., aggregate pixel similarity score) are better covered. The score can indicate the sufficiency of the reading or measurement of the blood pressure, pulse rate, among other health features of the user, at the pixel position associated with the score. In some cases, the score can represent a noise level (e.g., for a distance matrix—a high score can indicate a high noise level and a low score can indicate a low noise level), image quality, saturation level, among other indications of the quality of the sequence of images or the video. The configuration of whether a high score indicates poor quality and a low score indicates high quality, and vice versa, is based on the preference of the administrator of the application 114.

To determine which direction the user should move the finger, if not covering the lens properly, the computer system 100 can determine or compute an aggregate pixel similarity score for each pixel position of the sequence of images. As used herein, the aggregate similarity score can represent a measure of similarity or dissimilarity between a pixel position and the rest of (or other) pixel positions. For example, the computer system 100 can use the aggregation function a for computing the pixel score. The computer system 100 can determine that if the score for each pixel gets closer to zero, the pixel can be considered as good quality. On the other hand, if the score is high, the pixel can be considered poor quality. In this case, the computer system 100 can determine or compute a distance matrix, where a higher score can indicate a higher distance, higher variation, or having less correlation between pairs of pixel positions. In some implementations, the computer system 100 can use a resemblance matrix, such as a cross-correlation matrix, to determine the aggregate pixel similarity score for each pixel position. The computer system 100 can compute the distance matrix as:

$$\Delta_j^i = \Delta[i,j] = 1 - \Gamma[i,j] \qquad (16)$$

The distance Δ[i,j] presented above may not have a specific distribution. In other words, if two of the pixel positions greatly differ from each other, the computer system 100 may compute a corresponding high distance for the pixel positions. However, the actual value of the distance matrix may not be informative, for example, a high distance between a pair of pixel positions and a very high distance between another pair of pixel positions may correspond to a similar setup or result in the distance matrix.

The computer system 100 can use quantile estimation to determine the distance of a pixel position to other pixel positions of the downsampled image. For each pixel, the computer system 100 can compute the q-th quantile of the p distances of a pixel position to another. This yields to the aggregated penalty score (or aggregated similarity score) for each pixel i, as:

$$\pi_i = \alpha(\Delta)[i] = \Delta_{(qp)}^i \qquad (17)$$

Where $\Delta_{(j)}^i$ denotes the j-th element or entry of $\Delta^i$, where the entries of $\Delta^i$ are sorted in an ascending order. Therefore, by using the above formulas, the computer system 100 can determine a distance matrix and the aggregate pixel similarity scores for each of the pixel locations of the sequence of images.

In some implementations, the computing device can determine the respective aggregate pixel similarity score using the cross-correlation values associated with the pixel position. Responsive to determining the respective aggregate pixel similarity score, the computer system 100 can determine, for each pair of pixel positions, a respective distance score using the cross-correlation value. In this case, the respective distance between each pair of pixel locations can represent the cross-correlation between the pair of sequences of pixel intensity values. Further, the pair of sequences of pixel intensity values can represent pixel intensities of the pair of pixel positions over the time window. For example, the computer system 100 can cross-correlate between at least two of the pixel positions having pixel intensity values associated with the respective pixel positions. The computer system 100 can cross-correlate the pair of pixel positions over the time window. The computer system 100 can repeat the cross-correlation for other pairs of pixels of the sequence of images. By computing the cross-correlation, the computer system 100 can obtain or determine various cross-correlation values associated with each respective pixel position. Therefore, for each pixel position, the computer system 100 can determine the respective aggregate pixel similarity score as an aggregation of respective distance scores associated with the pixel position. According to the above formula, the computer system 100 can compute the negative of the aggregated cross-correlation values of each pixel position to determine a distance matrix for each of the corresponding pixel positions.

The computer system 100 can determine, using aggregate pixel similarity scores of various pixel positions of the sequence of downsampled images, a vector indicative of a position of a body part of a user (STEP 1708). The vector indicative of a position of a body part can include or refer to an orientation vector. The body part can be a finger as referred to herein, for example. The computer system 100 can determine the orientation vector for assisting or guiding users to correctly placed their fingers by using formula (18).

$$\delta = \begin{pmatrix} \dfrac{\sum_i x_i \cdot \pi_i}{\sum_i \pi_i} \\ \dfrac{\sum_i y_i \cdot \pi_i}{\sum_i \pi_i} \end{pmatrix} \quad (18)$$

By using the orientation vector, the computer system 100 can derive a direction θ and an intensity I, such as in formula (19).

$$I=|\delta|=\sqrt{\delta_x^2+\delta_y^2} \quad (19)$$

$$\theta=\text{angle}(\delta)=a\tan 2(\delta_y,\delta_x).$$

Thus, by performing the techniques discussed above, the computer system 100 can reduce the complexity of the process by a factor n, compute the cross-correlation between pairs of pixel positions (e.g., vectors), the distance matrix, and the orientation vector to guide the user finger in an appropriate direction and distance for enhancing the quality of the bloodstream captured by the camera.

As depicted in equation (15), the computer system 100 can determine or compute a center of mass of the aggregate pixel similarity scores of the plurality of pixel positions of the downsampled images, which may be viewed as representing an estimate of the position of the finger (or other body part) relative to a desired position. The smaller the vector δ in magnitude, the closer is the position of the finger or body part to the desired position, and the larger the vector δ in magnitude, the farther is the position of the finger or body part from the desired position.

In some implementations, the computer system 100 can determine the angle of the vector δ indicative of a direction along which to move the finger or body part of the user. For example, the computer system 100 can determine that the finger of the user is not at the desired position on the lens (e.g., the center of the lens). The computer system 100 can determine the position of the finger based on the vector δ, where the magnitude of the vector δ can indicate how far (e.g., relatively) is the finger from the desired position and the angle θ of the vector δ can represent the direction along which the finger position is deviating from the desired position. Accordingly, the computer system 100 can determine the trajectory or angle (e.g., the angle θ of the vector δ) along which the finger has to move in order to reach or overlap with the desired position on the lens. In some implementations, the computer system 100 can determine the magnitude of the vector δ indicative of a relative distance separating the finger (or body part) position and the desired position. As such, the magnitude and angle of vector δ can provide an indication for the user regarding in which direction and by relatively how much to move the user's finger (or body part) to overlap the desired position on the lens of the camera. The computer system 100 can display an indication of the relative distance separating the finger position from the desired position on the lens, and/or an indication of the deviation angle θ. The farther the distance between the finger position and the desired position, the higher is the magnitude of the vector δ, as can be displayed on a UI for presentation to the user via the display device 112. In another example, if the finger position is near or in proximity to the desired position on the lens, the computer system 100 will provide a low magnitude of the vector δ indicating a small distance for the user to move their finger.

Figure 18B:
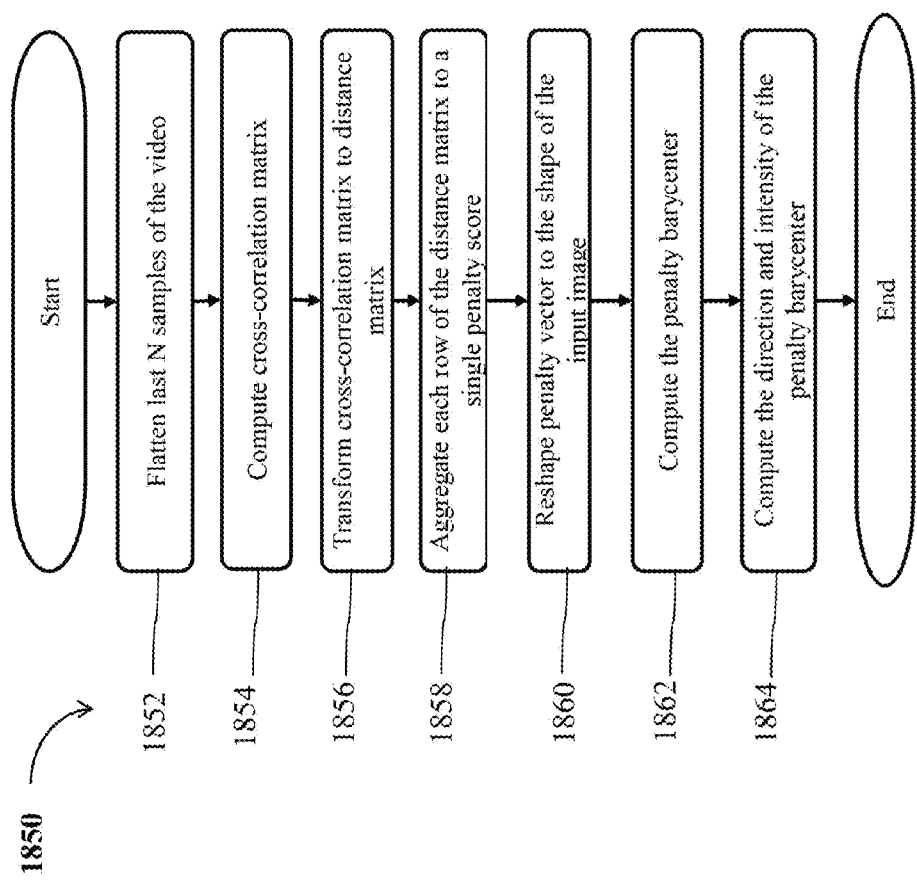
FIG. 18B shows a flowchart illustrating a method of computing a vector for assisting finger positioning of the user, according to example embodiments.

FIG. 18B shows a flowchart illustrating a method 1850 depicting an example implementation of method 1800 of FIG. 18A. At step 1852, the computer system 100 can transform each acquired image frame into a corresponding one-dimensional vector as discussed above with regard to the reshaping of the video sequence V. At steps 1854 and 1856, the computer system 100 can compute the cross-correlation matrix Γ as discussed above with regard to equations (13)-(15), and can compute the distance matrix Δ as discussed above in relation to equation (16), respectively. At step 1858, the computer system can compute the similarity (or penalty) scores $\pi_i$ as discussed above with regard to equation (17). At steps 1860 and 1862, the computer system 100 can reshape the computed similarity (or penalty) scores $\pi_i$ into a matrix having a size $(d_x \times d_y)$, and compute the barycenter (or the center of mass) vector δ of the matrix of the similarity (or penalty) scores $\pi_i$ as discussed above with regard to equation (18), respectively. At step 1864, the computer system 100 can compute the magnitude |δ| of the barycenter vector (or the relative distance between the finger position and the desired position) and the angle θ of the barycenter vector δ as discussed above with regard to equations (19).

In some implementations, the computer system 100 can provide a visual output generated using the vector δ to guide the user to move their finger or body part relative to a center of the photodetector lens. For example, the computer system 100 executing the application 114 can initiate a UI for display on the display device 112. The UI can include elements indicative of at least the position of the user finger (or body part), the desired finger position on the lens, the quality of the finger placement, and/or an indication or instruction regarding any action(s) to be taken by the user. The computer system 100 can display visual elements indicative of the desired position and the detected position of the user finger (or body part) on the lens of the camera. If the detected finger position does not coincide or overlap with the desired position on the lens (or the detected finger position is not "close enough" to the desired position), the computer system 100 can determine or estimate a displacement between the detected finger position and the desired position, and display a visual representation or indication of the determined or estimated displacement. An example illustration of the visual outputs that may be displayed to the user is shown in FIG. 18C.

Figure 18C:
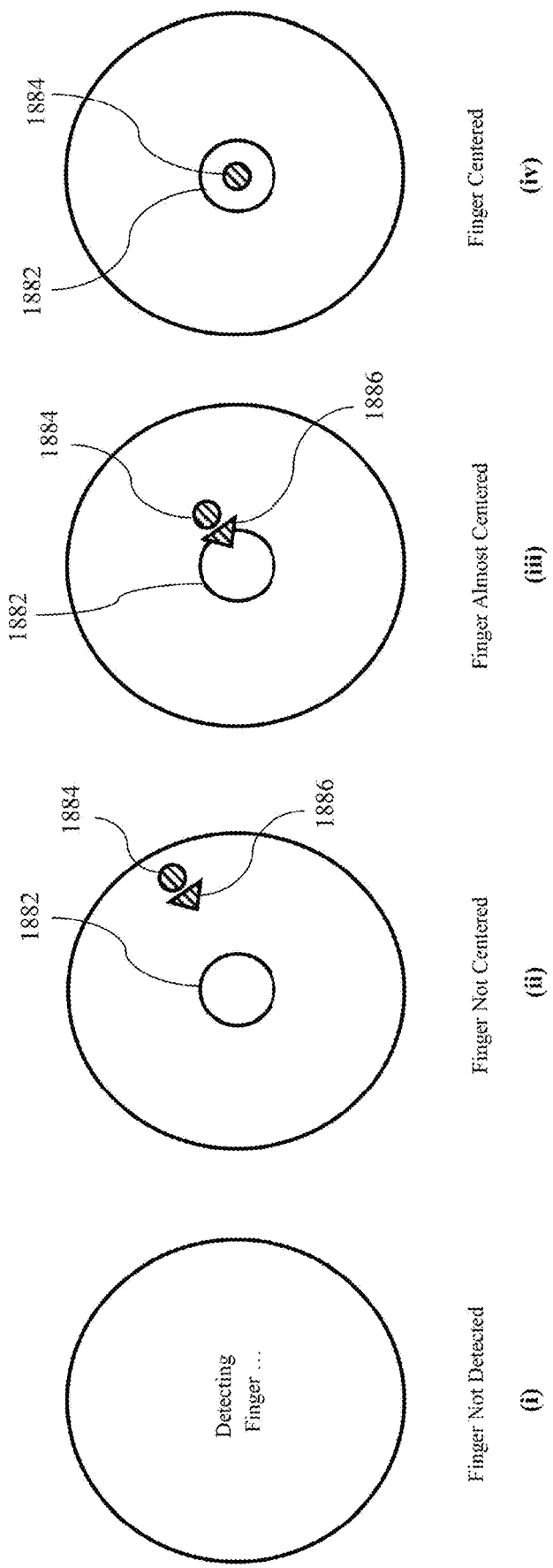
FIG. 18C illustrates an example of a user interface ("UP") for assisting finger positioning of the user, according to example embodiments.

FIG. 18C shows examples of user interfaces ("UIs") for assisting finger positioning of the user, according to example embodiments. The UIs can be generated by the application 114 based on videos or a sequence of images captured by the camera 110 of the computer system 100. The computer system 100 can present or display the UIs to the user via a display device 112. The UIs can include at least a first visual element 1882 (e.g., a circle) indicative of a desired position for the finger and a second visual element 1888 (e.g., a circle) indicative of the detected finger position. The UIs can further include another visual element 1886 (e.g., arrow or triangle) indicative of a direction for moving the user finger towards the desired position. In some implementations, the direction for moving the user finger towards the desired position can be inferred based on the relative positions of the first and second visual elements 1882 and 1884 (e.g., without the visual element 1886). The desired position of the finger (or other body part) can be at the center of the lens of the camera or photodetector 110 (or other locations based on the configuration of the lens and/or configurations set by the administrator or operator of the application 114 or the computer system 100).

The computer system 100 can display the UI (i) in FIG. 18C when the data acquisition process is initiated but before the user finger is detected (or before sufficient image frames to detect the finger position are acquired). The computer system 100 can display the UI (ii) of FIG. 18C once the finger position is detected as discussed above. The user can move his (or her) finger towards the desired position, and the computer system can display the UI (iii) to show an updated position of the finger relative to the desired position. The UI (iv) of FIG. 18C indicates that the detected finger position coincides or overlaps with the desired position. While FIG. 18C, shows only four UIs, the computer system 100 can display any number of UIs as the user finger moves. In some implementations, the UIs can display an indication (e.g., text or a color bar) of a finger placement quality.

The computer system 100 can determine or estimate the finger position based on the aggregate pixel similarity scores (as discussed above) and/or based on the cross-correlation values Γ[t,i,j]. The computer system 100 can determine or detect the position of the user finger (or body part) based on the highest aggregated similarity score for each pixel position. Further, if the detected finger position does not coincide or overlap with the desired position, the computer system 100 can determine and output the magnitude and/or orientation of the vector δ (or displacement) between the detected finger position and the desired position. The orientation can indicate which direction to move the finger and the magnitude can indicate the distance to move the finger. The higher the magnitude, the more distance the finger should travel, and vice versa.

The computer system 100 can generate a finger placement quality meter (or color bar) indicating, for example, a quality of the user finger placement, a quality of user finger detectability and/or a quality of the acquired sequence of images. The computer system 100 can update the quality meter responsive to changes in the detected finger position, changes in the detectability of the finger and/or changes in the quality of captured images. Once the gauge of the quality metric reached a threshold, the computer system 100 can indicate to the user, either at the quality metric or other portion of the UI (e.g., via text), for the user to maintain position or keep still. In other words, the computer system 100 can notify the user that the measurement is in progress and for the user not to move to maintain the stability of the measured results and avoid invalid or unstable measurement data. Accordingly, the computer system 100 can present the UI to assist users with their finger positioning.

The computer system 100 can notify the user of different states of the finger, based on at least the detected positioning of the finger and/or the pressure applied to the camera. The detected finger position is correlated to the quality of the signal or images that the computer system 100 captures. The pressure applied on (or distance of the finger from) the camera can affect the quality of the signal or images. For example, poor positioning and application of the finger on the camera may result in the computer system 100 capturing a poor quality signal or images. On the other hand, a well-positioned and application of the finger on the camera 110 may result in the computer system 100 capturing a good quality signal or images. The computer system 100 can discriminate between different finger placement states including, for example, a well_placed_finger state, a misplaced_finger state, and an unknown_position state of the finger. The computer system 100 can discriminate and notify the user of the different states based on the aggregate penalty score (or aggregate discrimination score) for each of the pixel position in the sequence of images. The penalty score can include, refer to, or be based on the distance score and/or the cross-correlation values. For example, the computer system 100 can detect and/or output the well_placed finger state or condition when most or all (e.g., 80%, 85%, 90%, 95% or 100%, among other ratios/percentages) of the pixel positions have a low or relatively small aggregate penalty score (or aggregate similarity score), e.g., compared to a first threshold score. The computer system 100 can detect and/or output the misplaced_finger state when at least a portion (e.g., 35%, 30%, 25% of the total pixel positions, among other ratios/percentage) of the total pixel positions have a high or large aggregate penalty score (or aggregate similarity score), e.g., compared to a second threshold score. The computer system 100 can detect and/or output the unknown_position state when most or all (e.g., 70%, 75%, 80%, 85%, 90%, 95% or 100%, among other ratios/percentages) of the pixel positions of the image sequence have a high aggregate penalty score, e.g., compared to the second threshold score. The computer system 100 can display a message indicating the state of the finger placement to the user.

To determine the state, the computer system 100 can determine or obtain the penalty score for each image frame captured by the camera 110. The aggregate penalty score can refer to or include one or more scores (e.g., distance score or correlation score, in some cases) for each of the pixel positions in the image. The computer system 100 can determine an aggregate penalty score similar to determining the aggregate pixel similarity score or the distance score, such as discussed above in relation with FIG. 18A. The penalty score matrix can be denoted as A, which can have a size of ($d_x$, $d_y$).

The computer system 100 can use one or more parameters for determining different states of the finger. The parameters can include, for example, a penalty high quantile, a penalty low quantile, a penalty high threshold, and a penalty low threshold. The penalty high quantile can refer to a quantile used for estimating the highest penalty score for a pixel. For example, the computer system 100 can use the high quantile of the penalty scores (or high quantile of aggregate similarity scores) to identify images with detected finger placement or position close enough to the desired position. The high quantile of the penalty scores can be denoted as $q_{high}$h. The high quantile of the penalty scores (or the aggregate similarity scores) can be dependent on the penalty score used, and can be configured or preset to 100% or in some cases, lower than 100%. The computer system 100 can use the low quantile of the aggregate similarity scores (or) for estimating the intermediate penalty score for a pixel. For example, the computer system 100 can use the low quantile of the penalty scores (or the aggregate similarity scores) to identify images where the detected finger position is relatively far from the desired position to assist with the finger placement of the user. The low quantile of the penalty scores (or the aggregate similarity scores) can be denoted as $q_{low}$. The low quantile of the penalty scores (or the aggregate similarity scores) can also depend on the penalty score used, and can be configured or preset to 30% or other percentages (e.g., either higher or lower).

The computer system 100 can use penalty thresholds to discriminate between pixel positions with "good" or relatively low penalty scores and pixels with "bad" or relatively high penalty scores. For example, the computer system 100 can use a high penalty threshold to identify pixel positions considered to have "good" or low penalty scores. The high penalty threshold can be denoted as $β_{high}$, which can be dependent on the penalty score used. The computer system 100 can be configured to use 0.04 (e.g., among other values)

for a cross-correlation-based penalty score. In another example, the computer system 100 can use a low penalty threshold to identify pixel positions considered to have "bad" or high penalty scores. The penalty low threshold can be denoted as $\beta_{low}$, which can also be dependent on the penalty score used. The computer system 100 can be configured with a low penalty threshold of 0.15 (e.g., configurable among other values) for a cross-correlation-based penalty score. Based on any penalty score used, the $q_{high}$ can be greater than the $q_{low}$ and the $\beta_{high}$ can be smaller than the $\beta_{low}$.

As part of the steps for determining the state of the user finger or body part (e.g., the position, pressure applied, or distance from the lens), the computer system 100 can compute or determine multiple aggregation metrics based on the penalty matrix $\Delta$. The aggregation metrics can include $\delta_{high}$=quantile ($\Delta$; $q_{high}$) and $\delta_{low}$=quantile ($\Delta$; $q_{low}$). By using the property that $q_{high} > q_{low}$, the computer system 100 can obtain $\delta_{high} > \delta_{low}$. Responsive to computing the $\delta_{high}$ and $q_{low}$, the computer system 100 can classify one or more conditions of $\delta_{high}$ and $\delta_{low}$ with an associated state (sometimes referred to as a finger helper state). The classification of the conditions can be as shown in Table 3 below.

TABLE 3

Classification of Finger States

| Condition | Finger helper state |
|---|---|
| $\begin{cases} \delta_{high} < \beta_{high} \\ \delta_{low} < \beta_{low} \end{cases}$ | WELL_PLACED_FINGER |
| $\begin{cases} \delta_{high} \geq \beta_{high} \\ \delta_{low} < \beta_{low} \end{cases}$ | MISPLACED_FINGER |
| $\begin{cases} \delta_{high} \geq \beta_{high} \\ \delta_{low} \geq \beta_{low} \end{cases}$ | UNKNOWN_POSITION |
| $\begin{cases} \delta_{high} < \beta_{high} \\ \delta_{low} \geq \beta_{low} \end{cases}$ | Impossible case |

The last case or condition in Table 3 is impossible. Assuming that quantiles and thresholds meet the last condition of Table 3, then the quantiles and thresholds would satisfy: $\delta_{high} < \beta_{high} < \beta_{low} \leq \delta_{low} < \delta_{high}$. As seen in this case, the resulting condition is impossible as it requires $\delta_{high} < \delta_{high}$.

The computer system 100 can refer to the above classifications of the condition to determine the state of the user finger placement, based on the penalty scores (or aggregate similarity core) of the pixels of each image. The computer system 100 can output the classification as a visual illustration for the user. For example, based on the classification, the computer system 100 can provide at least one of the feedback to the user (e.g., via the application 114) indicating whether the finger is well placed (e.g., well_placed_finger state), misplaced (e.g., misplaced_finger state), or at an unknown location (e.g., unknown_position state). In the case of a misplaced_finger, the computer system 100 can rely on a vector with a direction and an amplitude, e.g., as discussed above with regard to vector $\delta$. Using the vector, the computer system 100 can indicate which direction and how far the finger is from the center of the lens (or other desired/preconfigured position that the center mass of the finger should be located). Therefore, the computer system 100 can hint the user to adjust their behavior for a better-placed finger on the camera lens.

D.3. Pulse and Pulse Features Extraction

A photoplethysmogram (PPG) signal can be obtained by processing images of a finger (or other body parts) of the user. The images can be captured using the camera 110, an RGB sensor (e.g., RGB sensor 312), or other optical devices. The computer system 100 can use the PPG signal to measure the blood pressure of the user based at least on changes in the blood volume. The computer system 100 can use the PPG signal to identify a succession of pulses. Further, the computer system 100 can split the PPG signal into individual pulses to analyze individual pulses separately. The computer system 100 can compute statistics based on the distribution of the metrics over the individual pulses.

By splitting the PPG signal, the computer system 100 can analyze the features and the quality of individual pulses (e.g., single pulse analysis). The signals representing one or more pulses can be described by their periodicity, such as a loop of a big ascending slope, followed by a slow descending slope. The computer system 100 can extract individual pulses from the PPG signal by detecting successions of the pulse events or features in the high-pass-filtered PPG signal. Other filters can be used for the PPG signal to extract features and qualities of the pulses. The computer system 100 can obtain or capture one or more PPG signals that pulses can be extracted from. The PPG signal can be denoted as a series $(x_k)_{1 \leq k \leq N}$ of length N. The parameter k can represent the indices of the PPG signal values. The computer system 100 can filter the PPG signal at a predetermined bandwidth. The bandwidth can be denoted as $[f_{low}, f_{high}]$. The bandwidth can be set to [0.4 Hz, 3.5 Hz], among other frequency settings. The bandwidth can be adjusted to obtain an optimal setting for extracting at least one pulse from the PPG signal. Responsive to filtering the PPG signal, the computer system 100 can determine, identify, or extract features of individual pulses within the PPG signal to output a list of pulses. The computer system 100 can determine the quality of the pulses based on the features extracted from the PPG signal.

Figure 19:
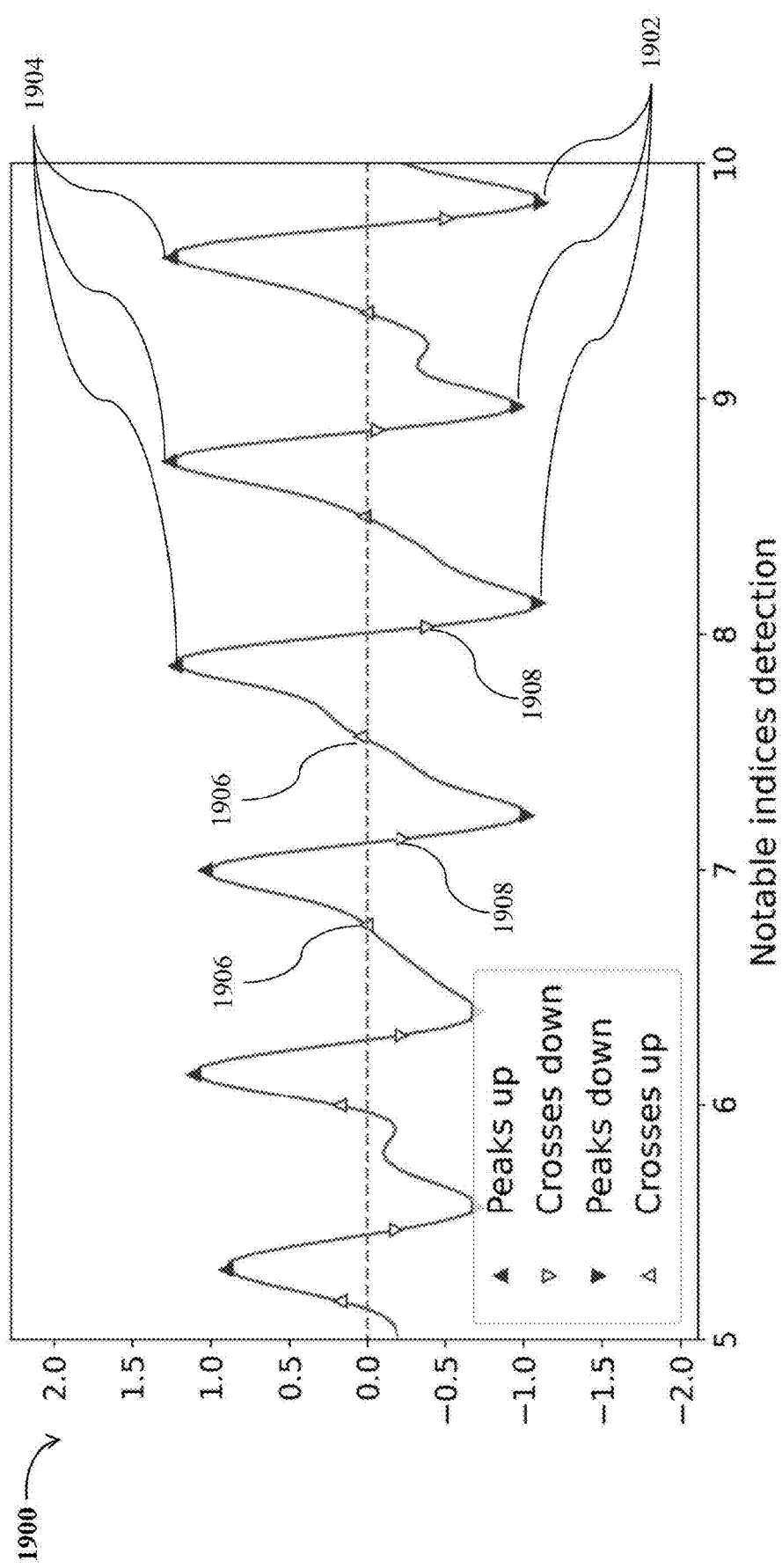
FIG. 19 illustrates an example plot for an extraction of pulse indices, according to example embodiments.

FIG. 19 shows a plot 1900 of an example PPG signal with signal features (also referred to as notable indices) used to identify separate pulses of the PPG signal, according to example embodiments. The pulse events or pulse features used can include troughs (or peaks down) 1902, peaks 1904 and zero-crossings up 1906 and zero-crossings down 1908.

Figure 20A:
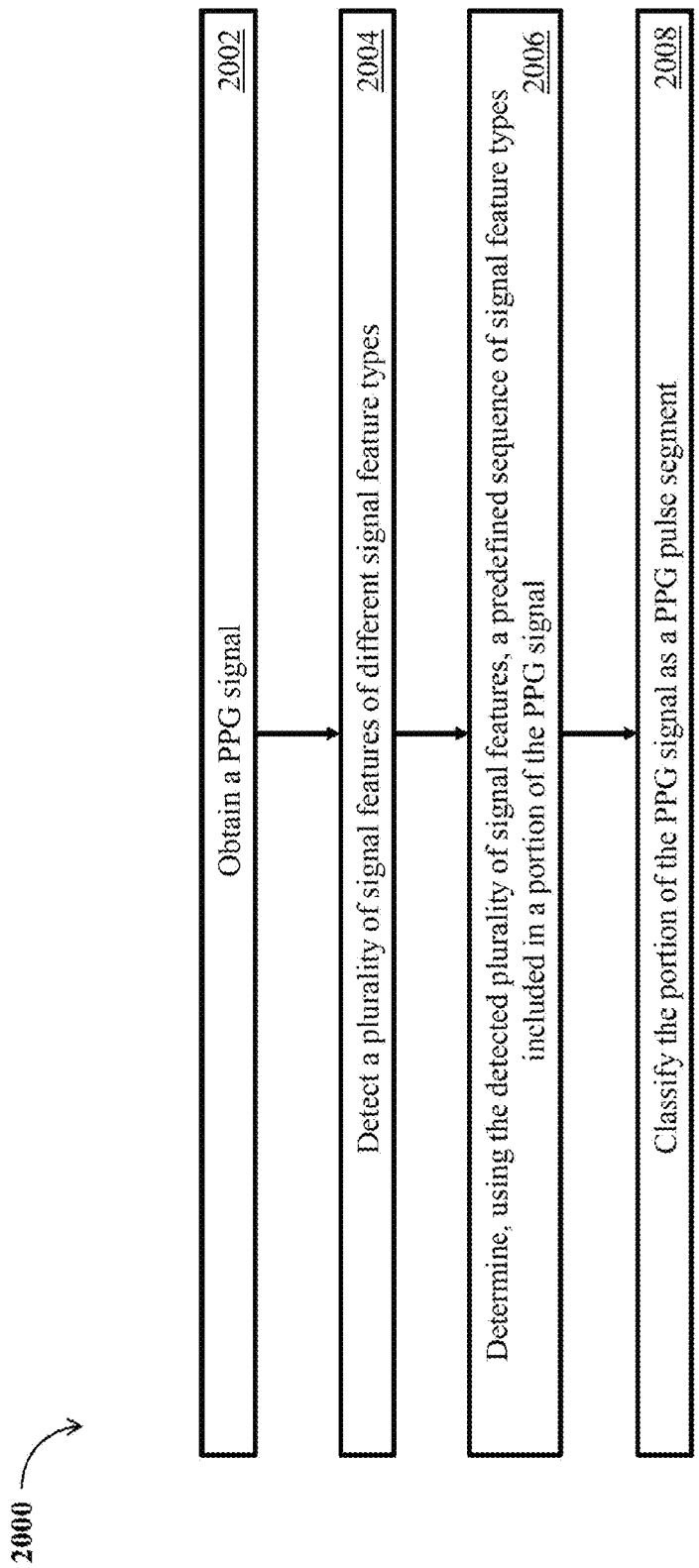
FIG. 20A shows a flowchart illustrating a method of detecting pulses in a PPG signal, according to example embodiments.

Referring to FIG. 20A, a flowchart illustrating a method 2000 of detecting pulses in a PPG signal is shown, according to example embodiments. The method 2000 can include obtaining a PPG signal generated from a sequence of images acquired using a photodetector (STEP 2002). The method 2000 can include detecting various signal features of different signal feature types of the PPG signal (STEP 2004). The method 2000 can include determining, using the detected signal features, a predetermined (or predefined) sequence of signal feature types included in a portion of the PPG signal (STEP 2006). The method 2000 can include classifying the portion of the PPG signal as a PPG pulse segment (STEP 2008). The method 2000 can be performed by the computer system 100 or the corresponding processor 102, for example, upon executing the application 114. The method 2000 can be performed by other components (e.g., memory 104, BUS 106, light source 108, camera device 110, or display device 112) of the computer system 100, in conjunction with FIG. 1. The method 2000 can be performed by a remote device or a remote server. In some implementations, the method 2000 can be performed by a computer system 100 and a remote server. For example, the computer system 100 can be in communication with the remote server to delegate one or more tasks to the remote server. In this case, the remote server can perform the one or more tasks, such as performing at least one of STEPS 2002-2008 and transmit an output to the computer system 100. The method 2000 can be performed by other components discussed herein and perform features and functionalities in conjunction with at least one of FIGS. 1-19, for example. The method 2000 can be performed in conjunction with, sequential, or prior to at least one of other methods discussed herein, such as methods 400, 1200, 1600, etc.

Still referring to FIG. 20A, in further detail, the computer system 100 can obtain a PPG signal generated from a sequence of images acquired using a photodetector (STEP 2002). The photodetector can include or be at least one of an RGB sensor 312 or a camera. For example, the computer system 100 can capture a sequence of images (e.g., a video) of a finger for a period of N samples. The computer system 100 can obtain or generate the PPG signal using a sequence of images with a single color channel, such as only green or only red. In some cases, the computer system 100 can obtain the PPG signal using a sequence of images with multiple color channels (e.g., R, G, and/or B).

Prior to obtaining or generating the PPG signal, the computer system 100 can process raw images captured using the photodetector. For example, the computer system 100 can generate a sequence of downsampled color frames corresponding to the sequence of images by downsampling a respective color frame for each image of the sequence of images. The computer system 100 can downsample the images to reduce the resolution of the image for generating the PPG signal. By reducing the resolution (e.g., reduced to 5×5 pixels), the computer system 100 can decrease latency and reduce resource consumption when processing the sequence of downsampled color frames. The downsampled color frames may include only one color channel, such as green or red. In some cases, the downsampled color frames may include multiple color channels.

Responsive to generating the sequence of downsampled color frames, the computer system 100 can identify, in each downsampled color frame of the sequence of downsampled color frames, a respective image block representing a central image region of the downsampled color frame and having a first size smaller than a second size of the downsampled color frame. The respective image block can include or be referred to as a portion of the respective downsampled color frame. The central image region of the respective image block may be located at the center of the downsampled color frame. For example, in a 5×5 pixels image (among other sizes), the computer system 100 can determine that the central image region is located at the inner 3×3 pixels of the downsampled color frame. In another example, the computer system 100 can determine that the central image region is not located at the center or the inner portion of the downsampled color frame. Instead, the computer system 100 can identify the center image region located edges of the downsampled color frame. The central image region may be of any size smaller than the downsampled color frame. For example, if the downsampled color frame is 10×10 pixels, the central image region can be 5×5 pixels, 5×9 pixels, 7×4 pixels, among others.

The computer system 100 can generate a color intensity signal using the respective image blocks of the sequence of downsampled color frames. For example, the computer system 100 can identify, within the central image region of each respective image block, the color value or intensity value associated with image blocks. Based on the color value or the intensity value, the computer system 100 can generate a color intensity signal having at least one of the color values or the intensity value associated with the color intensity signal. Accordingly, the computing device can generate the PPG signal using the color intensity signal to determine a blood pressure value.

The computer system 100 can apply a filter on the PPG signal generated using the sequence of images. The filter can be a pass-band filter, among other filtering techniques, such as a low-pass filter, high-pass filter, etc. For example, the computer system 100 can input the PPG signal into the pass-band filter set to predetermined low and high frequencies thresholds (e.g., 0.4 Hz and 3.5 Hz as the lower threshold and higher threshold, respectively). These thresholds can be referred to as cut-off frequencies $[f_{low}, f_{high}]$. The computer system 100 can obtain or implement the pass-band filter by using two infinite impulse response ("IIR") filters successively. The computer system 100 can apply the high-pass exponential filter causally and then anti-causally with cut-off frequency $f_{low}$. Similarly, the computer system 100 can apply the low-pass exponential filter causally and then anti-causally with cut-off frequency $f_{high}$. By applying the filter causally, the computer system 100 can generate an output that depends on past and current inputs but not future inputs. By applying the filter anti-causally, the computer system 100 can generate an output that depends only on future input values. In other words, the computer system 100 can apply the filters to PPG signals previously captured and PPG signals that will be obtained by the photodetector. Accordingly, the computer system 100 can obtain a filtered PPG signal without high variations. The global or general shape of the signal can be maintained, the signal can be centered around zero, and small irregularities presented in the signal can be filtered out.

The predetermined thresholds can be configured by the operator or the administrator of the computer system 100, for example. By passing the PPG signal through the pass-band filter, the computer system 100 can filter PPG signals below the low-frequency and above the high-frequency thresholds. Using the pass-band filter, the computer system 100 can eliminate quick variations of the signal to obtain a more stable and smoother PPG signal.

The computer system 100 can detect various signal features of different signal feature types of the PPG signal (STEP 2004). The signal features can include or be referred to as notable indices. The computer system 100 can extract the signal features from the PPG signal to identify individual pulses for extraction or division. To extract the features, the computer system 100 can compute one or more normalization features from the filtered PPG signal. Normalization features can refer to features computed from a normalized signal, such as PPG signal centered around the zero. For example, the computer system 100 can compute a minimal prominence of the peaks (e.g., trough and high peak) of the signal. The minimal prominence can be preconfigured to 5% the range of values taken in input PPG $x$:$p=0.05 \times (x_{(95\%)} - x_{(5\%)})$. In this case, the range can be the difference between the $5^{th}$ and $95^{th}$ percentile of the signal values. The range can be configured to other percentiles of the signal values, such as between the $10^{th}$ and $90^{th}$ percentile, $3^{rd}$ and $97^{th}$ percentile of the signal values, among other values. In some cases, the minimal prominence can be configured to the highest value and the lowest values of the signal values. The computer system 100 can compute the minimal pulse duration via the following equation: $d=0.5 \times f_s$, where $f_s$ is the sampling frequency.

Referring to FIG. 19, the computer system 100 can extract some notable indices or feature types from the signal, such as the features 1902, 1904, 1906 and 1908. The signal feature types can include at least a peak (sometimes referred to as peaks top), a trough (sometimes referred to as peaks down), a zero-crossing up, and a zero-crossing down. The computer system 100 can detect other features obtainable from the signal. The computer system 100 can extract peaks top in the signal with a prominence of at least p and a distance from peaks down of at least d. Similarly, the computer system 100 can extract peaks down in the signal with a prominence of at least p and a distance from peaks top of at least d.

The computer system 100 can identify or determine one or more points of interest, based on the extract features of different feature types. The one or more points of interest can include at least the start of the pulse, a systolic peak, the start of the next pulse, the start of reflective pulse, a diastolic peak, the end of a pulse, a systolic peak max slope, a notch max slope, and a diastolic max slope. The start of the pulse can refer to an index of the start of a pulse or a time point at which the PPG signal starts to increase (e.g., from the trough). In some cases, the start of the pulse can begin at other locations within the slopes of the PPG signal, indicative of the pulse, such as at the systolic peak. The systolic peak can refer to an index at which the signal reaches its maximum value. The systolic peak can include or be the peaks up of the signal. The start of the next pulse can be an index at the next time point similar to the start of the pulse. The start of the next pulse can be referred to as a start of a second pulse. The start of a reflective pulse can be an index after the systolic peak at which signal second derivative reaches its maximum. The diastolic peak can be an index at which the signal second derivative reaches its minimal value after the reflective pulse. The end of a pulse can be an index at which the slope of the signal has come back to a stationary state. Depending on the start of the pulse (e.g., the index position starting the pulse), the end of the pulse can be located before the start of the next pulse, but after the diastolic max slope. The systolic peak max slope can be an index of maximal slope in the PPG signal between the start of the pulse and the systolic peak. The notch max slope can be an index of maximal slope in the PPG signal after the dicrotic notch. The diastolic max slope can be an index of the maximal slope of the diastolic descent within the PPG signal. With at least the aforementioned pulse features, the computer system 100 can identify one or more pulses from the PPG signal generated using a sequence of images.

The computer system 100 can determine, using the detected signal features, a predetermined (or predefined) sequence of signal feature types included in a portion of the PPG signal (STEP 2006). The predetermined sequence of signal feature types can be used to indicate, describe, or in some cases, define PPG pulse segments. The sequence of signal feature types can be predetermined by the operator or administrator of the computer system 100. The predetermined sequence of signal feature types can include a ordered sequence of feature types, such as a first peak (e.g., peaks up) 1904, a zero-crossing down 1908, a trough (or a peak down) 1902, a zero-crossing up 1906 and a second peak (e.g., second peaks up) 1904. In some cases, the predetermined sequence of signal feature types can include an ordered sequence of a first trough 1902, a zero-crossing up 1906, a peak 1904, a zero-crossing down 1908, and a second trough 1902. The predetermined sequence of signal feature types can start at any of the feature types and end at the next feature of the same feature type.

In some implementations, the ordered sequence of feature types may not include a second peak. For example, the computer system 100 can determine a predetermined sequence of signal feature types of the trough, zero-crossing up, peak, zero-crossing down, and an index indicating the end of the pulse. In some implementations, the computer system 100 can determine a predetermined sequence of signal feature types in other portions of the PPG signals, such as after the second peak or second trough.

In some implementations, the portion of the PPG signal indicative of a potential pulse can be a first portion that ends at or before a first signal feature (e.g., index of the start of the next pulse). The computer system 100 can determine, using the detected signal features, the predefined sequence of signal feature types in a second portion of the PPG signal. The second portion can be different from the first portion of the PPG signal and may include one or more feature types different from the first portion. The second portion of the PPG signal can start at the first signal feature. The computer system 100 can extract one or more features from the second portion for classification. Based on whether the features of the second portion follow or include an ordered sequence of feature types similar to the predetermined ordered sequence, the computer system 100 may classify the second portion of the PPG signal as a second PPG pulse segment.

The computer system 100 can classify the portion of the PPG signal as a PPG pulse segment based on the predetermined ordered sequence of signal feature types included in a portion of the PPG signal (STEP 2008). For example, after extracting the features of different feature types from the signal, the computer system 100 can determine the sequence of the feature types within the portion of the PPG signal. If the sequence of feature types identified in the signal matches the predetermined ordered sequence of signal feature types, the computer system 100 can classify the portion of the PPG signal as a pulse. In some cases, if a first portion of the PPG signal does not satisfy the predetermined ordered sequence, the computer system 100 can extend the first portion of the PPG signal until the remaining feature types are included in the first portion. In other words, the computer system 100 can keep identifying features successively and extending the first portion to include the include additional identified features until the first portion includes or satisfies the predetermined ordered sequence of signal feature types. The computer system 100 can then classify the first portion of the PPG signal as a pulse.

Figure 20B:
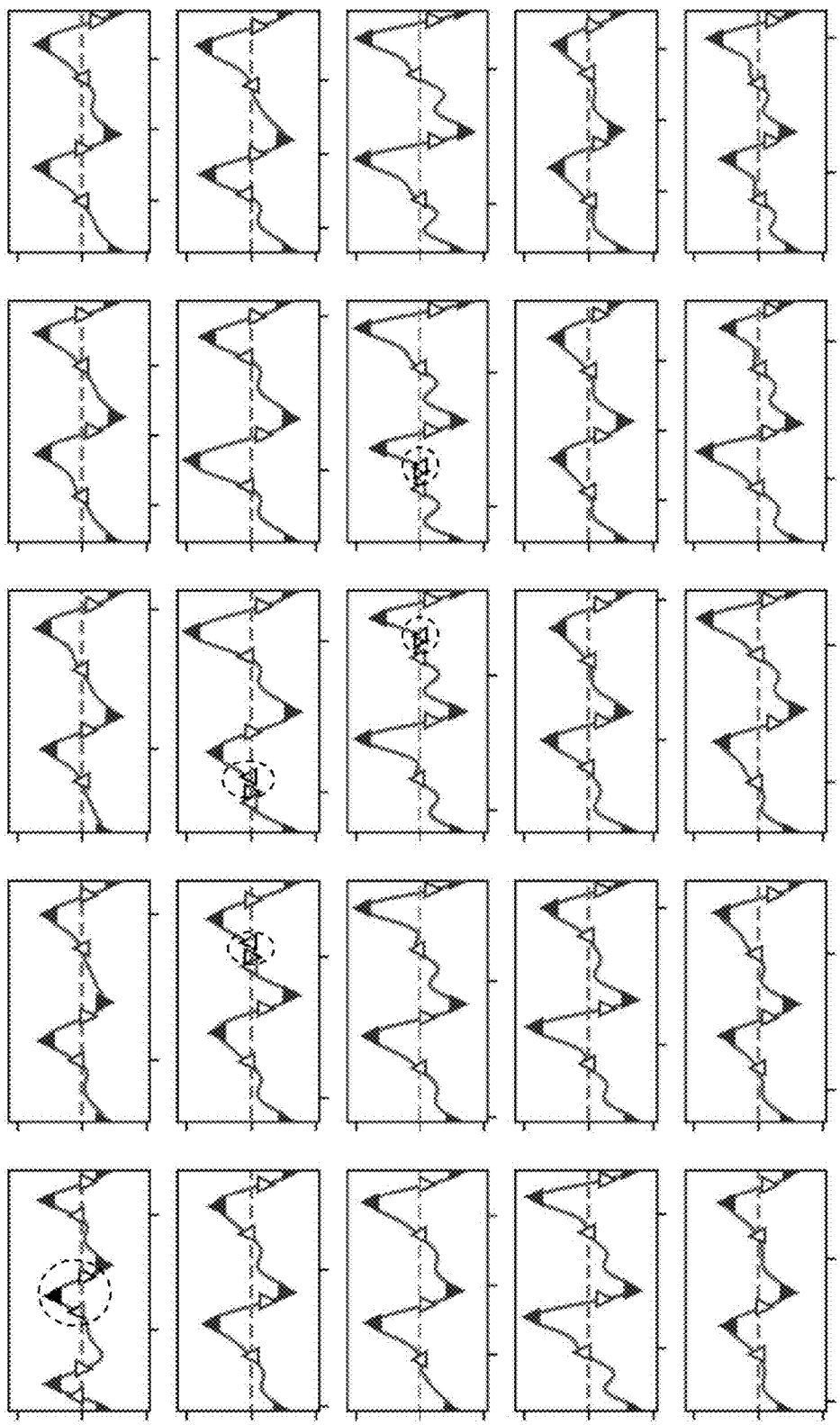
FIG. 20B shows example subplots of extracted pairs of pulses, according to example embodiments.

Referring to FIG. 20B, various examples of identified pairs of pulses are shown, according to example embodiments. The computer system 100 can extract pulses in successive pairs (e.g., multiple portions of the signal), such as to bypass any phase shift in the pulses. The successive pairs can refer to multiple portions of the signal, which may be classified as two pulses, a single pulse, or no pulses (e.g., in cases where the ordered sequence is not satisfied). Using successive pairs, the computer system 100 can extract the pulse starting at any feature type, such as the peak 1904 instead of the trough 1902. With successive pairs, the computer system 100 can extract the whole pulse starting at any feature type, instead of just part of the pulse, for example, when the extraction starts from the peaks 1904. The computer system 100 (or a corresponding computing device) can screen out feature types to detect the successions of at least i) peak down or trough 1902, ii) zero-crossing up 1906 (e.g., a point where negative value turns positive), iii) peak up or peak 1904 (e.g., the peak or summit of the portion of the signal), iv) zero-crossing down 1908 (e.g., a point where positive value turns negative), v)trough 1902, vi) zero-crossing up 1906, vii) peak 1904, viii) zero-crossing down 1908, and ix) trough (or peak down) 1902 again. In this case, the computer system 100 can identify the successive pairs of pulses starting at the trough (or peak down) 1902. The computer system 100 can identify each pulse as the predefined sequence of feature types: trough 1902, zero-crossing up 1906, peak 1904, zero-crossing down 1908 and trough 1902 again. The computer system 100 can identify the successive pairs of pulses starting at any of the feature types discussed herein. For example, the pairs of pulses (or pulses) can start and end with peaks 1904, the pairs of pulses can start and end with zero-crossings up 1906, or the pairs of pulses can start and end with zero-crossings down 1908. The computer system 100 can use similar logic to identify other pulses (or other pairs of pulses) within the PPG signal by successively identifying features of the different feature types until the predefined sequence of feature types is identified for each new pair of pulses.

In some implementations, in identifying the predetermined ordered sequence of feature types, the computer system 100 can identify additional features in between due to irregularities in an identified pulse or an identified pair of pulses. The dashed circles in FIG. 20B refer to such irregularities or additional features. For example, the pair of pulses in the top left corner of FIG. 20B include the features of a zero-crossing up, a peak and a zero-crossing down (shown within the dashed circle) as additional or extra features that are identified between a zero-crossing down and a trough of the predetermined ordered sequence of feature types. In other words, the pair of pulses includes 12 features instead of nine features. Referring to the second and third plots in the second row of FIG. 20B, each of these pairs of pulses includes an extra two features, namely an extra zero-crossing down and an extra zero-crossing up. Both pairs of pulses include 11 features instead of nine features. Other irregularities are depicted in the third and fourth plots in the third row of FIG. 20B. When facing or detecting such irregularities, the computer system 100 can continue searching for the next features in the PPG signal until the predefined or predetermined ordered sequence of feature types is identified. In other words, the computer system can ignore the extra features (or extra feature types) and keep looking for the missing features in the predefined or predetermined ordered sequence of feature types. Accordingly, some of the identified pulses or pairs of pulses may include more features than those corresponding to the predefined ordered sequence of feature types.

The computer system 100 can determine the pulse duration by computing a difference between two timestamps corresponding to the respective two feature types (e.g., same family of feature type), such as two of the same feature types. In some cases, the computer system 100 can calculate the duration of the pulse as a difference between a first timestamp of a first index representing the start of the pulse and a second timestamp of a second index representing the end of the pulse. The second index can also represent the start of the next pulse.

In some implementations, the computer system 100 can compute, using the various signal features of at least one of the different signal feature types of the PPG signal, the characteristics of the pulses of the user. For example, the computer system 100 can determine the following characteristics of the pulses: duration between time points (e.g., indicating a pulse or a heartbeat), differences of amplitudes, relative differences of amplitudes, slopes and relative slopes at one or more feature types, slopes and relative slopes between different feature types, and accelerations and relative accelerations at one or more feature types. The computer system 100 can compute other characteristics using the extracted features of the PPG signal. These characteristics can be used to determine the quality of the pulse or the health of the user. In some implementations, the pulses discussed above can be referred to as different PPG pulse segments corresponding to the respective portions of the PPG signal. The computer system 100 can classify other portions of the PPG signal as different PPG pulse segments based on the ordered sequence of feature types.

In some implementations, if the portion (e.g., PPG pulse segment or an indication of a pulse) of the PPG signal starts at a first peak 1904 and ends at a second peak 1904 (e.g., the peaks up), the computer system 100 can determine a duration of the PPG pulse segment based on a length of time between the first peak and the second peak. If the portion of the PPG signal starts at a first trough and ends at a second trough, the computer system 100 can determine the duration of the PPG pulse segment based on the length of time between the first trough and the second trough. The duration of the PPG pulse segment can reflect the duration of a pulse. In some cases, the duration of the PPG pulse segment may not indicate just the duration of a pulse but also the duration of the pulse and the stable state of the signal (e.g., after the heartbeat) up until the beginning of a second pulse.

In some implementations, the computer system 100 can generate, from the PPG signal, one or more PPG pulse segments indicative of at least the respective one or more pulses. Each PPG pulse segment can include signal features (e.g., at least one peak, at least one trough, at least one zero-cross up, and at least one zero-crossing down). The signal features in the PPG pulse segment can include the predetermined ordered sequence of signal feature types. The predetermined ordered sequence of feature types can be configured by the administrator of the computer system 100.

In some implementations, the computer system 100 can determine that a time duration between a first feature of a first type and a second feature of a second type within a PPG pulse segment exceeds a time duration threshold. For example, the first type can be a trough and the second type can be a peak up. The computer system 100 can identify a time duration threshold associated with the first type and the second type of features. The time duration threshold can indicate either a minimum time or a maximum time between the first type and the second type for a normal pulse. If the duration between the first type and the second type does not satisfy at least one of the minimum time or the maximum time, the computer system 100 can set a flag (e.g., indicating a corrupt or bad pulse) to the PPG pulse segment, such as responsive to determining that the time duration exceeds the time duration threshold.

A physiological pulse has several characteristics that distinguishes it from noise or false positives. For instance, the slope at a zero-crossing downward is very steep, implying that the duration between a peak up and a zero-crossing down is very short. Accordingly, the computer system 100 can check whether the following inequalities are satisfied:

$$\begin{cases} 30\,\text{ms} \le \text{zero} - \text{crossing } down_0 - peak_0 \le 250\,\text{ms} \\ 30\,\text{ms} \le \text{zero} - \text{crossing } down_1 - peak_1 \le 250\,\text{ms} \end{cases},$$

where the zero-crossing $down_0$ and zero-crossing $down_1$ represent successive zero-crossings down of the notable indices (or features of the predefined ordered sequence of feature types), and the $peak_0$ and $peak_1$ represent successive peaks (or peaks up) of the notable indices (or features of the predefined ordered sequence of feature types). If any of the above inequalities is not satisfied, the computer system 100 can declare the corresponding pulse segment as a corrupted pulse or can reject the pulse segment as not a valid pulse. In some implementations, the computer system 100 can use other inequalities and/or durations between other features to determine whether a pulse segment is corrupt or a valid pulse.

Figure 20C:
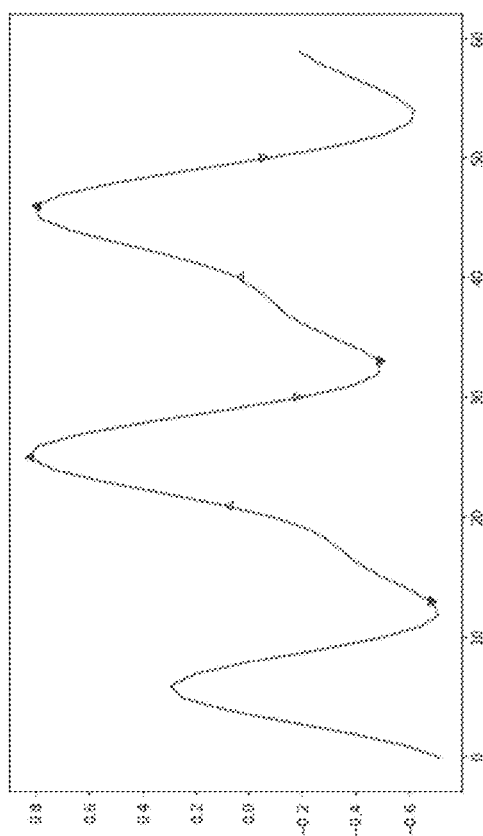
FIG. 20C shows examples of a corrupted pulse and valid or good a pulse, according to example embodiment.
Figure 20C:
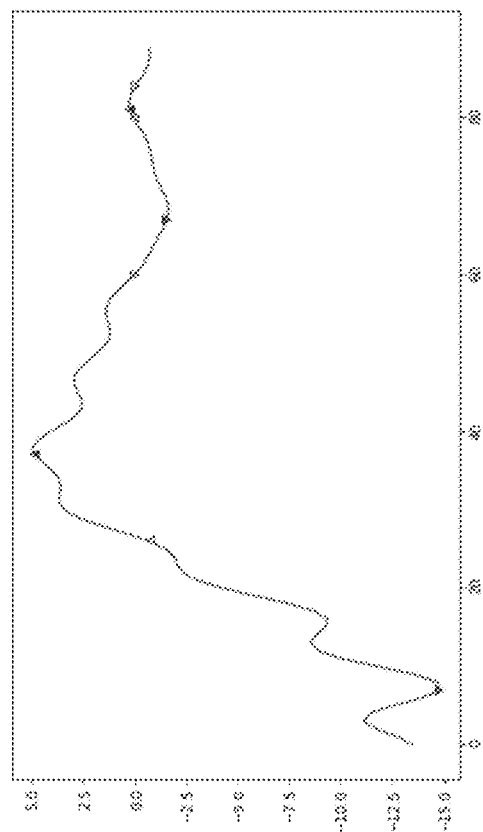

Referring to FIG. 20C, examples of a corrupted pulse and valid or good a pulse are shown, according to example embodiment. The plot on the left side illustrates an example of a corrupted pulse, while the plot on the right side of FIG. 20C illustrates an example valid or good pulse.

In some implementations, the first type and the second type can be other types of features, such as zero-crossing up or zero-crossing down. In this case, the computer system 100 can compare the time between these features to a second time duration threshold, different from the aforementioned time duration threshold for a trough and a peak feature types. In some implementations, if the time duration between the first feature and the second feature satisfies the time duration threshold, the computer system 100 may not set a flag to the PPG pulse segment (e.g., as corrupted or not valid pulse).

In some implementations, the computer system 100 can determine the duration of the PPG pulse segment based on the length of time between a first signal feature and a last signal feature of the predetermined (or predefined) sequence. The first signal feature and the last signal feature of the predetermined sequence can be the same feature type. In some other cases, the first signal feature and the last signal feature may not be the same type, but rather, the last signal feature can be a feature type before the start of the next pulse. Similar to the above, the computer system 100 can compare the duration between the first signal feature and the last signal feature of the predetermined sequence to a time duration threshold. Based on the duration of the PPG pulse segment not satisfying the time duration threshold, the computer system 100 can set a flag to the PPG pulse segment. Otherwise, the computer system 100 can proceed to analyze the next PPG pulse segment for irregularities or to measure the blood volume or pulses of the user. Accordingly, by performing the aforementioned techniques, the computer system 100 can compute raw estimates of the duration of individual pulses, the location of where the pulses are measured from (e.g., part of the user body), and the quality of the individual pulses. The quality of individual pulses can refer to the consistency of the pulses, the length of each pulse, the pulse rate, among other characteristics of the pulse, which can be used, in part, as an indicator of the user's health. By extracting different features from the PPG signal, the computer system 100 can improve the precision of measuring or computing the characteristics and qualities of individual pulses.

Individual pulses can carry information about the blood pressure or other vital conditions of the user. By using the pulse division formula or algorithm, the computer system 100 can identify or divide the signal (e.g., PPG signal) into multiple pulses (sometimes referred to as rough pulses). In some implementations, the signal may be corrupted, may not be of good quality, or may not contain precise features, e.g., caused by an algorithm processing the signal. In this case, the computer system 100 can use or rely on one or more pulse positions (e.g., from the original signal as a start) for refining the pulse features and removing the corruption.

Figure 21:
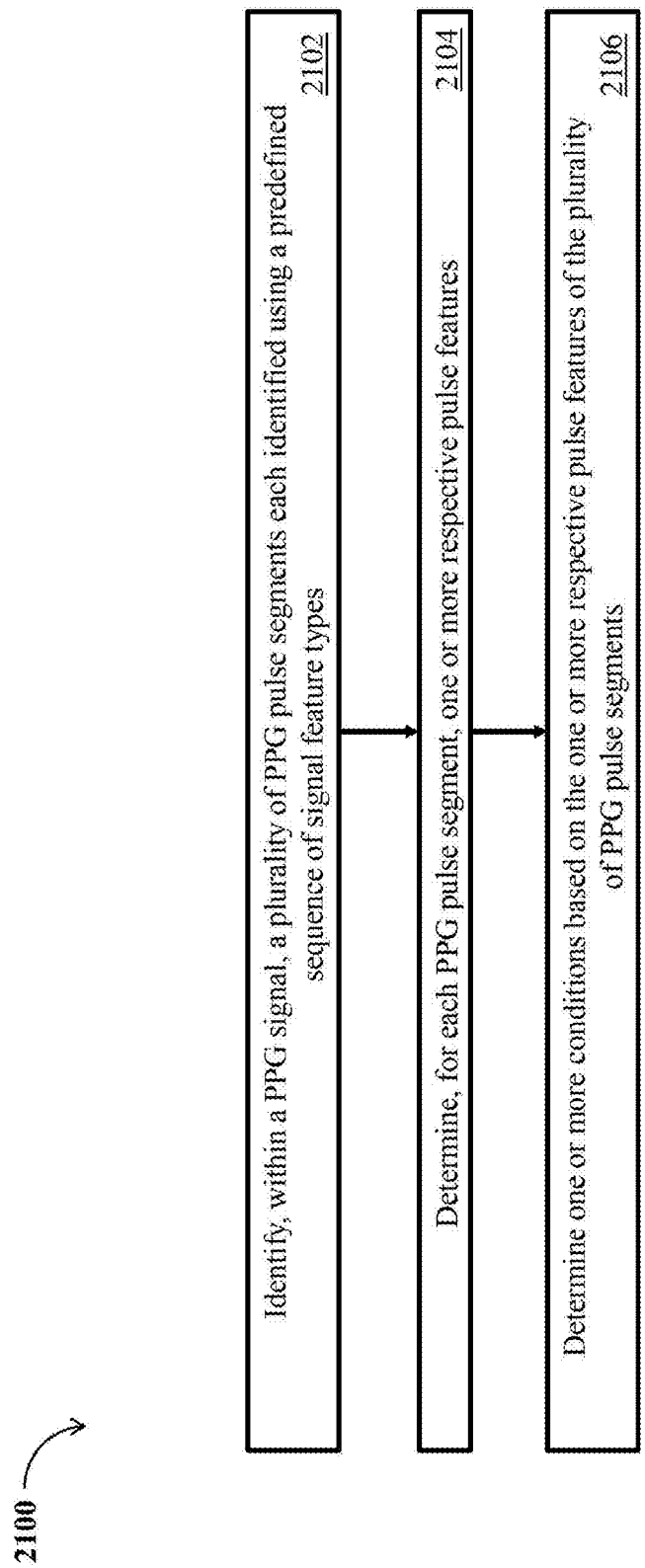
FIG. 21 shows a flowchart illustrating a method of determining one or more error conditions based on features of pulse segments of the PPG signal, according to example embodiments.

The computer system 100 can refine the pulse features herein, using a window (e.g., small window) in the PPG signal by using pulse division indices, such as discussed in at least one of FIG. 20A or FIG. 21. By using the small window in the PPG signal, the computer system 100 can identify notable indices (sometimes referred to as signal features) with better accuracy using raw PPG signal. The computer system 100 can perform one or more steps herein to refine the pulse or signal features. The one or more steps can be performed either sequentially, consecutively, in parallel, or in any other order, for example.

The computer system 100 can prepare the pulse for boundary extraction (e.g., indications of where individual pulses start or stop). For example, as a first step, the computer system 100 can gather a number of frames used for cropping the PPG signal around the start of a pulse. This number of frames can be denoted as n. The computer system 100 may set n as $2\times f_s$ (e.g., two times the sampling frequency $f_s$) frames of the original PPG signal, among other values. The start of the gathered n frames of the original PPG signal can be set as an offset of a window for cropping the PPG signal. In this case, the offset can be referred to as l herein. The start of the gathered n frames can start at l frames before the rough pulse start. The rough pulse start or the rough start of the pulse can be or include the general area where the pulse starts or divides from other pulses. For example, the rough pulse start can be located at the trough, the systolic slope, among others. The l can be configured or preset at 0.3 seconds (e.g., $0.3 \times f_s$), among other offset times of the window, before the rough start of the pulse.

Subsequent to gathering n frames, the computer system 100 can upsample the PPG signal to a target frequency. The target frequency can be the frequency at which the PPG signal should be upsampled, which can be denoted as $f_{up}$. The $f_{up}$ can be configured or preset to 500 Hz among other frequencies for upsampling the PPG signal, such as greater than or less than 500 Hz. The target frequency can be configured with an interpolation of order 6. In some cases, the target frequency can be configured with other interpolation orders. By upsampling the signal, the computer system 100 can increase the smoothness of the signal and the first derivative of the signal. Responsive to upsampling the signal, the computer system 100 can compute the first two derivatives of the signal. Accordingly, the computer system 100 can prepare the pulse for the extraction of pulse boundaries.

Figure 22A:
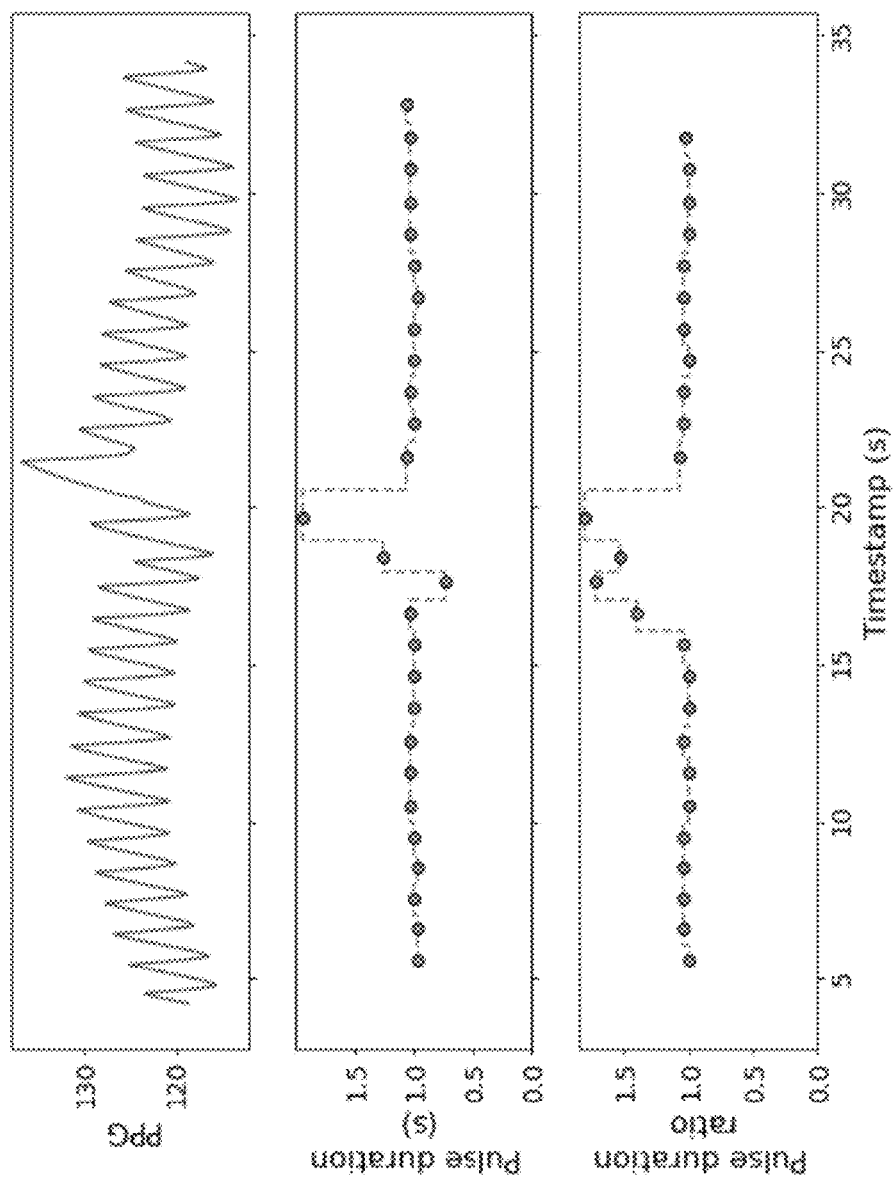
FIG. 22A shows plots illustrating an example PPG signal, variation in respective pulse durations and variations in ratios of durations of consecutive pulses, according to example embodiments.
Figure 22B:
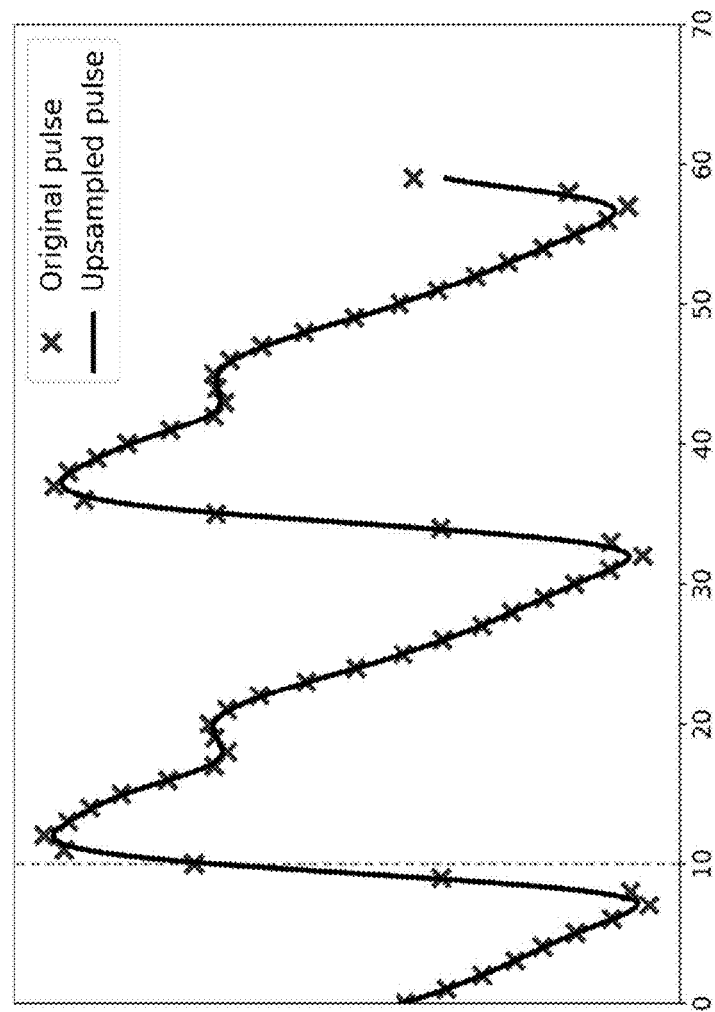
FIGS. 22B-G show plots illustrating an example upsampled PPG signal with extracted features and characteristics, according to example embodiments.

As shown in FIG. 22B, a plot of an example PPG signal can be illustrated, according to example embodiments. The plot can include various original pulses (e.g., data points of the PPG signals) for graphing the various pulses. With the various original pulses or data points, the computer system 100 can generate the upsampled pulse, presented as the continuous line in this example. The example plot can the PPG signal upsampled to 500 Hz with a b-spline interpolation in the order of 6. The computer system 100 can determine, identify, or configure the rough pulse start at the systolic slope positioned at 10 frames (or 333 ms for a frame rate of 30 fps). The computer system 100 can use or refer to plot for extracting the pulse boundaries.

Figure 22D:
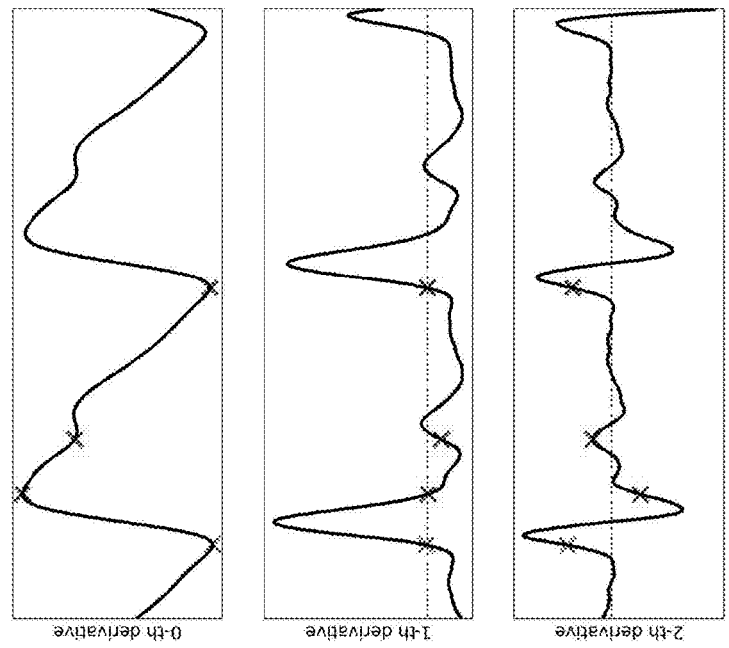
Figure 22C:
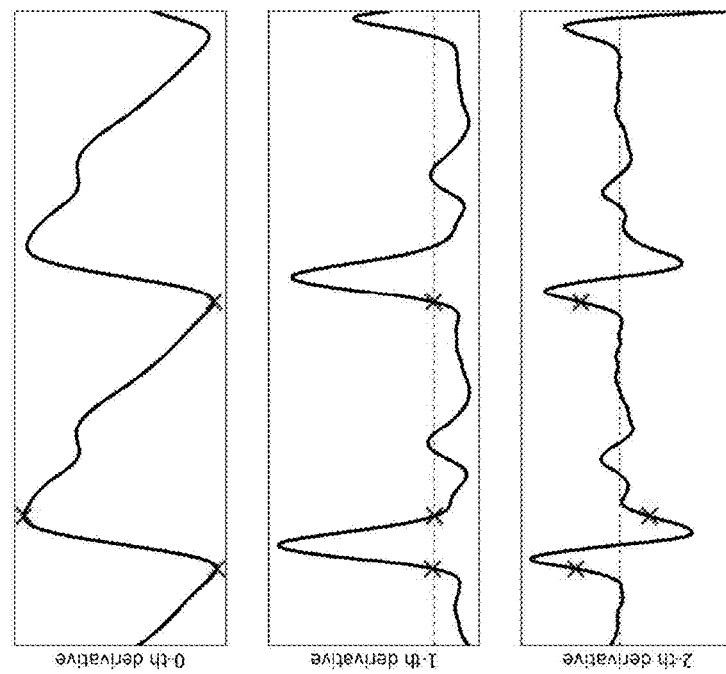

After upsampling and computing the successive derivatives (e.g., the first and the second derivative of the PPG signal), the computer system 100 can find the indices of pulse boundaries. FIG. 22C illustrates an example extraction of the pulse boundaries (or the indices of the pulse boundaries) according to example embodiments. The upsampled PPG signal can be illustrated in a first subplot. Further, a second subplot and a third subplot can represent examples of the first and second derivatives of the upsampled PPG signal of the first subplot, respectively. To find the indices of the pulse boundaries, the computer system 100 can be configured with one or more criteria for identifying one or more indices of the pulse boundaries. For example, the start of the pulse (e.g., which can be the first trough of the PPG signal) can include a height of 90% of the signal amplitude (e.g., lower height or minimum height). The signal amplitude can refer to the averaged, among other aggregation techniques for the amplitudes of the signal throughout the signal, for example. The systolic peak of the pulse (e.g., the first peak of the signal) can include a height of 90% of the signal amplitude (e.g., upper height or maximum height). The start of the next pulse can be an index located at the second trough with a similar height as the first trough (e.g., 90% of the signal amplitude). The computer system 100 can extract other pulse boundaries as discussed herein, based on the configuration or the definition of individual indices (e.g., the percentage or ratio of the signal amplitude, among other points of the signal). The extracted pulse boundaries can be extracted and marked according to the example illustrations of FIG. 22C.

Figure 22F:
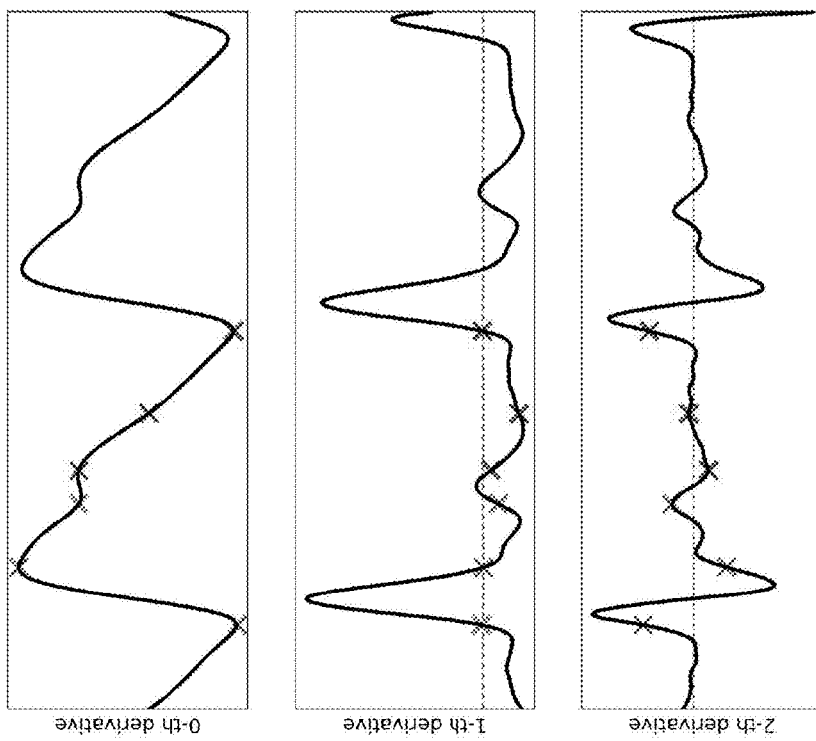
Figure 22E:
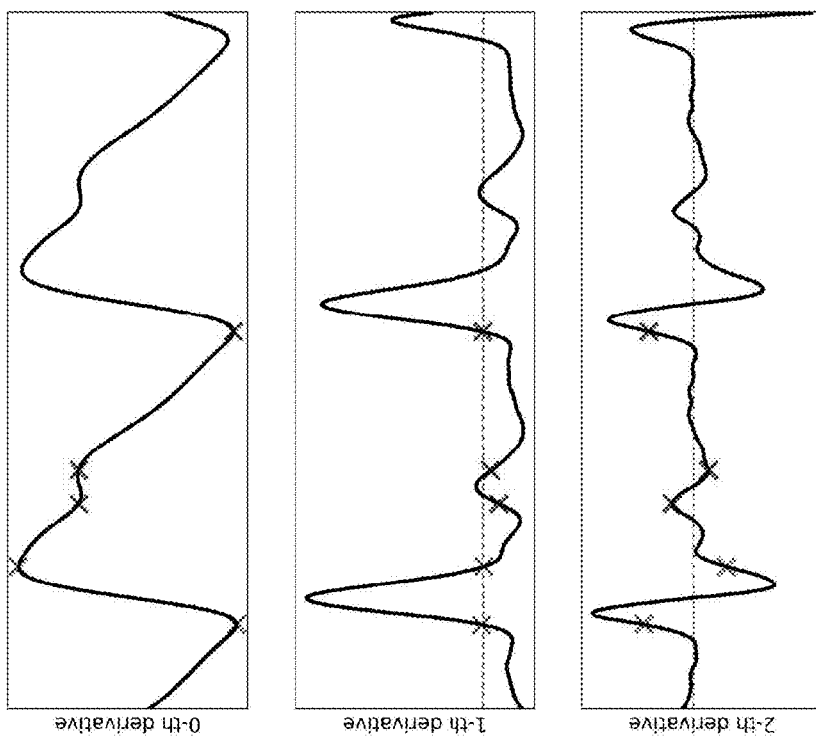

The computer system 100 can extract one or more characteristic features of the pulse responsive to extracting the pulse boundaries or after segregating individual pulses. For example, the computer system 100 can extract at least the notch (sometimes referred to as a pulse notch), the diastolic peak (sometimes referred to as a pulse diastolic peak), and the end of the pulse (sometimes referred to as pulse end) of the PPG signal. For example, the notch can be described as the index between the systolic peak and the start of the next pulse where the second derivative reaches its maximal value. Extraction of the pulse notch can be illustrated in the example plot in conjunction with FIG. 22D. The diastolic peak can be described as the index between the notch and the start of the next pulse where the second derivative reaches its minimal value. Extraction of the pulse diastolic peak can be illustrated in the example plot in conjunction with FIG. 22E. The end of the pulse can be described as the index between the diastolic peak and the start of the next pulse where the second derivative reaches its maximal value. Extraction of the pulse end can be illustrated in the example plot in conjunction with FIG. 22F. The computer system 100 can extract other characteristic features of the PPG signals discussed herein.

Figure 22G:
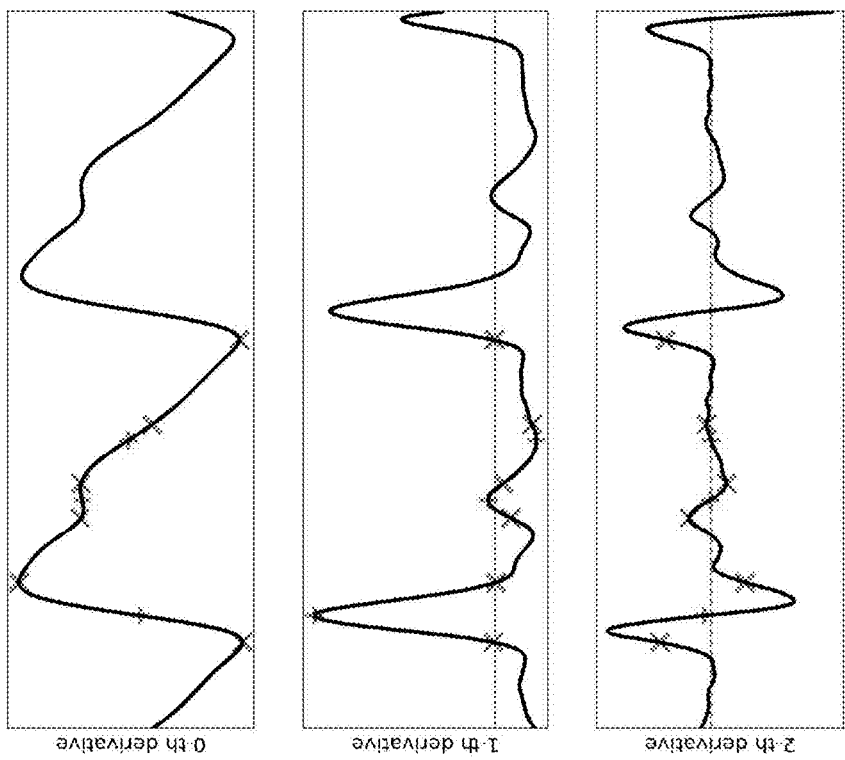

Responsive to extracting the characteristic features, the computer system 100 can determine the characteristic slopes based on the characteristic features. FIG. 22G illustrates examples of the characteristic slopes in the $0^{th}$, $1^{st}$, and $2^{nd}$ derivatives of the upsampled PPG signal. To determine the slope, the following indices can be described for the computer system 100 to calculate the slope. For example, the systolic max slope index can be described as the index between the start of the pulse and the systolic peak where the first derivative reaches its maximal value. The notch max slope index can be described as the index between notch and diastolic peak where the first derivative reaches its maximal value. The diastolic max slope index can be described as the index between the diastolic peak and the end of the pulse where the first derivative reaches its minimal value. Based on the description of the aforementioned slope indices, the computer system 100 can determine the characteristic slopes based on the characteristic features. The characteristic slopes can be illustrated, flagged, or marked as shown in the one or more subplots of FIG. 22G.

The computer system 100 can augment the features for refining the features of the PPG signal or pulses within the PPG signal. For example, the computer system 100 can obtain or determine the cross features or relative features by computing different combinations between the characteristic slopes or characteristic features, such as $F_j = f_j(t_1, x_1, t_2, x_2, \ldots, t_n, x_n)$, where $F_1$ can denote a cross feature, $f_j$ can denote a function for aggregating different primary features and indices into cross features, and $t_i$ and $x_i$ can denote indices and corresponding feature values (e.g., PPG, slope, etc.), respectively. For example, to compute the systolic peak duration, the computer system 100 can use the following formula: Peak duration=$t_{sys\ peak} - t_{pulse\ start}$. The computer system 100 may use one or more features (e.g., primary features) in the cross feature. In some implementations, the computer system 100 may not use certain features in the cross feature. Accordingly, by performing the refinement process, the computer system 100 can efficiently obtain an improved estimate of the blood pressure, heart rate, among other vital signs of the user based on the features or characteristics of the PPG signal.

D.4. Pulse Based Conditions

To measure a PPG or a PPG signal, a finger (or other body parts) should be present on the camera lens or other photodetectors for capturing images of the finger. However, in certain cases, the user finger may not be present on the lens, the user may not be still (e.g., moving around), the user may remove their finger before the computer system 100 finish with analyzing the blood volume of the user based on the PPG signals, or other conditions may arise that would degrade the quality of the captured images or data for processing by the computer system 100. Therefore, to make sure that the recording of the finger is performed under expected conditions, the computer system 100 can analyze a color intensity signal (or PPG signal) generated from the sequence of images to determine if, for example, the finger is on the lens or the user is keeping still while performing blood volume measurement.

The computer system 100 can obtain, receive, or identify one or more pulses within the PPG signal. The computer system 100 can identify one or more pulses from a list of pulses. Each pulse can be associated with a portion or a PPG pulse segment of the PPG signal. The computer system 100 can determine the duration of individual pulses within a sequence of pulses as discussed in at least STEPS 2006 and 2008 in conjunction with FIG. 20A, for example. The list of pulse durations can be denoted as $(D_i)_{i \geq 0}$ herein. The index i in this case can refer to or represent the pulse index of a pulse whose pulse duration is denoted $D_i$.

The computer system 100 can use one or more parameters to determine one or more conditions that can be used to alert the user. In some cases, the computer system 100 can use the parameters to determine if at least one error condition is present. The one or more parameters can include at least a consecutive duration ratio outlier quantile, a consecutive duration ratio threshold, an overall duration quantile, and a duration consecutive ratio threshold. A quantile can refer to or indicate a cut point dividing between value ranges. For example, a 5% quantile can divide or separate the maximum or minimum 5% of all values from the rest of the values. The consecutive duration ratio outlier quantile can refer to a quantile used for eliminating extreme duration ratios between two consecutive pulses, denoted as $q_{cdr}$. The duration between two consecutive pulses can refer to a time duration between the start of a pulse and the end of the pulse for two consecutive pulses. In some cases, the time duration can be from the start of a first pulse to the start of the second pulse. Using $q_{cdr}$, the computer system 100 can determine the magnitude of variation in pulse duration for consecutive pulses or consecutive pairs of pulses. The ratio between two consecutive pulses can be calculated by dividing a first pulse duration of a first pulse by a second pulse duration of a second pulse where the first and second pulses are consecutive pulses. The computer system 100 can eliminate, discard, or ignore ratios above a maximum quantile or below a minimum quantile, for example.

In some implementations, the $q_{cdr}$ can indicate whether the user is positioning the finger (or body part) properly on the lens. The $q_{cdr}$ can provide indication of other conditions that, for example, contribute or lead to the extreme (or relatively large) values of $q_{cdr}$. In some cases, the computer system 100 can notify or ask the user to readjust the position of their finger or remain still during the measuring process, based on determined values of the $q_{cdr}$.

The consecutive duration ratio threshold can refer to or represent a threshold value for pulse duration ratios for pairs of consecutive pulses, which can be denoted as $\theta_{cdr}$. If at least one computed duration ratio for a pair of consecutive pulses is above $\theta_{cdr}$, the computer system 100 can raise the ARRHYTHMIA condition, indicating that the user may potentially have arrhythmia based on the characteristics of the pulses (e.g., the durations of subsequent pulses).

The overall duration quantile can refer to a quantile used for eliminating or identifying extreme pulse durations within a recorded PPG signal, denoted herein as $q_{od}$. The computer system 100 can measure or compute the pulse durations as discussed above in subsection D.3. In some implementations, the computer system 100 can compute or determine extremal pulse durations using the overall duration quantile, as discussed in further detail below. The computer system 100 can use the extremal pulse durations to detect additional conditions. For instance, the computer system 100 can use the extremal pulse durations to detect presence of an irregular heart rate condition. Specifically, a relative large difference or relatively large ratio between the extremal pulse durations can be indicative of the irregular heart rate condition. The computer system 100 can compare both extremal pulse durations of a PPG signal to detect irregular heart rate.

The computer system 100 can compute or determine a maximal duration ratio representing a ratio between the extremal pulse durations of the PPG signal. This computer system 100 can use a maximal duration ratio threshold denoted as $\theta_{odr}$. The maximal duration ratio threshold $\theta_{odr}$ can be configured or predefined by the administrator of the computer system 100. If the computer system 100 determines that the maximal duration ratio is greater than the threshold $\theta_{odr}$, the computer system 100 can raise an IRREGULAR_HEART_RATE condition indicating that the user has irregular heart rate. The conditions raised can be displayed on a display device 112 of the computer system 100 as part of the UI of the application 114, for example. Based on at least one of the thresholds above, the computer system 100 can output a boolean value corresponding to one or more error conditions, such as ARRHYTHMIA or IRREGULAR_HEART_RATE. These error conditions can be transmitted to the administrator or used by the computer system 100 to train a machine learning model for enhancing the accuracy of identifying error conditions discussed herein.

Referring to FIG. 21, a flowchart illustrating a method 2100 of determining one or more error conditions based on features of pulse segments of the PPG signal is shown, according to example embodiments. The method 2100 can include identifying, within a PPG signal generated from a sequence of images acquired using a photodetector, various PPG pulse segments, each of the PPG pulse segments identified using a predetermined (or predefined) sequence of signal feature types (STEP 2002). The method 2100 can include determining, for each PPG pulse segment, one or more respective pulse features (STEP 2004). The method 2100 can include determining one or more conditions based on the one or more respective pulse features of the various PPG pulse segments (STEP 2006). The method 2100 can be performed by the computer system 100 or the corresponding processor 102, for example, upon executing the application 114. The method 2100 can be performed by other components (e.g., memory 104, BUS 106, light source 108, camera device 110, or display device 112) of the computer system 100, in conjunction with FIG. 1. The method 2100 can be performed by a remote device or a remote server. In some implementations, the method 2100 can be performed by a computer system 100 and a remote server. For example, the computer system 100 can be in communication with the remote server to delegate one or more tasks to the remote server. In this case, the remote server can perform the one or more tasks, such as performing at least one of STEPS 2002-2006, and transmit an output to the computer system 100. The method 2100 can be performed by other components discussed herein and perform features and functionalities in conjunction with at least one of FIGS. 1-20, for example. The method 2100 can be performed in conjunction with, sequential, or prior to at least one of other methods discussed herein, such as methods 400, 1100, 1500, etc.

Still referring to FIG. 21, in further detail, the computer system 100 can identify, from a PPG signal generated from a sequence of images acquired using a photodetector, various PPG pulse segments. The computer system 100 can identify each of the PPG pulse segments using a predetermined (or predefined) sequence of signal feature types (STEP 2002). The signal feature types can include at least a trough (e.g., peak down), zero-crossing up, peak (e.g., peak up), and zero-crossing down. The computer system 100 can identify the PPG pulse segments by classifying portions of the PPG signal as the PPG pulse segments based on the features in a predetermined ordered sequence of feature types. The computer system 100 can classify the portions of the PPG signal as the PPG pulse segments similar to STEP 1908 in conjunction with FIG. 20A.

The computer system 100 can determine, for each of the PPG pulse segments, one or more respective pulse features determined from the PPG pulse segment (STEP 2004). The one or more respective pulse features can include at least the respective pulse duration for each PPG pulse segment based on a length of time between a first signal feature and a last signal feature of the predefined sequence. The first signal feature and the last signal feature can be from the same family of feature types (e.g., from peak to peak, trough to trough, etc.). In some cases, the first signal feature and the last signal feature can be of different feature types, such as from an index of the start of a pulse to an index of the end of the pulse. The index indicating the end of the pulse can be different from (e.g., located before) the index for the start of the next pulse. The index indicating the end of the pulse can be located between the diastolic max slope and the start of the next pulse.

In some embodiments, the respective pulse features can include the duration between two consecutive pulses or multiple pairs of consecutive pulses. For example, the computer system 100 can calculate a first duration between the start of a first pulse to the start of a second pulse. The computer system 100 can then calculate a second duration between the start of the second pulse to the start of a third pulse. The computer system 100 can compare the first duration and the second duration to determine a ratio or the variation between the durations of two pairs of consecutive pulses, in this case. The ratio (or duration ratio) can of the durations between consecutive pulses (e.g., a pulse pair) can represent a quantitative relation between the duration of the pair of consecutive PPG pulse segments. The computer system 100 can use the respective duration ratios for each of the pairs of consecutive PPG pulse segments to determine a reference duration ratio. The reference duration ratio can include at least one of the maximum (or the minimum) of the respective duration ratios for the plurality of pairs of consecutive pulse segments. In some implementations, the reference duration ratio can include a quantile (e.g., the magnitude or percentage) of the respective duration ratios for the pairs of consecutive pulse segments.

Using the respective ratio for the pairs of consecutive PPG pulse segments, the computer system 100 can detect if the user has a condition, such as an arrhythmia, based on the calculated ratio. For example, the computer system 100 can compare the reference duration ratio (or one or more duration ratios of at least a pair of consecutive PPG pulse segments) to a threshold value. The computer system 100 can determine if the arrhythmia condition should be raised based on the comparison of the reference duration ratio to the threshold value. In this case, the threshold value can be $\theta_{odr}$.

In some embodiments, the computer system 100 can determine a first pulse duration of a first PPG pulse segment and a second pulse duration of a second PPG pulse segment to detect the condition of the user. For example, the first pulse duration can be a minimum pulse duration of respective pulse durations of the PPG pulse segments. The second pulse duration can be the maximum pulse duration of respective pulse durations of the PPG pulse segments. In some cases, the first pulse duration can be a first quartile of respective pulse durations of the PPG pulse segments and the second pulse duration can be a second quantile of respective pulse durations of the PPG pulse segments. The computer system 100 can determine a relative variation between the first pulse duration and the second pulse duration based on a comparison between the maximum and the minimum pulse duration from various PPG pulse segments. The computer system 100 can compare the relative variation between the first and second pulse durations to a threshold to determine whether to raise a condition (e.g., irregular heartbeat condition) based on a relative variation between the first pulse duration and the second pulse duration.

In some implementations, the computer system 100 can determine, for each pair of consecutive pulse segments, various PPG pulse segments. Each PPG segment or PPG pulse segment can include signal features that include the predetermined sequence of signal feature types. For example, the predetermined sequence of signal feature types can be in the order of trough, zero-crossing up, peak (e.g., peak up), zero-crossing down, and trough. In another example, the predetermined sequence of signal feature types can be in the order of peak, zero-crossing down, trough, zero-crossing up, and peak. The predetermined sequence can start with any other feature type.

The computer system 100 can compute the duration of individual pulses as discussed above with regard to subsection D.4. The computer system 100 can use variation in pulse durations of consecutive pulses to detect one or more conditions such as arrhythmia. High variation in pulse durations of consecutive pulse can be indicative of an abnormal condition of the user. The computer system 100 can compute a high ratio between the pulse durations of pairs of consecutive pulses. Having a high pulse duration ratio may suggest that something happened physiologically to the user and/or that the measurement may not be reliable.

The computer system 100 can compute the high pulse duration ratio between two successive pulse durations as:

$$r_i = \max\left(\frac{D_i}{D_{i+1}}, \frac{D_{i+1}}{D_i}\right). \tag{20}$$

The ratio $r_i$ can represent the maximum or higher ratio of $$\frac{D_i}{D_{i+1}} \text{ and } \frac{D_{i+1}}{D_i}.$$

The ratio $r_i$ can be equal to $$\frac{D_i}{D_{i+1}}$$

if $D_i$ is greater than $D_{i+1}$, or can be equal to $$\frac{D_{i+1}}{D_i} \text{ if } D_{i+1}$$

is greater than $D_i$. The computer system 100 can then compute the maximal consecutive duration ratio as a high quantile $q_{cdr}$ of the $(r_i)_{i \geq 0}$. The maximal consecutive duration ratio (or $q_{cdr}$-th quantile of the ratios $r_i$) can be denoted as $r^*$. The computer system 100 can detect one or more conditions based on whether the maximal consecutive duration ratio $r^*$ exceeds a threshold (e.g., a consecutive duration ratio threshold $\theta_{odr}$). For example, the computer system 100 may detect and raise (or report) a condition of Arrhythmia if $r^*$ exceeds the consecutive duration ratio threshold $\theta_{cdr}$.

As in normal circumstances, the pulse duration of users may vary throughout time due to changes in the pulse rate, physiological state of the user, among other contributing factors to the user's blood volume. Further, with high variation in pulse duration, this may suggest that the user is not at rest (e.g., not still or moving while taking measurement). In this case, the measurement may not be reliable as it should be, and the computer system 100 may notify the user to retry the measurement or raise a condition indicating for the user to remain still while taking the measurement, for example. The computer system 100 can compute extremal durations between pulses, such as $D^{min}$ for the minimum (or relatively short) pulse duration and $D^{max}$ for the maximum (or relatively long) pulse duration from the PPG pulse segments. The $D^{min}$ and $D^{max}$ may be computed as the $q_{od}^{th}$ and $(1-q_{od})^{th}$ quantiles, respectively. The $q_{od}$ can represent the quantile used to identify extremal pulse durations. The $q_{od}$ can be preset and configured, for example, to 1%, 2%, 3%, etc. In some cases, the $q_{od}$ may be at least one of the highest or lowest values within the PPG pulse segments. The computer system 100 can determine the maximal duration ratio as:

$$R = \frac{D^{max}}{D^{min}}. \tag{21}$$

Based on the maximal duration ratio R, the computer system 100 can detect or raise (e.g., report) a condition indicative of irregular hear rate. For example, the computer system 100 can detect irregular heart rate if R is greater than a corresponding threshold.

The computer system 100 can determine or detect one or more conditions based on the one or more respective pulse features of the various PPG pulse segments (STEP 2006). The one or more conditions can include at least an arrhythmia condition or irregular heartbeat (or heart rate) condition. For example, the computer system 100 can determine or check if the maximal consecutive duration ratio r* exceeds the threshold $\theta_{cdr}$. If $r^* > \theta_{cdr}$, the computer system 100 can detect or raise the error condition of ARRHYTHMIA. In other words, the computer system 100 can detect the arrhythmia condition based on the comparison of the maximal consecutive duration ratio to the threshold value of $\theta_{cdr}$. The computer system 100 can display the error condition on the display device 112 for the user. In some cases, the computer system 100 can transmit the error condition to an administrator for analysis. In some other cases, the computer system 100 can transmit the results and error conditions to a machine learning model as a training data sample.

The computer system 100 can determine if R exceeds the maximal duration ratio threshold $\theta_{or}$. For example, if $R > \theta_{or}$, the computer system 100 can raise an error condition of IRREGULAR_HEART_RATE. In other words, the computer system 100 can detect and raise the irregular heartbeat condition based on a relative variation between the first pulse duration and the second pulse duration. The relative variation between the first and second pulse durations can include or refer to a ratio of the second pulse duration over the first pulse duration. In some cases, the relative variation between the first and second pulse durations can include or refer to a difference between the first pulse duration and the second pulse duration. In some other cases, the relative variation between the first and second pulse durations can include or refer to a normalized difference between the first pulse duration and the second pulse duration. The computer system 100 can normalize the difference, for example, by dividing the difference with a maximum pulse duration, a minimum pulse duration, the median of the pulse durations, among other normalization techniques. Similar to the ARRHYTHMIA error condition, the computer system 100 can display the error condition to the user, transmit the error condition to the administrator, or provide as an input to the machine learning model either for training or further processing to determine any false positive or false negative in the analysis of the pulse durations. In some implementations, the computer system 100 can determine and raise other conditions based on the duration or magnitude of the pulses. The one or more conditions discussed above can be related to the physiology of the user.

In some cases, the conditions can include or refer to the condition of the computer system 100, such as irregular data captured by the photodetector. In this case, the computer system 100 may notify and request the user to reattempt the measurement. In some cases, since some users may not be aware of some of the conditions (e.g., hand stability when taking measurements, etc.), the computer system 100 can notify some conditions as a hint to the user, such as to maintain the stability of the finger for more accurate measurement. Thus, based on the duration of individual pulses, the computer system 100 can determine one or more potential conditions that the user may have using the PPG pulse segments. An illustrative example of the pulse durations and the pulse duration ratios computed based on pairs of pulse durations can be shown in FIG. 22.

In some implementations, the computer system 100 can identify or determine if there are a sufficient number or enough pulses for computing the pulse duration ratio for detecting at least the arrhythmia condition or the irregular heart rate condition. The computer system 100 can determine if there is either enough or insufficient number of pulses based on the number of extracted pulses, the duration of the measured signal, or a total number of captured frames. For example, the computer system 100 can compare the total number of pulses to a threshold. If the total number of pulses is less than the threshold, the computer system 100 can alert the user of an insufficient number of pulses condition (sometimes referred to as NOT_ENOUGH_PULSE condition). If there are a sufficient number of pulses, the computer system 100 can proceed to determine the pulse duration ratio, among other conditions or measurements, for example. In another example, the total number of pulses can be associated with the total number of frames. In this case, the computer system 100 can compare the total number of frames to a threshold. If the total number of frames is less than the threshold, the computer system 100 can alert the user of an insufficient number of pulses condition. If there are a sufficient number of frames, the computer system 100 can proceed to determine the pulse duration ratio, among other conditions or measurements. In some embodiments, the computer system 100 can compare the total duration of capturing the PPG signal to a threshold. Similar to the previous example, if the total duration satisfies the threshold, the computer system 100 can proceed to other steps in at least one of error checking (e.g., checking other conditions) or performing a measurement. Otherwise, if the total duration does not satisfy the threshold, the computer system 100 can alert the user of the insufficient number of pulses condition.

FIG. 22 shows plots illustrating an example PPG signal, variation in respective pulse durations and variations in pulse duration ratios, according to example embodiments. The example illustration can include a first subplot having a PPG signal, a second subplot having the pulse durations, and a third subplot having the pulse duration ratios. The features and functionalities discussed herein, such as capturing the PPG signal, generate PPG pulse segments, compute the pulse durations, or determine the pulse duration ratios can be performed by the computer system 100 executing the application 114. In some implementations, the features and functionalities discussed herein can be performed by a server or a remote computing device, or the combination of the server and the computer system 100. The computer system 100 can receive the PPG signal including various PPG pulse segments. The PPG pulse segments can represent or include a pulse with a duration from the start of the pulse to either the end of the pulse or the beginning of the next pulse. The end of the pulse and the beginning of the next pulse may be the same index within the PPG signal.

In the second subplot, the computer system 100 can determine the pulse duration for each of the PPG pulse segments from the PPG signal of the first subplot. The computer system 100 can calculate a pulse duration ratio for each pair of pulse durations, as presented in the third subplot. The computer system 100 can use the pulse duration ratio to determine if the user has at least one of the conditions (e.g., irregular heartbeat or arrhythmia). For example, through the measured period of time, the computer system 100 can determine that the pulse duration is generally at 1 second. By commuting the ratio between a first pulse duration and a second pulse duration of around 1 second, the pulse duration ratio can be 1:1 (e.g., pulse duration ratio of 1). However, at approximately 17 to 20 seconds, the computer system 100 can detect the variation of the user's pulse duration based on the computed ratio, such as 1:0.7, 0.7:1.2, 1.2:2, and 2:1 for example. The ratios can be represented as values, such as 1.43, 1.71, 1.67, and 2, respectively in this case. The computer system 100 can determine if the user has arrhythmia, based on a comparison between at least one ratio greater than a threshold $\theta_{cdr}$. For example, if $\theta_{cdr}$ is 1.7 and the previous ratios are calculated, the computer system 100 can determine that the user may have an arrhythmia, thereby raising or alerting the arrhythmia condition to the user. Otherwise, if the ratios from the PPG signal are less than $\theta_{cdr}$, the computer system 100 can continue measuring the blood volume of the user. In some cases, the computer system 100 can notify the user that no arrhythmia condition is detected. In some implementations, the computer system 100 may be configured to raise the arrhythmia condition after calculating a predetermined number of ratios exceeding $\theta_{cdr}$, such as 2, 3, 5, 10, etc.

In another example, the computer system 100 can determine if the user has an irregular heartbeat to raise the irregular heartbeat condition, based on at least one of a ratio, a difference, an average, or a normalization between the maximum duration and the minimum duration within the PPG signal. The computer system 100 can use other metrics, aggregation, differentiation, or measurement techniques to determine if the user has a condition. The computer system 100 can normalize the maximum and minimum durations of the PPG signal by dividing the result of, for example, the difference between the maximum and the minimum durations by at least one of the average, the difference, the median, the maximum, or the minimum durations. The computer system 100 can normalize the maximum and minimum durations by other normalization techniques. Based on the two durations, the computer system 100 can compute a ratio or a value for comparison with a threshold $\theta_{odr}$. Referring to the previous example, the maximum duration can be 2 seconds and the minimum duration can be 0.7 seconds. In this case, the ratio would be 2.86. The computer system 100 can compare this result to the threshold $\theta_{odr}$. If the ratio is above (or equal to) the threshold $\theta_{odr}$, the computer system 100 can raise the irregular heartbeat condition and alert the user of the condition. Otherwise, if the ratio is below the threshold $\theta_{odr}$, the computer system 100 may continue measuring the blood volume of the user or complete the measurement process.

D.5. Blood Perfusion Based Conditions

A good signal (e.g., PPG signal) can be or refer to a signal that includes much more information compared to noises. In other words, good signals can have a high signal-to-noise ratio ("SNR") (e.g., more signal than noise). To compute or analyze data from the signals, the computer system 100 can determine if the signal is of good quality (e.g., large SNR) or if there are more noises than the signal itself. The computer system 100 can measure the perfusion (e.g., blood flow rate or the volume of blood per unit time) from a body part of the user, such as the finger. Perfusion measurement can revolve around having a PPG signal with a large SNR, such that the signal has a great amplitude for the computer system 100 to compute or provide an accurate measurement.

The perfusion can be a measure of the amplitude of the signal. The computer system 100 can determine the perfusion by using the log of the PPG signal as a measure of the absorbance to compare the amplitudes of the signal without being biased by the average value of the signal. For example, if the luminosity is 100 for a signal around 1000 (e.g., 1000 values or points), the variation of this luminosity should not weigh more than a variation of 1 for a signal around 10. To determine the perfusion, the computer system 100 can capture a sequence of images to calculate or determine the PPG signal used as input. The PPG signal can be denoted as X, which can include a length of T. The computer system 100 can consider one or more parameters, such as the variation threshold, the window size, and the variation quantile when determining the perfusion. The computer system 100 can consider other parameters discussed herein to determine the perfusion of the signal.

The variation threshold can include or be a threshold for the variation metrics of the PPG signal or values to be considered as having a good amplitude. The variation threshold can be denoted as $\theta$ herein. The variation metric can include at least a value or a metric indicating the variation (e.g., difference, standard deviation, average, among others) between the upper and lower values of individual PPG pulse segments, for example. The variation metric can be based on the variation quantile discussed herein. The computer system 100 can compare the variation metric to $\theta$, such as to determine if the PPG signal should be used for calculating the blood volume, pulse rate, or other characteristics of the pulse. The window size can include or refer to the duration of a window over which the variations are computed. The window size can be denoted as n herein. The window size can be set to 1s, 30 frames, 60 frames, among other values or durations. In some cases, the window size can depend on the shutter speed of the camera. The window size can be configured by the administrator of the computer system 100. The variation quantile can include or be a quantile of the distribution of amplitudes used for the variation metric. The variation quantile can be denoted as $q_{var}$ herein. The variation quantile can be configured to 0.5 (e.g., a cutoff point at 50% or the median of the distribution of amplitudes).

Based on the input signal and the parameters, the computer system 100 can calculate or determine the perfusion of the PPG signal. The perfusion can be denoted as P herein. The perfusion can be a single value used to determine whether the PPG signal should be used to calculate the characteristics of the user's blood such as blood pressure, among other features of the blood flow. In some cases, the perfusion can include or be the variation metric for comparison with $\theta$. With P, the computer system 100 can determine a boolean value associated with an error condition of COLD_FINGER (sometimes referred to generally as cold finger condition). The computer system 100 can alert the cold_finger condition to the user via the UI of the application 114 responsive to determining the error condition, for example.

Figure 23:
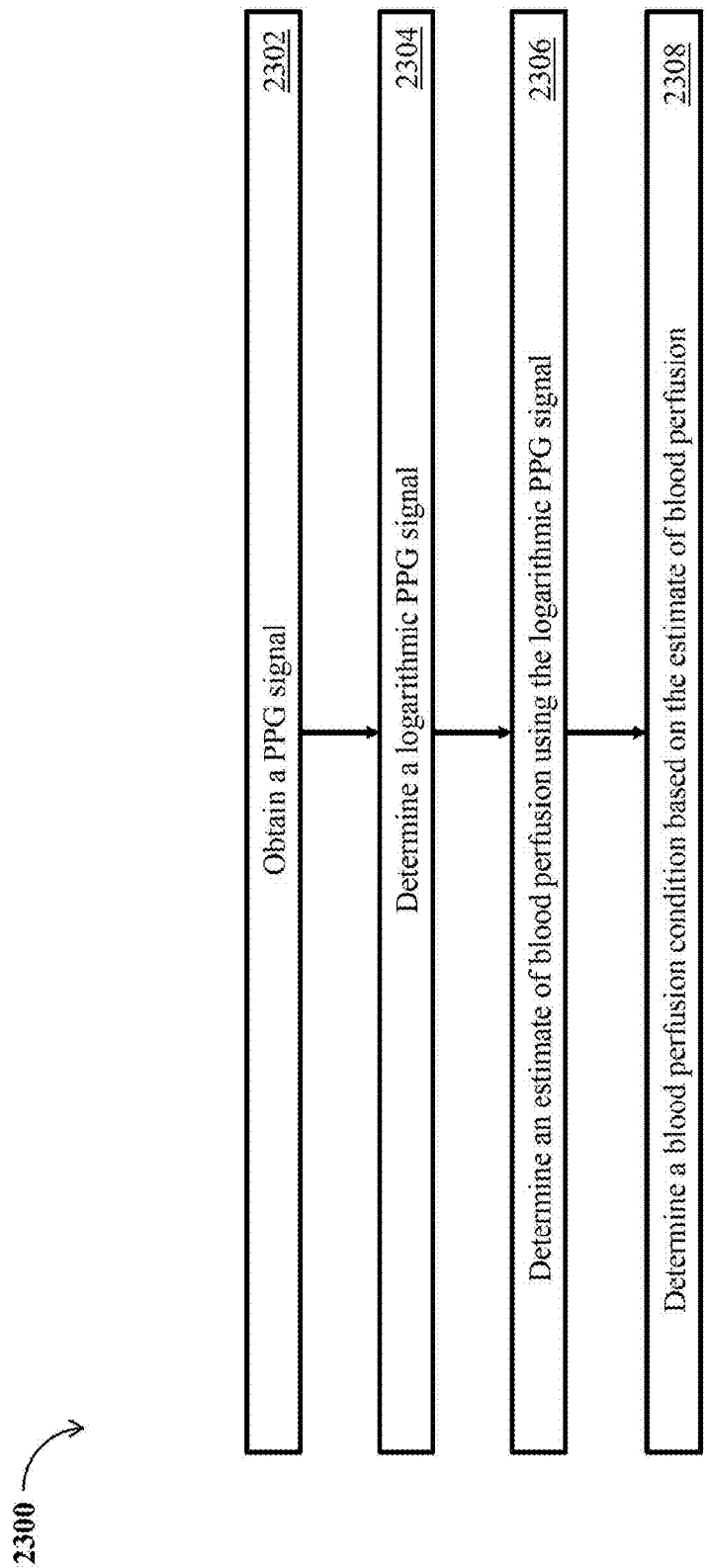
FIG. 23 shows a flowchart illustrating a method of determining perfusion of a PPG signal, according to example embodiments.

Referring to FIG. 23, a flowchart illustrating a method 2300 of determining perfusion of a PPG signal is shown, according to example embodiments. The method 2300 can include obtaining a PPG signal (STEP 2302). The method 2300 can include determining a logarithmic PPG signal (STEP 2304). The method 2300 can include determining an estimate of blood perfusion using the logarithmic PPG signal (STEP 2306). The method 2300 can include determining a blood perfusion condition based on the estimate of blood perfusion (STEP 2308). The method 2300 can be performed by the computer system 100 or the corresponding processor 102, for example, upon executing the application 114. The method 2300 can be performed by other components (e.g., memory 104, BUS 106, light source 108, camera device 110, or display device 112) of the computer system 100, in conjunction with FIG. 1. The method 2300 can be performed by a remote device or a remote server. In some implementations, the method 2300 can be performed by a computer system 100 and a remote server. For example, the computer system 100 can be in communication with the remote server to delegate one or more tasks to the remote server. In this case, the remote server can perform the one or more tasks, such as performing at least one of STEPS 2302-2308, and transmit an output to the computer system 100. The method 2300 can be performed by other components discussed herein and perform features and functionalities in conjunction with at least one of FIGS. 1-22, for example. The method 2300 can be performed in conjunction with, sequential, or prior to at least one of other methods discussed herein, such as methods 400, 1100, 1500, etc.

Still referring to FIG. 21, in further detail, the computer system 100 can obtaining, by a computing device, a PPG signal generated from a sequence of images acquired using a photodetector (e.g., camera or RGB sensor 312) while a body part (e.g., a finger) is placed in proximity and in the field of view of the photodetector (STEP 2302). In some cases, the computer system 100 can obtain the PPG signal similarly to at least STEP 1902 in conjunction with FIG. 20A. For example, the computer system 100 can capture a sequence of images (e.g., a video) of a finger for a period of N time. The computer system 100 can obtain or generate the PPG signal using a sequence of images with a single color channel, such as only green or only red. In some cases, the computer system 100 can obtain the PPG signal using a sequence of images with multiple color channels (e.g., R, G, and/or B).

Prior to obtaining or generating the PPG signal, the computer system 100 can process raw images captured using the photodetector. For example, the computer system 100 can generate a sequence of downsampled color frames corresponding to the sequence of images by downsampling a respective color frame for each image of the sequence of images. The computer system 100 can downsample the images to reduce the resolution of the image for generating the PPG signal. By reducing the resolution (e.g., reduced to 5×5 pixels), the computer system 100 can decrease latency and reduce resource consumption when processing the sequence of downsampled color frames. The downsampled color frames may include only one color channel, such as green or red. In some cases, the downsampled color frames may include multiple color channels.

Responsive to generating the sequence of downsampled color frames, the computer system 100 can identify, in each downsampled color frame of the sequence of downsampled color frames, a respective image block representing a central image region of the downsampled color frame and having a first size smaller than a second size of the downsampled color frame. The respective image block can include or be referred to as a portion of the respective downsampled color frame. The central image region of the respective image block may be located at the center of the downsampled color frame. For example, in a 5×5 pixels image (among other sizes), the computer system 100 can determine that the central image region is located at the inner 3×3 pixels of the downsampled color frame. In another example, the computer system 100 can determine that the central image region is not located at the center or the inner portion of the downsampled color frame. Instead, the computer system 100 can identify the center image region located edges of the downsampled color frame. The central image region may be of any size smaller than the downsampled color frame. For example, if the downsampled color frame is 10×10 pixels, the central image region can be 5×5 pixels, 5×9 pixels, 7×4 pixels, among others.

The computer system 100 can generate a color intensity signal using the respective image blocks of the sequence of downsampled color frames. For example, the computer system 100 can identify, within the central image region of each respective image block, the color value or intensity value associated with image blocks. Based on the color value or the intensity value, the computer system 100 can generate a color intensity signal having at least one of the color values or the intensity value associated with the color intensity signal. Accordingly, the computing device can generate the PPG signal using the color intensity signal to determine a blood pressure value.

The computer system 100 can determine a logarithmic PPG signal by computing a logarithm of the PPG signal (STEP 2304). The logarithmic (sometimes referred to generally as a log) PPG signal can be proportional to the blood absorbance of light. For example, to estimate the blood perfusion, the computer system 100 can use at least one of the following metrics among other metrics for a PPG signal. The metric can include a transmitted light $T \propto X$, which can be directly proportional to the RGB values yielded or captured by the photodetector (e.g., the camera or the RGB sensor 312). The metric can include an absorbance of the tissue, as in formula (22).

$$A = -\log_{10}(T) \propto \log(X) \qquad (22)$$

The absorbance value can be denoted as A. The A can be proportional to the logarithm of the transmitted light based on formula (22) for A.

With A being proportional to the logarithm of the transmitted light, when T is subject to variations of the amplitude (e.g., with changes of incoming light or with changes of the multiplicative factor), A can be more robust (e.g., higher light absorbance by the tissue, which can reflect higher amplitudes for the PPG signal), with both the changes in incoming light or the multiplicative factor resulting only in variations of the offset, for example. In other words, variation in T can increase the robustness or absorbance level of A, with the changes in incoming light and multiplicative factor variating the offset of A. An example of the PPG absorbance A can be illustrated in part in FIG. 24A, for example. The PPG absorbance A can refer to the logarithmic PPG signal computed from $\log_{10}$ of T and X according to the formula discussed above.

The computing device can determine an estimate of blood perfusion in the body part using the logarithmic PPG signal (STEP 2306). As an example, the body part can be the user's finger, among other body parts. The estimate of blood perfusion can be based on the logarithmic PPG signal (or PPG absorbance A) calculated from the logarithm of the PPG signal. For example, the computer system 100 can determine the estimate of blood perfusion based on the amplitude calculated from the logarithmic PPG signal or the PPG absorbance A. In some cases, the estimate of blood perfusion can include or refer to the amplitude of the PPG absorbance A. For example, the computer system 100 can determine the estimate of blood perfusion by determining an envelope of the logarithmic PPG signal. The envelope can refer to the amplitude of the logarithmic PPG signal, e.g., the difference between the upper value of A and the lower value of A for each of the segments or portions of the logarithmic PPG signal. Accordingly, the computer system 100 can determine the estimate of blood perfusion using the envelope of the logarithmic PPG signal. In other words, the envelope may be indicative of the amplitude of the logarithmic PPG signal or at least a segment of the logarithmic PPG signal.

In some implementations, determining the envelope of the logarithmic PPG signal can refer to or include determining, for each time interval of various time intervals of the logarithmic PPG signal, a respective maximum and a respective minimum of the logarithmic PPG signal. For example, the logarithmic PPG signal can include various time intervals, each representing an interval of a PPG absorbance A, such as a pulse of A. For each time interval, the computer system 100 can determine the minimum (e.g., trough) and the maximum (e.g., upper peak) of A.

The computer system 100 can use the respective maximum and minimum to determine the envelope of the logarithmic PPG signal. In some cases, the computer system 100 can use the respective maximum and minimum of the logarithmic PPG signal to determine the estimate of blood perfusion in the body part.

The computer system 100 can compute the amplitude of the logarithmic PPG signal using the envelope of the signal. The computer system 100 can determine the envelope, denoted as $A_{lower}$ and $A_{upper}$, by computing the sliding maxima and sliding minima over a time period. In other words, the computer system 100 can use the maxima and the sliding minima as the estimate blood perfusion, e.g., based on the amplitude of the signal over time. The time period can refer to the time through the logarithmic PPG signal. The $A_{lower}$ and $A_{upper}$ of the envelope can be computed using formula (23).

$$A_{lower}(t) = \min_{t' \in [t-\frac{dt}{2}, t+\frac{dt}{2}]} A(t'), \quad (23)$$

$$A_{upper}(t) = \min_{t' \in [t-\frac{dt}{2}, t+\frac{dt}{2}]} A(t').$$

The computer system 100 can determine, for each of the time intervals, a respective local variation of the envelope of the logarithmic PPG signal. The respective local variation can be equal to a difference between the respective maximum and the respective minimum of the logarithmic PPG signal within the time interval. The local variation can be referred to as, or used interchangeably with other descriptive terms, such as a local width or an amplitude of the envelope of the logarithmic PPG signal. Formula (24) can be used to compute the local variation.

$$\Delta(t) = A_{upper}(t) - A_{lower}(t). \quad (24)$$

Accordingly, the computer system 100 can use the amplitude, which can be indicative of the blood perfusion, or the estimate of the amplitude to determine the blood perfusion condition.

Figure 24A:
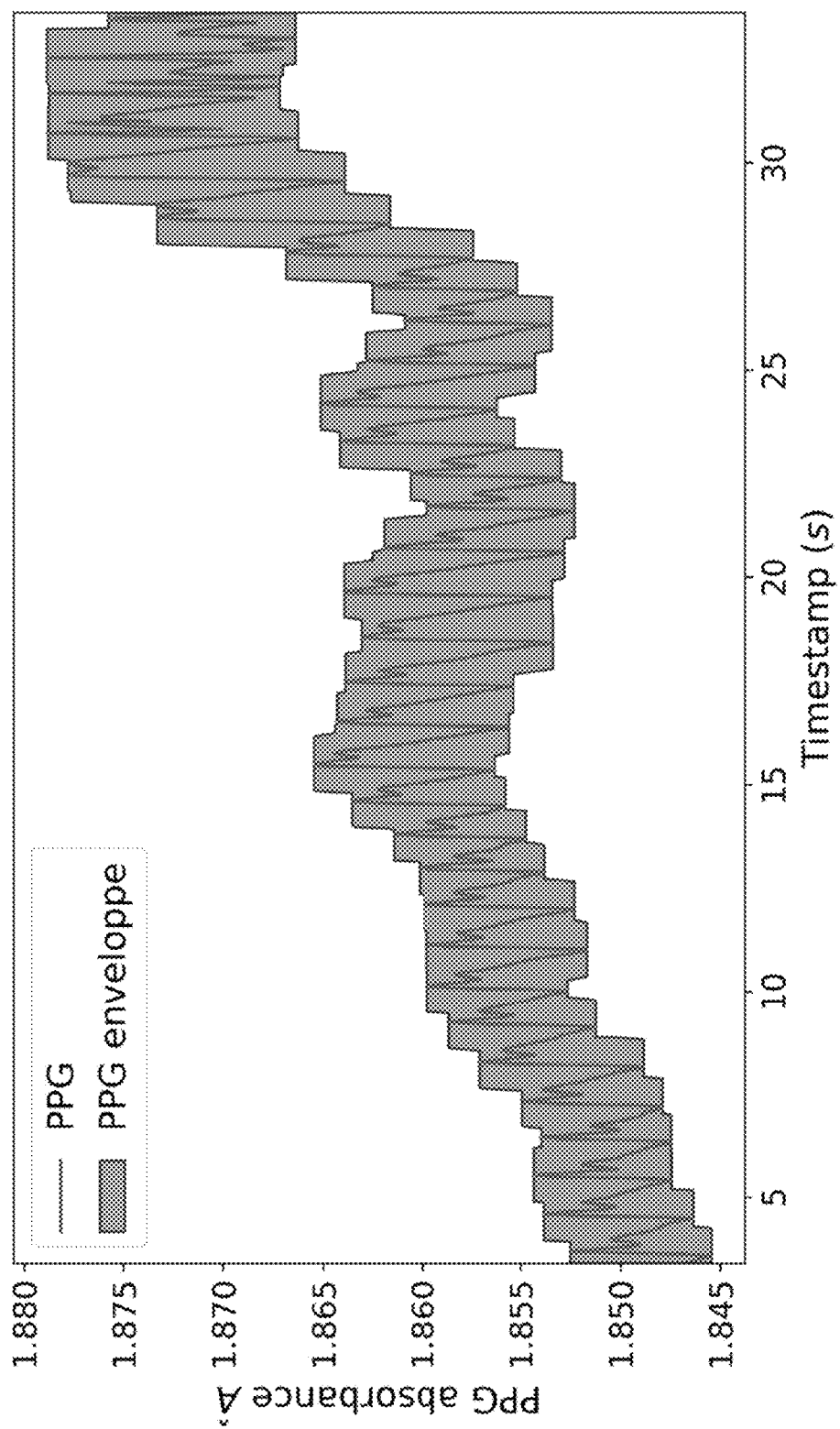
FIG. 24A illustrates an example of a negative logarithmic PPG signal (or PPG absorbance A) and the respective envelope, according to example embodiments.
Figures 24B, 24C:
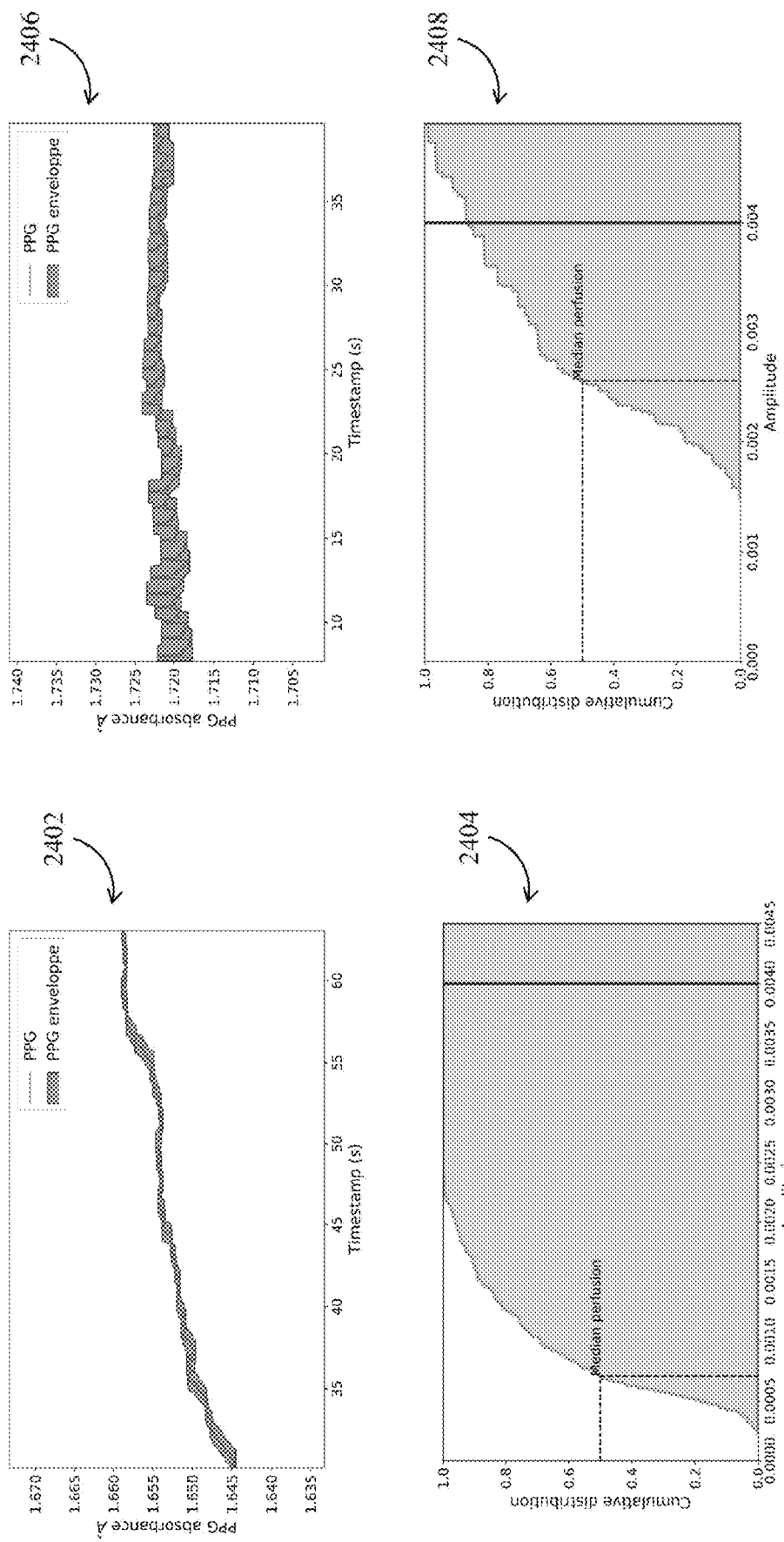
FIGS. 24B-E show plots illustrating various logarithmic PPG signals and respective amplitude distributions, according to example embodiments.
Figure 24D:
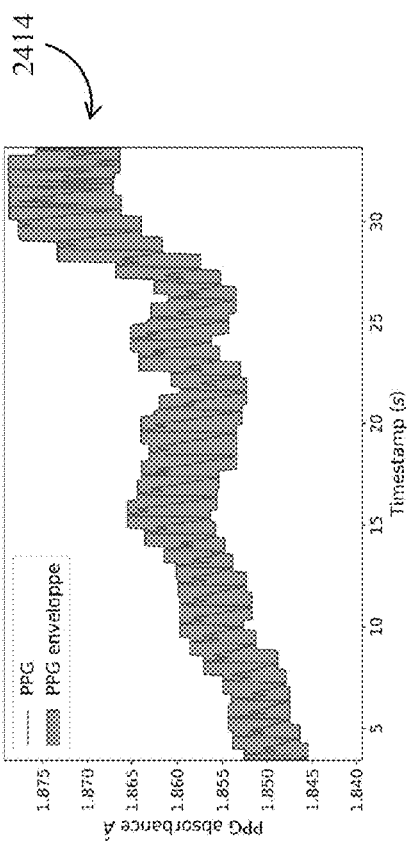
Figure 24D:
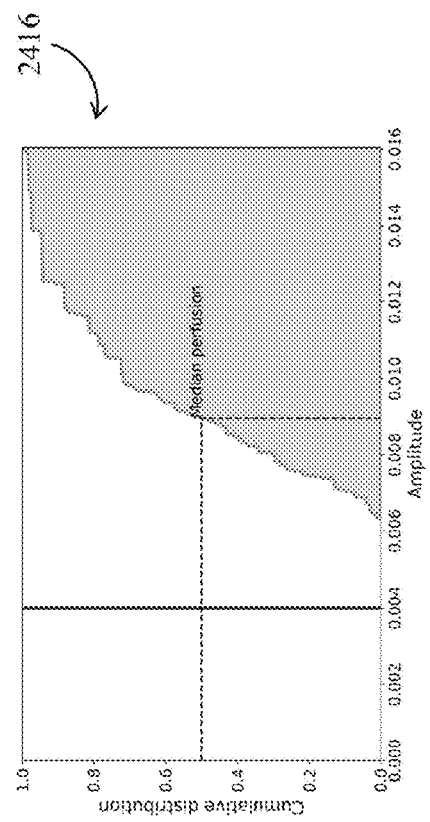
Figure 24D:
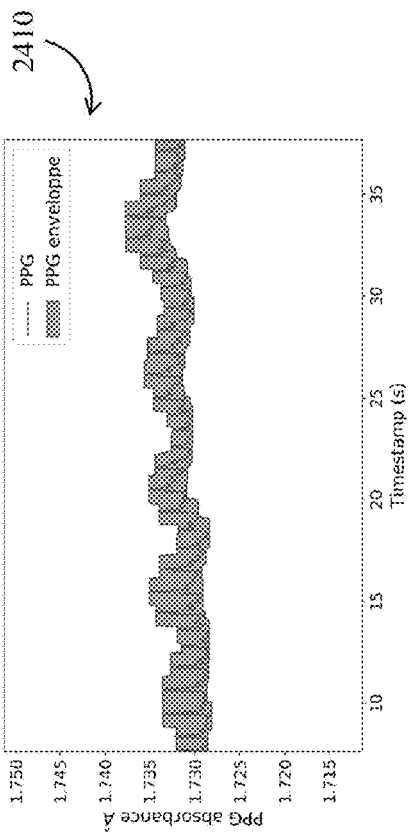
Figure 24E:
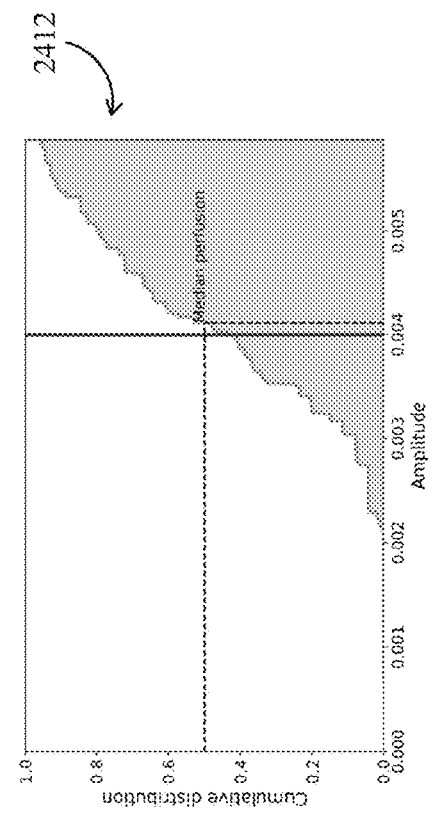

FIG. 24A illustrates an example of the logarithmic PPG signal (or PPG absorbance A) and the respective envelope, according to example embodiments. For example, the illustration of FIG. 24A can include a plot of PPG absorbance A over time (e.g., timestamp in seconds). In this example, the range of A can be from 1.845 to 1.880 and the length of time can be from 1 second to 35 seconds. Throughout the plot, the computer system 100 can compute and generate the logarithmic PPG signal denoted generally as the PPG (signal) in the plotted line. The computer system 100 can compute the envelope of the using the logarithmic PPG signal within the time intervals. As shown, for each of the time intervals, the envelope may vary in amplitude and offset. The computer system 100 can compute the offset of the logarithmic PPG signal based on the changes of incoming light or with changes of the multiplicative factor, since A is proportional to the logarithm of the transmitted light, for example. The width, girth, amplitude, or height of the envelope can vary through each of the time intervals within the logarithmic PPG signal. In particular, the computer system 100 can use the envelope indicative of the difference between the upper A and the lower A to determine the amplitude. As such, the computer system 100 can compute the amplitude for each of the time intervals of the logarithmic PPG signal. With the amplitude throughout the logarithmic PPG signal, the computer system 100 can generate a plot or a metric of the cumulative distribution of the amplitudes, indicating the number or a count for different magnitudes of amplitudes, as in the illustrative examples of FIGS. 24B-E.

In some implementations, determining the envelope of the logarithmic PPG signal can include applying a low-pass filter to the logarithmic PPG signal. The computer system 100 can apply the low-pass filter for each of various time intervals of the logarithmic PPG signal. For example, for each time interval, the computer system 100 can apply a first low pass filter to the logarithmic PPG signal, thereby discarding or ignoring values beyond the maximum value of A for the respective time interval in the logarithmic PPG signal. The computer system 100 can flip, reverse, or compute the negative of the logarithmic PPG signal, such that the minimum value becomes the maximum value, and vice versa, in this case. The computer system 100 can apply a second low-pass filter, which can discard or ignore the values beyond the maximum value of A (previously the minimum). The computer system 100 can revert the logarithmic PPG signal to positive. Accordingly, the computer system 100 can use the low-pass filter to determine the envelope of the logarithmic PPG signal. The computer system 100 can use other types of filters to determine the envelope of the logarithmic PPG signal.

The computer system 100 can determine the estimate of the amplitude (or the blood perfusion) of the logarithmic PPG signal using at least one other technique. For example, the computer system 100 can determine the estimate of the blood perfusion as a predetermined quantile (e.g., 5%, 10%, 90%, 95%, etc.) of the respective local variations of the envelope of the logarithmic PPG signal within the time intervals. In some implementations, the computer system 100 can determine the estimate of the blood perfusion as a median (e.g., quantile of 0.5 or 50%) of the respective local variations of the envelope of the logarithmic PPG signal within the time intervals. In some implementations, the computer system 100 can determine the estimate of the blood perfusion as an average or a mean of the respective local variations of the envelope of the logarithmic PPG signal within the time intervals. In some implementations, the computer system 100 can determine the amplitude of the logarithmic PPG signal as an average or a mean of the respective local variations of the envelope of the logarithmic PPG signal within the time intervals. In some implementations, the computer system 100 can determine the estimate of the blood perfusion as a maximum (e.g., maximum value) of the respective local variations of the envelope of the logarithmic PPG signal within the time intervals. In some implementations, the computer system 100 can determine the estimate of the blood perfusion as a minimum (e.g., minimum value) of the respective local variations of the envelope of the logarithmic PPG signal within the time intervals.

After computing the amplitude of the logarithmic PPG signal, the computer system 100 can determine the distribution of the amplitudes of different time intervals within the logarithmic PPG signal. For example, the computer system 100 can distribute amplitudes calculated from each of the time intervals of the logarithmic PPG signal in a graph having the cumulative distribution of the amplitudes. Examples of the graph can be shown in FIGS. 24B-E. The distribution of the amplitudes may be similar to a normal distribution, e.g., with some location and scale (e.g., x-axis and y-axis scaling), and some outliers. In this case, the location may represent the perfusion, which can be an amplitude with respect to the cumulative distribution.

The computer system 100 can determine an estimate of blood perfusion in the body part using respective local variations (e.g., amplitudes) of the envelope of the logarithmic PPG signal within the time intervals. Each local variation can correspond to the respective time interval of the logarithmic PPG signal. The computer system 100 can determine the blood perfusion condition (sometimes generally referred to as the perfusion indicated by the amplitude within the cumulative distribution of amplitudes) of the body part based on the estimate of the amplitude of the logarithmic PPG signal. As an example, to obtain a good estimate of the perfusion without many outliers, the computer system 100 can compute the median (e.g., a quantile of 0.5 or 50%) of the distribution to obtain the median perfusion. The computer system 100 can estimate the blood perfusion as:

$$P = \underset{t}{med}\,(\Delta(t)). \quad (25)$$

The "med" can denote the median of the distribution, which can be a value such that 50% of the distribution is below or equal to it and 50% is above or equal to the respective value. The median can be an example value or quantile used in this case. Instead of using the median, the computer system 100 can use other quantiles $q_{var}$ to estimate the amplitude so that at least a proportion $1-q_{var}$ of the signal has at least some amplitude P. Accordingly, the median can be a particular case with $q_{var}=0.5$, and other quantiles (e.g., $q_{var}=0.4, 0.45, 0.49, 0.51, 0.55, 0.6$, etc.) can be used to determine the perfusion based on the distribution of amplitudes.

The computer system 100 can determine a blood perfusion condition of the body part based on the estimate of blood perfusion (STEP 2308). The blood perfusion condition can include or indicate a low blood perfusion condition indicative of a cold body part. Based on the estimate of the blood perfusion (e.g., the estimate of the amplitude of the cumulative distribution of amplitudes), the computer system 100 determine if the blood perfusion condition, such as the user having low blood perfusion, should be raised. Examples of acceptable or unacceptable perfusions based on logarithmic PPG signals can be shown in FIGS. 24B-E.

For example, the computer system 100 can compare the estimate of the amplitude or the estimate of the blood perfusion (e.g., the value of P) of the logarithmic PPG signal to a threshold value $\theta$ to determine if the perfusion of the user is low or normal. The computer system 100 can determine the blood perfusion condition of the body part (e.g., whether the user has a low perfusion or a normal perfusion) based on the comparison of the estimate of the amplitude of the logarithmic PPG signal to the threshold value. If $P \leq \theta$ based on the comparison, the computer system 100 can determine that the perfusion is low. Otherwise, if $P > \theta$, the computing device can determine that the perfusion is normal. In some implementations, if P is above a second threshold configured by the administrator, different from $\theta$, the computer system 100 may determine that the perfusion is high, which may raise a different blood perfusion condition (e.g., high blood perfusion condition indicative of an abnormally hot body part).

The threshold $\theta$ can be configured by the administrator. In some implementations, the threshold $\theta$ can be determined by a machine learning model. For example, the computer system 100 can feed various samples of PPG signals with PPG absorbance A having different amplitudes. These samples of PPG signals can be marked or labeled indicating one or more features of the PPG signals, such as the peak up, peak down, zero-crossing up, zero-crossing down, duration of the PPG pulse segments, among others. The machine learning model can attempt to compute these features from the sample PPG signals having the respective PPG absorbance A with different amplitudes. Based on the performance (e.g., the accuracy) of feature extractions, the machine learning model can determine, provide, or indicate a threshold $\theta$ predetermined or preset for the computer system 100, such that perfusion above the threshold $\theta$ can be accepted. Hence, the computer system 100 can provide an accurate measurement of the blood characteristics using acceptable perfusion calculated from the logarithmic PPG signal.

The computer system 100 can provide, responsive to determining the blood perfusion condition, an alert to the user placing the finger on the lens. The alert can indicate a cold body part or that the body part on the lens is cold, which may produce a lower accurate measurement. In some implementations, the alert can include one or more instructions for warming up the body part. Accordingly, the computer system 100 can inform or alert the user to retry the measurement with increased perfusion (e.g., increase the temperature of the body part used for measurement), for example. By performing the features and functionalities discussed above, and using the estimate of blood perfusion to determine the blood perfusion condition, the computer system 100 can capture good quality PPG signals with high SNR for increasing the accuracy of blood volume measurement for identifying any conditions of the user.

Referring to generally to FIGS. 24B-E, example illustrations of the logarithmic PPG signal, the envelope of the logarithmic PPG signal, and their corresponding PPG amplitude distribution are shown, according to inventive concepts of this disclosure. The example illustrations can include plots (e.g., graphs or subplots) 2402-2416, where plots 2402, 2406, 2410, and 2414 corresponds to plots 2404, 2408, 2412, and 2416, respectively. The features, functionalities, operations, or techniques performed in relation to the example illustrations can be performed by the computer system 100 executing the application 114, a remote server, among other components herein. In some cases, the features and functionalities can be performed by the combination of the computer system 100 and the remote server. The features and functionalities discussed herein can be performed in conjunction with methods and operations discussed in at least one of FIGS. 1-22G, for example.

The computer system 100 can compute the logarithmic PPG signals for plots 2402, 2406, 2410 and 2414 based on the respective PPG signals. Using the logarithmic PPG signals, the computer system 100 can compute the respective envelopes as shown in the plots 2402, 2406, 2410 and 1414. The computer system 100 can compute the respective amplitudes of an envelope for each of the time intervals within the logarithmic PPG signal. With the respective amplitudes for each logarithmic PPG signal, the computer system 100 can determine the distribution of the amplitudes, as presented in plots 2402, 2408, 2412 and 2416, for example.

The computer system 100 can determine the perfusion of the distribution of amplitude based on a predetermined quantile indicative of the perfusion. In the example illustrations, the quantile can be configured to 0.5 or 50%. With a quantile of 0.5, the computer system 100 can determine an estimate of the amplitude or a value at the median or 50% of where all amplitudes fall within the plot. In some other implementations, the computer system 100 can be configured to determine the perfusion at a different quantile, such as the average/mean of all amplitudes, a quantile of 0.4, 0.6, 0.55, among other quantiles. In some embodiments, the computer system 100 can determine the median perfusion for plot 2404 as approximately 0.0007 amplitude, for plot 2408 as approximately 0.0026, for plot 2412 approximately 0.0042, and for plot 2416 approximately 0.009.

The computer system 100 can compare the perfusion to a threshold to determine if the condition (e.g., low perfusion condition, sometimes referred to as cold finger condition) should be raised. The threshold may be configured by the administrator of the computer system 100 or determined by a machine learning model trained using historical PPG signals, historical logarithmic PPG signals, among other samples. Further from the previous examples, the computer system 100 can compare the determined perfusion to a threshold of 0.004. The threshold can be presented in the plots 2404, 2408, 2412 and 2416 as a perpendicular line at the x-axis value of 0.004. Perfusions less than or equal to the threshold can be considered as low perfusion, which may trigger a low perfusion condition. Perfusions higher than the threshold can be considered normal perfusion.

Based on the calculated median perfusions, the computer system 100 can determine that the median perfusions of plots 2404 and 2408 are lower than the threshold and that the median perfusions of plots 2412 and 2416 are higher than the threshold. Accordingly, the computer system 100 can alert or notify the user of the low perfusion condition for logarithmic PPG signals of FIGS. 24B-C. As for FIGS. 24D-E, the computer system 100 can proceed to measure the results of the blood volume or other conditions of the user using the respective PPG signal captured from the body part (e.g., the finger) of the user.

In some implementations, the computer system 100 can compare the perfusion to a second threshold representing the maximum allowed perfusion (not shown). For example, the computer system 100 can determine that the perfusion at the preconfigured quantile (e.g., median, average, etc.) higher than the second threshold can indicate a high perfusion condition or that the finger is too hot, in some circumstances. Therefore, similar to the previous example, the computer system 100 can alert the user of high perfusion conditions if the estimate of blood perfusion exceeds or equal to the second threshold. Otherwise, the computer system 100 can proceed to determine other conditions or to measuring the blood volume results for the user if the perfusion is below the second threshold.

D.6. Saturation Based Conditions

For a PPG signal to be considered as a good PPG signal, the signal should be in the linear range of the camera or exhibit linear characteristics between the incident physical light and measured light. Therefore, the saturation of the images should be balanced, such as not too dark and not too bright. The features, functionalities, operations, or techniques discussed herein can be performed by the computer system 100, a remote server, or the combination of the computer system 100 and the remote server. As an example, the computer system 100 can achieve at making the digitalized signal, which is a transformation of the physical signal, as close to a linear transformation as possible. The computer system 100 can determine, for each image frame of a sequence of image frames, if pixel values of the image are within the linear range or exhibit non-linear characteristics.

The computer system 100 can capture and downsample images of the body part (e.g., a finger of the user) from the camera. The downsampled images can include or be preconfigured to a size of 5×5 pixels, for example. The computer system 100 can downsample the images to any other size based on the configuration for downsampling images. To determine the level of saturation for each of the image frames, the computer system 100 can be configured with one or more thresholds, such as a dark saturation threshold or a bright saturation threshold. The computer system 100 can compare the macropixel data or the pixel color values of each image to the thresholds. The dark saturation threshold and the bright saturation threshold can be preconfigured by an operator/administrator or determined by a machine learning model analyzing the threshold values (e.g., upper and lower values) for the color values to be within the linear range, such as in the measured light to the incident physical light spectrum. The dark saturation threshold can be denoted as $\theta_{min}^c$, where c can denote the color channel, e.g., $\theta_{min}^{green}$, $\theta_{min}^{red}$. By comparing the macropixel data to $\theta_{min}^c$, the computer system 100 can determine if the macropixel data is too low for being in the linear range.

The $\theta_{min}^c$ can be predetermined or preset to a value, such as 5, 10, 15, 20, among other values lower than the bright saturation threshold. In this case, the values for the macropixel data and the thresholds may range from 0 to 255 for 8-bits colors, for example. In other cases, the values for the macropixel data and the threshold may have a higher or lower range, depending on the bit size of the color spectrum or color values captured by the camera. The thresholds (e.g., dark saturation threshold or bright saturation threshold) can be set for each color channel or for a combination of multiple color channels.

The bright saturation threshold can be denoted as $\theta_{max}^c$, which can be the threshold for the maximum macropixel data. The computer system 100 can use $\theta_{max}^c$ to determine if the macropixel data is too high for being in the linear range. The $\theta_{max}^c$ can be a threshold for each of the color channel, e.g., $\theta_{max}^{green}$, $\theta_{max}^{red}$. The $\theta_{max}^c$ can be preconfigured or preset to a value, such as 240, 245, 250, among other values. In this case, the maximum value may not exceed 255. Further, to determine if a saturation condition should be raised, the computer system 100 can determine if a threshold or a total number of maximal incorrect frames is exceeded based on a sequence of images compared to $\theta_{min}^c$ and $\theta_{max}^c$. The maximal incorrect frames can be denoted as Nsat. The computer system 100 can compare the total number of frames that do not satisfy $\theta_{min}^c$ or $\theta_{max}^c$ to Nsat to determine if there are too many incorrect frames. The Nsat can be preconfigured to any number of image frames, such as 30, 60, 90, 120, among other numbers of image frames. When comparing the total number of frames that do not satisfy $\theta_{min}^c$ or $\theta hd max^c$ to Nsat, the total number of frames may be consecutive image frames or non-consecutive image frames within a sequence of images. Accordingly, with the parameters discussed above, including the thresholds and Nsat, the computer system 100 can determine if an error condition (e.g., isDarkSaturating or isBrightSaturating) should be raised.

In further detail, the computer system 100 can capture images of the user's finger using a camera or a photodetector. The camera can be a device that transforms a continuous physical value (e.g., light intensity) into a discrete numerical value. Referring back to FIG. 11, a plot of a transfer function between incident physical light (e.g., light intensity or value emitted by the light source 108 or the light going into the camera) and the measured light (e.g., light intensity or value captured by the camera) can be shown. The data of the plot can be presented on a logarithmic scale (e.g., increment of the power of 10). The camera can transform the continuous physical value into a discrete numerical value from 0 to 255, however, the light emitted by the light source 108 can exceed beyond an intensity or the value of 255.

Still referring to FIG. 11 as an illustrative example, the plot can include three lines noted as no quantization, pixels with noise and quantization, and pixels without noise and quantization. First, with no quantization line, no quantization nor transformation has occurred in this case, which the transfer function can be the identity function. Hence, the no quantization line can be the reference line for an ideal case with linear characteristics at any range presented in the plot. In a second case, if individual pixels are taken without any noise nor binning (e.g., no averaging multiple pixels or no downsampling), the transfer function would have a stair-like representation (e.g., non-linear characteristics). In this second case, the transfer function can be very rough at the low incident physical light and measured light values (e.g., labeled as artifacts range due to quantization) and thresholded at the higher values (e.g., beyond the 250 value or other values in the thresholding range).

In a third case, if pixels are subject to some noise and averaged locally (e.g., downsampled or averaged between multiple pixels), while the transfer function may be represented with stair-like characteristics low values, the transfer function can be smoother than in the second case. For example, the higher the incident intensities (e.g., higher incident physical light value or measured light value), the pixel values of the pixels can be more smoothly until the thresholded value or range. In this third case, the medium range (e.g., labeled as a linear range) of pixel values can better represent or achieve the linearity characteristic of the identity transfer function. The linear range can be from 100 to 150, 90 to 160, among other ranges which can be predetermined based on analysis of historical transfer functions.

By downsampling the image for determining the saturation, the computer system 100 can evaluate the saturation of the image based on the third case discussed above, such as with noisy individual pixels and aggregation of batches of pixels into a single macro pixel by downsampling the image. The computer system 100 can limit the spread of values to an acceptable range in the approximatively linear portion of the transfer function, e.g., within the linear range, as shown in FIG. 11. To determine if the pixel values are in the acceptable range or within the linear range, the computer system 100 can classify one or more images into multiple non-disjoint and non-exhaustive categories, such as too bright, too dark, a combination of too bright and too dark, or normal light intensity.

For example, the computing device can determine if the color value, such as red or green is less than $\theta_{min}^{c}$ of the respective color channel. If at least one macro-pixels is too dark (e.g., red<$\theta_{min}^{red}$ or green<$\theta_{min}^{green}$), the computer system 100 can flag the image as isDarkSaturating or raise the dark saturation condition (e.g., DARK_SATURATION) indicating that at least a portion of the image is too dark. In another example, the computer system 100 can determine if the color value is greater than $\theta_{max}^{c}$, which indicates that at least a portion of the image is too bright. If at least one macro-pixels is too bright (e.g., red>$\theta_{max}^{red}$ or green>$\theta_{max}^{green}$), the computer system 100 can mark or flag the image as isBrightSaturating or raise the light saturation condition (e.g., LIGHT_SATURATION) indicating that at least a portion of the image is too bright. By comparing the color values to the thresholds, the computing device can determine a boolean value corresponding to the respective error condition, such as to raise or not to raise the error condition. The threshold can be set to $\theta_{min}^{green}=\theta_{min}^{red}=10$ and $\theta_{max}^{green}=\theta_{max}^{red}=245$, for example. The threshold can be set to other values, such as a minimum of 100 and a maximum of 150, a minimum of 140 and a maximum of 200, etc.

Subsequent to raising at least one of the conditions, the computer system 100 may alert the user of the error condition(s). For example, the computer system 100 can alert the user of the light_saturation or the dark_saturation condition based on the determined condition. By alerting the user, the user can maneuver the finger to correct or address the alerted condition. In some cases, the computer system 100 can provide a hint to the user, such as to better cover the lens with the finger if the image is too bright, increase the light intensity, or cover a portion of the finger on the light source 108, if the image is too dark. In some implementations, the computer system 100 can aggregate the flagged or marked images within a sequence of images to determine the total number of images that are too bright or too dark. The computer system 100 can compare the total number of images marked with at least one error condition to Nsat. If the total number of flagged images exceeds the threshold of Nsat, the computer system 100 can alert the user of at least one of the respective error conditions. The computer system 100 can alert the user with the error condition that are presented the most or with any error condition that is flagged. The total number of flagged images can consecutive flagged images or may not be consecutive images (e.g., total number of flagged images within the single sequence of images).

By determining whether the pixel values of an image are within the linear range, the computer system 100 can reduce the likelihood of artifacts due to the camera hardware. Further, by alerting the user of the error conditions or hinting the user of how to resolve the error conditions (e.g., readjust the placement of the finger), the computer system 100 can obtain images with pixel values within the linear range. If no error condition is detected in this case, the computer system 100 can determine if other error conditions are triggered or proceed to measure the PPG of the user. Thus, the computer system 100 can increase the accuracy of measuring the PPG of the user. The features and functionalities discussed herein can be performed independently, concurrently, or as a part of other features or functionalities described, for example, in other methods or other error detection techniques.

D.7. Accelerometer Based Conditions

To obtain a good PPG signal, the user or at least a body part (e.g., a finger) of the user present on the photodetector should be still. In other words, the user's finger should not move during the measurement process. As such, an accelerometer can be used to capture the movement or measure the stillness of the user. The features, functionalities, operations, or techniques discussed herein can be performed by the computer system 100, a remote server, or the combination of the computer system 100 and the remote server. For example, the computer system 100 executing the application 114 can detect the movement of the user using an accelerometer which may be built-in, adapted, or connected to the computer system 100. In this case, the acceleration of the computer system 100 can reflect or correspond to the acceleration or changes in the movement of the user. The acceleration can be measured in meter per second squared, inches per second squared, or other units for measuring acceleration.

The computer system 100 can capture one or more acceleration amplitudes associated with the time of capturing a sequence of images. The acceleration amplitude can be a metric (sometimes referred to as an acceleration metric) that measures the overall movement amplitude based on variations around acceleration at rest. The acceleration metric can be used to estimate the average movement intensity. The acceleration amplitude can increase (or decrease) proportionally to the changes in the user's position, such that extensive position changes can greatly increase the metric and short position changes may not increase the metric at least by a noticeable amount (e.g., short position changes have a small impact towards the average movement intensity).

In further detail, the computer system 100 can capture an acceleration signal from an accelerometer coupled to or in electrical communication with the computer system 100. The acceleration signal can be denoted as X, which can have a length of T. The acceleration signal or data can be plotted in a graph including or composed of three components (e.g., three individual signals) corresponding to the respective x, y, and z axes from the device. The three components can be individual acceleration signals measuring the acceleration of the computer system 100 or the user on the respective axis.

When capturing the acceleration, the acceleration data can be polluted or affected by the earth's gravity or gravitational acceleration. Ignoring terms (e.g., ignoring variables or expression from the calculation) created by the variation of the orientation of the computer system 100 (e.g., ignoring the angular acceleration), formula (26) can be presented for use by the computer system 100 to determine the measured acceleration for each axis.

$$\begin{cases} a_x^{measured}(t) = a^{device}(t) \cdot x(t) + g \cdot x(t) \\ a_y^{measured}(t) = a^{device}(t) \cdot y(t) + g \cdot y(t) \\ a_z^{measured}(t) = a^{device}(t) \cdot z(t) + g \cdot z(t) \end{cases} \quad (26)$$

In this case, the formula can include the gravity variable g for the acceleration formula of each axis. The constant gravity g can be modulated by the direction of the computer system 100 (e.g., g·x(t), g·y(t), or g·z(t)). To remove g, the computer system 100 can separate g from the direction of the computer system 100 by constructing or using formula (27).

$$\begin{aligned} \|a^{measured}\|^2 &= (a^{device}(t) \cdot x(t) + g \cdot x(t))^2 + \\ &\quad (a^{device}(t) \cdot y(t) + g \cdot y(t))^2 + \\ &\quad (a^{device}(t) \cdot z(t) + g \cdot z(t))^2 \\ &= \|a^{device}\|^2 + \|g\|^2 + 2 \cdot a^{device} \cdot g. \end{aligned} \quad (27)$$

With the above formula separating g from the direction of the computer system 100, the computer system 100 can use a high-pass filter on $\|a^{measured}\|^2$ to remove the component $\|g\|^2$ in formula (27). Hence, the computer system 100 can allow for values proportional to the acceleration of the device $\|a^{device}\|$ to be considered when calculating for $\|a^{measured}\|^2$, for example. The high-pass filter can be set at a cutoff frequency of 2.5 Hz, for example. In some cases, the cutoff can be set to a different frequency, such as 3 Hz, 4 Hz, 5 Hz, etc. The cutoff frequency can be denoted as $f_c$. Accordingly, by using the high-pass filter, the computer system 100 can filter out the gravity acceleration $\|g\|^2$. The high-passed filtered signal with a cutoff frequency $f_c$ can be denoted as ã.

With the above formula removed of $\|g\|^2$, the computer system 100 can determine ã by using the acceleration of the device to calculate for ã. The computer system 100 can use at least one of the accelerations from a respective axis, multiple accelerations from the respective axes, or an averaged acceleration between the axes, for example. The high-passed filtered signal ã can be computed for various portions and timeframe of the acceleration signal. Thus, the computer system 100 can compute or obtain various variations of amplitudes (e.g., envelope) of the acceleration signal distributed across a time period.

After computing the filtered acceleration ã, the computer system 100 can compute the median amplitude of the filtered acceleration ã based on the predetermined quantile of the distribution of acceleration values (sometimes referred to as an acceleration amplitude quantile). The acceleration amplitude quantile can be denoted as q and used for determining the variation metric or the amplitude of the distribution of amplitude values in the acceleration signal. In this case, the quantile can be preconfigured to 0.5 or 50%, which represents the median amplitude across the distribution of amplitude values. Formula (28) can be used to determine the acceleration amplitude.

$$A = \underset{t}{med} |\tilde{a}(t)|. \quad (28)$$

The "med" can denote the median of the distribution, e.g., the value such that 50% of the distribution is below or equal to it and 50% is above or equal to the median value. In this case, the median amplitude can be the acceleration amplitude denoted as A representing a value of the acceleration amplitude of the signal. The median can be a particular case with q=0.5. The computer system 100 can use other quantiles (e.g., the average, the mode, among other values, such as 0.45, 0.48, 0.52, 0.55, etc.) to estimate the amplitude A at q of at least a portion of the acceleration signal.

Responsive to or immediately after determining the amplitude A, the computer system 100 can compare A to a threshold value to determine if the movement of the device or the user is low or high. The amplitude A can be in the same unit as the acceleration, such as meter per second squared. The threshold can refer to an acceleration amplitude threshold, denoted as θ. The computer system 100 can use the threshold θ to determine if the user is still or in motion (e.g., extensive movement or not stable). The threshold can be predetermined by the administrator or a machine learning model. For example, the machine learning model can be trained using sample data. The sample data can include PPG signal data and historical acceleration data having various acceleration amplitudes. The machine learning model can use the sample data with various acceleration amplitudes as references to determine different acceleration amplitudes that yield good or poor results for identifying, extracting, or analyzing features from the PPG signal, for example. In another example, the threshold θ can be preconfigured to 0.05, which by having an amplitude below this value can be considered to yield good results when measuring the PPG of the user. Other values can be used as the threshold θ, such as 0.04, 0.045, 0.055, 0.06, etc.

For example, if A≥θ, the computer system 100 can determine that the boolean value for "isMovementDetected" (sometimes referred to as MOVEMENT condition) is true (e.g., a value of 1). In this case, the computer system 100 can raise the movement condition indicating that the user is not stable or moving during the measurement. By raising the movement condition, the computer system 100 can alert the user of the error condition. In some cases, the computer system 100 can provide the user with a hint to avoid the error condition in the next measurement attempt. The hint can include notifying the user to be more stable or stay still, avoid movement, place the device (e.g., the computer system 100) on a flat/stable surface, among other suggestions.

In some cases, the computer system 100 can determine that A<0. In this case, the computer system 100 can determine if any other error conditions should be raised or proceed to measure the PPG of the user. Accordingly, the computer system 100 can determine how still the user is based on the acceleration data and the amplitude of the acceleration based on the quantile of the distributed acceleration values. In some implementations, the computer system 100 can extract the envelope of the acceleration signals, similar to extracting the envelope for PPG absorbance. By extracting the envelope of the acceleration signals, the computer system 100 can determine at least a region or a portion of the measurement time when the user is still. Thus, if the user is not still or moving at times during the measurement, the computer system 100 can use at least the region when the user is still to measure the PPG of the user, such that accurate PPG measurements can be obtained at least for the respective region.

D.8. Detection of Data Error Conditions Using a Color-Based Penalty

In subsection D.2, a cross-correlation based approach is described for detecting or estimating a relative position of a body part (or finger) of user based on an acquired sequence of images. The computer system 100 can use the estimated or the detected relative position of the body part (or finger) to provide feedback to the user. The feedback allows the user to properly place their body part (or finger) against the lens of the camera or photodetector to ensure a sequence of images of a quality that allows accurate and reliable detection or estimation of the blood pressure (or other vital signs) of the user.

In this subsection a color based approach for determining the relative position of the body part or finger with respect to a desired position (e.g., relative to the lens of the camera or the photodetector) is described. The computer system 100 can compute or determine penalty scores for various pixel positions based on color differences between color values of pixels corresponding to the pixel positions and a desired or predefined color value representing a color of light emitted or reflected from the body part towards the photodetector.

A finger or other body part well placed on the lens is a key factor for getting or generating a good quality PPG signal to allow for an accurate and/or reliable measurement of blood pressure. To that end, methods and systems described herein include processing a captured image sequence in order to help the user properly placing or positioning their finger or body part on the lens of the camera or photodetector. A finger helper approach can be based on the idea that when the finger (or body part) is well positioned, light goes through (and gets reflected from) the flesh giving it an orange color. When some of the light does not go through the finger it most likely keeps its original color (e.g., white). Accordingly, the computer system 110 can use color as an indicator of well or proper positioning or placement of the finger or other body part.

Figure 25A:
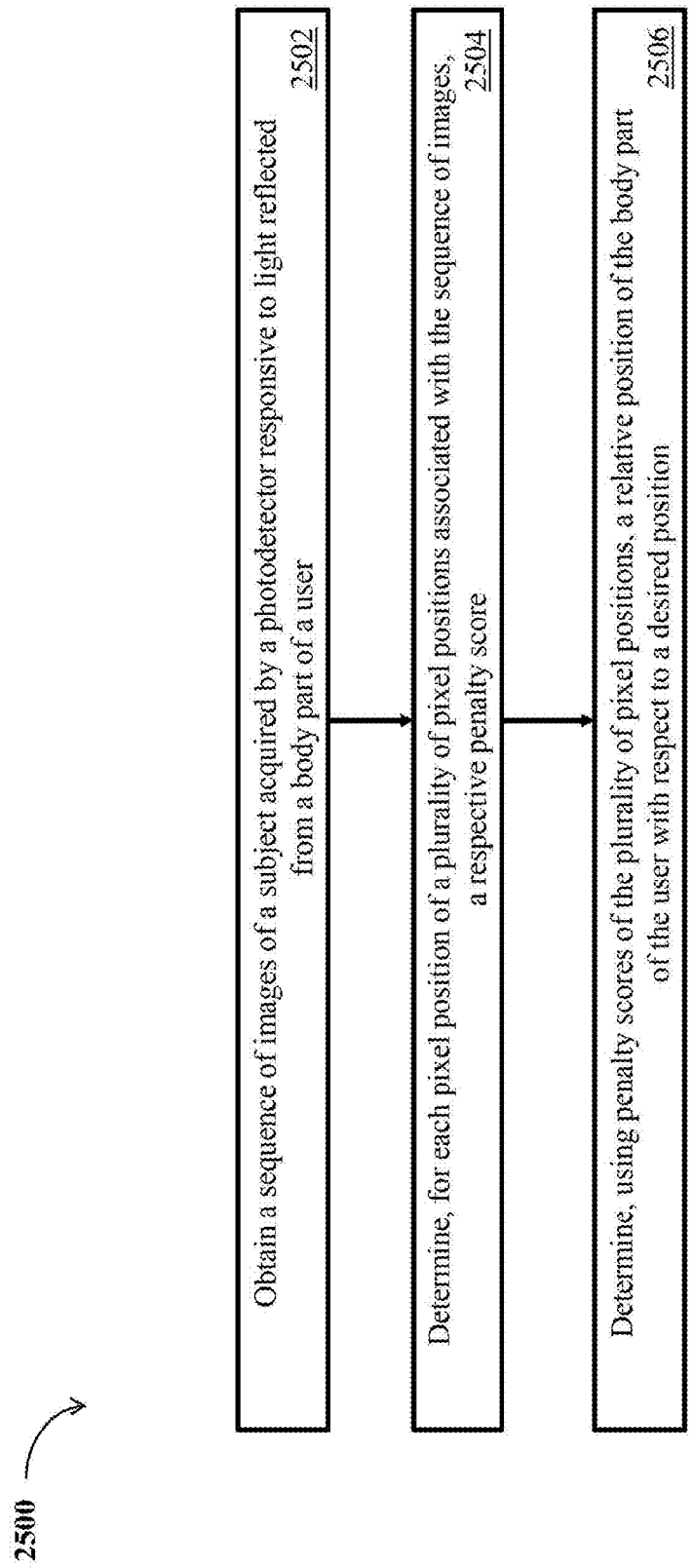
FIG. 25A shows a flowchart illustrating a method of detecting placement of a body part (e.g., a finger) facing a photodetector, according to example embodiments.

Referring now to FIG. 25A, a flowchart illustrating a method 2500 of detecting placement of a body part (e.g., a finger) facing a photodetector is shown, according to example embodiments. In a brief overview, the method 2500 can include obtaining a sequence of images acquired by the photodetector responsive to light emitted by or reflected from the body part (STEP 2502). The method 2500 can include determining, for each pixel position of a plurality of pixel positions associated with the sequence of images, a respective penalty score indicative of a similarity between a color value of a pixel of the pixel position and a desired color value (STEP 2504). The desired color value can represent a color property of light emitted by or reflected from body parts when placed opposite to the photodetector. The method 2500 can include determining, using penalty scores of the plurality of pixel positions, a relative position of the body part of the user with respect to a desired position (2506). The method 2500 can be performed by the computer system 100 or a computing device thereof. The method 2500 can be performed, or executed, by the computing device hosting the photodetector or camera 110 or another computing device (e.g., a remote server, desktop or laptop, among others) that is communicatively coupled to the device capturing or recording the sequence of images.

The method 2500 can include the computer system 100 obtaining a sequence of images acquired by the photodetector responsive to light emitted by or reflected from the body part (STEP 2502). The photodetector or camera 110 can acquire the sequence of images as discussed above, for example, with regard to step 402 of FIG. 4, step 1602 of FIG. 16 or step 1802 of FIG. 18. The computing device hosting the photodetector 110 or another computing device can obtain the acquired or recorded sequence of images. The computer system 100 can process image frames of the sequence of images sequentially as they are received.

In some implementations, the method 2500 can further include the computer system 100 downsampling each image frame of the sequence of images to generate a corresponding sequence of downsampled images, e.g., as discussed above with regard to steps 404, 1604 and/or 1804 of FIGS. 4, 16 and 18. Downsampling the sequence of images can lead to significant reduction in the method 2500.

The method 2500 can include determining, for each pixel position of a plurality of pixel positions associated with the sequence of images, a respective penalty score indicative of a similarity between a color value of a pixel of the pixel position and a desired color value (STEP 2504). The desired color value can represent a color property of light emitted by or reflected from body parts when placed opposite to the photodetector. In some implementations, the color property can be (or can include) the orange color.

The computer system 100 can generate for each image of the sequence of images a corresponding penalty matrix. The penalty matrix can have a size equal to the size of each image (or color frame) of the sequence of images or the size each downsampled image (or downsampled color frames). For example, if each downsampled image frame has a size of $(d_x, d_y, 3)$ or $(d_x, d_y)$, then each penalty matrix can have a size $(d_x, d_y)$. The penalty matrix can be denoted as $\Delta$, and can include penalty scores for pixels (or pixel positions) of a corresponding downsampled image frame (or corresponding image frame of the sequence of images). For instance, each pixel in the downsampled image frame can have a corresponding penalty score in the corresponding penalty matrix Δ.

Figure 25B:
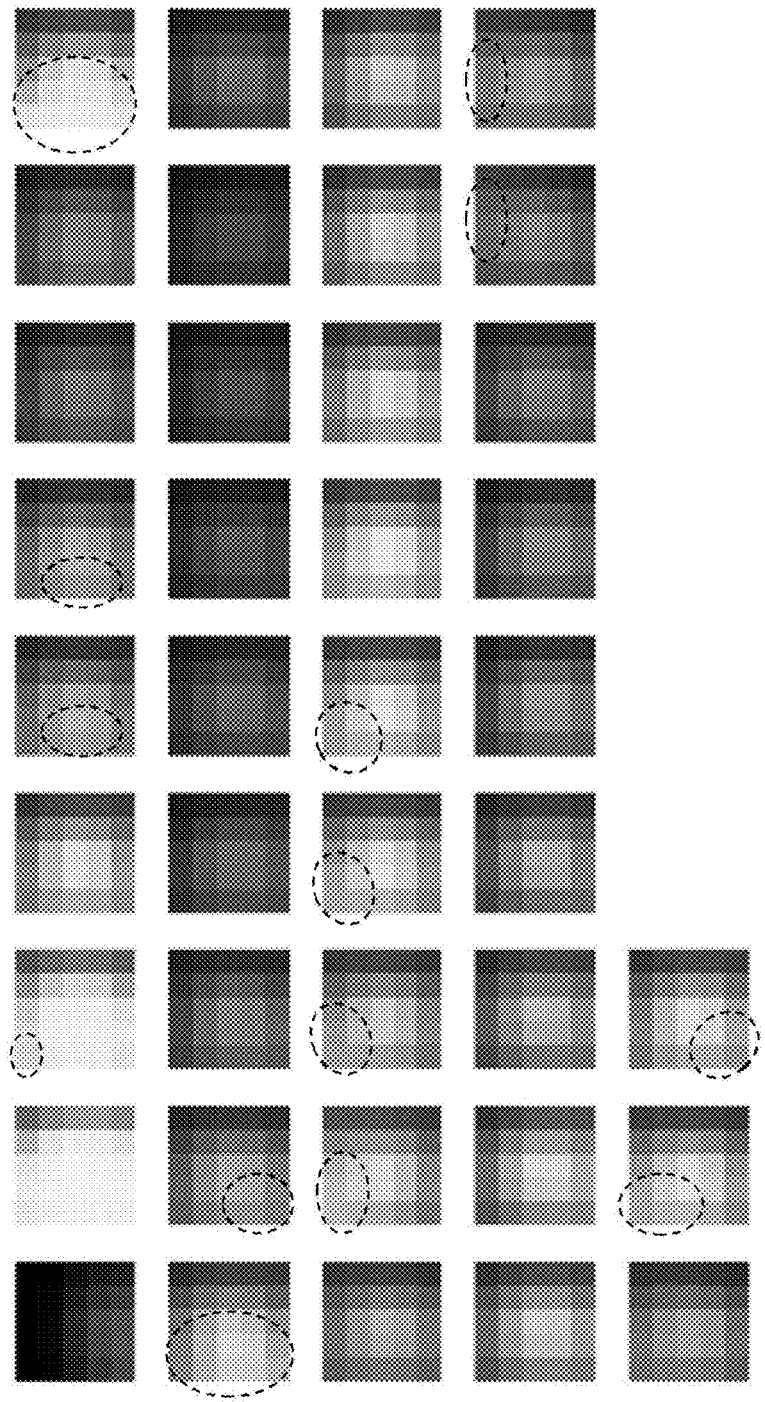
FIG. 25B shows raw images captured while a user moves his finger across a lens of a camera, according to example embodiments.

In some implementations, with a corrected white balance applied by the application 114 (or other module associated with the camera 110) the white color may be detected by the camera or photodetector 110 as green. Referring to FIG. 25B, raw images captured while a user moves his finger across the lens of the camera are shown. Some exposure adjustments occurred during the process. The green pixels (e.g., portions indicated via the dashed circles) correspond to portions of the image where the finger is not properly stuck to the lens. Light bounces off (or is reflected by) the finger, without going through the finger, and gets in the lens to the photodetector. The images in FIG. 25B provide an illustration that color can be a good indicator of whether or not the finger is well positioned or placed against the lens.

In the RGB color space, determining the color of the finger (or other body part) may not be straightforward. For instance, the finger color (whether as a color value or a color range) cannot be specified or determined using a single color channel among the red, green and blue channel. In contrast, the hue, saturation, luminance (HSL) color space allows for determining or specifying the finger (or other body part) color. In general, the HSL color space defines colors more naturally than other color spaces. The hue channel carries or reflects the color of captured light. The saturation channel, as the name suggests, depicts saturation or color purity. The luminance channel represents brightness.

Figure 25C:
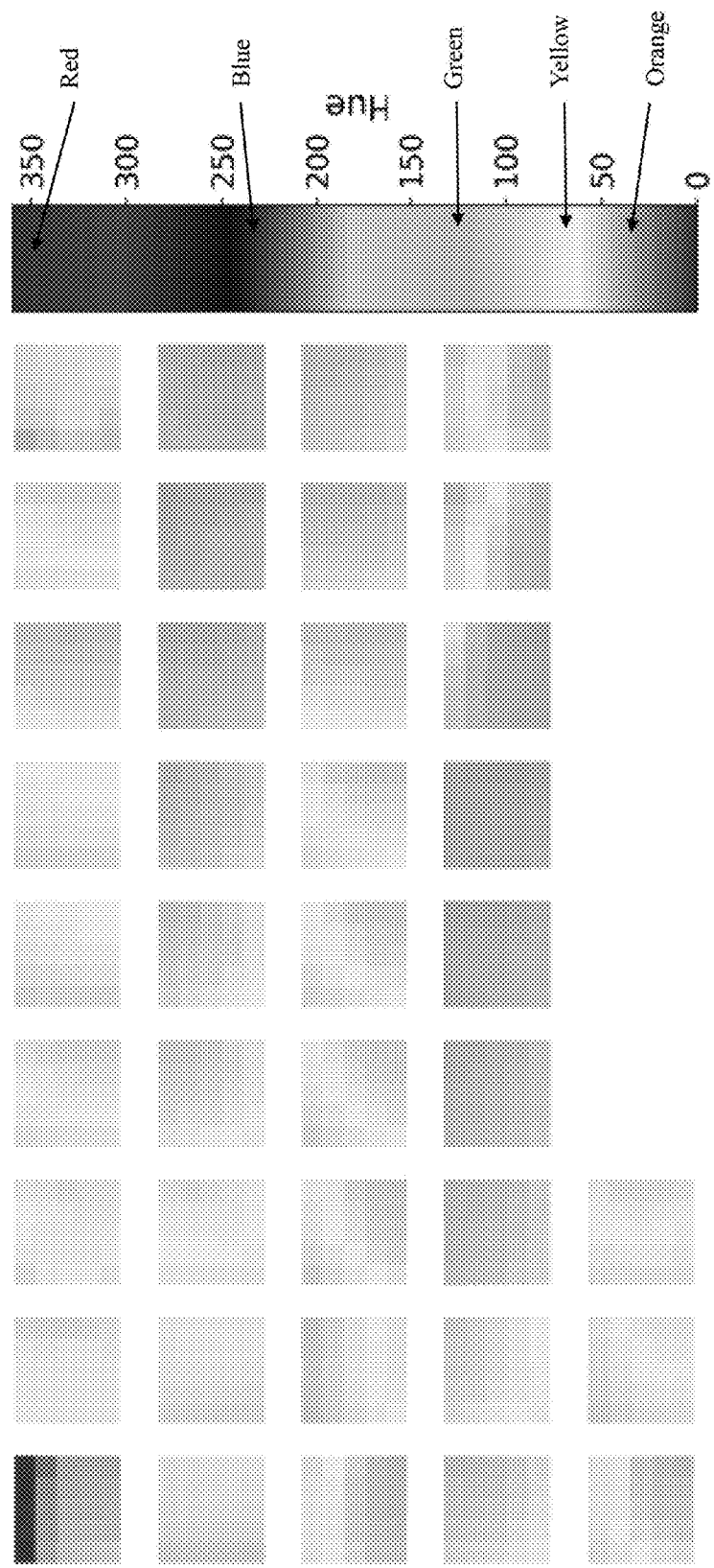
FIGS. 25C-E show the images of FIG. 25B in the HSL color space.
Figure 25D:
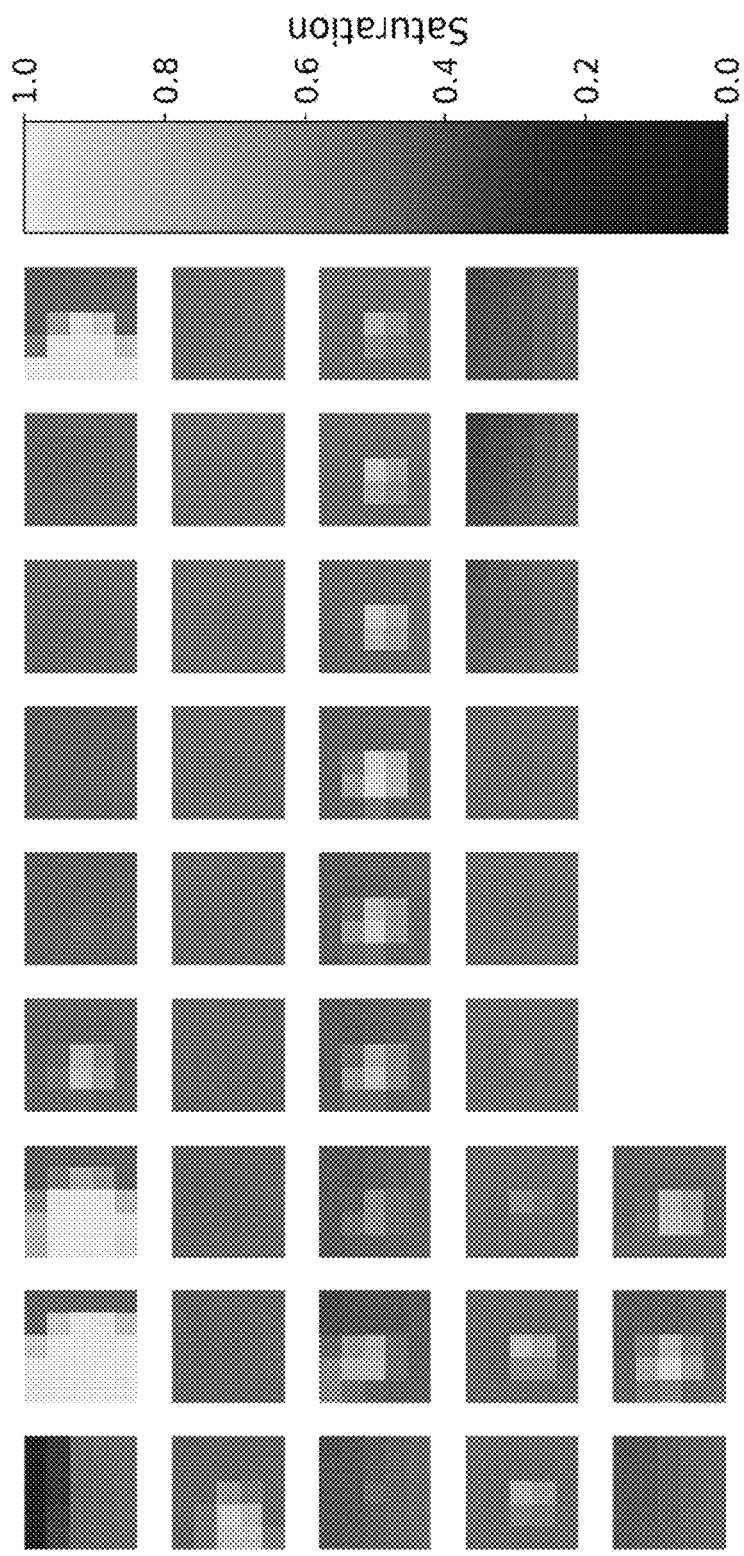
Figure 25E:
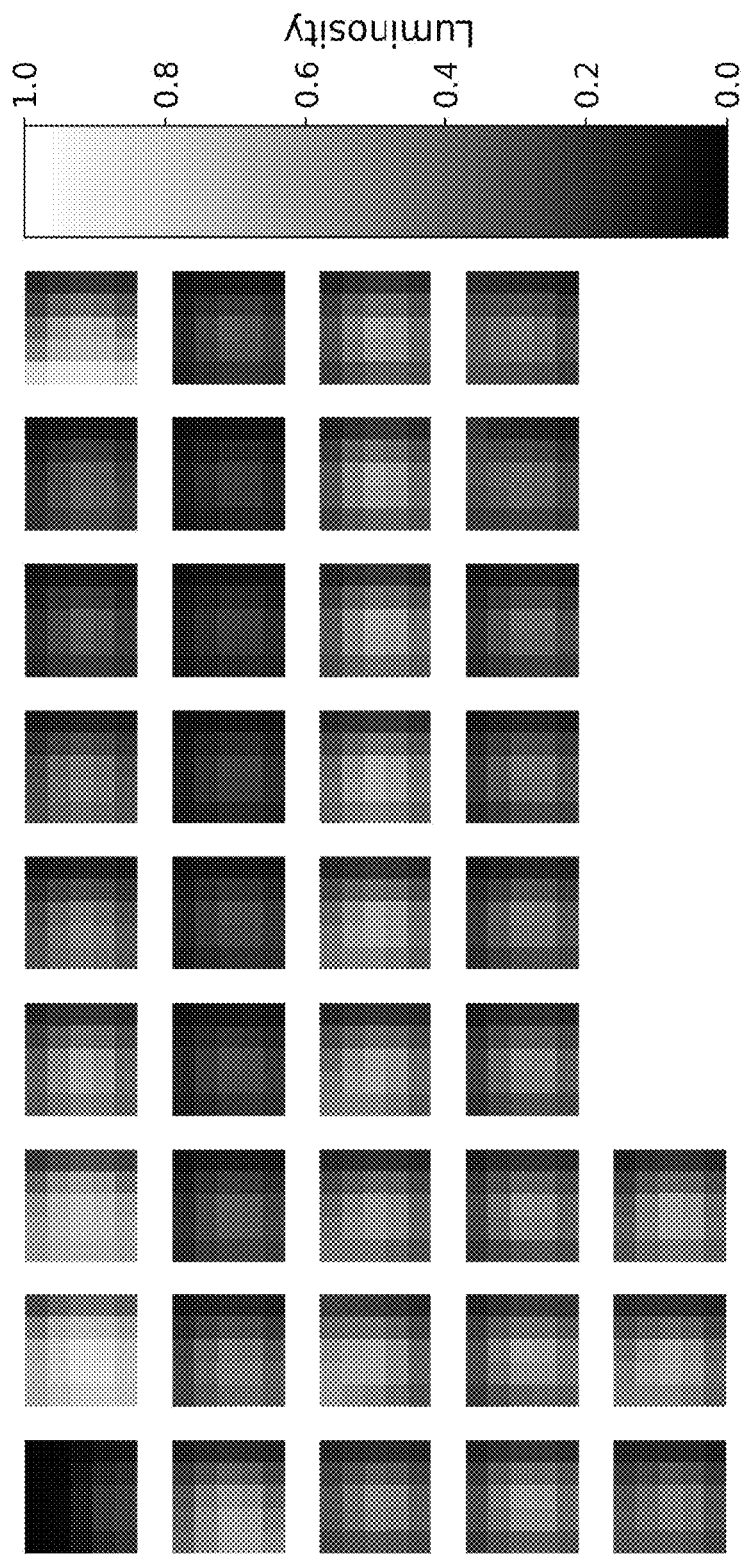

FIGS. 25C-E show the images of FIG. 25B in the HSL space. FIG. 25C shows the hue components of the images of FIG. 25B. The orange color represents light that was absorbed by the finger (or other body part) and then reflected back to be received by the photodetector. Pixels whose color drifts towards the green color are indicative of regions where light was not properly absorbed by the finger, and suggest that the finger (or other body part) should be moved toward that specific region.

FIG. 25D shows the saturation components of the images of FIG. 25B. The images of FIG. 25D show that some of the pixels are saturating when too much light comes into them. FIG. 25E show the luminance components of the images of FIG. 25B. The luminance components depict brightness at each. It is to be noted that in most of the images of FIG. 25E, the central region of the images is generally the one with highest luminance or brightness. The images in FIGS. 25B-E correspond to a downsampled sequence of images.

Referring back to FIG. 25A, the method 2500 can further include the computer system 100 transforming the sequence of images or the corresponding downsampled sequence of images to the HSL color space. For instance, the computer system 100 can convert the RGB color channels to hue, saturation and luminance color channels. The transformation is nonlinear, and the color of each pixel is depicted in the corresponding hue value of the pixel. To perform the transformation, the computer system 100 can define or determine the Chroma C in terms of the extremal RGB channel values. Specifically, the computer system 100 can determine m as the minimum color value among the R, G and B color channels, e.g., m=min (R,G,B), and determine M as the maximum color value among the R, G and B color channels, e.g., M=max (R,G,B). The computer system 100 can then determine the Chroma C as C=M−m. The Chroma can be viewed as representing an absolute amount of pure color in all colors.

Figure 25F:
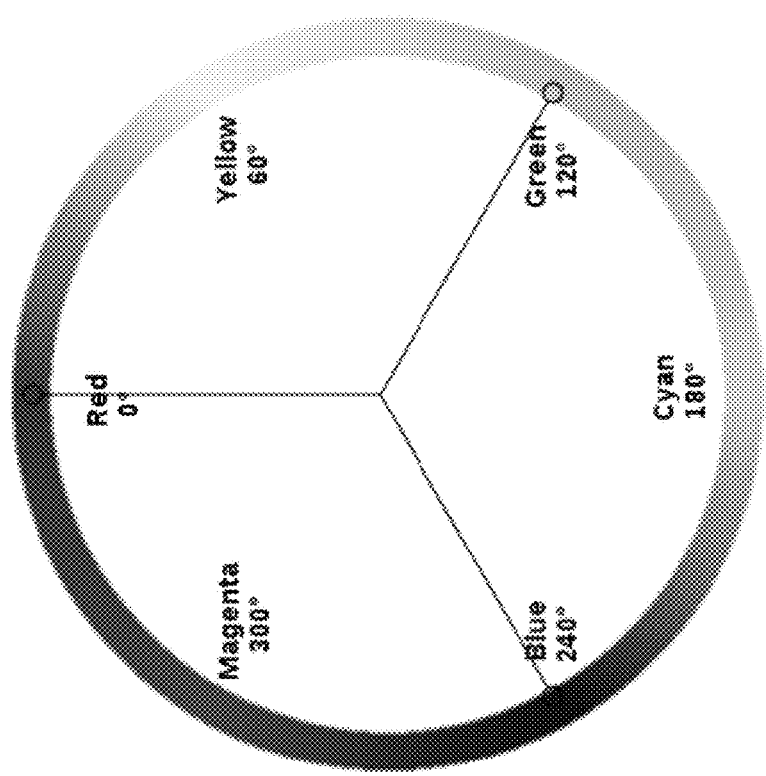
FIG. 25F shows a diagram illustrating the chromatic circle.

Referring now to FIG. 25F, a diagram illustrating the chromatic circle is shown. The chromatic circle is designed so that different colors are assigned different degrees in the circle. The computer system 100 can determine the hue value H for each pixel as an angle of a corresponding color on the chromatic circle:

$$H = 60° \cdot \begin{cases} 0 & \text{if } C = 0 \\ \dfrac{G-B}{C} \bmod 6 & \text{if } M = R \\ \dfrac{B-R}{C} + 2 & \text{if } M = G \\ \dfrac{R-G}{C} + 4 & \text{if } M = B \end{cases} \quad (29)$$

Equation (29) is designed so that a different degree is assigned for each separate pure color as depicted in FIG. 25F. Also, the degenerate colors like black, white and gray colors are assigned the degree 0°.

$$L = \frac{M+m}{2}.$$

The computer system 100 can determine the luminance for each pixel as Luminance can be used to estimate the power of the color or the amount of light contained in it. The computer system 100 can determine the saturation as:

$$S = \begin{cases} 0 & \text{if } L = 0 \text{ or } L = 1 \\ \dfrac{C}{1-|2i-1|} & \text{otherwise} \end{cases} \quad (30)$$

While Chroma represents an absolute color purity value, saturation can be viewed as representing relative color purity. In some implementations, the computer system 100 can determine or construct only hue color frames but not the saturation and luminance color frames.

Referring back to FIG. 25A, the computer system 100 can determine, for each pixel position of an image of the sequence of images or of a downsampled image of the sequence of downsampled images, a corresponding penalty score indicative of the similarity between a color intensity value of the pixel at the pixel position and the desired color value. The color value can represent a hue color value of the pixel of the pixel position and the desired color value can be a desired hue color value. The desired hue color value can represent the hue color value of fingers (or other body parts) when they are properly placed against the lens or opposite to (or facing) the photodetector 110.

The computer system 100 can compute or determine the penalty score for each pixel of an image or a downsampled image as a function of the absolute difference $|H-T_H|$ between the hue value H of the pixel and the desired hue color $T_H$. Specifically, and considering the cyclic nature of the hue values as depicted in FIG. 25F, the computer system 100 can compute or determine the penalty score for each pixel of an image or a downsampled image as a function of $\min(|H-T_H|, 360-|H-T_H|)$. Multiple penalty scores can be defined based on pixel hue values.

Figure 25G:
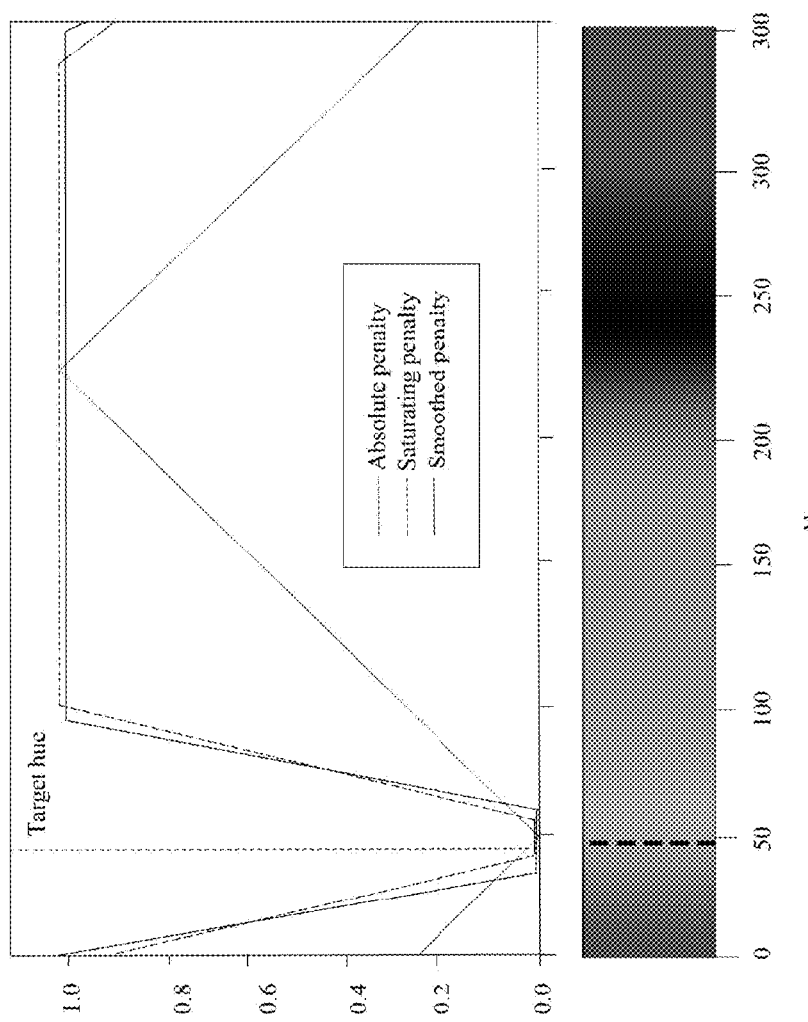
FIG. 25G shows plots for three different penalty scores expressed as functions of pixel hue values, according to example embodiments.

FIG. 25G shows plots for three different penalty scores expressed as functions of pixel hue values, according to example embodiments. The desired hue value $T_H$ is referred to in FIG. 25G as the target hue and is equal to 45. A first penalty score is referred to as the absolute penalty and is defined as:

$$\Delta_{abs} = \frac{1}{180} \min(|H - T_H|, 360 - |H - T_H|). \tag{31}$$

Other penalty scores can be defined as functions of the absolute penalty, e.g., $\Delta_i = f_i(\Delta_{abs})$. For instance, the saturating penalty $\Delta_{sat}$ (shown in FIG. 25G) can be viewed as a transformation function based on two parameters $\rho_1$ and $\rho_2$. The computer system 100 can determine or compute the saturating penalty as:

$$\Delta_{sat} = \begin{cases} 0, & \text{if } \Delta_{abs} < \rho_1 \\ \frac{\Delta_{abs}}{\rho_2 - \rho_1}, & \text{if } \rho_1 < \Delta_{abs} < \rho_2. \\ 1, & \text{if } \rho_2 < \Delta_{abs} \end{cases} \tag{32}$$

The smooth penalty $\Delta_{smooth}$ (also shown in FIG. 25G) can be defined as a transformation function of $\Delta_{abs}$ with two scale parameters $\mu$ and $\sigma$. The computer system 100 can determine or compute the smooth penalty score for each pixel of an image or a downsampled image as $$\Delta_{smooth} = f_{smooth}(\Delta_{abs}; \mu, \sigma) = \tanh\left(\frac{\Delta_{abs} - \mu}{\sigma}\right). \tag{33}$$

In some implementations, the penalty score for each pixel of an image or a downsampled image can be defined in terms of a difference between the color value of the pixel and the desired color value, regardless of whether the pixel color value and the desired color value are hue values or other color values. For example, the desired color value can include desired red, green and blue values that represent finger (or other body part) color. The computer system 100 can determine or compute the penalty score for each pixel in terms of a distance (or differences) between the pixel red, green and blue values $R_{pixel}$, $G_{pixel}$ and $B_{pixel}$ and the desired or target red, green and blue values $R_{target}$, $G_{target}$ and $B_{target}$ (e.g., in terms of $|R_{pixel} - R_{target}|$, $|G_{pixel} - G_{target}|$ and $|B_{pixel} - B_{target}|$). In some implementations, the computer system 100 can use a different color space (e.g., other than the HSL color space) to determine or compute the penalty scores for different pixels.

The computer system 100 can arrange the penalty scores into a matrix $\Delta$ having a size or dimension $(d_x, d_y)$. Note that the penalty matrix $\Delta$ described in this subsection has a different size or dimension than the penalty matrix described in subsection 8.2.

Referring back to FIG. 25A, the method 2500 can include the computer system 100 determining, using penalty scores of the plurality of pixel positions, a relative position of the body part of the user with respect to a desired position (2506). The computer system 100 can determine a position vector (or orientation vector) indicative of the relative position of the finger or body part with respect to a desired position in a similar way as discussed above in subsection D.2, e.g., with regard to equation (18). Specifically, the computer system 100 can determine or compute the relative position (or position vector) of the finger or body part as the center of mass or barycenter of the penalty scores for the pixels of the image or the corresponding downsampled image, e.g., as $$\delta = \begin{pmatrix} \frac{\sum_{i,j} i \cdot \Delta(i,j)}{\sum_{i,j} \Delta(i,j)} \\ \frac{\sum_{i,j} j \cdot \Delta(i,j)}{\sum_{i,j} \Delta(i,j)} \end{pmatrix}. \tag{34}$$

The computer system 100 can compute a position vector (or a relative position) of the finger or body part for each acquired image frame (or the corresponding downsampled image frame). The computer system 100 may further compute the magnitude and/or the angle (e.g., direction or orientation) of the position vector $\delta$ as discussed above in subsection D.2 with regard to equation (19).

The computer system 100 can provide a visual output indicative of the relative position for display on the display device 112 to assist or guide the users to correctly place their fingers (or other body part). For instance, the computer system can cause display of visual output as discussed above in subsection D.2, e.g., with regard to FIG. 18C. The visual output can include an indication of a classification of the relative position of the finger or body part. The computer system 100 can determine the classification of the relative position of the finger or body part as discussed above in subsection D.2, e.g., with regard to Table 3. The visual output can include an indication (e.g., a color bar) of a metric representing a quality of the placement of the finger or other body part on the lens of the camera.

The computer system 100 can cause display of the visual output for each received image of the sequence of images. For instance, when the user moves his or her finger (or body part) responsive to the visual output, the visual output determined based on following images will reflect the movement of the finger or body part.

D.9. Detection of Data Acquisition Conditions Using a Machine Learning Model

The approaches or processes described in subsections D.1 through D.8 allow for detection of various conditions associated with the acquisition of optical (or transdermal) data of a user for use to measure the blood pressure of the user. The detected conditions can relate to the positioning or placement of the finger (or other body part) of the user on the lens of the camera, physiological conditions of the user (e.g., cold finger, Arrhythmia or irregular heart beat) or light conditions (e.g., dark or light saturation conditions), among others. These conditions (also referred to as error conditions) are indicative of potential issues or problems with the data acquisition that could lead to acquired data that wouldn't be good or reliable for measuring or determining blood pressure or other vital signs. The detected conditions can be used by the computer system 100 to provide visual or other type of output for the user to help or instruct the user take some action to enhance the quality of the acquired transdermal optical data. It is to be noted that in all the approaches descried in section D the output provided to the use can be a visual output, audio output or some other type of output.

Each of the approaches in subsections D1-D8 can detect one or small subset of the possible conditions. To check for all or most of the conditions, one may need to use many of the approaches or methods discussed in subsections D1-D8. In this subsection a more comprehensive machine learning approach is described. The machine learning approach allows for detecting various conditions at once.

Figure 26:
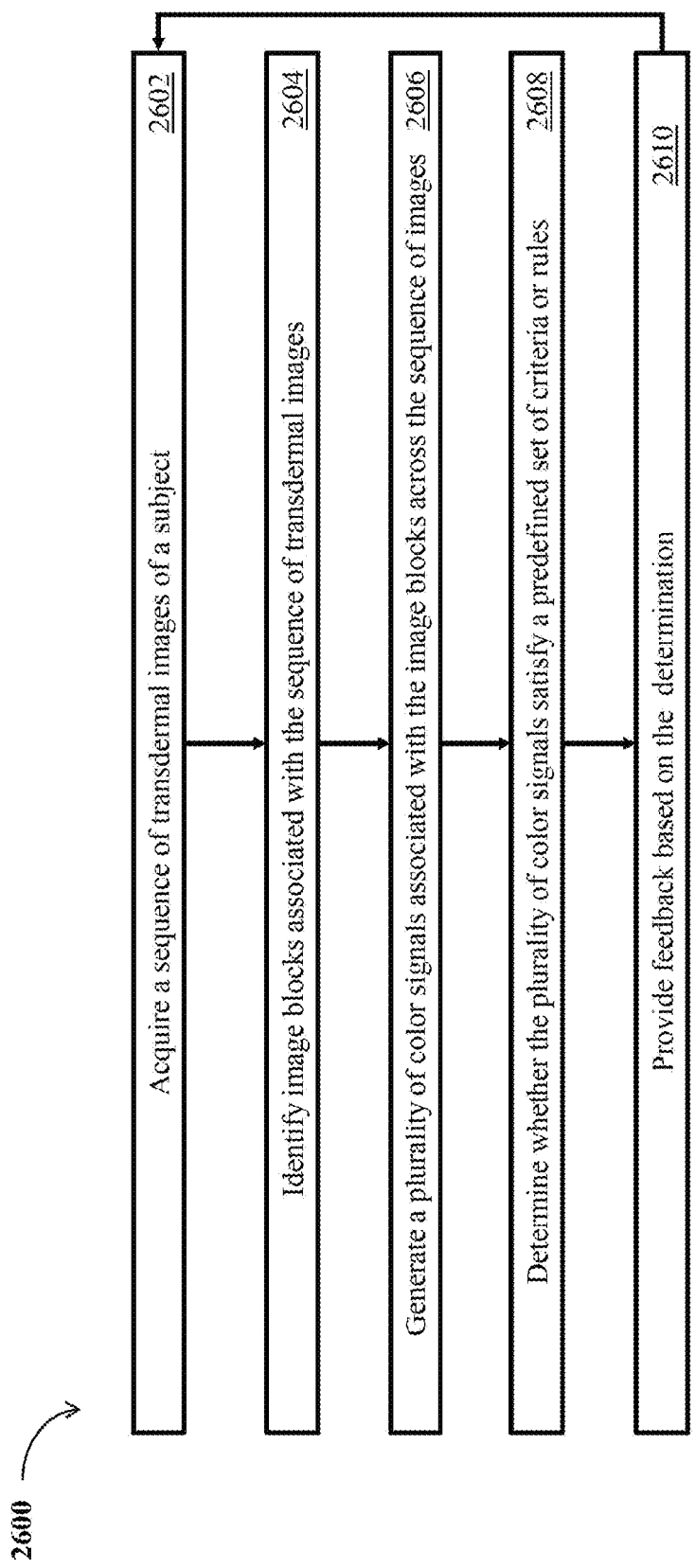
FIG. 26 shows a flowchart illustrating a method for enhancing acquisition of transdermal optical data, according to example embodiments.

Referring now to FIG. 26, a flowchart illustrating a method 2600 for enhancing acquisition of transdermal optical data is shown, according to example embodiments. The method 2600 can include obtaining a sequence of images representing transdermal optical data of a subject and acquired by a photodetector (STEP 2602). The method 2600 can include identifying a plurality of image regions across the sequence of images (STEP 2604). The method 2600 can include generating a plurality of color intensity signals associated with the plurality of image regions across the sequence of images (STEP 2606). The method 2600 can include determining, using a machine learning model and the plurality of color intensity signals associated with the plurality of image regions, a condition associated with acquisition of the sequence of images (STEP 2608), and providing feedback for presentation to a user based on the condition associated with the acquisition of the sequence of images (STEP 2610).

The method 2600 can include the computer system 100 or the application 114 obtaining a sequence of images representing transdermal optical data of a subject (STEP 2602), and identifying a plurality of image regions across the sequence of images (STEP 2604). The photodetector or camera 110 can acquire the sequence of images as discussed above, for example, with regard to step 402 of FIG. 4, step 1602 of FIG. 16 or step 1802 of FIG. 18. The acquisition of the sequence of image frames can be performed, e.g., by the data acquisition module 502, in a similar way as STEP 402 of method 400 in FIG. 4. The computing device hosting the photodetector 110 or another computing device can obtain the acquired or recorded sequence of images. The computer system 100 can process image frames of the sequence of images sequentially as they are received.

Identifying the plurality of image regions across the sequence of images can include the processing module 504 downsampling, for each acquired image frame, the respective color frames (e.g., R and G frames) to obtain corresponding downsampled color frames. In some implementations, the downsampled color frames can have a size of 9×9, 6×6 or other size. The computer system 100 can identify the plurality of image regions across the sequence of downsampled color frames. In some implementations, the computer system 100 can forego downsampling and identify the image regions within or across the original color frames of the sequence of images (e.g., not downsampled image frames). In some implementations, the computer system can identify the plurality of image regions across green and red color frames (or corresponding downsampled versions) of the acquired image sequence. In some implementations, the computer system 100 can identify the plurality of image regions across color frames (or corresponding downsampled versions) of other color spaces (e.g., other than the RGB color space).

In some implementations, the color frames or the corresponding downsampled versions in which the image regions are identified can belong to a plurality of color spaces. For example, the computer system 100 can identify the image regions across green, red and hue color frames of the acquired image sequence. The computer system 100 can determine or compute the hue color frames as discussed above with regard to equation (29). In general, the computer system 100 can apply transformations from one color space to one or more other color spaces to determine color frames across multiple color spaces.

Figure 27:
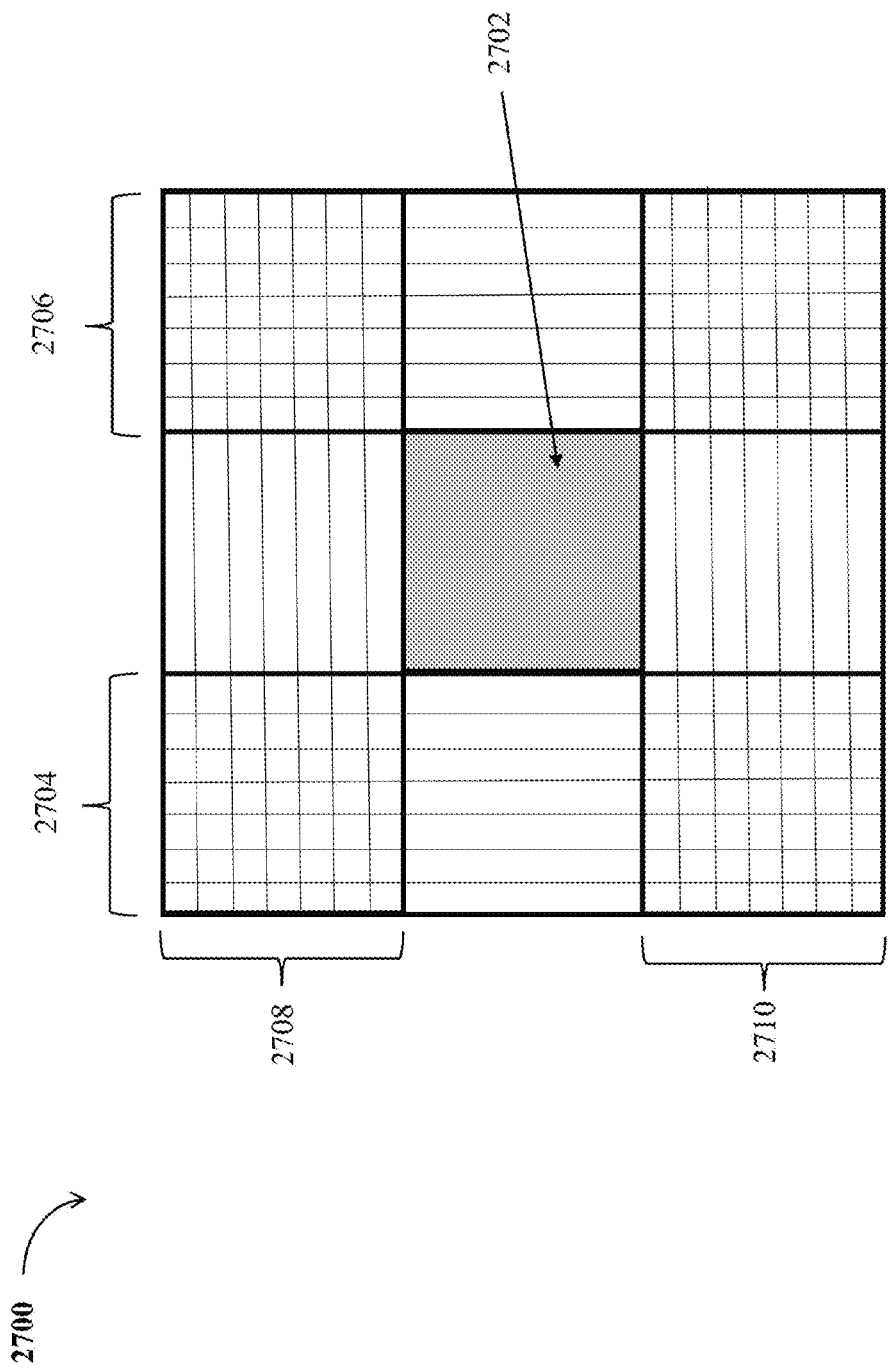
FIG. 27 shows a diagram illustrating an example approach of dividing an image block into a plurality of corresponding sub-regions, according to example embodiments.

Referring now to FIG. 27, a diagram illustrating an example approach of dividing a color (or image) frame (or a downsampled version thereof) 2700 into a plurality of corresponding image regions. The pattern for dividing each color or image frame into the corresponding plurality of image regions can be the same (e.g., in terms of size, shape and location within the color frames) across various image or color frames. The image regions can include a central image region and one or more side image regions. For instance, the signal-generating module 506 can identify a central image region 2702, a left-side image region 2704, a right-side image region 2706, a top-side image region 2708, and a bottom-side image region 2710 as depicted in FIG. 27. The left-side image region 2704 can include one or more left columns of the image or color frame (or corresponding downsampled version) 2700, and the right-side image region 2706 can include one or more right columns of the image or color frame 2700. The top-side image region 2708 can include one or more top rows of the image or color frame (or the corresponding downsampled version) 2700, and the bottom-side image region 2710 can include one or more bottom rows of the image region (or corresponding downsampled version) 2700.

In some implementations, the computer system 100 can use a different pattern for dividing the image or color frames into the corresponding image regions. The number, the size and the shapes of the images regions in each image frame can be different from the number, size and shapes of the image regions 2702, 2704, 2706, 2708 and 2710 of FIG. 27. For example, the computer system 100 can identify a number of image regions of equal size in each image or color frame.

The method can include determining, by the computing device, using a machine learning model and the plurality of color intensity signals associated with the plurality of image regions, a condition associated with acquisition of the sequence of images. The machine learning model can receive the plurality color intensity signals as input and provide an indication of the condition as output. The method can include providing, by the computing device, feedback for presentation to a user based on the condition associated with the acquisition of the sequence of images.

Referring back to FIG. 26, the method 2600 can include the computer system 100 or the signal-generating module 506 generating a plurality of color intensity signals associated with the plurality of image regions across the sequence of images (STEP 2606). The signal-generating module 506 can generate each color intensity signal using a corresponding image region defined across color frames of a given color of the image sequence. For instance, the computer system 100 can generate one or more red intensity signals using one or more corresponding image regions defied across red color frames (or corresponding downsampled versions) of the acquired image sequence, and/or one or more green intensity signals using one or more corresponding image regions defied across green color frames (or corresponding downsampled versions) of the acquired image sequence. In some implementations, the computer system 100 can generate one or more hue intensity signals using one or more corresponding image regions defied across hue color frames (or corresponding downsampled versions) of the acquired image sequence.

In some implementations, the computer system 100 or the signal-generating module 506 can generate a color intensity signal associated with an image region across the sequence of images by averaging pixel color values of the image region for each image frame (or each corresponding color frame) of the sequence of images. In some implementations, the computer system 100 or the signal-generating module 506 may apply weighted averaging for an image region across color frames of the sequence of images to generate the corresponding color signal.

Referring back to FIG. 27, the computer system 100 or the signal-generating module 506 can average the pixel values in each of the image regions 2702, 2704, 2706, 2708 and 2710, for both R and G color frames (or corresponding downsampled versions) to generate corresponding red and green intensity signals. In some implementations, the signal-generating module 506 can generate color signals for a subset of the image regions identified at step 2604 and/or a subset of the color frames. For example, the signal-generating module 506 can generate one or more green intensity signals using one or more identified image regions (e.g., 2702, 2704, 2706, 2708 and 2710) across the green color frames (or corresponding downsampled versions) of the sequence of images, one or more red intensity signals using one or more identified image regions (e.g., 2702, 2704, 2706, 2708 and 2710) across the red color frames (or corresponding downsampled versions) of the sequence of images or a combination thereof. The signal-generating module 506 can generate one or more hue intensity signals using one or more identified image regions (e.g., 2702, 2704, 2706, 2708 and 2710) across the hue color frames (or corresponding downsampled versions) of the sequence of images. The color frame-image region pairs for which to generate corresponding color intensity signals can be predefined.

The method 2600 can include the computer system 100 determining, using a machine learning model and the plurality of color intensity signals associated with the plurality of image regions, a condition associated with acquisition of the sequence of images (STEP 2608). The machine learning model can receive the plurality of generated color intensity signals as input and provide an indication of the condition as output. The machine learning model can be trained using a second plurality of color intensity signals generated from one or more second image sequences. The second plurality of color intensity signals can be associated with the plurality of image regions across the one or more second image sequences or respective color frames. The color frames and the images regions of the one or more second image sequences used to generate the second plurality of color intensity signals (for training the machine learning model) can correspond to or can be similar to the image regions and the color frames used at steps 2604 and 2606. In some implementations, the method 2600 can further include the computer system 100 training the machine learning model using the second plurality of color intensity signals.

The training data (e.g., the second plurality of color intensity signals) can be labeled data. For instance various sets of training color intensity signals can be associated with known corresponding error conditions (e.g., finger placement condition or state, blood perfusion condition, light saturation or dark conditions, Arrhythmia, irregular heart rate, etc.). The machine learning model can include a neural network, a Bayesian network, a statistical model or other type of machine learning model that can be trained using training data. The machine learning model, once trained, can receive a plurality of color intensity signals corresponding to a plurality of predefined color frame-image region pairs of a sequence of images, and generate one or more indications of one or more conditions associated with acquisition of the sequence of images.

The conditions can include conditions of the generated color signals indicative of relative placement of the user finger (or other body part). For example, proper placement of the finger or body part can require that the central R signal (corresponding to central R image region 2702) to be greater (in corresponding values) than the central G signal (corresponding to the central image region 2702), and the central R signal to be greater than the bottom-side G signal corresponding to bottom-side image region 2710. Proper placement of the finger or other body part may require the central G signal to be greater than the left-side G signal (e.g., corresponding to left-side image region 2704). Proper placement of the finger or other body part can require the central G signal to be greater than the right-side G signal (e.g., corresponding to the right-side image region 2706). Proper placement of the finger or other body part can require the central G signal to be greater than the top-side G signal (e.g., corresponding to the top-side image region 2708). Accordingly, the machine learning model ca detect improper placement of the finger or other body part on the lens based on the input color intensity signals generated at step 1606. The machine learning model can detect other conditions, such as Arrhythmia, irregular heart rate, blood perfusion, or light saturation or dark conditions, among others, based on the plurality of color intensity signals generated at step 2606 and provided as input to the machine learning model.

Figure 28A:
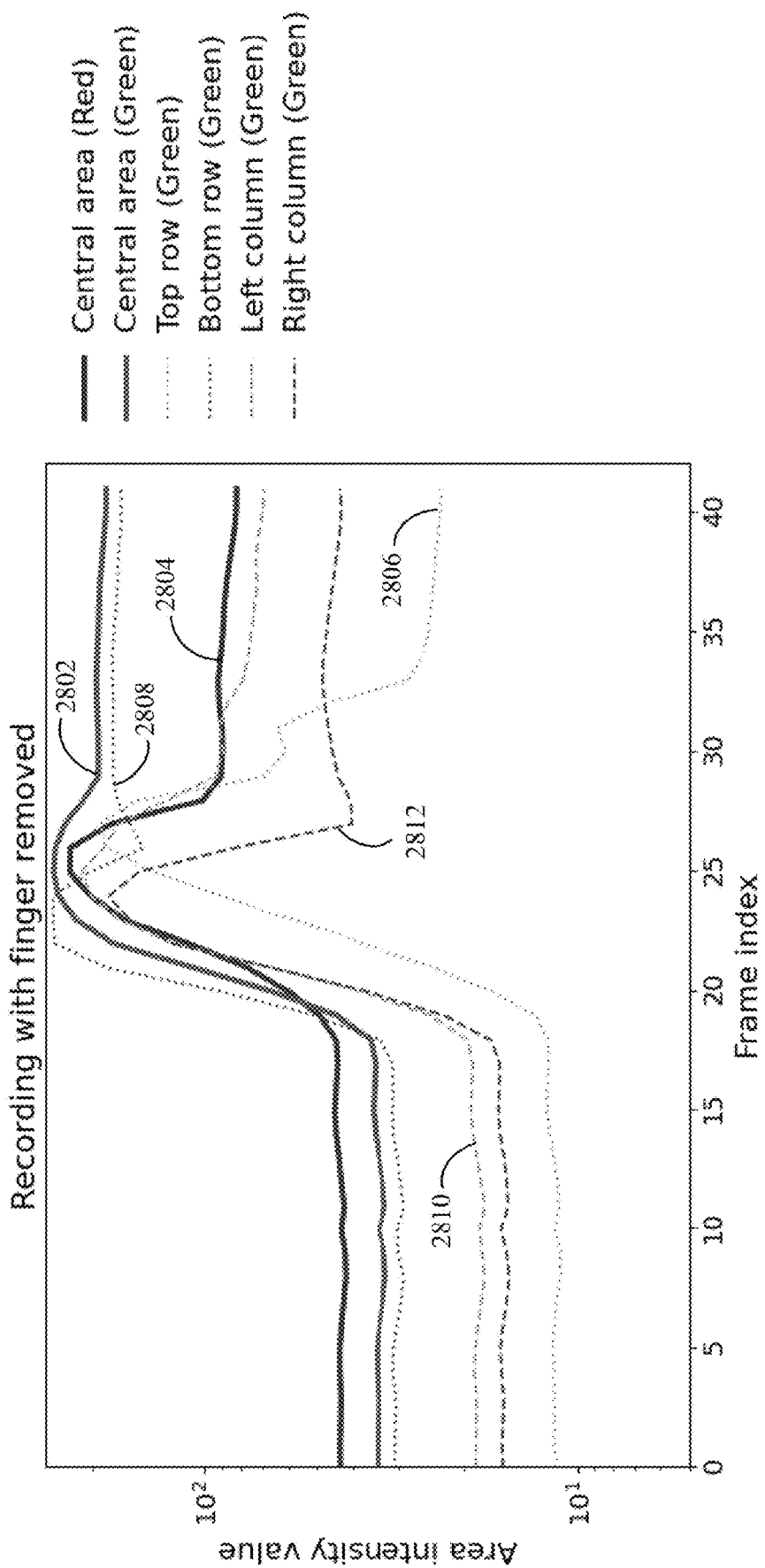
FIGS. 28A-G show plots of color signals associated with various image blocks and different data quality conditions, according to example embodiments.

Referring to FIGS. 28A-G, various color intensity signals 2802-2812 illustrating various scenarios are shown, according to example embodiments. In each of FIGS. 28A-G, six color signals, mainly the central G signal 2802, the central R signal 2804, the top-side G signal 2806, the bottom-side G signal 2808, the left-side G signal 2810 and the right-side G signal 2812 are shown. FIG. 28A illustrates a scenario where the user finger was removed from the lens during the data acquisition process. The removed of the finger is reflected through a sudden jump (or increase in intensity) in all the color intensity signals 2802, 2804, 2806, 2808, 2810 and 2812.

Figure 28B:
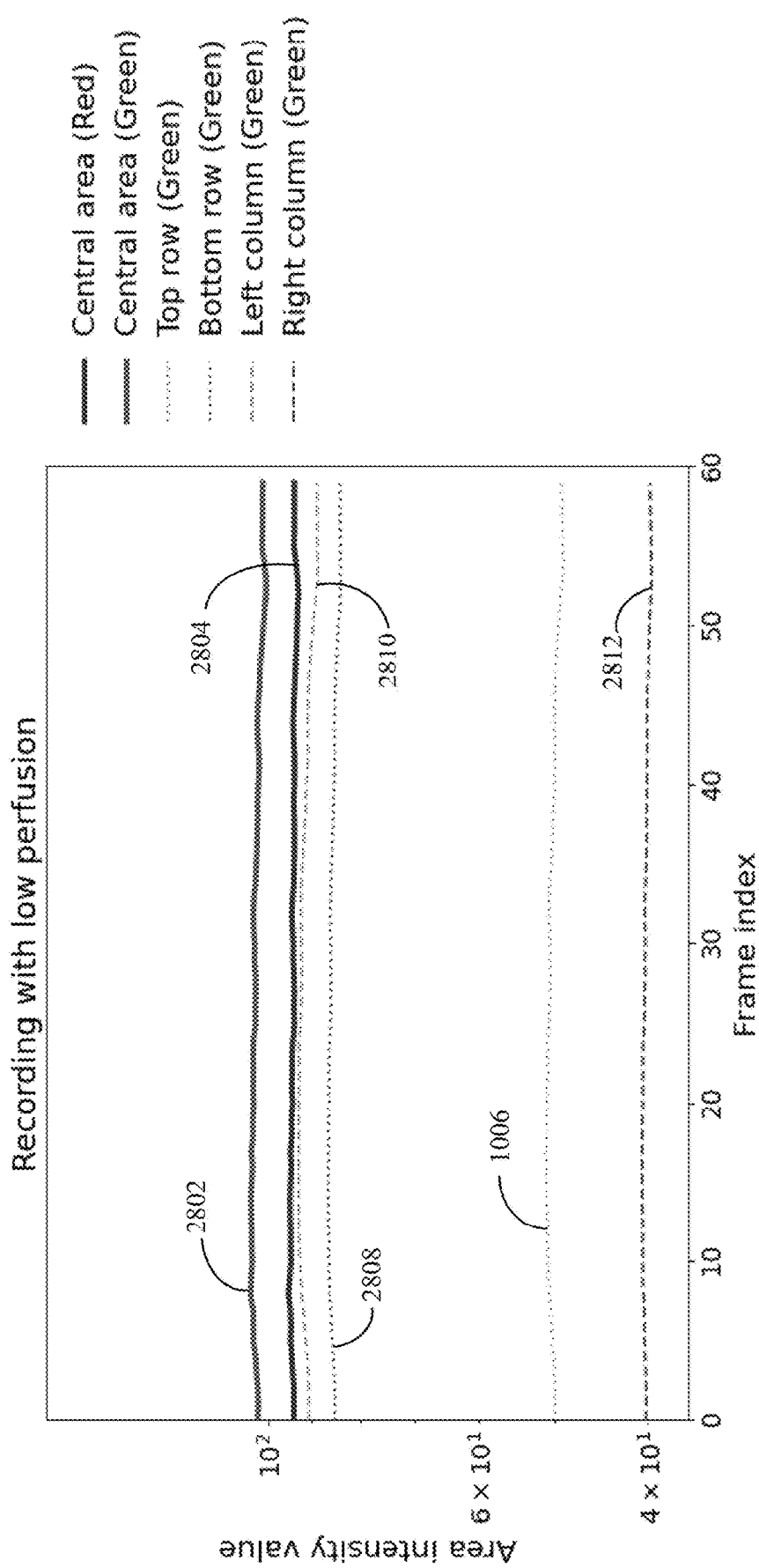
Figure 28C:
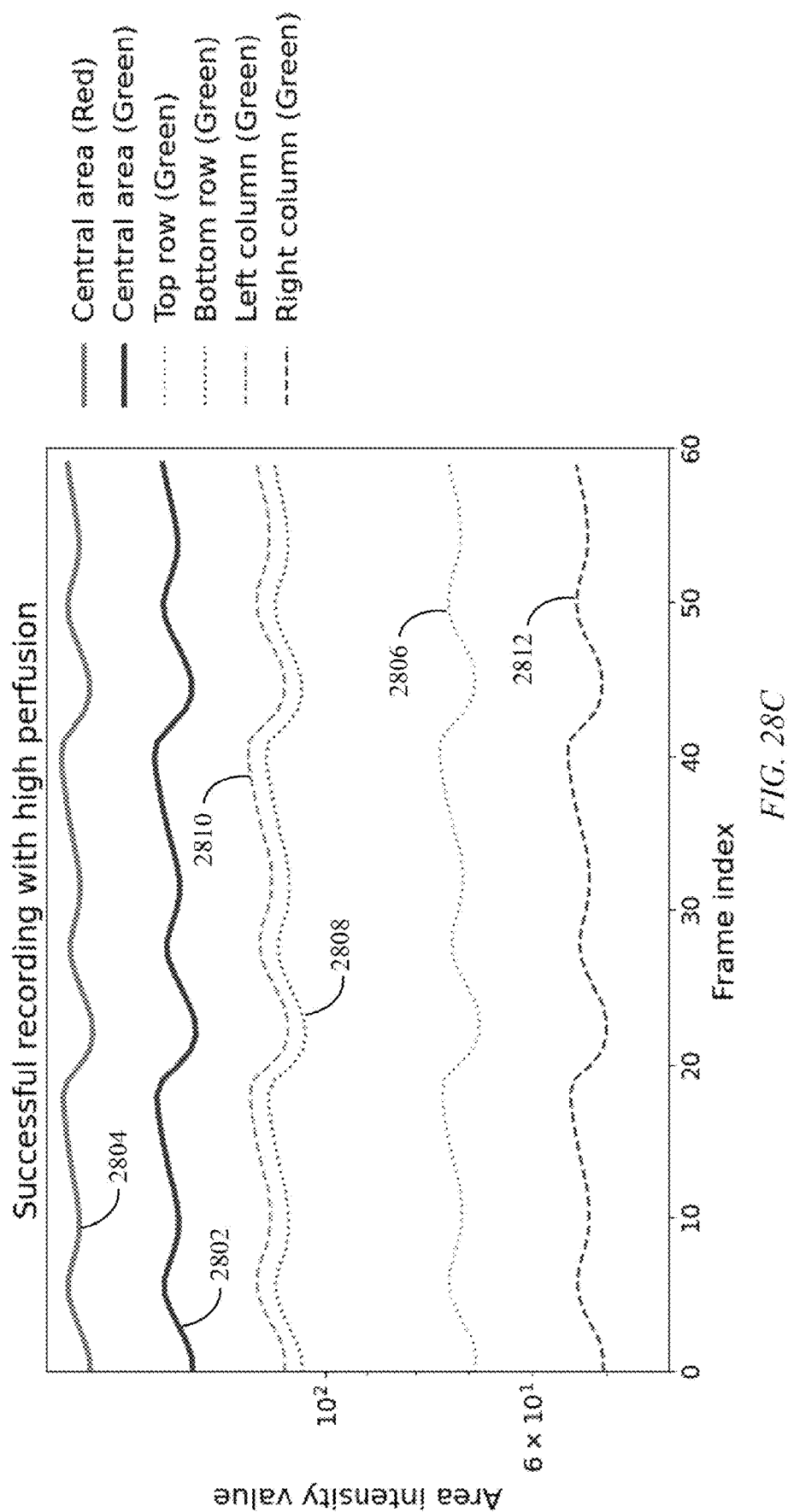

FIGS. 28B and 28C show the color intensity signals 2802, 2804, 2806, 2808, 2810 and 2812 for a low blood perfusion scenario and high perfusion scenario, respectively. The relative positions of these color intensity signals are different in FIGS. 28B and 28C. For instance, in the case of low blood perfusion (e.g., corresponding to cold finger), the central G signal 2802 is greater than the central R signal 2804 and the magnitude of both signals is around 100. In the case of high blood perfusion (FIG. 28C), the central G signal 2802 is smaller than the central R signal 2804 and the magnitude of both signals is higher compared to FIG. 28B.

Figure 28D:
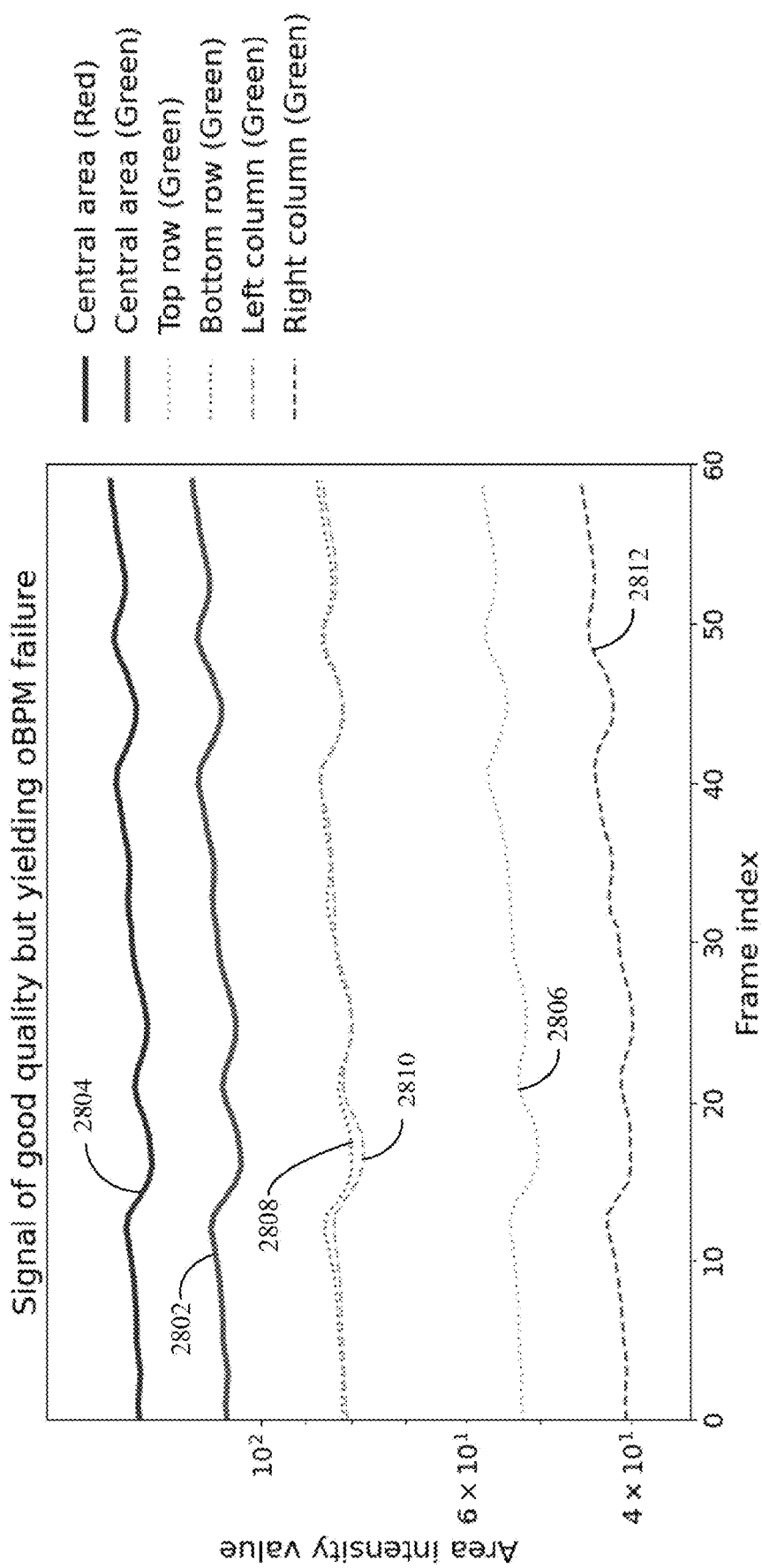

FIG. 28D shows a scenario where the color intensity signals 2802, 2804, 2806, 2808, 2810 and 2812 seem to be of good quality, but still lead to a failure of the OBPM model in providing a blood pressure measurement.

Figure 28E:
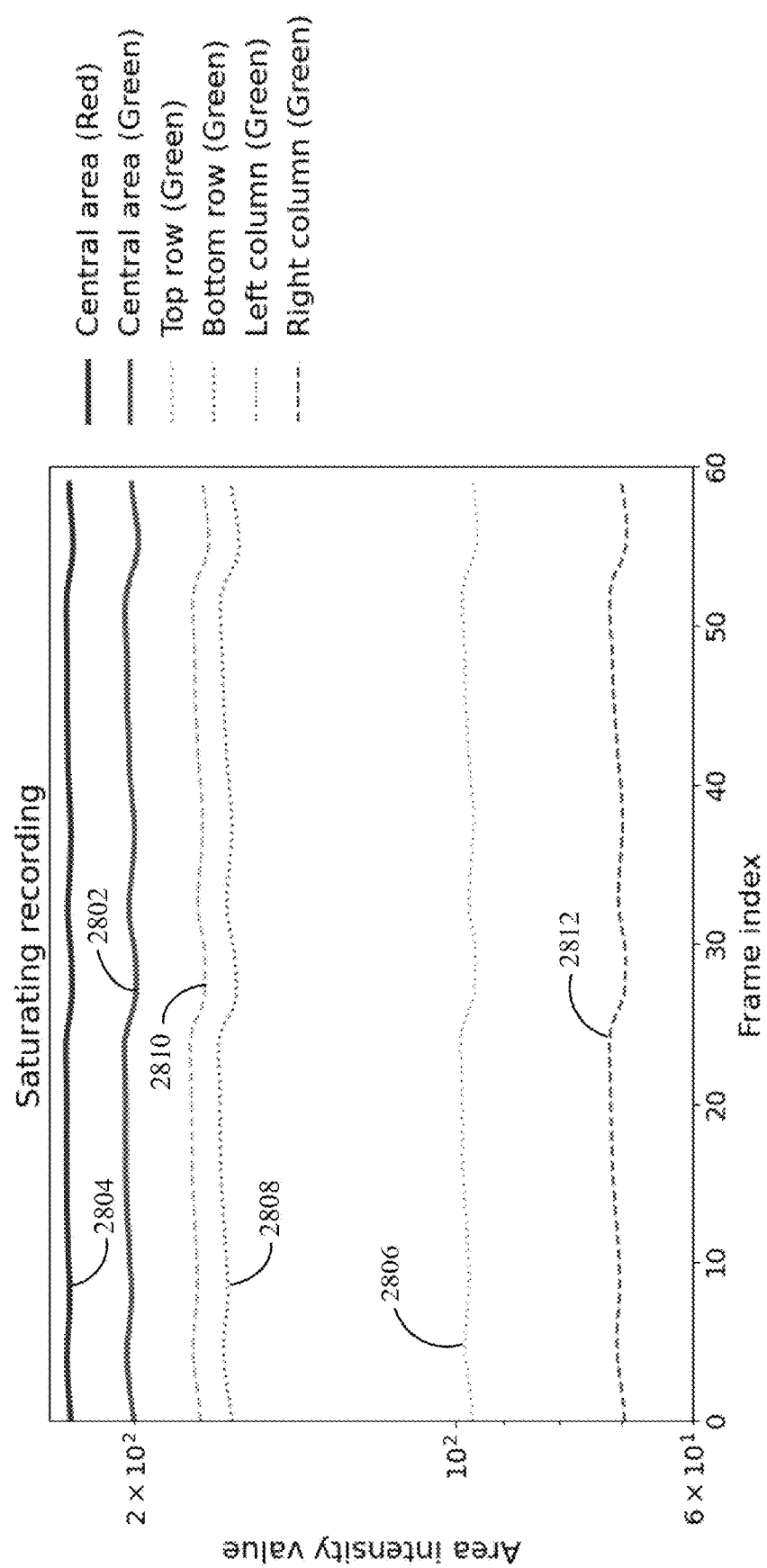
Figure 28F:
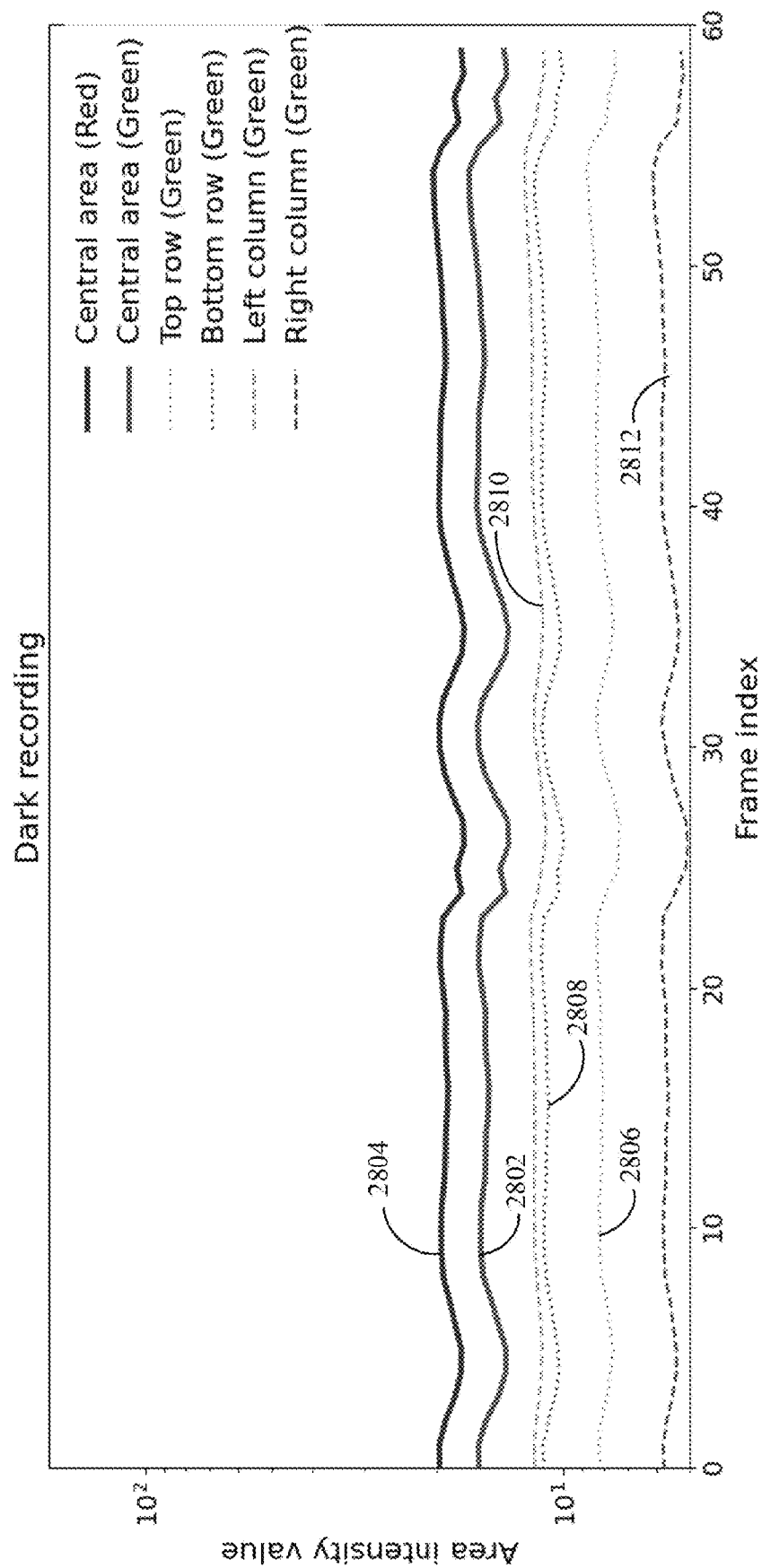
Figure 28G:
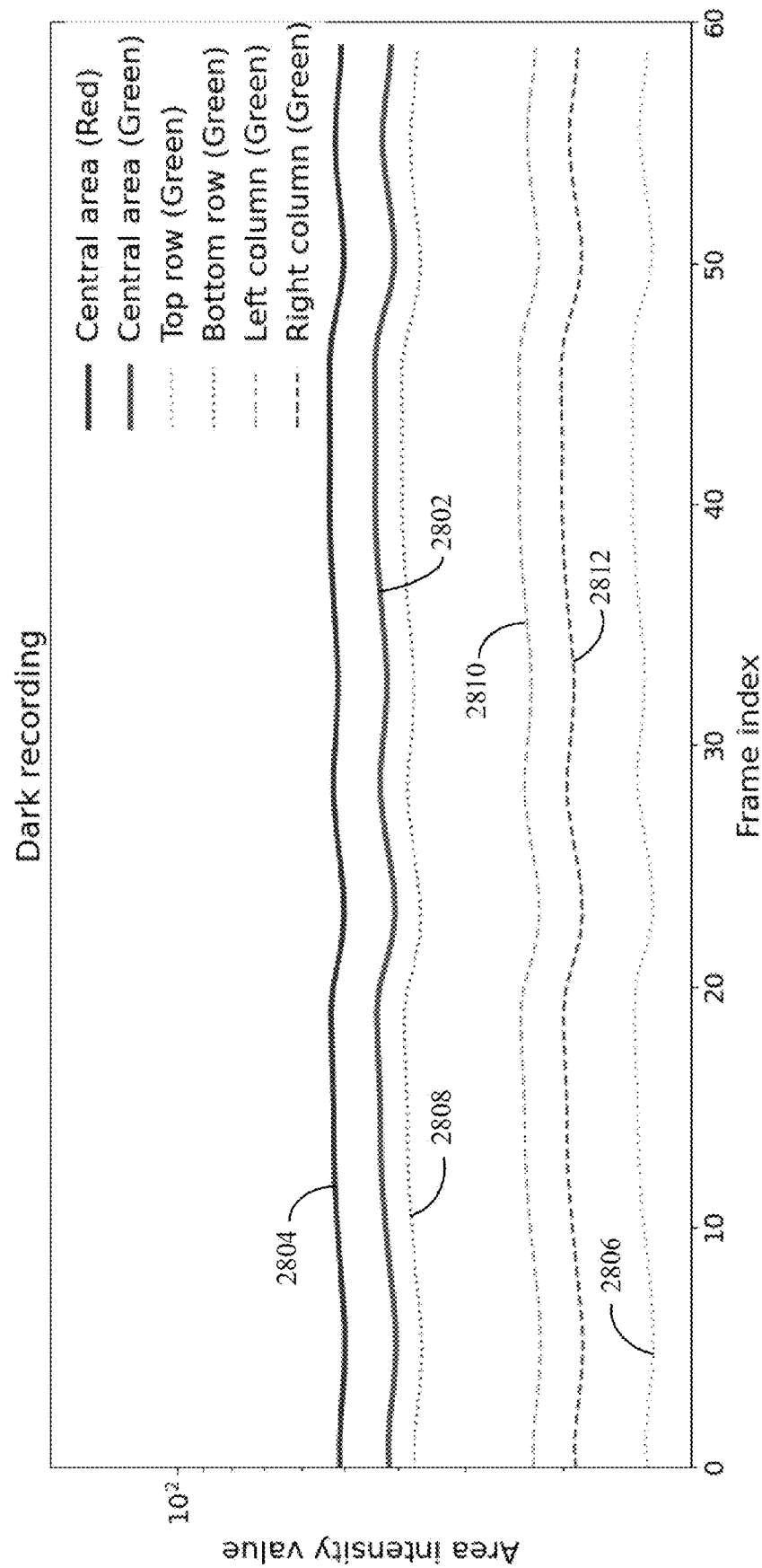

FIGS. 28E, 28F and 28G illustrate various lighting scenarios. FIG. 28E shows the color intensity signals 2802, 2804, 2806, 2808, 2810 and 2812 for a light saturation condition (e.g., high light intensity resulting in saturation in recorded color intensities). FIGS. 28F and 28G shows the color intensity signals 2802, 2804, 2806, 2808, 2810 and 2812 for two relatively dark lighting conditions. The magnitudes and relative positions of the color intensity signals 2802, 2804, 2806, 2808, 2810 and 2812 in FIG. 28E are significantly different from those in FIGS. 28F and 28G.

FIGS. 28A-G illustrate that the color intensity signals generated at step 2606 can provide indications of various underlying conditions. Using training data, e.g., including a various sets of color intensity signals and indications of corresponding underlying conditions, a machine learning model can be trained (e.g., by the computer system 100 or other computer system) to detect various error condition (or data acquisition conditions) based on color intensity signals generated as described in step 2606. The trained machine learning model can receive the plurality of color intensity signals (e.g., generated as discussed in relation with step 2606) and provide one or more indications of one or more conditions.

The condition can include at least one of a condition related to placement of a body part of the subject or user relative to the photodetector or a blood perfusion condition (e.g., indicative of a cold finger or body part) of the subject. The condition can include a lighting condition, such as a saturation or dark condition. In some implementations, the condition can include an Arrhythmia condition and/or an irregular heart rate condition.

Referring back to FIG. 26, the method 2600 can include providing, by the computing device, feedback for presentation to a user based on the condition associated with the acquisition of the sequence of images (STEP 2610). The method 2600 can include the output module 512 or the computer system 100 providing feedback based on the determined condition(s). The output module 512 can provide feedback or instructions for presenting to the user via the application UI indicative of (or associated with) the detected condition. The output module 512 can provide general feedback or instructions to indicate that the finger is not properly placed. The UI may provide the option (e.g., upon user selection) to render detailed instructions or a demo illustrating how the user finger should be placed relative to the camera device 110 and/or the flash device 206. In some implementations, the output module 512 can present specific feedback or instructions depending on the detected condition. For instance, if the finger is detected to be shifted to the left side of the camera 110, the output module 512 can present specific feedback to indicate the left shift of the finger, or can instruct the user to move the finger slightly to the right.

The method 2600 or steps thereof can be performed by the computer system 100 in combination with any of the methods described in this disclosure. In general, any combination of the methods or processes described in this disclosure can be performed by the computer system 100.

E. Assessing PPG Signal Quality for Initiating Blood Pressure Measurement

Even when applying processes to enhance the accuracy or fidelity of acquired optical transdermal data, e.g., as discussed with regard to Section C above, the corresponding generated PPG signal may still show distortions and fail to accurately depict the pulse wave of the user. To improve the accuracy of measured blood pressure, the computer system 100 or the signal quality assessment module 508 can check if the generated PPG signal is suitable for biosensing analysis by verifying or inspecting one or more features of the PPG signal. In some implementations, the computer system 100 or the signal quality assessment module 508 can employ a threshold for a corresponding signal feature to predict the quality of the PPG signal quality. The use of thresholds allows for fast detection of poor signal quality, for example, caused by low blood perfusion in the finger due to cold hands or generally low vascularity. The signal quality assessment module 508 can determine based on the assessment of the quality of the PPG signal whether or not to feed the PPG signal or portion thereof to the OBM module 510 for use to estimate blood pressure.

The PPG signal is expected to be periodic with a base frequency equal to that of the user heart rate. However, the heart rate is not constant over time and evolves slowly due to respiratory rate or user activity, among other factors. The change in heart rate over time can induce artifacts in the frequency spectrum of the PPG signal, for example, with respect to the locations of corresponding peaks. This fact, calls for a signal assessment approach that can estimate the local quality, e.g., local period, of the PPG signal.

Figure 29:
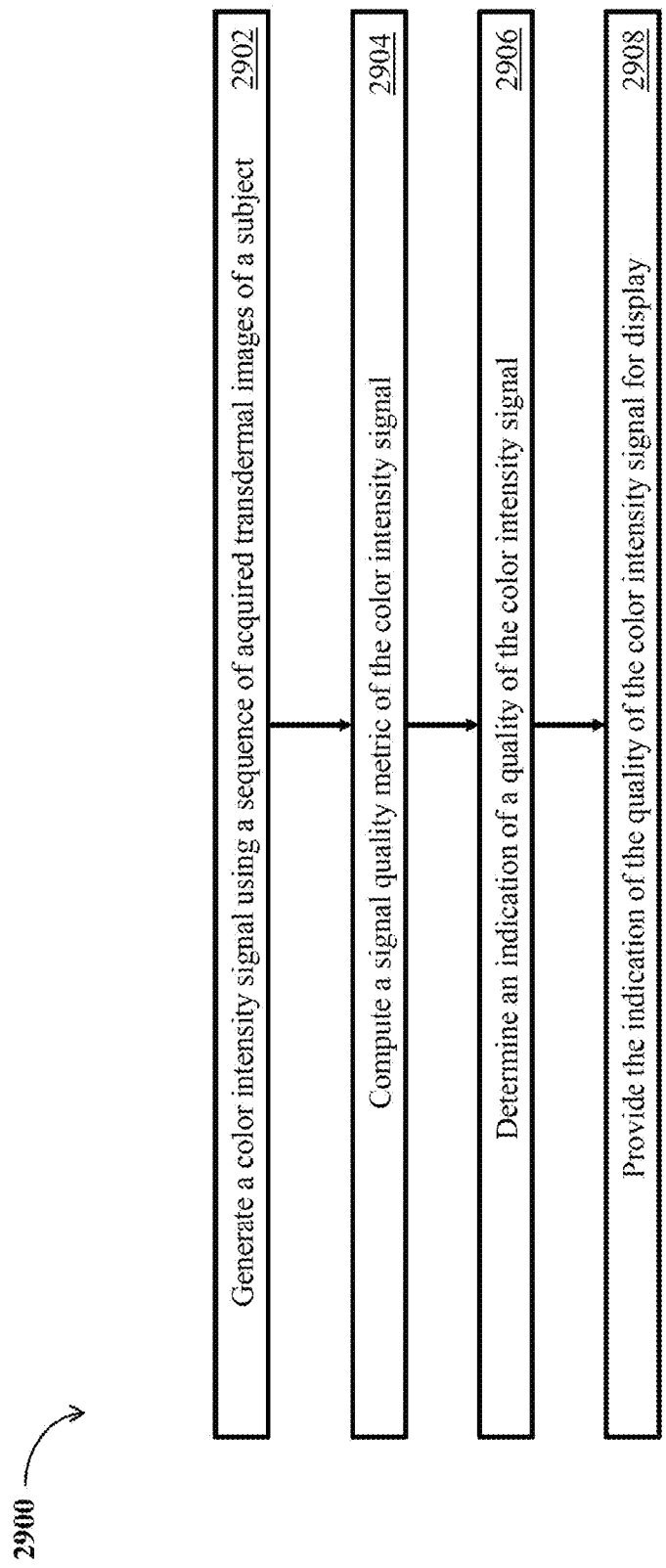
FIG. 29 shows a flowchart illustrating a method for assessing PPG signal quality for use to estimate blood pressure, according to example embodiments.

FIG. 29 shows a flowchart illustrating a method 2900 for assessing a signal quality for use to estimate blood pressure, according to inventive concepts of the current disclosure. In brief overview, the method 2900 can include generating a color intensity signal using a sequence of acquired transdermal images of a subject (STEP 2902), and computing a signal quality metric of the color intensity signal (STEP 2904). The method 2900 can include determining an indication of a quality of the color intensity signal (STEP 2906), and providing the indication of the quality of the color intensity signal for display (STEP 2908).

In further detail, the method can include the computer system 100 or the signal-generating module 508 generating the color intensity signal (STEP 2902). The data acquisition module 502 can acquire the sequence of transdermal images as discussed above with regard STEP 402 of FIG. 4. The processing module 504 can identify an image block across the sequence of transdermal images, and the signal-generating module 506 can generate the color intensity signal based on the image block as discussed above with regard to STEPs 404 and 406 of FIG. 4.

The method 2900 can include the signal quality assessment module 508 computing a signal quality metric of the color intensity signal (STEP 2904). The signal quality metric of the color intensity signal can include a normalized autocorrelation metric or score as shown in equation (38) below, a peak or maximum of the normalized autocorrelation metric or score within a predefined time window or time interval, a spectrum entropy based metric as described in equations (39) and (40) below or a combination thereof. The signal quality assessment module 508 can compute a plurality of values of the signal quality metric. For instance, the signal quality assessment module 508 can evaluate the signal quality metric iteratively using a different set of generated samples of the color intensity at each iteration.

In some implementations, the signal quality assessment module 508 can compute a plurality of normalized autocorrelation metrics or parameters of the color intensity signal. Using the normalized autocorrelation metrics, the computer system 100 or the signal quality assessment module 508 can determine local features of the generated color intensity (or PPG) signal. For instance, the signal quality assessment module 508 can compute the normalized autocorrelation parameters using a sliding window of a given size n, where n is an integer representing the number of signal samples in the sliding window.

Figure 30:
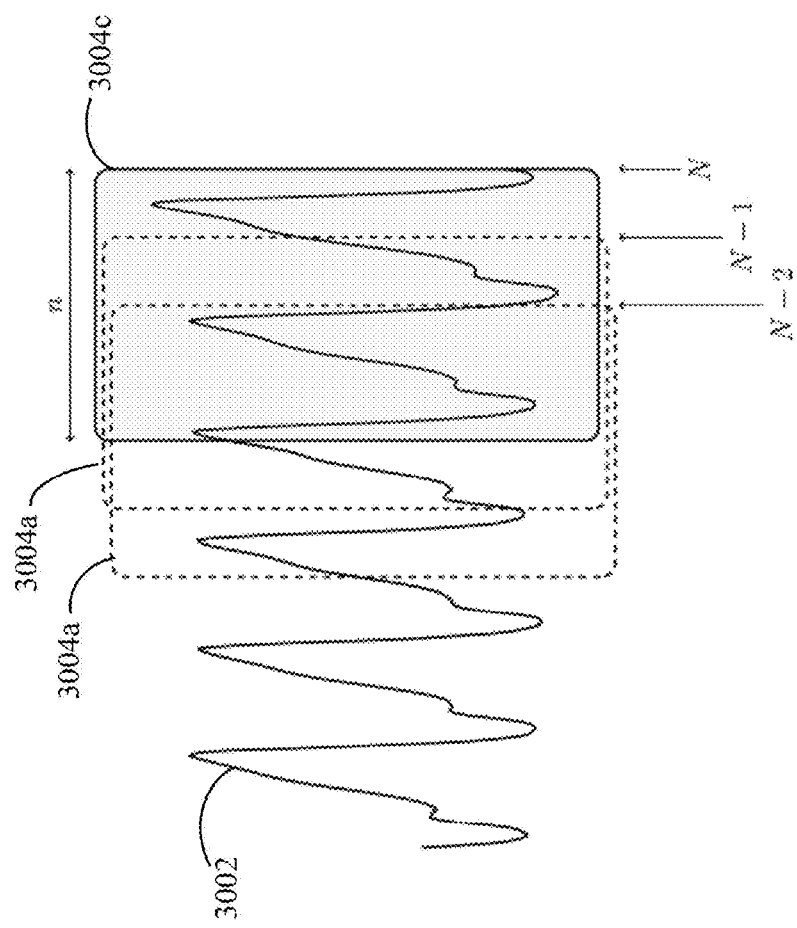
FIG. 30 shows an example diagram illustrating the use of a sliding window to compute the normalized autocorrelation metrics or parameters, according to example embodiments.

Referring to FIG. 30, a diagram illustrating the use of a sliding window to compute the normalized autocorrelation metrics or parameters is shown, according to inventive concepts of the current disclosure. The signal 3002, referred to hereafter as x[.], represents the PPG signal. The windows 3004a-3004c represent different versions of the sliding window associated with different timestamps N−2, N−1 and N, respectively. In some implementations, the timestamp of each version of the sliding window can represent the index of the last signal sample in that version of the sliding window. For instance, the last signal sample in the sliding window version 3004c, having timestamp N and referred to as $W_N$, is $x[N]$, and the last signal sample in the sliding window version 3004b, having timestamp N-1 and referred to as $W_{N-1}$, is $x[N-1]$.

For each time window $W_N$, the computer system 100 or the signal quality assessment module 508 can compute a plurality of corresponding covariance values $Q_N(i)$ for a plurality of integer values i. For each integer i ($0 \le i \le n-1$), the covariance value $Q_N(i)$ can represent the covariance between the window $W_N$ and the window $W_{N-i}$, and may be described as:

$$Q_N(i) = \frac{1}{n}\sum_{j=0}^{n-1}(x[N-j]-M_N)(x[N-i-j]-M_{N-i}), \quad (35)$$

where $M_N$ represents the average of the signal values in the window $W_N$, and $M_{N-i}$ represents the average of the signal values the window $W_{N-i}$. Equation (29) can be re-written as:

$$Q_N(i) = \frac{1}{n}\sum_{j=0}^{n-1}x[N-j]x[N-i-j]-M_N M_{N-i}. \quad (36)$$

In some implementations, the computer system 100 or the signal quality assessment module 508 can compute the covariance values $Q_N(i)$ iteratively to reduce the computational cost. Specifically, considering equation (30), the signal quality assessment module 508 can compute the covariance value $Q_N(i)$ in terms of the covariance value $Q_{N-1}(i)$ as in formula (31).

$$Q_N(i) = Q_{N-1}(i) + \frac{1}{n}x[N]x[N-i] + \quad (37)$$
$$M_{N-1}M_{N-1-i} \pm \frac{1}{n}x[N-n]x[N-n-i] - M_N M_{N-i}.$$

The iterative approach described in equation (31) reduces the computational complexity significantly. According to equation (31), the signal quality assessment module 508 can compute each new covariance value $Q_N(0)$ using only four multiplications and four additions provided that the values covariance values $Q_{N-1}(i)$ and the mean values $M_{N-1}$ through $M_{N-n}$ are stored in the memory 104. As such, the gain in computational complexity, when using equation (31) instead of equation (30), is in the order of n; the size of the sliding windows. In fact, the computational cost of computing the covariance values $Q_N(i)$ for all N and i is of order O (N.K) operations, where N is the size of the signal and K the number of delayed windows for which we want to compute autocorrelation.

The signal quality assessment module 508 can then compute, for each time window $W_N$, the corresponding normalized autocorrelation metrics or parameters, as:

$$q_N(i) = \frac{Q_N(i)}{\sqrt{Q_N(0)}\sqrt{Q_{N-i}(0)}}, \quad (38)$$

for each integer i where $0 \le i \le n-1$.

Figure 31A:
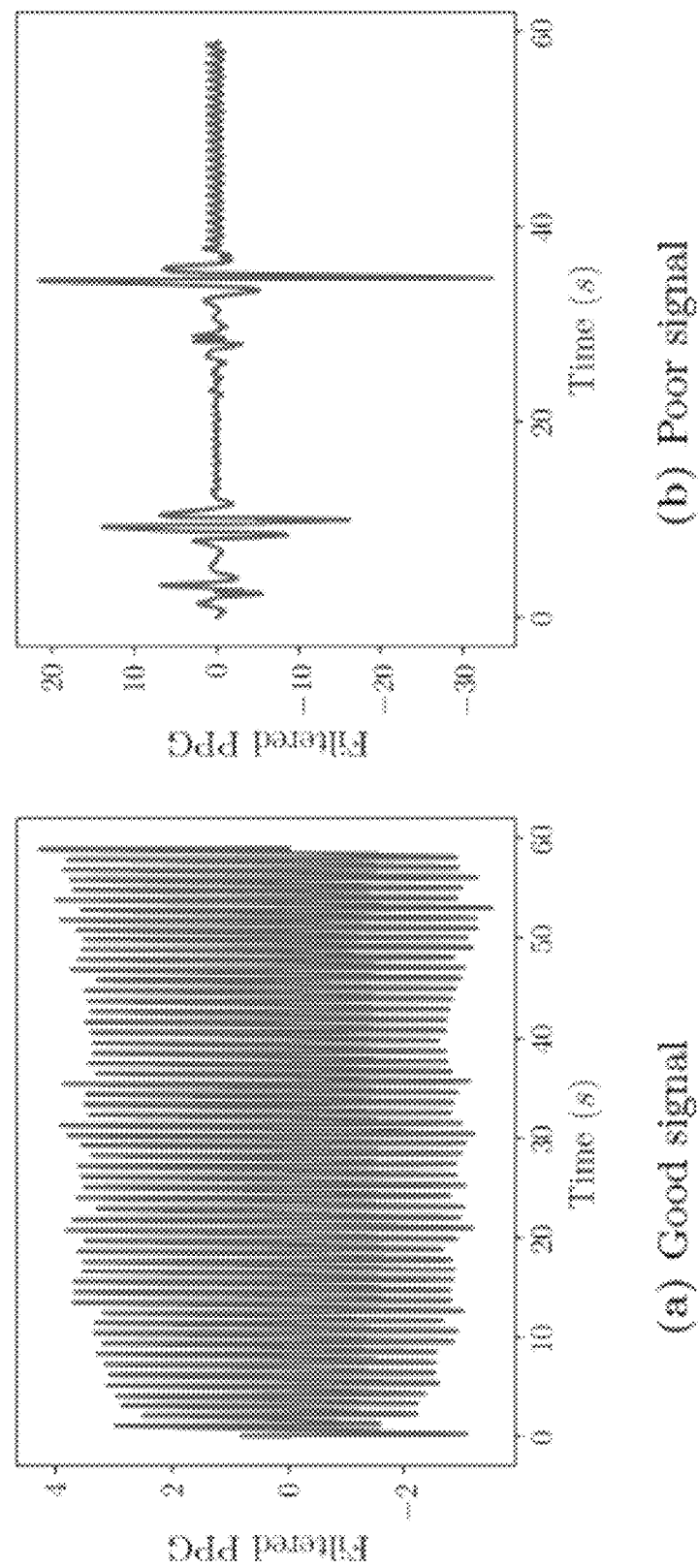
FIGS. 31A-B show examples of two examples of filtered PPG signals and the corresponding normalized autocorrelation metrics or parameters $q_N(i)$ for a given time window $W_N$, according to example embodiments.
Figure 31B:
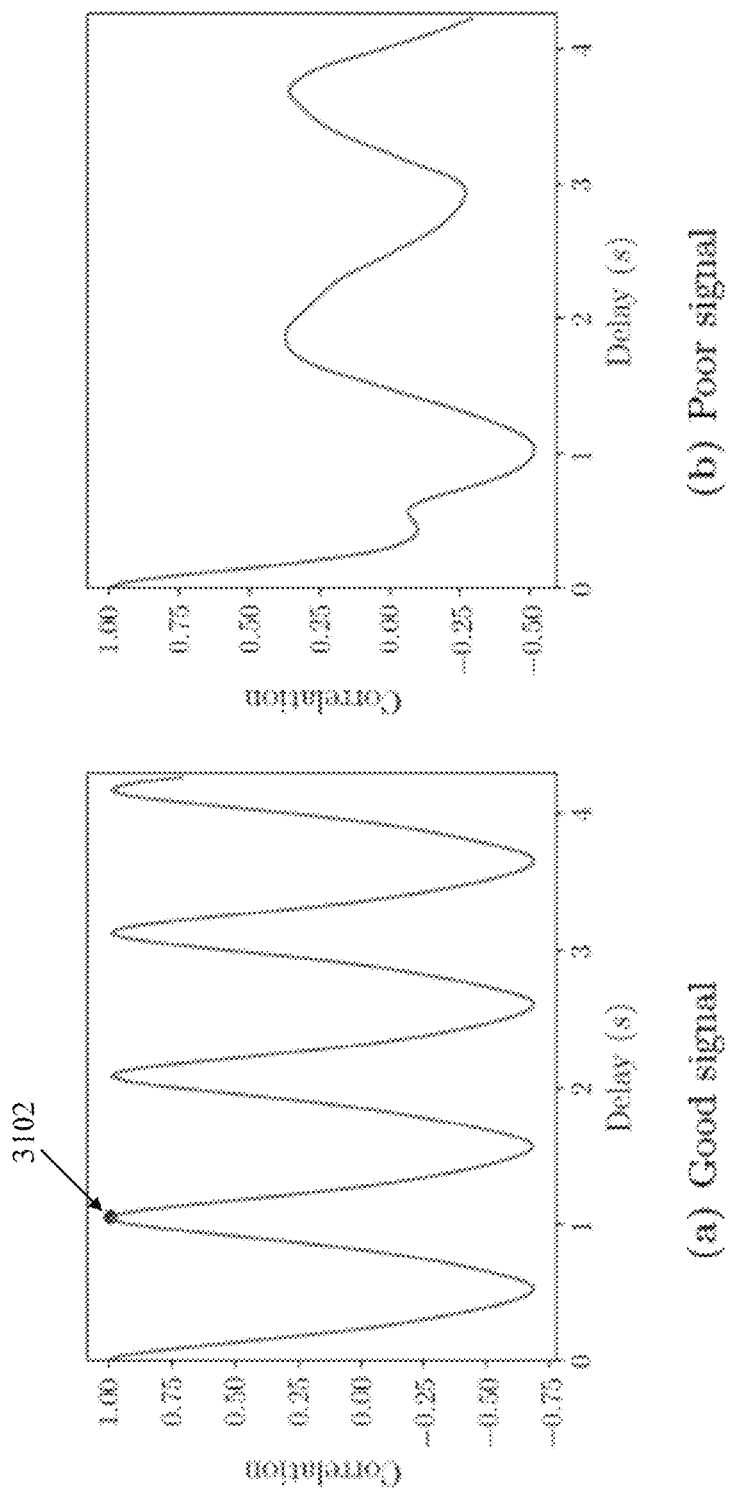

Referring now briefly to FIGS. 31A and 31B, FIGS. 31A and 31B show two examples of filtered PPG signals and the corresponding normalized autocorrelation metrics or parameters $q_N(i)$ for a given time window $W_N$. The PPG plot at the left side of FIG. 31A represents an example of a good quality PPG signal, while the plot at the right side of FIG. 31A represents an example of a bad PPG signal. In FIG. 31B, the plot on the left represents the normalized autocorrelation metrics or parameters $q_N(i)$ for the left PPG signal of FIG. 31A. The plot on the right of FIG. 31B represents the normalized autocorrelation metrics or parameters $q_N(i)$ for the right PPG signal of FIG. 31A. If the PPG signal is of good quality, the corresponding $q_N(i)$ has several successive valleys and peaks reaching very high correlation values close to 1.

In some implementations, the computer system 100 or the signal quality assessment module 508 can define values around the peak, e.g., as a polynomial of degree 2, and interpolate the values of $q_N(i)$ around the peak with such a polynomial, to achieve sub-frame precision. The computer system 100 or the signal quality assessment module 508 can then extract a sub-frame maximum by finding the maximum of the interpolation function. In FIG. 31B, the point 3102 represents the first peak of $q_N(i)$ for the good-quality PPG signal. In FIG. 31B (b), no peak of $q_N(i)$ for the bad-quality PPG signal, other than the first peak, reaches a high value close to 1.

In some embodiments, the computer system 100, or the signal quality assessment module 508, can employ a signal quality metric based on spectrum entropy. A periodic signal can be viewed as composition of unit pure periodic signals or sinusoids that can be considered as symbols. Based on information theory, the amount of information contained in this superposition of symbols can be related to Shannon entropy. Specifically, the signal quality metric based on spectrum entropy can be described as:

$$H(X) = \sum_{k=0}^{N-1}\hat{P}[k]\log \hat{P}[k], \quad (39)$$

where $\hat{P}[k]$ represents the normalized power spectrum of the Fourier transform $\hat{X}[k]$ at the frequency $f_k$ and can be defined as:

$$\hat{P}[k] = \frac{|\hat{X}[k]|^2}{\sum_{l=0}^{N-1}|\hat{X}[l]|^2}. \quad (40)$$

The computer system 100 or the signal quality assessment module 508 can compute H(X) according to equations (39) and (40).

In some implementations, the computer system 100 or the signal quality assessment module 508 can compute a plurality of values of H(X) iteratively as the camera 110 acquires new image frames. For example, when computing the Fourier transform $\hat{X}$, the computer system 100 or the signal quality assessment module 508 can use a different set, or a different sliding window, of samples of the color intensity signal at each iteration. The computer system 100 or the signal quality assessment module 508 can compute, for each computed $\hat{X}$, a corresponding value of H(X). As such, the computer system 100 or the signal quality assessment module 508 does not need to wait for acquisition of the whole color intensity signal to compute H(X), but can evaluate H(X) iteratively as new samples of the color intensity signal (or PPG signal) are generated.

The method 2900 can include the computer system 100 or the signal quality assessment module 508 determining the indication of the quality of the color intensity signal (STEP 2906). The indication of the quality of the color intensity signal can be a signal quality level, such as poor or good. The computer system 100 or the signal quality assessment module 508 can determine the indication of the quality of the color intensity signal using the signal quality metric. For instance, the computer system 100 or the signal quality assessment module 508 can determine the quality level of the color intensity signal using a peak of the normalized autocorrelation score or parameter $q_N(i)$ over each time window $W_N$. Peaks of $q_N(i)$ for each time window $W_N$ usually occur at the local period of heart pulsation of the user or subject.

Figure 31C:
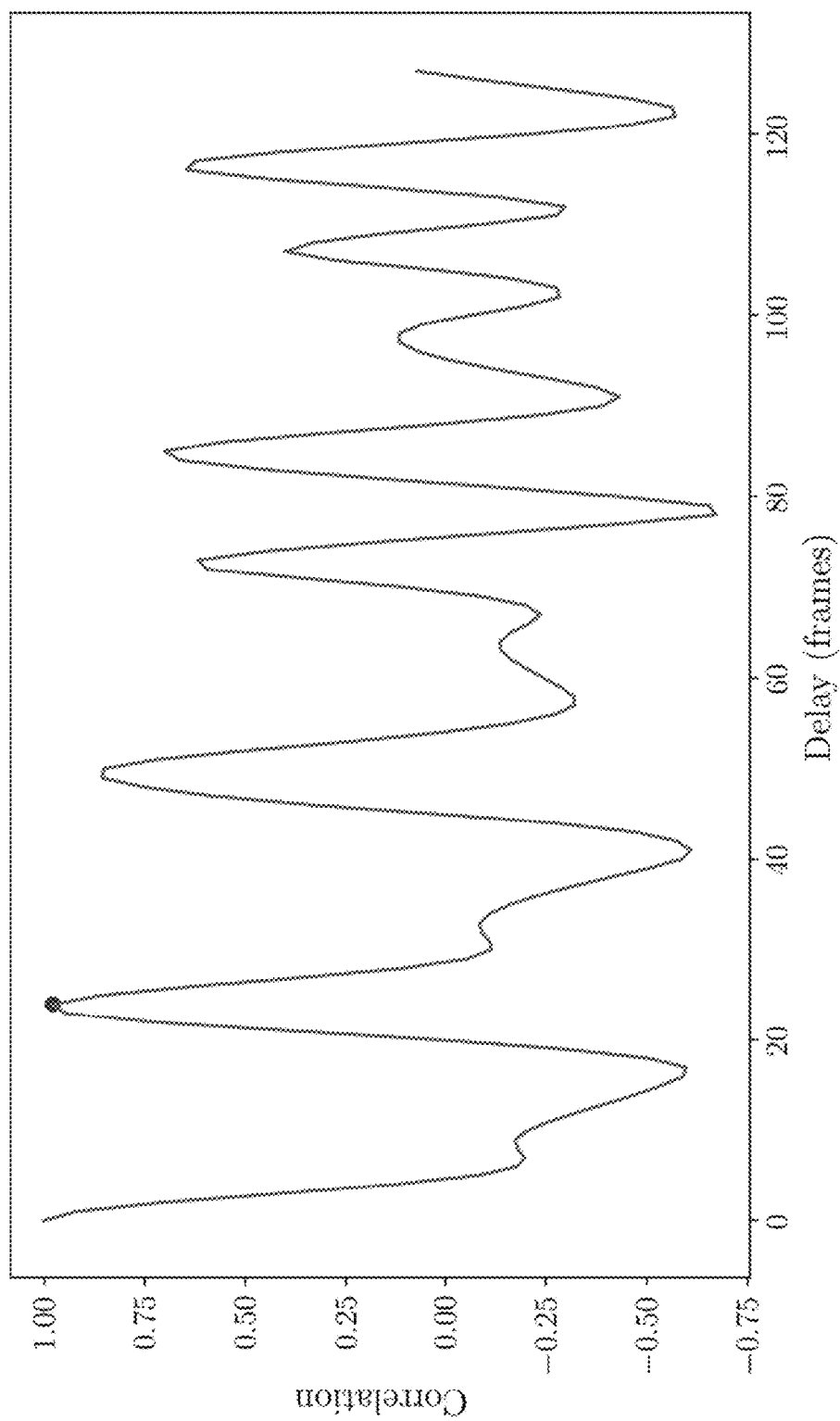
FIGS. 31C-D shows examples of peak detection in example autocorrelation arrays, according to example embodiments.
Figure 31D:
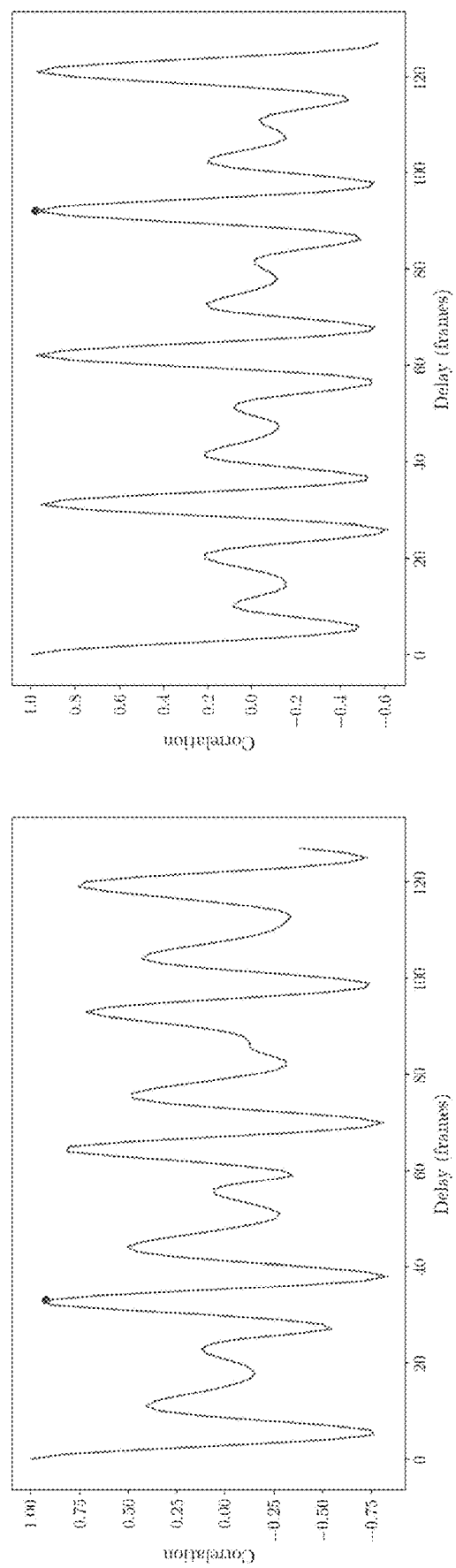

The autocorrelation array $q_N(i)$ always has a value of 1 at its first entry because a signal window (e.g., window 3004c) has a correlation of 1 with itself. When determining the quality indication, is to find the next peak in the autocorrelation array $q_N(i)$. One approach is to detect the second in height (e.g., the maximum of the array $q_N(i)$ without the first entry) and take it as the autocorrelation peak. The computer system 100 or the signal quality assessment module 508 can determine or identify the second highest peak of the autocorrelation array $q_N(i)$ for each time window. FIG. 31C shows an example autocorrelation array where the second highest peak is used to detect the local period of the heart pulsation. However, such approach (e.g., second highest peak) may not always accurately detect the local period of the heart pulsation. Referring to FIG. 31D, plots of two example autocorrelation arrays are shown. For the autocorrelation array on the left, the second highest peak occurs at the local period of the heart pulsation. However, for the autocorrelation array on the right, the second highest peak does not coincide with the local period of the heart pulsation because the color intensity signal contains harmonics of high order. In fact, FIG. 31D shows a degenerate case where the second highest peak is not the peak of interest, and illustrates the importance of a penalization of the peaks with higher index.

To avoid errors in detecting the peak of interest (e.g., due to higher signal harmonics), the computer system 100 or the signal quality assessment module 508 can determine or identify the index of the peak of interest in the autocorrelation array $q_N(i)$ as:

$$\hat{i} = \operatorname*{argmax}_{i} \frac{q(i)}{i^{\theta}}, \quad (41)$$

where $\theta > 0$, and $i^\theta$ is an equalizing factor that penalizes peaks that are too far from the first peak (or first entry) of the autocorrelation array $q_N(i)$. The penalization avoids errors in estimating the period of the pulses.

The computer system 100 or the signal quality assessment module 508 can compare the peak of $q_N(i)$ within each time window $W_N$ to a corresponding threshold value, such as 0.85, 0.9 or other value smaller than but close to 1. The computer system 100 or the signal quality assessment module 508 can determine that at least a portion of the color intensity signal to be of poor quality if the peak of $q_N(i)$ is smaller than the threshold value for one or more consecutive time windows. For example, the computer system 100 or the signal quality assessment module 508 can determine that at least a portion of the color intensity signal to be of poor quality if the peak of $q_N(i)$ is smaller than the threshold value for a sequence of consecutive time windows corresponding to a predefined data acquisition period or number of consecutive seconds. In some implementations, the computer system 100 or the signal quality assessment module 508 can determine that at least a portion of the color intensity signal to be of poor quality if the peak of $q_N(i)$ is smaller than the threshold value for one or more consecutive time windows, or if the variation in the local pulsation period exceeds a predefined variation threshold.

In some implementations, the computer system 100 or the signal quality assessment module 508 can compare each computed value of H (X) to an entropy threshold, such as −0.06, −0.041 or another number smaller than but close to zero. The computer system 100 or the signal quality assessment module 508 can determine that at least a portion of the color intensity signal to be of poor quality if one or more values (or a multiple consecutive values) of H(X) are determined to be smaller than the entropy threshold. In some embodiments, the computer system 100 or the signal quality assessment module 508 can determine that at least a portion of the color intensity signal to be of poor or good quality based on the comparison of a peak of $q_N(i)$ within a time window $W_N$ to the corresponding threshold value, variation in the local pulsation period, comparison of a value of H(X) to the entropy threshold or a combination thereof.

Figure 32:
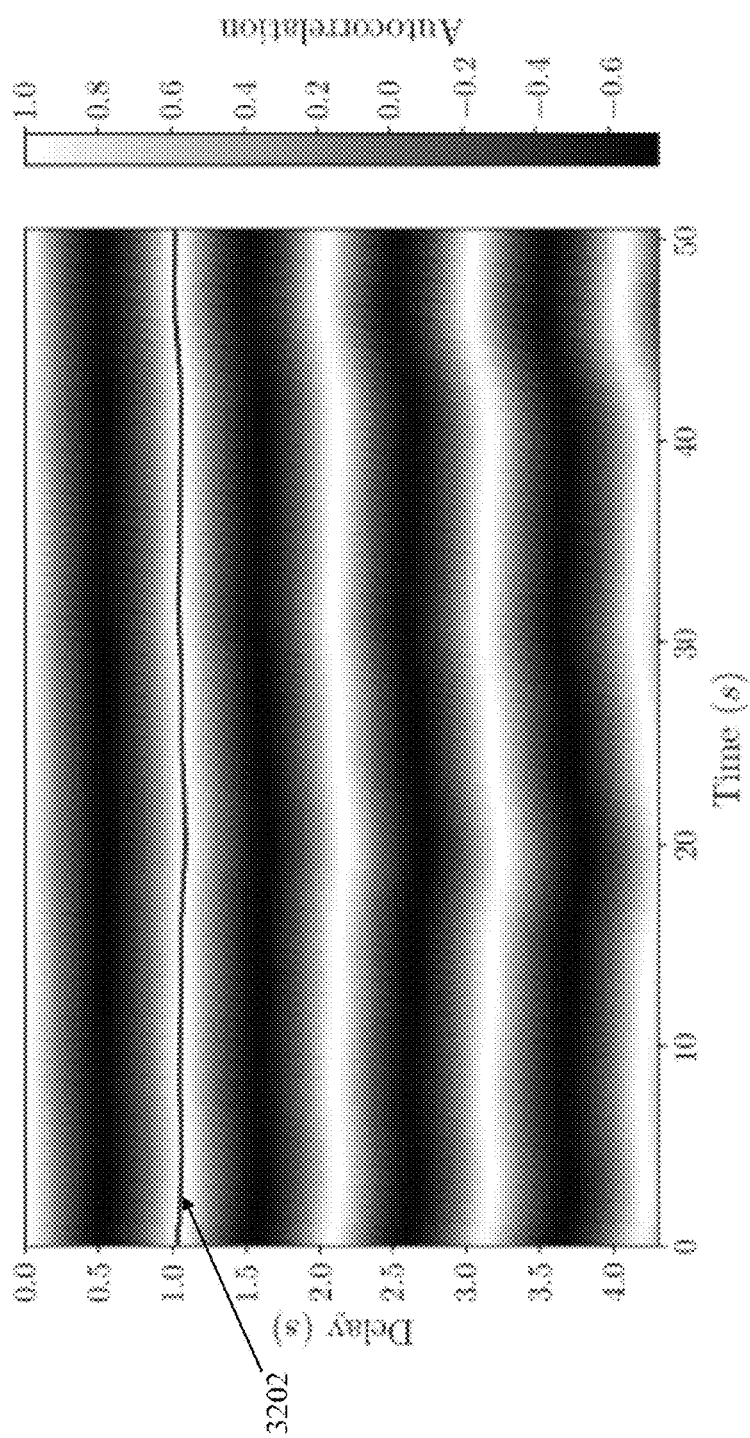
FIG. 32 shows an example image depicting individual normalized autocorrelation parameters $q_N(i)$ for a plurality of time windows $W_N$, according to example embodiments.
Figure 33A:
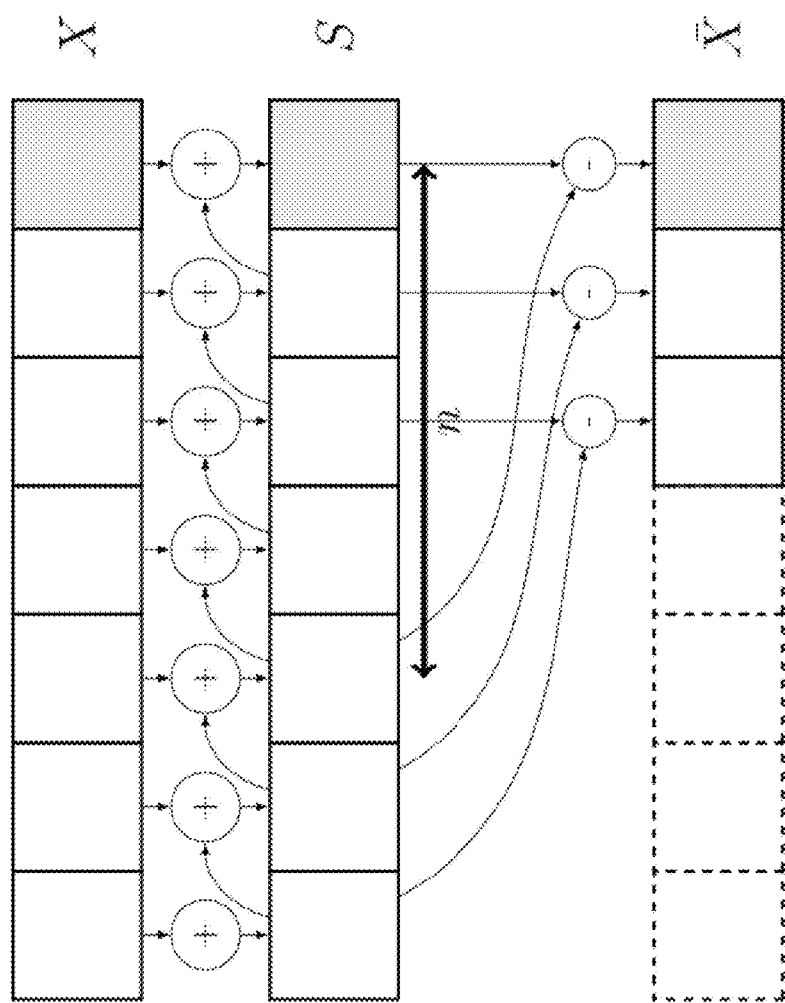
FIGS. 33A-B illustrate example implementations the computation of autocorrelation coefficients, according to example embodiments.
Figure 33B:
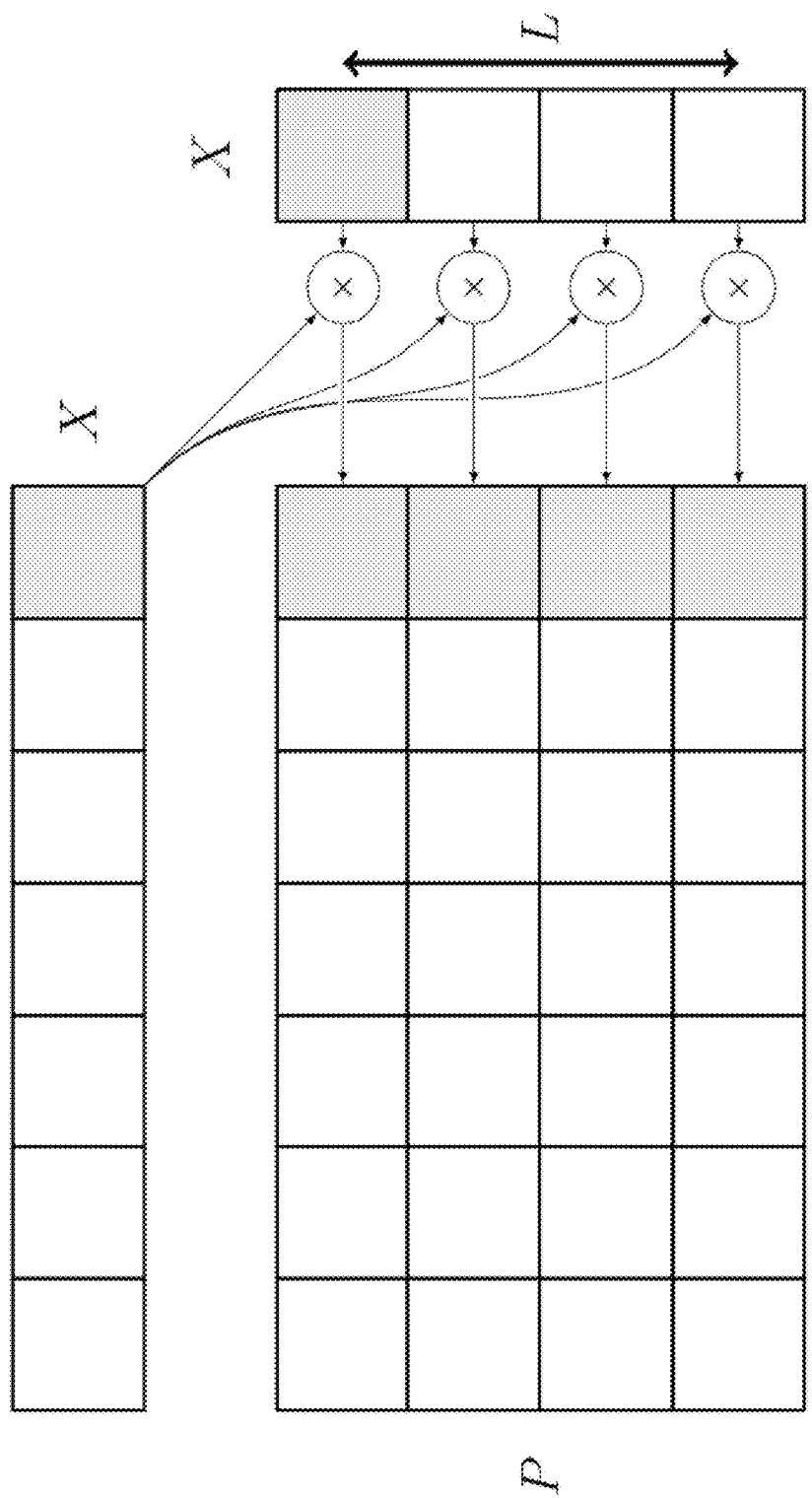

FIG. 32 shows an image depicting individual normalized autocorrelation parameters $q_N(i)$ for a plurality of time windows $W_N$. The horizontal axis represents the timestamps N of the time windows. The vertical axis represents the delay i between a current window $W_N$ and a comparative window $W_{N-i}$. The brighter a pixel with coordinates (N, i), the more correlated are the windows $W_N$ and $W_{N-i}$. The line 1402 represent the peak of $q_N(i)$ for each time window $W_N$.

The method 2900 can include the computer system 100 or the signal quality assessment module 508 providing the indication of the quality of the color intensity (or PPG) signal for display. The computer system 100 can continuously display indications of the signal quality as the camera 110 acquires new video frames. The display of the indications of the signal quality during the data acquisition process allows for detection of inadequate placement of the finger or other body part over the camera lens, and providing immediate notifications to the user of the computer system 100. As such, the user can quickly adjust the placement of his/her finger (or other body part) over the camera lens.

In some embodiments, the computer system 100 or the signal quality assessment module 508 can abort the data acquisition process (e.g., acquisition of the image frames and generation of samples of the color intensity signal) if the signal quality is determined to be poor (or of low level) for a predefined cumulative time period. For example, the computer application 114 can be configured to cause the computer system 100 to acquire data for a total of 30 seconds. To generate a reliable and accurate measurement of blood pressure or pulse, at least 60% of the measured color intensity (or PPG) signal should be of good quality. As such, if at any point during the data acquisition period the generated color intensity (or PPG) signal is determined to be of poor (or low) quality over a cumulative time period of 12 seconds or more (e.g., 40% of 30 seconds), the computer system 100 or the signal quality assessment module 508 can abort the data acquisition (or blood pressure measuring) process, and display a message or indication to the user about the termination of the process.

Figure 34:
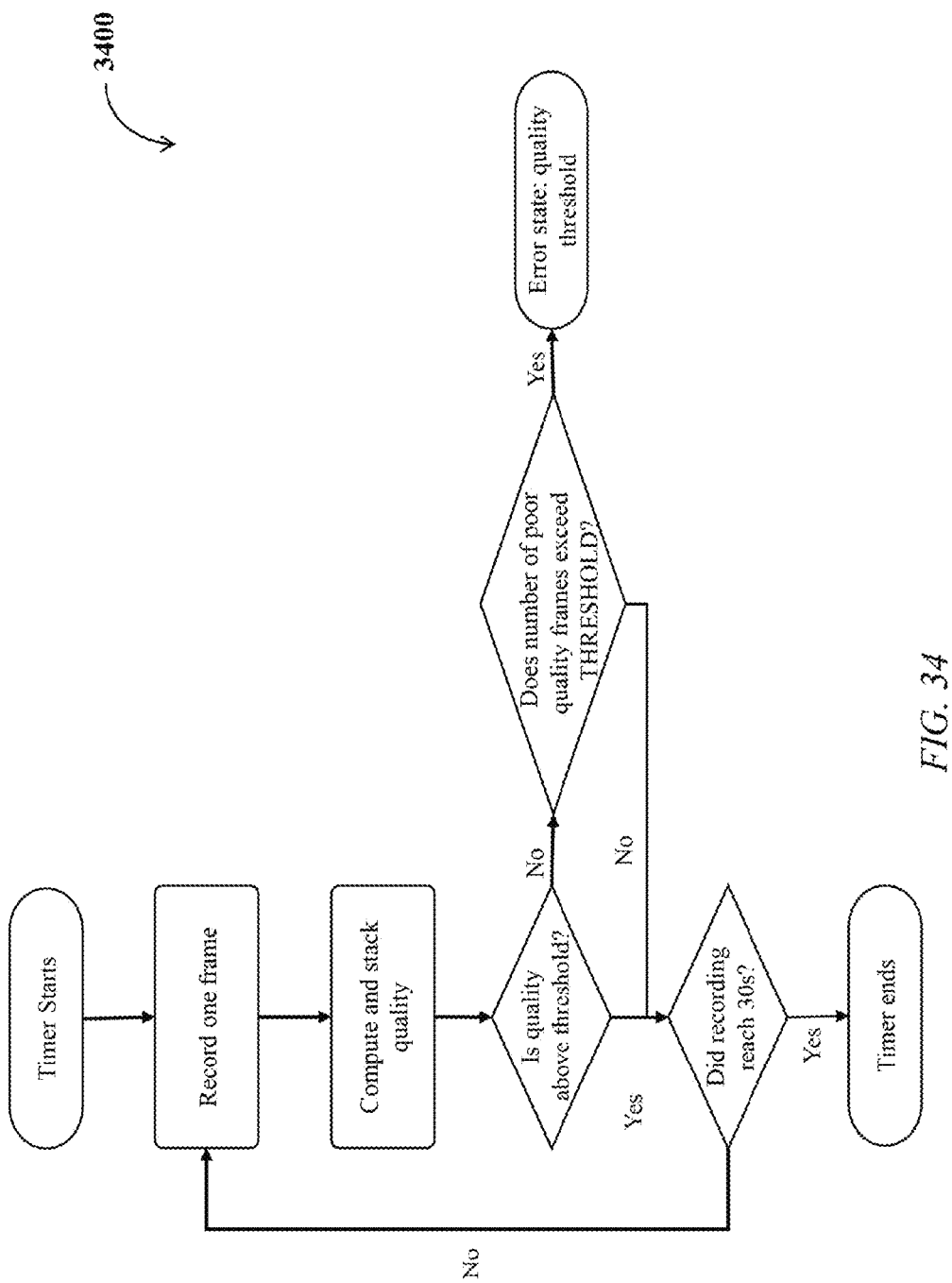
FIG. 34 shows a flowchart illustrating a method of measuring the quality of an acquired PPG signal, according to example embodiments.

Referring to FIG. 34, a flowchart illustrating a data acquisition method 3400 is shown, according to example embodiments. When data acquisition is initiated or triggered, the computer system 100 can start or set a timer (STEP 3402). The computer system 100 can iteratively record or acquire image frames (STEP 3404). For each recorded image frame, the computer system can compute and store a corresponding quality value or quality indication (STEP 3406) and compare the quality value to a quality threshold (STEP 3408). If the quality value is below the threshold, the computer system can increment a counter of poor quality frames and check whether the counter exceeds a maximum allowed number of poor quality frames (STEP 3410). If the counter exceeds the maximum allowed number of poor quality frames, the computer system 100 can abort the data acquisition and display an error message indicating poor quality data (STEP 3412). If the quality is found to exceed the quality threshold at STEP 3408 or if the counter does not exceed the maximum allowed number of poor quality frames at STEP 3410, the computer system 100 can proceed to STEP 3414 and check if the timer reached a predefined time duration (e.g., 30 second). If yes the computer system can stop the time and end data acquisition (as a successful acquisition), otherwise the computer system 100 loop back to STEP 3404 to acquire a new image frame.

Figure 35C:
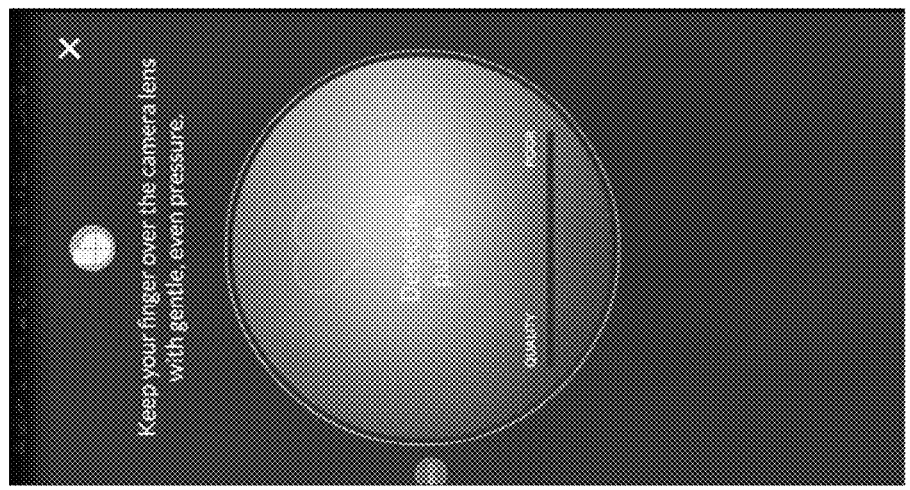
FIGS. 35A-L are screenshots of a user interface (UI) of the computer application at various phases of the acquisition of transdermal optical data, according to example embodiments.
Figure 35B:
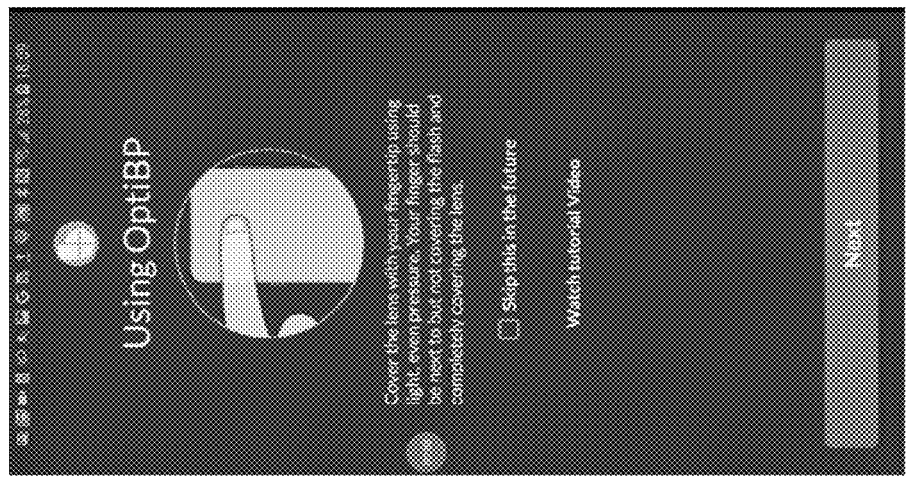
Figure 35A:
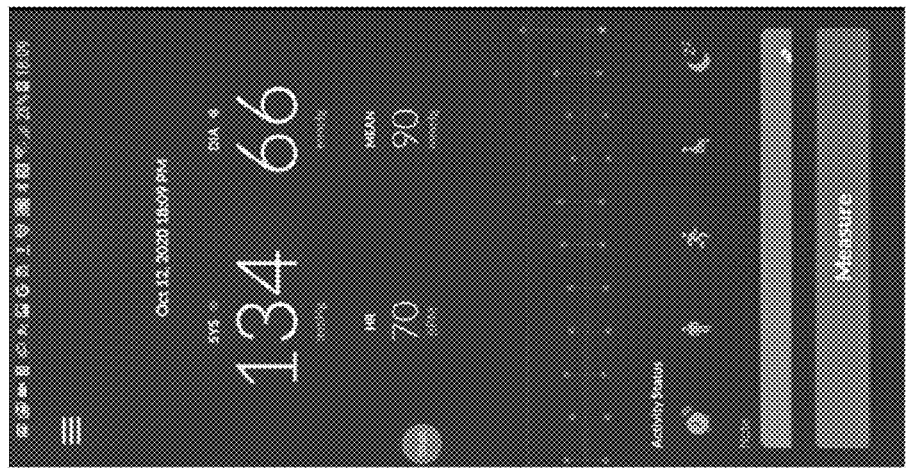

Referring to FIGS. 35A-L, screenshots of a user interface (UI) of the computer application 114 at various phases of the acquisition of transdermal optical data are shown, according to example embodiments of the current disclosure. The application 114, when executed, can cause the computer system 100 to display instructions and/or feedback to the user during in association with the data acquisition process. FIG. 35A shows a screenshot of an example home screen. When the computer application 114 is started or initiated on the computer system 100, e.g., by user action, the computer application 114 can cause the computer system 100 to display the UI shown in FIG. 35A. The UI can include the last blood pressure measurement and the data and time of such measurement. The UI may show a plot or graph of previous measurements of the user. The UI may include a tab or icon, e.g., the "Measure" tab, to initiate a new measuring process of blood pressure. For instance, the user can click or tap on the "measure" icon to trigger a new measuring process.

Upon actuation of the "Measure" tab or icon, the computer application 114 can cause the computing device to display the instructions UI in FIG. 35B. The instructions UI can include instructions or directions for the user regarding how place a finger or other body part against the camera 110 of the computer system 100. The instructions or directions can include an image depicting an example or a desired placement of the finger or other body part against the camera 110. The instructions or guidelines can include textual instructions explaining how to place the finger or other body part against the camera 100. The instructions UI can present an option to play or watch, e.g., via the "Watch tutorial video" tab or icon, a tutorial video that depicts finger (or other body part) placement and/or other instructions/information on how to use the computer application 114. The instructions UI can include a selectable icon to skip the instructions UI in future measurements of the blood pressure. The instructions UI can include an interactive item, e.g., the "Next" tab or icon, to initiate the measuring process when the user is ready.

Upon initiation of the measuring process, the computer application 114 can cause the computing device 110 to detect PPG signal quality, e.g., using methods or techniques discussed above, and display a representation of a quality meter depicting an indication or value of the quality of measured PPG signal. The screenshots in FIGS. 35C-I show instances of feedback UI at various time instances of the measuring process. The feedback UI can include the visual representation of the quality meter, e.g., the disc including a signal quality bar. In some implementations, the PPG signal quality as depicted by the signal quality bar can vary between poor and good. For example, the computer system 100 may consider the PPG signal quality to be good when the normalized autocorrelation score $q_N(i)$ is over 85% (or over 0.85). In some implementations, the signal quality bar can depict poor signal quality with blue color and/or the term "Poor" and depict good signal quality with green color and/or the term "Good."

In some implementations, the computer system 100 can start recording the measured PPG signal once the quality first reaches the "Good" level, e.g., when the normalized autocorrelation score $q_N(i)$ first exceeds 85%. Referring to FIGS. 35C and 35D, screenshots of the UI depicting PPG signal detection leading to potential start of signal recording. Initially, the feedback UI or the quality meter can indicate that the computer system 100 is in the process of "Detecting pulse" while detected PPG signal is still poor.

Figure 35F:
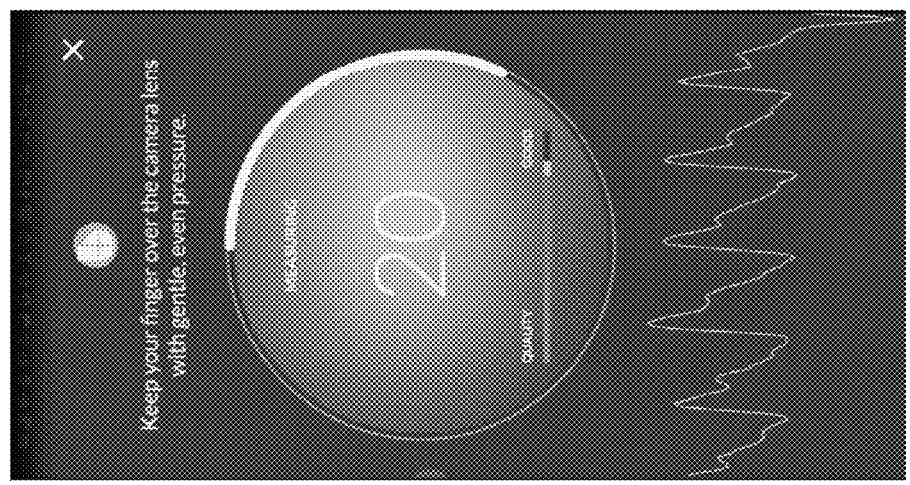
Figure 35E:
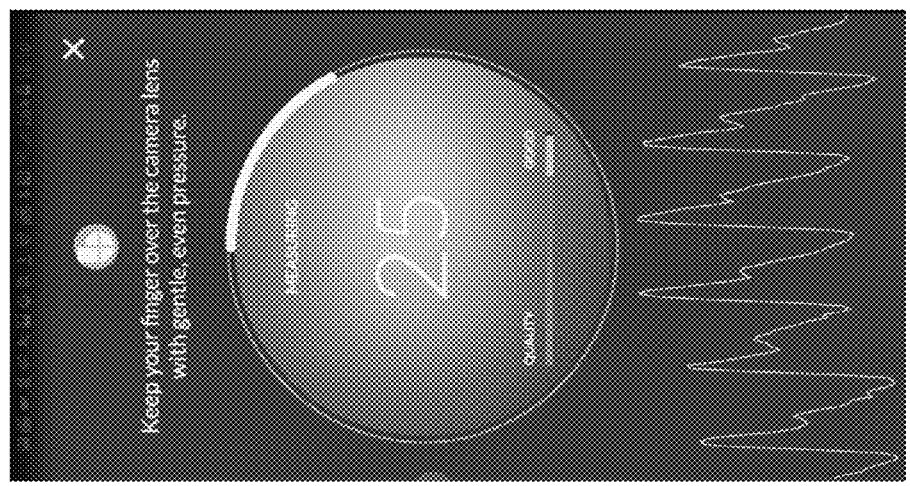
Figure 35D:
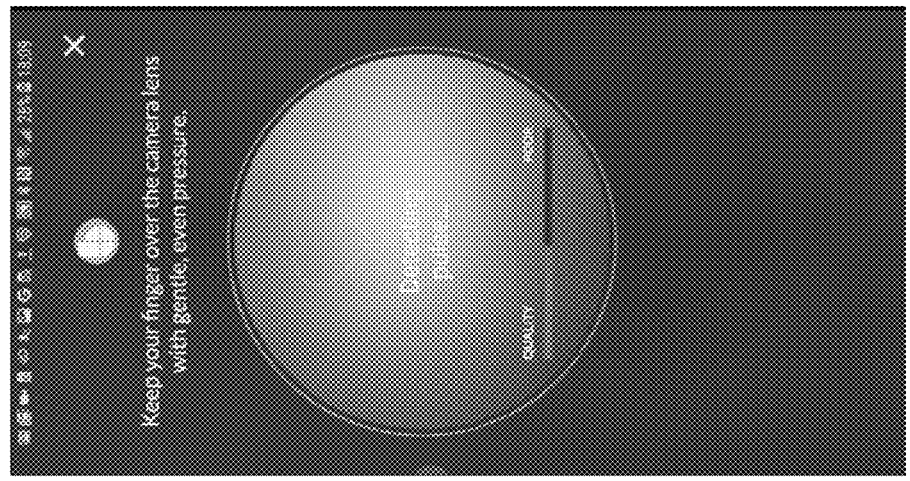

Once the measured PPG signal quality reaches a good quality level, the feedback UI can indicate the start of PPG signal recording, for example, by rendering the term "Measuring" as part of the quality meter, as illustrated in FIGS. 35E and 35F. The quality meter can display, via the signal quality bar, the current detected signal quality. The feedback UI may also display a plot or graph of a most recent recorded portion of the PPG signal. Throughout the signal detection and recording process, the feedback UI can render a text (or other visual indication) to remind the user to keep the finger (or other body part) over the camera lens with gentle and even pressure. After the signal recording process starts, the quality meter can display a timer, e.g., a decreasing counter, indicating time left in the data acquisition process.

Figure 35I:
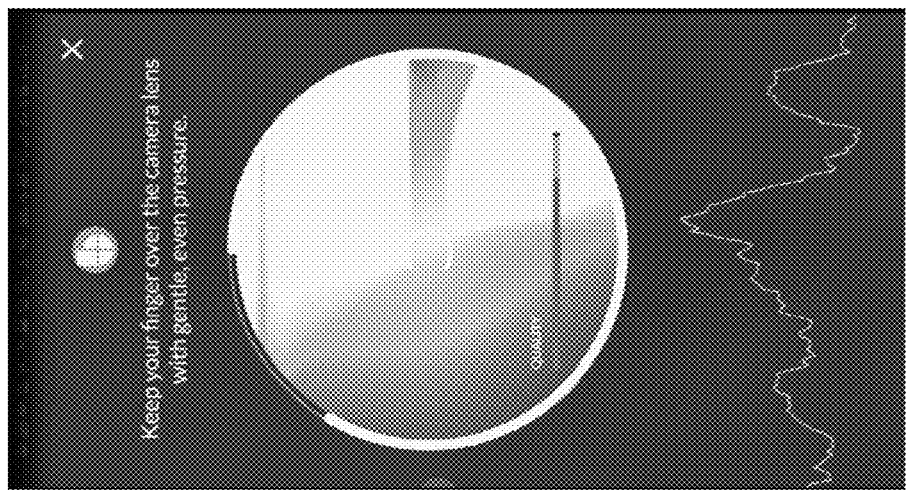
Figure 35H:
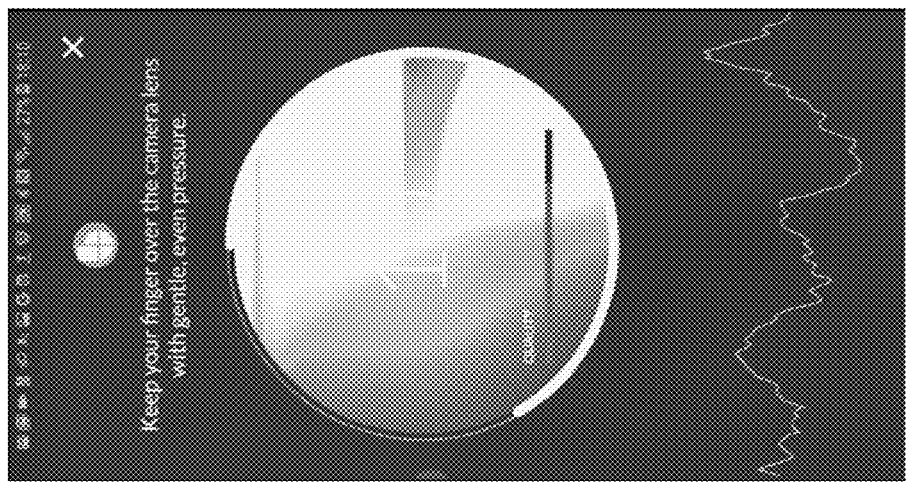
Figure 35G:
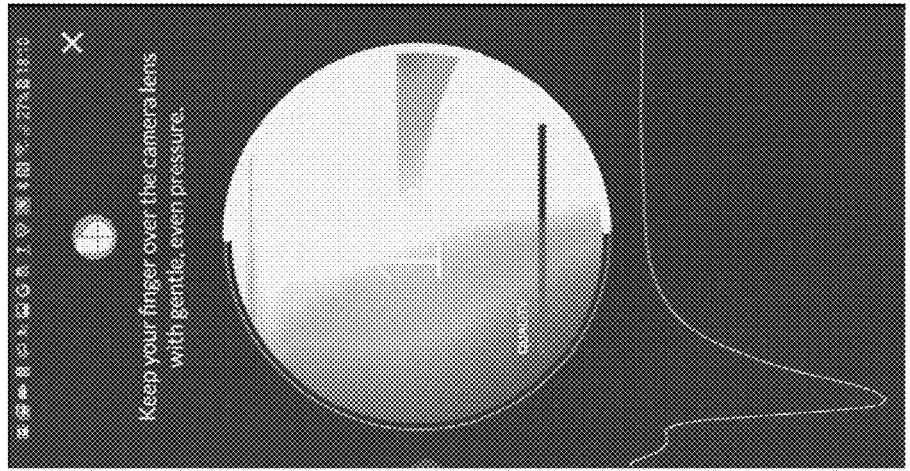

If the detected signal quality goes below 85% for a predefined time duration, e.g., x consecutive seconds, the quality meter or the signal quality bar can display an indication of the poor quality. As such, the user is notified of the poor quality and can promptly adjust the finger (or other body part) placement relative to the camera lens. The feedback UI can continue to render the plot or graph of the recorded PPG signal even if the detected quality is poor, as illustrated in FIGS. 35G-I.

Figure 35L:
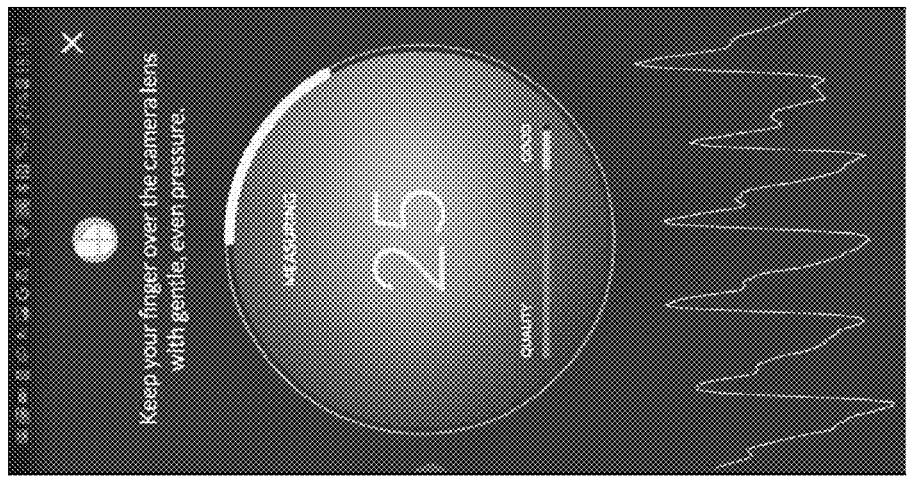
Figure 35K:
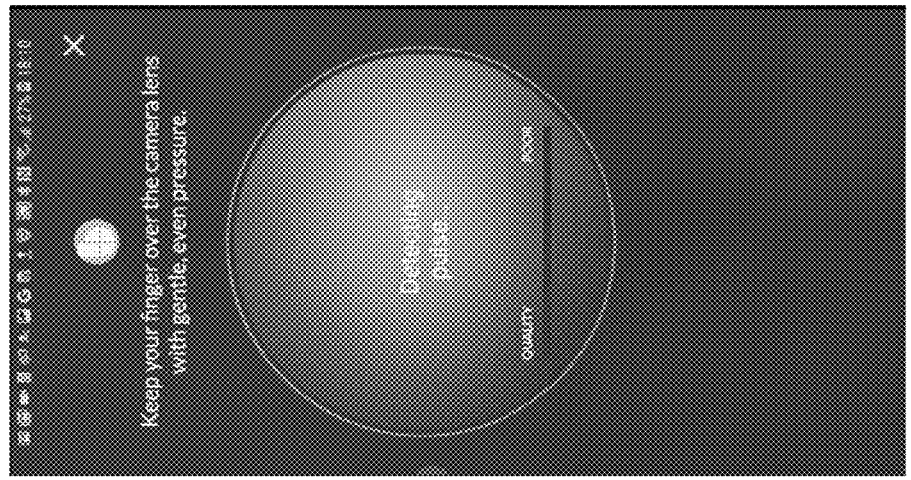
Figure 35J:
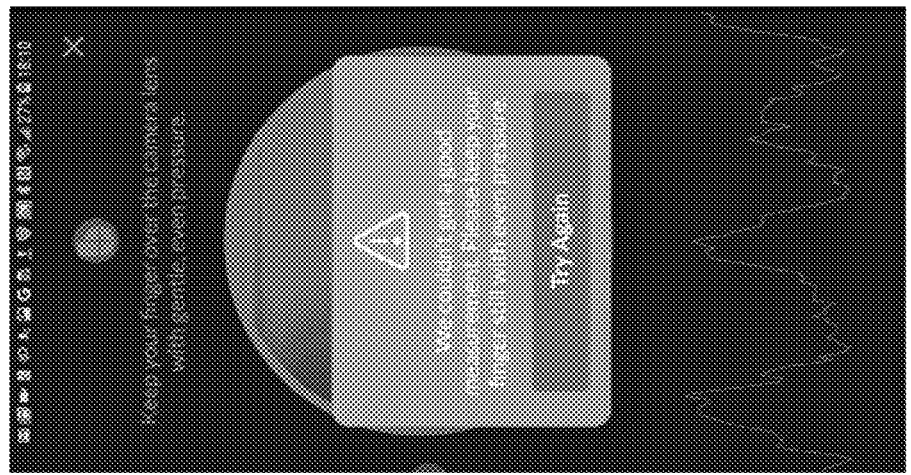

If the signal quality is poor for a predefined cumulative time period, e.g., y cumulative seconds, the computer system 100 can stop the signal recording process. Once the signal recording is stopped, the computer application 114 can cause the computer system 100 to display or render a message indicative of the termination of the signal recording. FIG. 35J shows an example of such message displayed by the computer system 100. The message can include an interactive item, e.g., icon, allowing the user to start or initiate a new signal recording process. If the user interacts with the interactive item, the computer system 100 can restart the signal detection and signal recording process, and display corresponding UIs as illustrated in FIGS. 35K and 35L. If the measured PPG signal has a good quality for at least a predefined cumulative time duration, e.g., 60% or more of the total recording duration, the computing device can use the recorded signal to measure the user's blood pressure and/or the user's pulse and display the measurements in a measurement UI. For example, the total recording duration can be equal to 30 seconds, and the computer system 100 can keep track of the signal quality metric(s) during this time period. Considering the predefined cumulative time duration, the computer system 100 may abort signal recording if bad signal is detected for a cumulative time period of 12 seconds.

In some implementations, the computer system 100 can record or store displayed feedback, plots of measured signal, computed normalized autocorrelation score $q_N(i)$ and/or other parameters in a document or data structure, such as a Firebase database or data storage. The document can include a tab "Poor Signal Quality" for accessing information related to poor signal quality, and/or a tab "End of measurements" to access information related to termination of PPG signal recording, such as time of termination or reason for termination, among others. The document or data structure can be maintained in the computer system 100 or on a remote computer server.

In some implementations, the computer application 114 can cause the computer system 100 to notify the user, e.g., via the feedback UI, if a detection is made indicating that that the finger (or other body part) is not placed correctly or is not fully covering the camera lens. The UI may instruct the user to adjust the placement of his/her finger or body part, or indicate to which direction the finger or body part is to be shifted. The computer application 114 may be configured to detect finger tremor that prevents recording of a good quality PPG signal, and notify the user of such fact via the feedback UI. In some implementations, the computer application 114 may be configured to detect that the signal amplitude is weaker than normal, e.g., finger feels cold and blood flow in the finger is sub-optimal, and notify the user the user via the feedback UI. In general, the computer application 114 may be configured to provide detailed feedback to the user that specifies the reason or cause of a bad quality signal.

F. Improving Accuracy of Blood Pressure Measurements Using Smartoffset Calibration Based on Reference Signals Generated Using a Blood Pressure Measurement Device The OBPM algorithm used to estimate blood pressure measurements based on the recorded (or generated) PPG signal, is able to accurately track blood pressure change, but does not provide accurate measurements (or estimates) of the absolute pressure. This calls for the use of calibration processes to enhance the accuracy of measurements of absolute blood pressure.

Figure 36:
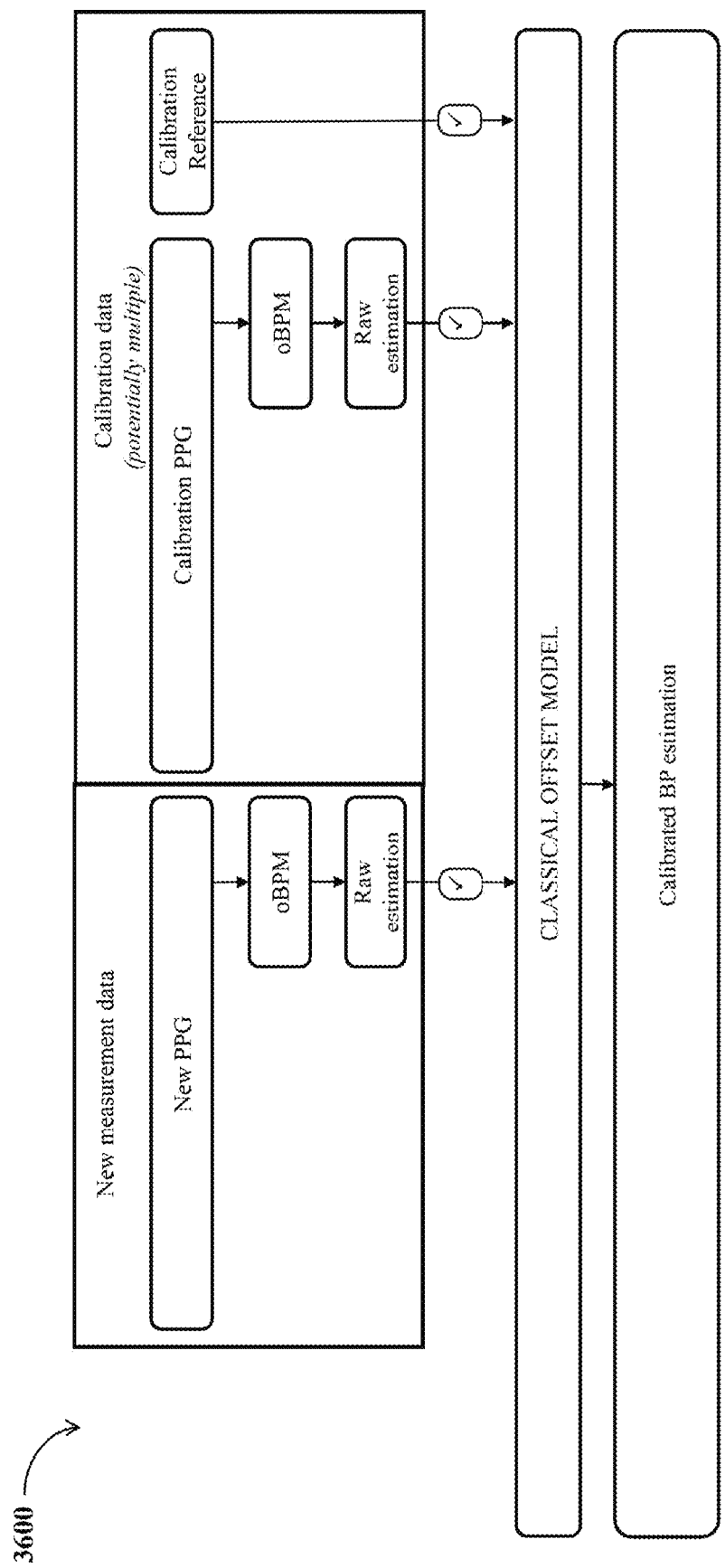
FIG. 36 illustrates an example of a classical offset calibration model, according to example embodiments.

A classical calibration approach includes determining a calibration offset, and adding the determined calibration offset to each blood pressure measurement. FIG. 36 shows a block diagram of a classical calibration model 3600. The computing system can obtain a calibration blood pressure measurement, referred to herein as reference calibration 3602 or $Cuff_{calibration}$, that is provided by a cuff-based blood pressure measuring device. The computer system 100 can generate, approximately at the same time or within a short time period of measuring the calibration reference 3602, a second calibration blood pressure measurement 3604 generated using a calibration PPG signal (e.g., determined using the OBPM algorithm). The second calibration signal 3604 is referred to herein as $OBPM_{calibration}$. The classical calibration model 3600 can receive $Cuff_{calibration}$ and $OBPM_{calibration}$ as input calibration parameters, and determine a calibration offset as the difference between $Cuff_{calibration}$ and $OBPM_{calibration}$. When the classical calibration model 3600 receives a new blood pressure measurement 3606 (denoted as OBPM), e.g., estimated by the OBPM algorithm using a recording PPG signal, the computer system 100 or the calibration model 3600 can compute a calibrated blood pressure measurement 3608 (denoted as $BP_i$) as:

$$BP_i = OBPM_i + (Cuff_{calibration} - OBPM_{calibration}). \quad (42)$$

Equation (42) can be viewed as a simple linear regression with a weight of +1 for $OBPM_i$ and $Cuff_{calibration}$ and a weight for −1 for $OBPM_{calibration}$. In some implementations, multiple calibration offsets determined based on multiple calibration pairs ($Cuff_{calibration}$, $OBPM_{calibration}$) can be used.

Figure 37:
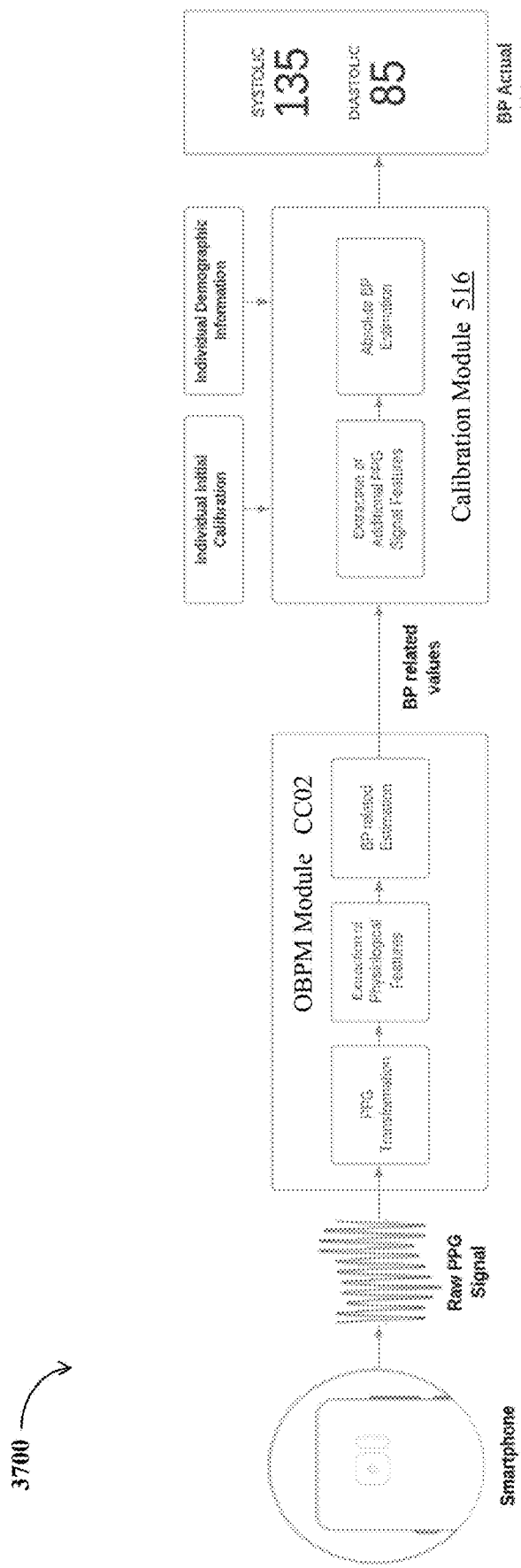
FIG. 37 is block diagram illustrating an example a blood pressure calibration system, according to example embodiments.

In the current disclosure, more complex calibration models are used to improve the accuracy of absolute blood pressure measurements based on recorded PPG signals. Referring to FIG. 37, a block diagram illustrating a calibration system 3700 is shown, according to example embodiments. The calibration system 3700 can include an OBPM module (or algorithm) 3702 and calibration module 516. The calibration module 516 can include a feature extraction module 3704 and an absolute blood pressure estimation module 3706 (e.g., calibration model, calibration free estimation model or classification model). The calibration module 516 can receive calibration measurements, e.g., $Cuff_{calibration}$ and $OBPM_{calibration}$, a calibration PPG signal, user demographic information, a recording PPG signal and a blood pressure estimate/value generated by the OBPM module 3702 based on recording PPG signal as input, and provide the systolic and/or diastolic blood pressure measurement(s) as output.

Figure 38:
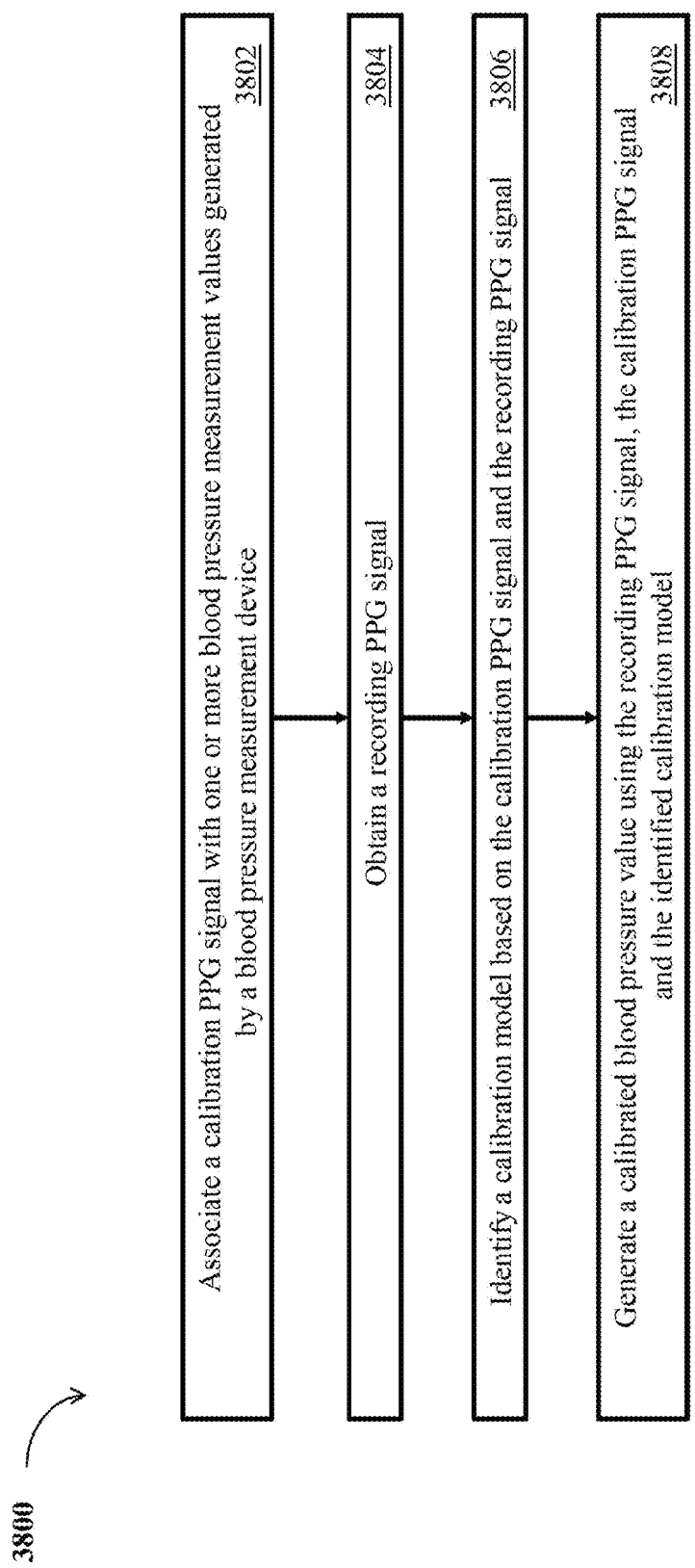
FIG. 38 shows an example flowchart illustrating a blood pressure calibration method, according to example embodiments.

Referring to FIG. 38, a flowchart of a calibration method 3800 is shown, according to example embodiments. In brief overview, the method 3800 can include associating a calibration PPG with one or more measurement values generated by a blood pressure measurement device (STEP 3802), and obtaining a recording PPG signal (STEP 3804). The method 3800 can include identifying a blood pressure calibration model based on the calibration PPG signal and the recording PPG signal (STEP 3806), and generating a calibrated blood pressure value using the recording PPG signal, features associated with the calibration PPG signal and the identified blood pressure calibration model (STEP 3808).

Figure 39:
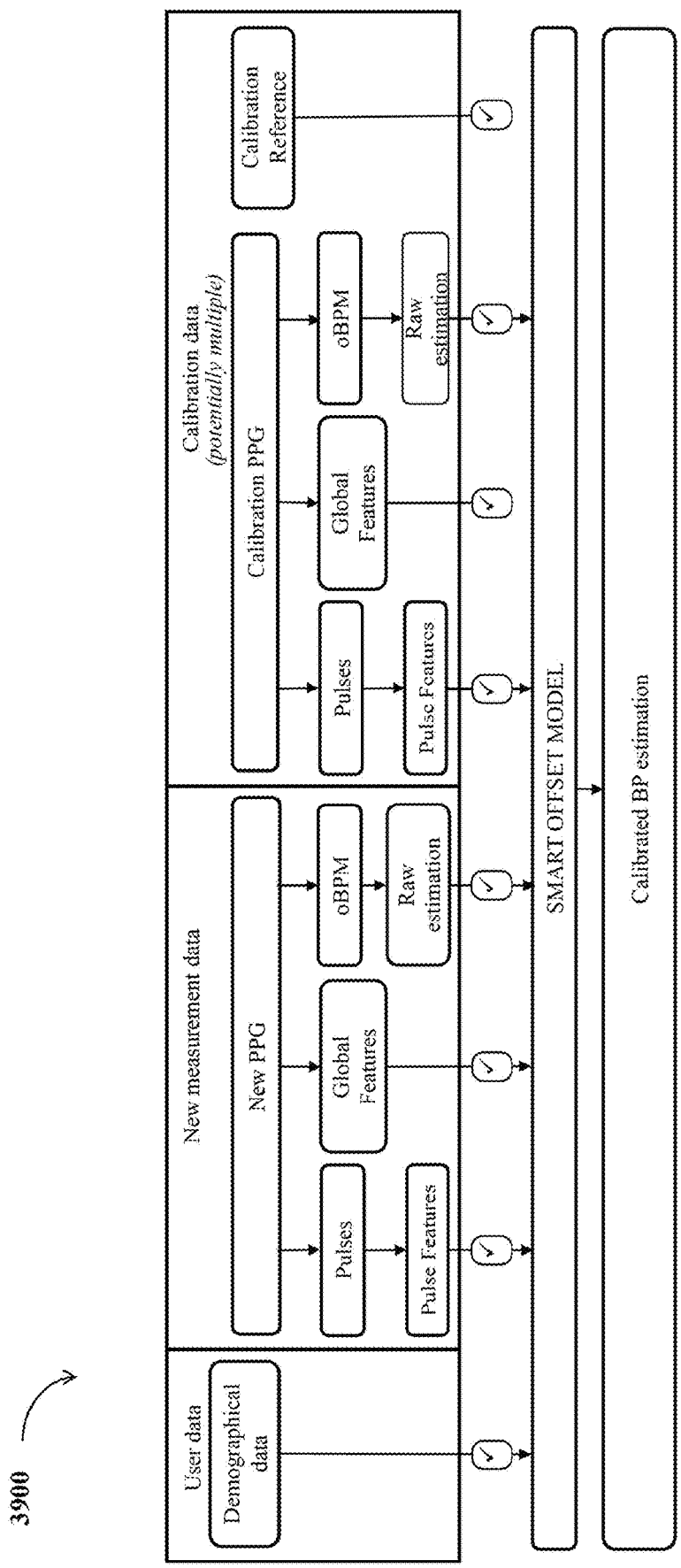
FIG. 39 illustrates an example of a smart offset calibration model, according to example embodiments.

FIG. 39 shows a block diagram illustrating a blood pressure calibration model 3900, according to example embodiments. The calibration model 3900 is also referred to herein as a smart offset calibration model 3900. The calibration model 3900 can be a linear regression model, a nonlinear regression model, a RandomForest regressor, a support vector machine regressor, a multi-layer perceptron or a neural network among others.

Referring now to FIGS. 37-39, the method 3800 can include the computer system 100 or the calibration module 516 associating a calibration PPG signal generated from a first sequence of image frames obtained from photodetector 110 of the computer system 100 with one or more calibration measurement values (or calibration references) 3902 generated by a blood pressure measurement device different from the computer system 100 (STEP 3802). The one or more calibration measurement values or calibration references 3902 (e.g., systolic and/or diastolic) can represent blood pressure measurement(s) of a user of the computer system 100 generated by a cuff based blood pressure measurement device. The calibration reference(s) can be referred to as $Cuff_{calibration}$. The computer system 100 can generate a calibration PPG signal of the user at the same time or within a short time period of measuring the calibration reference(s) 3902 or $Cuff_{calibration}$. The calibration PPG signal can be generated by the computer system as dicussed above with regard to FIGS. 4 and 7. The computer system 100 or the calibration module 516 can associate the calibration reference(s) 3902 or $Cuff_{calibration}$ to the calibration PPG signal. For instance, the computer system 100 can store the calibration PPG signal in association with the calibration reference(s) 3902 or $Cuff_{calibration}$, e.g., using a data structure. The association can indicate that both the calibration PPG signal and the calibration reference(s) 3902 or $Cuff_{calibration}$ were generated simultaneously or within a short time period (e.g., with 5 minutes or within 10 minutes) of each other.

The calibration module 516 receive both the calibration PPG signal and the calibration reference(s) 3902 or Cuff$_{calibration}$ as input calibration data.

The method 3800 can include the computer system 100 obtaining a recording PPG signal (or new PPG in FIG. 39) generated from a second sequence of image frames obtained from the photodetector 110 (STEP 3804). The second sequence of image frames can be acquired at a later time by the computer system 100 for measuring the blood pressure of the user. The computer system 100 can generate the recording PPG signal using the second sequence of image frames as discussed above with regard to FIGS. 4 and 7. The calibration module 516 can receive the recording PPG signal as input recording data for measuring the blood pressure of the user.

The method 3800 can include the computer system 100 or the calibration module 516 identifying a calibration model from a plurality of blood pressure calibration models based on the calibration PPG signal and the recording PPG signal (STEP 3806). The computer system 100 or the calibration module 516 can maintain or have access to the plurality of blood pressure calibration models. The plurality of blood pressure calibration models can include one or more linear regression models, one or more nonlinear regression models, one or more trained machine learning models or a combination thereof. The plurality of blood pressure calibration models can include one or more one or more trained machine learning regression models.

The computer system 100 or the calibration module 516 can identify or select the calibration model, from the plurality of blood pressure calibration models, based on outputs of the OBPM module 3702 when fed with calibration PPG signal or the recording PPG signal as input. The OBPM module 3702 can receive a PPG signal (raw PPG signal) or a logarithmic PPG signal as input. A logarithmic PPG signal is a PPG signal to which a logarithmic function or transformation is applied. The computer system 100 or the OBPM module 3702 can generate, from the recording PPG signal, a logarithmic recording PPG signal, and generate, from the calibration PPG signal, a logarithmic calibration PPG signal. The OBPM module 3702 can separately use each of the calibration PPG signal, the logarithmic calibration PPG signal, the recording PPG signal and the logarithmic recording PPG signal as input and estimate (or attempt to estimate) a corresponding blood pressure measurement for each of these input signals. However, the OBPM module 3702 may not be successful in estimating a corresponding blood pressure measurement for each of these input signals.

The computer system 100 or the calibration module 516 can determine (i) whether the recording PPG signal generates a first blood pressure estimate, (ii) whether the logarithmic recording PPG signal generates a second blood pressure estimate, (iii) whether the calibration PPG signal generates a third blood pressure estimate, and (iv) whether the logarithmic calibration PPG signal generates a fourth blood pressure estimate. The computer system 100 or the calibration module 516 can identify or select the calibration model from the plurality of blood pressure calibration models based on the events (i), (ii), (iii) and (iv). For instance, the computer system 100 or the calibration module 516 can identify or select the calibration model from 12 different blood pressure calibration models according to Table 4 below.

TABLE 4

Events for Calibration Model Selection/Identification.

| | | Recording signal | | | |
|---|---|---|---|---|---|
| | | Group_raw&log | Group_raw | Group_log | Group_noObpm |
| Calibration signal | Group_raw&log_calib | Model 1 | Model 2 | Model 3 | Model 4 |
| | Group_raw_calib | Model 5 | Model 6 | Model 7 | Model 8 |
| | Group_log_calib | Model 9 | Model 10 | Model 11 | Model 12 |

The term "Group_raw&log_calib" means that the OBM module 3702 provides blood pressure estimates for both the raw calibration PPG signal and the logarithmic calibration PPG signal. The term "Group_raw_calib" means that OBM module 3702 provides a blood pressure estimate only for the raw calibration PPG signal but not for the logarithmic calibration PPG signal. The term "Group_log_calib" means that the OBM module 3702 provides a blood pressure estimate only for the logarithmic calibration PPG signal but not for the raw calibration PPG signal. The term "Group_raw&log" means that the OBM module 3702 provides blood pressure estimates for both the raw recording PPG signal and the logarithmic recording PPG signal. The term "Group_raw" means that the OBM module 3702 provides a blood pressure estimate only for the raw recording PPG signal but not for the logarithmic recording PPG signal. The term "Group_log_calib" means that the OBM module 3702 provides a blood pressure estimate only for the logarithmic recording PPG signal but not for the raw recording PPG signal. The term "Group_noOBPM" means that the OBM module 3702 fails to provide an estimate either for the recording PPG signal or for the logarithmic recording PPG signal.

The method 3800 can include the computer system 100 or the calibration module 516 generating a calibrated blood pressure value 3918 using the recording PPG signal, features associated with the calibration PPG signal and the identified calibration model (STEP 3808). Each blood pressure calibration model of the plurality of blood pressure calibration models can be associated with a corresponding set of parameter variables used to determine calibrated blood pressure values. The corresponding set of parameter variables for each blood pressure calibration model $M_j$ can be indicative (or can represent) a set of features that are provided as input to the blood pressure calibration model $M_j$ and are used by the calibration model $M_j$ to determine the blood pressure value(s) (e.g., systolic and/or diastolic) of the user. For example, a blood pressure calibration model $M_j$ can be a linear regression model where the blood pressure value of the user is determined as:

$$BP_i = M_j(\text{feature}_1, \ldots, \text{feature}_{n_j}) = \beta_0^j + \Sigma_{k=1}^{n_j} \beta_k^j \text{feature}_k. \quad (43)$$

The parameter variables $\text{feature}_1, \ldots, \text{feature}_{n_j}$ represent the set of features used by the blood pressure calibration model $M_j$ to estimate or determine the absolute calibrated blood pressure values, such as the absolute calibrated blood pressure value $BP_i$ of recording i. The parameters $\beta_0^j, \ldots, \beta_{n_j}^j$ represent the linear regression coefficients of the linear regression model $M_j$, and $n_j$ represents the total number of features associated with the calibration model $M_j$. In some implementations, the blood calibration model can be a linear regression model, a nonlinear regression model, a neural network, a machine learning model or a combination thereof.

The set of features of a blood pressure calibration model, such as model $M_j$, can include systolic and/or diastolic blood pressure estimates generated by the OBPM module 3702 responsive to an input signal equal to the raw recording PPG signal or the logarithmic recording PPG signal. For instance, the set of features can include a systolic blood pressure estimate generated using the recording PPG signal as an input signal, a diastolic blood pressure estimate generated using the recording PPG signal as an input signal, a systolic blood pressure estimate generated using a logarithmic recording PPG signal as input signal, a diastolic blood pressure estimate generated using the logarithmic recording PPG signal as input signal or a combination thereof.

The set of features of a blood pressure calibration model, such as model $M_j$, can include calibration features (or OBPM calibration measurements) such as systolic and/or diastolic blood pressure estimates generated by the OBPM module 3702 responsive to an input signal equal to the raw calibration PPG signal or the logarithmic calibration PPG signal. For instance, the set of features can include a systolic blood pressure estimate generated using the calibration PPG signal as an input signal, a diastolic blood pressure estimate generated using the calibration PPG signal as an input signal, a systolic blood pressure estimate generated using a logarithmic calibration PPG signal as input signal, a diastolic blood pressure estimate generated using the logarithmic calibration PPG signal as input signal or a combination thereof. The calibration features can include a systolic calibration reference and/or a diastolic calibration reference representing calibration blood pressure measurements provided by the cuff based device. The calibration features are listed in Table 5 below.

TABLE 5

Calibration Features.

| Name | Definition |
|---|---|
| Raw Sys_calib | Systolic output of OBPM for the calibration with the input being the raw calibration PPG signal |
| Raw Dia_calib | Diastolic output of OBPM for the calibration with the input being the raw calibration PPG signal |
| Log Sys_calib | Systolic output of OBPM for the calibration with the input being the log of the calibration PPG signal |
| Log Dia_calib | Diastolic output of OBPM for the calibration with the input being the log of the calibration PPG signal |
| Ref Sys_calib | Systolic references from the calibration |
| Ref Dia_calib | Diastolic references from the calibration |

The set of features of a blood pressure calibration model, such as model $M_j$, can include global PPG signal features of the recording PPG signal and/or global PPG signal features of the calibration PPG signal. The feature extraction module 3704 can extract global PPG signal features of the recording PPG signal from the logarithmic recording PPG signal, and can extract global PPG signal features of the calibration PPG signal from the logarithmic calibration PPG signal. The feature extraction module 3704 can determine the absorbance by computing the logarithm of a PPG signal, and normalize the absorbance by subtracting the corresponding mean across time and divide by the standard deviation across time to remove the effect of hardware configuration, distance from light source, intensity of light source or environment, among others. Considering Beer's Law $$A(\theta, t) = A_{tissue}(\theta) + A_{veinous}(\theta) + A_{arterial}(\theta, t) + A_{others}(\theta) \quad (44)$$

$$= A_{stat.}(\theta) + a_{art.blood}(\theta)L(t)$$

where $A_{tissue}(\theta), A_{veinous}(\theta), A_{others}(\theta)$ are the absorbance of stationary elements of the finger that can be aggregated in $A_{stat.}(\theta)$, $A_{arterial}(\theta, t)$ is the time dependent contribution of the arterial blood flow, $a_{art.blood}$ is the absorptivity constant of arterial blood, and $L(t)$ is the light path length depending blood flow and thus on time. With regard to the setting for measuring blood pressure the light path length depend on the relative position of the light source 108 and the photodetector 110, which makes it device specific and does not vary over time during a recording. In the other hand the concentration of the solution (or blood) depends on the amount of blood in the vessel, which varies over time.

The feature extraction module 3702 can apply the normalization to the Beer Law using the following equations:

$$A(t) = A_{stat.}(\theta) + a_{art.blood}(\theta)L(t). \quad (45)$$

$$\overline{A} = \frac{1}{n}\sum_{t=1}^{n} A(t) \quad (46)$$
$$= \frac{1}{n}\sum_{t=1}^{n}(A_{stat.} + a_{art.blood}(\theta)L(t))$$
$$= A_{stat.} + a_{art.blood}(\theta)\overline{L}.$$

$$\sigma(A) = \sqrt{\frac{1}{n}\sum_{t=1}^{n}(A(t) - \overline{A})^2} = a_{art.blood}(\theta)\sigma(L). \quad (47)$$

$$\frac{A(t) - \overline{A}}{\sigma(A)} = \frac{L(t) - \overline{L}}{\sigma(L)} = \frac{A_{stat.} + a_{artblood}(\theta)L(t) - A_{stat} + a_{artblood}(\theta)\overline{L}}{a_{art.blood}(\theta)\sigma(L)}. \quad (48)$$

The following mathematical definitions are used for defining features extracted from the normalized logarithmic (calibration or recording) PPG signal, first derivative of the normalized logarithmic (calibration or recording) PPG signal, the second derivative of the normalized logarithmic (calibration or recording) PPG signal and the Teager-Kaiser energy operator applied on the normalized logarithmic (calibration or recording) PPG signal. A list of possible global signal features of the calibration PPG signal or the recording PPG signal is provided in Table 6 below.

TABLE 6

Global Signal Features.

| Name | Definition |
|---|---|
| log_signal_signal_skew | Skewness of the logarithmic (log.) normalized signal |
| log_signal_signal_kurtosis | Kurtosis of the log. normalized signal |
| log_signal_signal_median | Median of the log. normalized signal |
| log_signal_kte_mean | Mean the KTE on the log. normalized signal |
| log_signal_kte_std | Std of the KTE on the log. normalized signal |
| log_signal_kte_skew | Skewness of the KTE on the log. normalized signal |
| log_signal_kte_kurtosis | Kurtosis of the KTE on the log. normalized signal |

TABLE 6-continued

Global Signal Features.

| Name | Definition |
| --- | --- |
| log_signal_kte_median | Median of the KTE on the log. normalized signal |
| log_signal_d1_mean | Mean of the 1st derivative of the log. normalized signal |
| log_signal_d1_std | Std Deviation of 1st derivative of the log. normalized signal |
| log_signal_d1_skew | Skewness of the 1st derivative of the log. normalized signal |
| log_signal_d1_kurtosis | Kurtosis of the 1st derivative of the log. normalized signal |
| log_signal_d1_median | Median of the 1st derivative of the log. normalized signal |
| log_signal_d2_mean | Mean of the 2nd derivative of the log. normalized signal |
| log_signal_d2_std | Std Deviation of 2nd derivative of the log. normalized signal |
| log_signal_d2_skew | Skewness of the 2nd derivative of the log. normalized signal |
| log_signal_d2_kurtosis | Kurtosis of the 2nd derivative of the log. normalized signal |
| log_signal_d2_median | Median of the 2nd derivative of the log. normalized signal |

The set of features of a blood pressure calibration model, such as model $M_j$, can include pulse related (or pulse-specific) features of pulses of the calibration PPG signal and/or pulse related (or pulse-specific) features of pulses of the recording PPG signal. Pulse related features can include pulse features described above in sub-section D.3. The computer system 100 or the feature extraction module 3702 can divide a PPG signal into single pulses and compute or extract respective pulse features, as described in sub-section D.3 above. Besides the pulse features of each pulse described in sub-section D.3, the feature extraction module 3702 can determine a quality metric of the pulse based on the autocorrelation method described in Section E. The computer system 100 or the feature extraction module 3702 can determine a weighted mean and a weighted standard deviation (across various pulse segments) for each pulse. The computer system 100 or the feature extraction module 3702 can use the quality metric as a weight.

The set of features of a blood pressure calibration model, such as model $M_j$, can include demographic features of the user of the computer system (e.g., the individual for whom blood pressure is measured). Example demographic features are listed below in Table 7.

TABLE 7

Demographic Features.

| Name | Definition |
| --- | --- |
| age | age of the subject in year (year of recording – year of birth) |
| height | the height of the subject in cm |
| weight | the weight of the subject in kg |
| sex | the gender at birth of the subject (male/female) |
| BMI | The Body mass index of the subject |

Once the calibration model is identified at STEP 3806, the feature extraction module 3704 can extract or determine the set of features for the selected calibration model 3900 (those used by the calibration model as input), and provide the features values to the calibration model 3900. As discussed above, the set of features can include one or more calibration references 3902, one or more calibration estimates 3904 (provided by OBPM based on calibration PPG signal), one or more global calibration signal features 3906 (of calibration PPG signal), one or more calibration pulse related features 3908 (of calibration PPG signal), one or more recording estimates 3910 (provided by OBPM based on recording PPG signal), one or more global recording signal features 3912 (of recording PPG signal), one or more recording pulse related features 3914 (of recording PPG signal), one or more demographic features 3916 or any combination thereof. The calibration model 3900 can use the feature values to determine blood pressure value(s) (e.g., systolic and/or diastolic).

Each calibration model 3900 can be built using a subset of a training set of features. The calibration models 3900 can be trained, using labeled data, to determine the subset of features and the corresponding weighting coefficients for use to determine blood pressure measurements. During the training process, the features' selection for each model can be performed using lasso algorithm or univariate feature selection. Once the model is trained, the final model to be used can be a regression model (e.g., linear regression model), RandomForest regressor, Support Vector machine regressor, Multi-layer perceptron or a model of other type that makes use of (or is defined in terms of) the selected subset of features during the training process. Different models, such as the 12 models in Table 4, can be different in terms of the corresponding subset of selected features, in terms of the model parameters (e.g., coefficients) and/or in terms of the model type.

G. Calibration-Free Improvement of Accuracy of Blood Pressure Measurement

Figure 40:
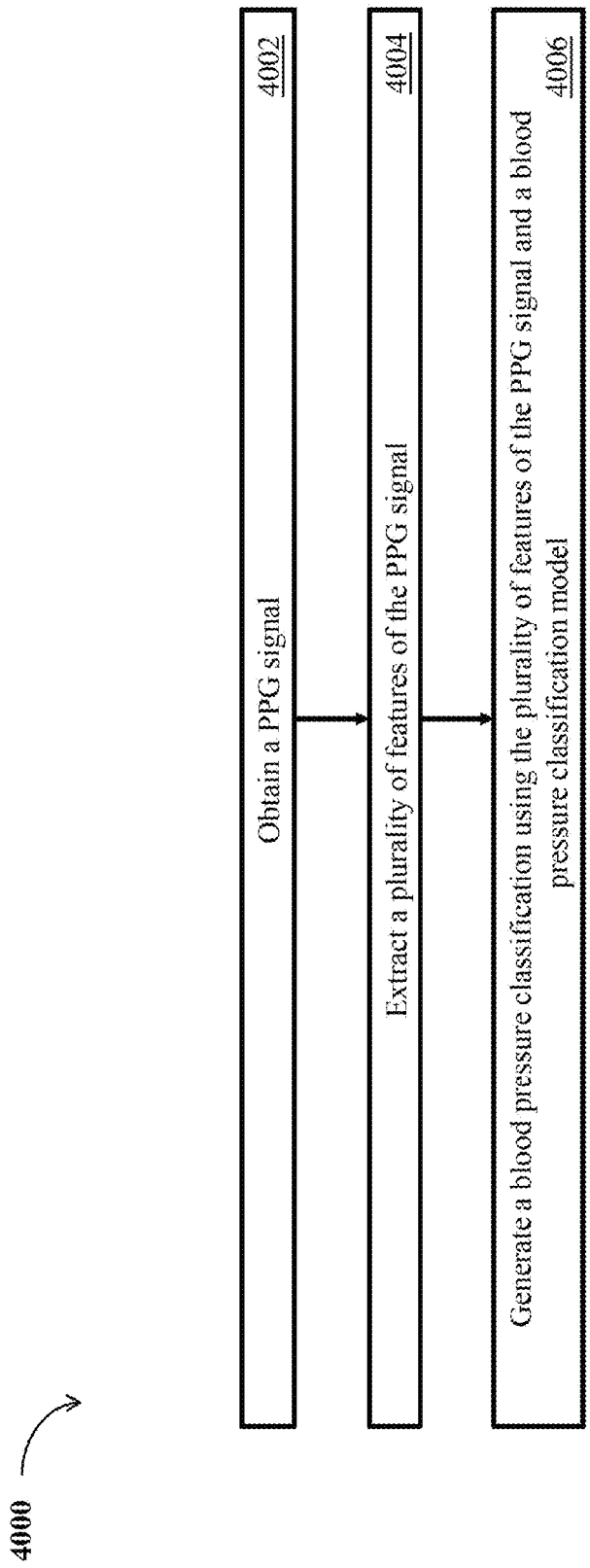
FIG. 40 shows a flowchart illustrating a method of generating a blood pressure classification based on a PPG signal and a classification model, according to example embodiments.

Referring to FIG. 40, a flowchart illustrating a method 4000 for calibration free estimation of blood pressure. In brief overview, the method 4000 can include obtaining a PPG signal (STEP 4002), and identifying a calibration free blood pressure estimation model based on the PPG signal (STEP 4004). The method 4000 can include generating a blood pressure value based using the identified calibration free blood pressure estimation model and the PPG signal (STEP 4008).

Figure 41:
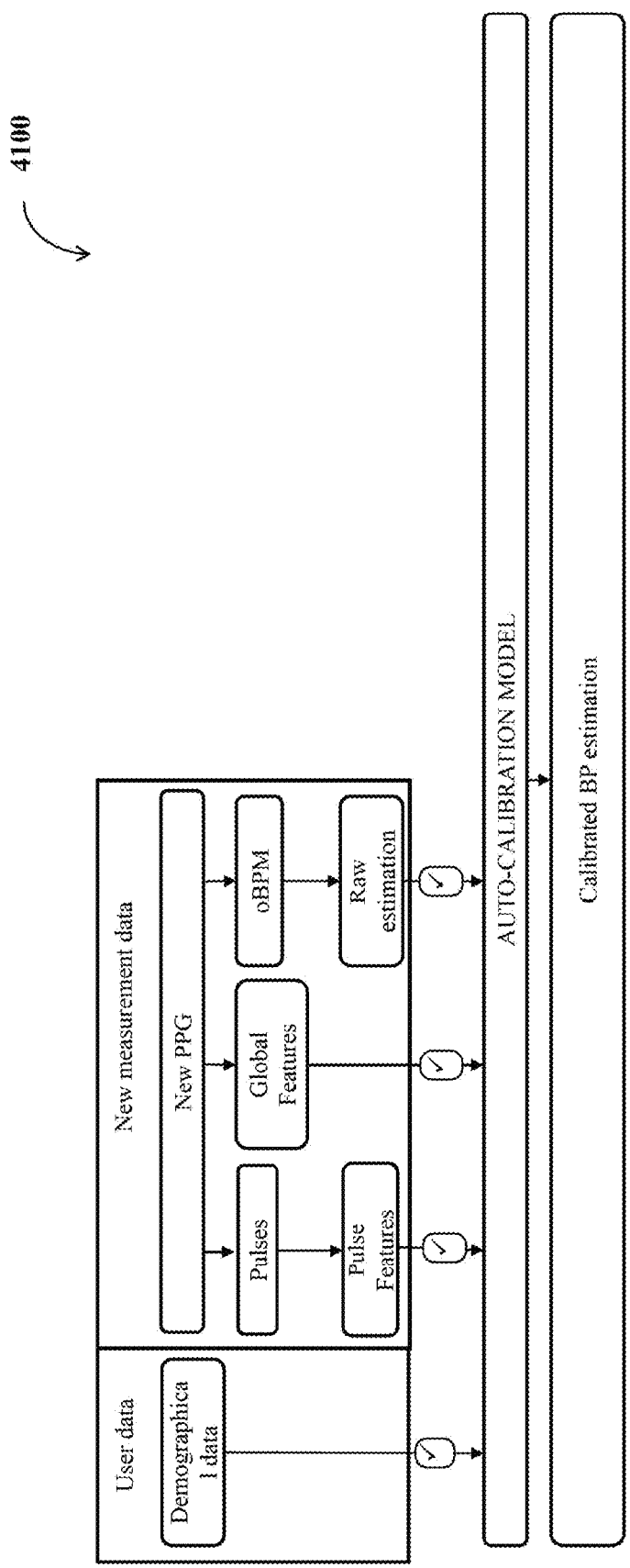
FIG. 41 illustrates an example of an auto-calibration model, according to example embodiments.

FIG. 41 shows a block diagram illustrating a calibration free blood pressure estimation model 4100, according to example embodiments. The estimation model 4100 is also referring to herein as a smart offset calibration model 3900. The calibration model 3900 can include a linear regression model, a nonlinear regression model, a RandomForest regressor, a support vector machine regressor, a multi-layer perceptron or a neural network among others. Unlike the calibration model 3900, the calibration free blood pressure estimation model 4100 does not make use of calibration data.

The method 4000 can include the computer system 100 obtaining a recording PPG signal (or new PPG in FIG. 41) generated from a sequence of image frames obtained from the photodetector 110 (STEP 4002). The sequence of image frames can be acquired by the computer system 100 for measuring the blood pressure of the user. The computer system 100 can generate the recording PPG signal using the sequence of image frames as discussed above with regard to FIGS. 4 and 7. The calibration/estimation module 516 can receive the recording PPG signal as input recording data for measuring the blood pressure of the user.

The method 3800 can include the computer system 100 or the calibration/estimation module 516 identifying a calibration free estimation model from a plurality of calibration free estimation models based on the recording PPG signal (STEP 4004). The computer system 100 or the calibration/estimation module 516 can maintain or have access to the plurality of calibration free estimation models. The plurality of calibration free estimation models can include one or more linear regression models, one or more nonlinear regression models, one or more RandomForest regressors, one or more support vector machine regressors, one or more multi-layer perceptrons, one or more neural networks or a combination thereof among others. The plurality of calibration free blood pressure estimation models can machine learning models trained using labeled data.

The computer system 100 or the calibration/estimation module 516 can identify or select the calibration model, from the plurality of blood pressure calibration models, based on outputs of the OBPM module 3702 when fed with recording PPG signal as input. The OBPM module 3702 can receive a PPG signal (raw PPG signal) or a logarithmic PPG signal as input. A logarithmic PPG signal is a PPG signal to which a logarithmic function or transformation is applied. The computer system 100 or the OBPM module 3702 can generate, from the recording PPG signal, a logarithmic recording PPG signal. The OBPM module 3702 can separately use each of the recording PPG signal and the logarithmic recording PPG signal as input and estimate (or attempt to estimate) a corresponding blood pressure measurement for each of these input signals. However, the OBPM module 3702 may not be successful in estimating a corresponding blood pressure measurement for each of these input signals.

The computer system 100 or the calibration/estimation module 516 can determine (i) whether the recording PPG signal generates a first blood pressure estimate and (ii) whether the logarithmic recording PPG signal generates a second blood pressure estimate. The computer system 100 or the calibration module 516 can identify or select the calibration free estimation model from the plurality of calibration free estimation models based on the vents (i) and (ii). For instance, the computer system 100 or the calibration module 516 can identify or select the calibration free estimation model from 4 different blood pressure calibration models according to Table 8 below.

TABLE 8

Calibration free model selection.
Recording signal

| Group_raw&log | Group_raw | Group_log | Group_noObpm |
|---|---|---|---|
| Model 1 | Model 2 | Model 3 | Model 4 |

Each of the plurality calibration free estimation models can be associated with (or defined in terms of) a corresponding set of parameter variables (corresponding to a subset of features specific to that model) used to determine calibrated blood pressure values. The subset of features of a calibration free estimation model can include systolic and/or diastolic blood pressure estimates generated by the OBPM module 3702 responsive to an input signal equal to the raw recording PPG signal or the logarithmic recording PPG signal. For instance, the set of features can include a systolic blood pressure estimate generated using the recording PPG signal as an input signal, a diastolic blood pressure estimate generated using the recording PPG signal as an input signal, a systolic blood pressure estimate generated using a logarithmic recording PPG signal as input signal, a diastolic blood pressure estimate generated using the logarithmic recording PPG signal as input signal or a combination thereof.

The subset of features of a calibration free estimation model can include global PPG signal features of the recording PPG signal. The feature extraction module 3704 can extract global PPG signal features of the recording PPG signal from the logarithmic recording PPG signal. The global PPG signal features of the recording PPG signal can include features from Table 6 above.

The subset of features of a calibration free estimation model, can include pulse related (or pulse-specific) features of pulses of the recording PPG signal. Pulse related features can include pulse features described above in sub-section D.3. The computer system 100 or the feature extraction module 3704 can divide a PPG signal into single pulses and compute or extract respective pulse features, as described in sub-section D.3 above. Besides the pulse features of each pulse described in sub-section D.3, the feature extraction module 3704 can determine a quality metric of the pulse based on the autocorrelation method described in Section E. The computer system 100 or the feature extraction module 3704 can determine a weighted mean and a weighted standard deviation (across various pulse segments) for each pulse. The computer system 100 or the feature extraction module 3704 can use the quality metric as a weight.

The set of features of a blood pressure calibration model, can include demographic features of the user of the computer system (e.g., the individual for whom blood pressure is measured). Example demographic features are listed above in Table 7.

Once the calibration model is identified at STEP 4004, the feature extraction module 3704 can extract or determine the subset of features for the selected calibration free estimation model 4100 (those used by the calibration free estimation model as input), and provide the feature values to the calibration free estimation model 4100. As discussed above, the subset of features can include one or more recording estimates 4102 (provided by OBPM based on recording PPG signal), one or more global recording signal features 4104 (of recording PPG signal), one or more recording pulse related features 4106 (of recording PPG signal), one or more demographic features 4108 or combination thereof. The calibration model 4100 can use the feature values to determine blood pressure value(s) 4110 (e.g., systolic and/or diastolic).

Each calibration free estimation model 4100 can be built using a subset of a training set of features. Each calibration free estimation model 4100 can be trained, using labeled data, to determine the subset of features and the corresponding weighting coefficients for use to determine blood pressure measurements. During the training process, the features' selection for each model can be performed using lasso algorithm or univariate feature selection. Once the model is trained, the final model to be used can be a regression model (e.g., linear regression model), RandomForest regressor, Support Vector machine regressor, Multi-layer perceptron or a model of other type that makes use of (or is defined in terms of) the selected subset of features during the training process. Different models, such as the 4 models in Table 8, can be different in terms of the corresponding subset of selected features, in terms of the model parameters (e.g., coefficients) and/or in terms of the model type.

H. Feature-Based Classification of User Blood Pressure

Figure 42:
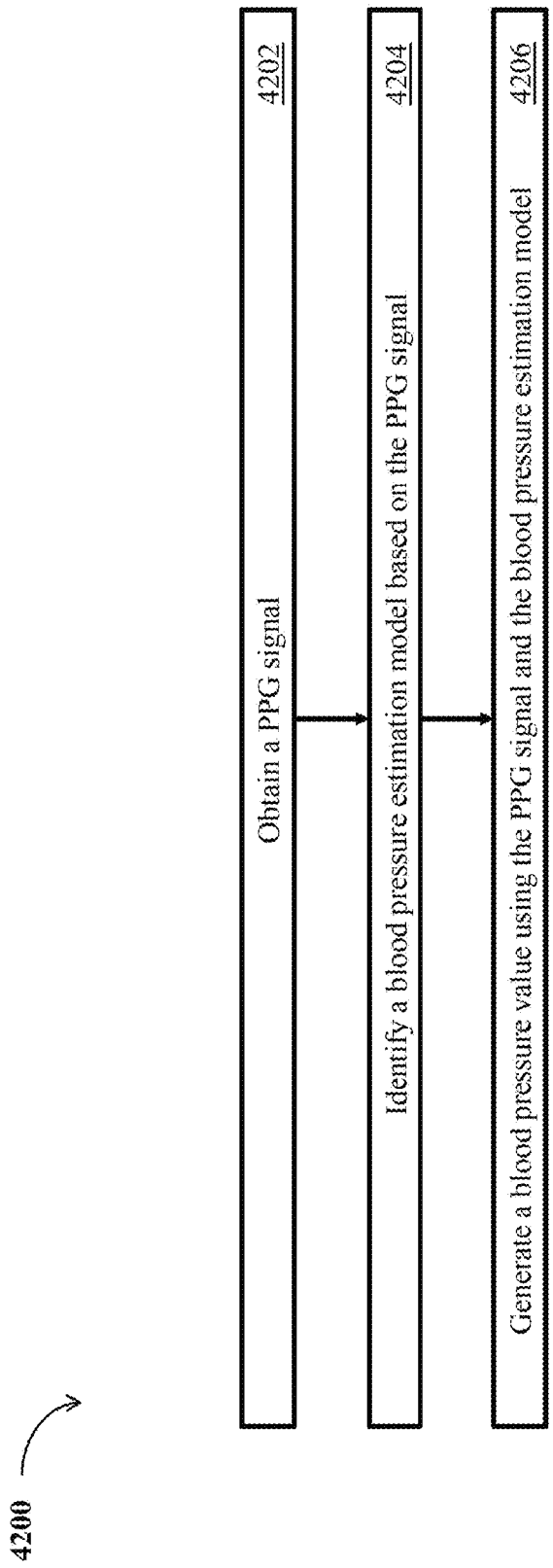
FIG. 42 shows a flowchart illustrating a method of generating a blood pressure value based on a PPG signal and an estimation model, according to example embodiments.
Figure 43B:
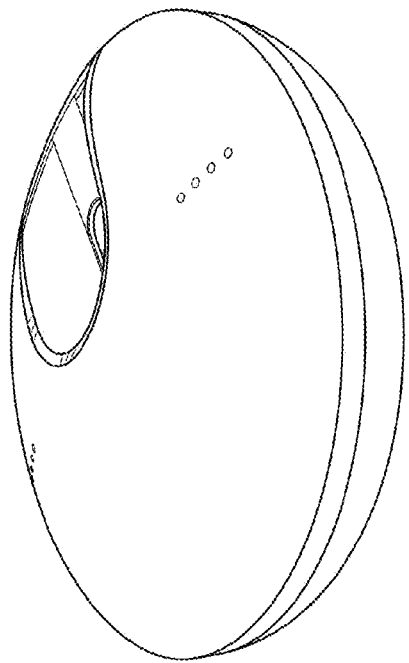
FIGS. 43A-H illustrate examples of a device for measuring vital signs of a user in various views, according to example embodiments.
Figure 43D:
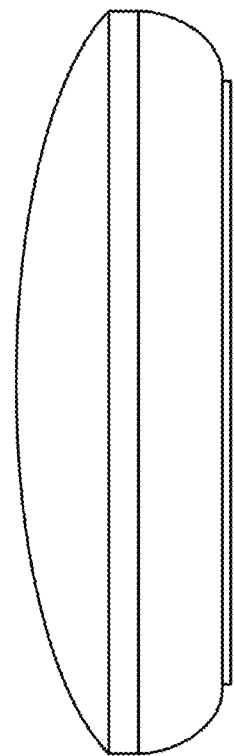
Figure 43A:
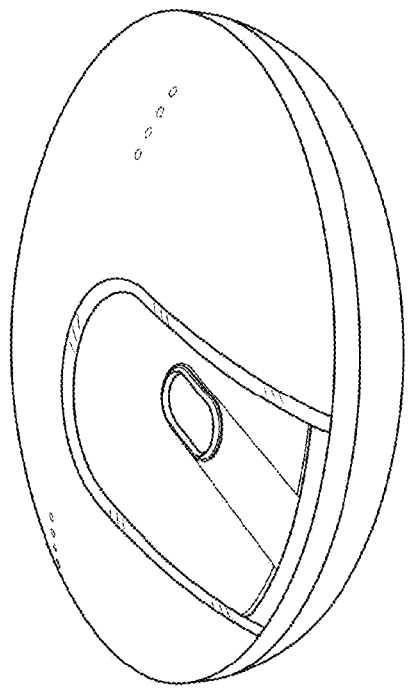
Figure 43C:
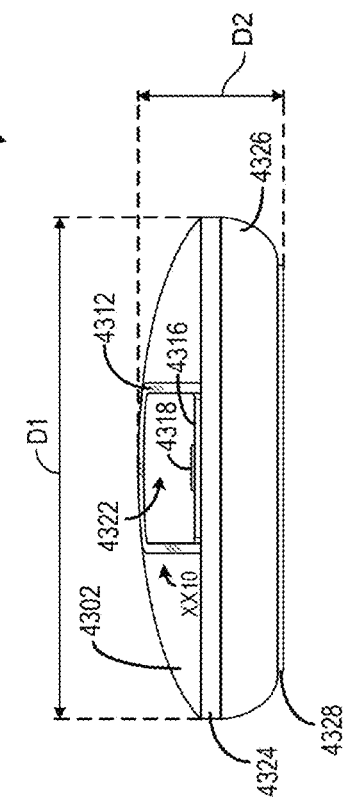
Figure 43F:
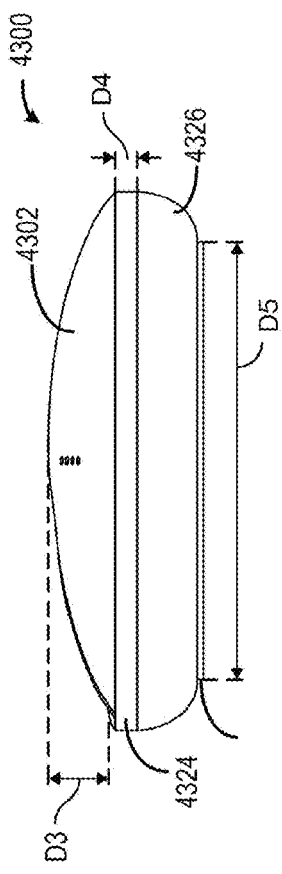
Figure 43H:
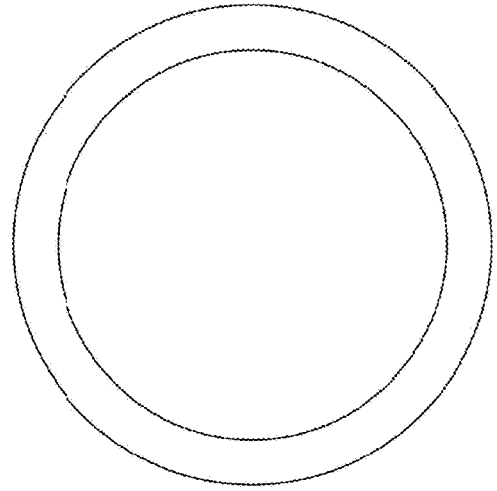
Figure 43E:
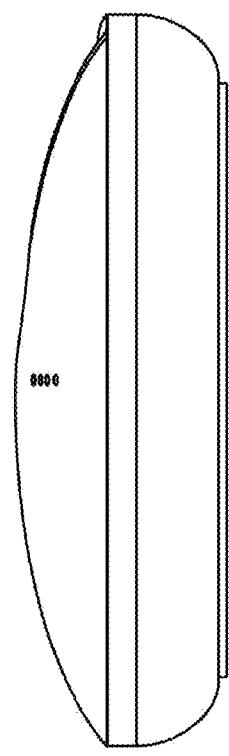
Figure 43G:
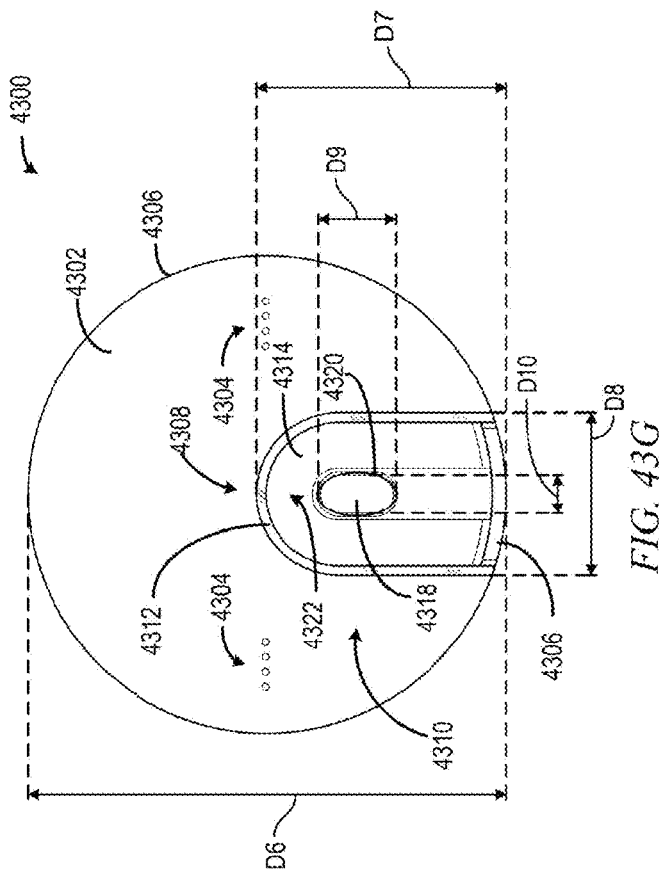
Figure 44B:
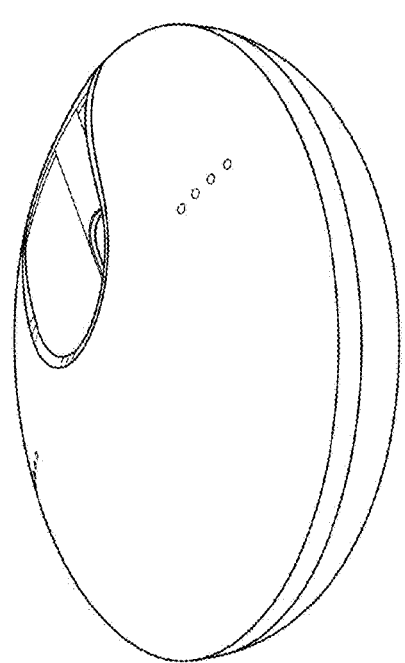
FIG. 44A-H illustrate different views of a device for measuring vital signs of a user, according to example embodiments.
Figure 44D:
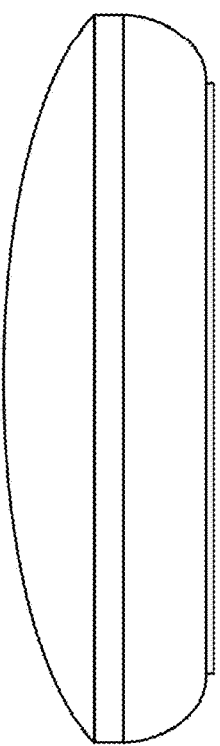
Figure 44A:
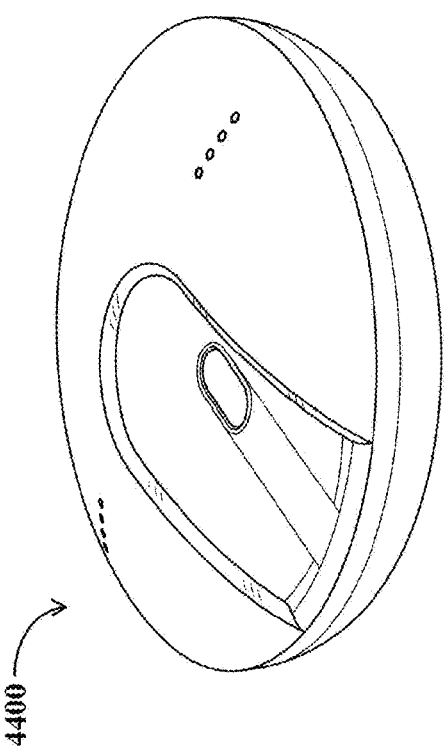
Figure 44C:
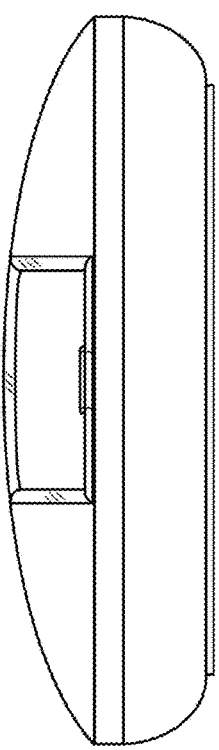
Figure 44F:
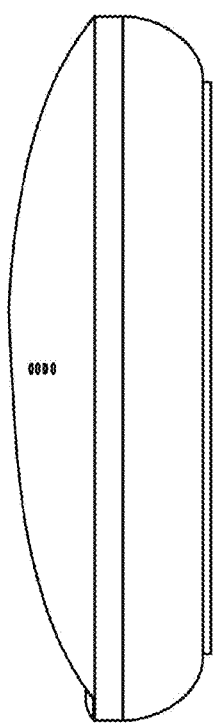
Figure 44H:
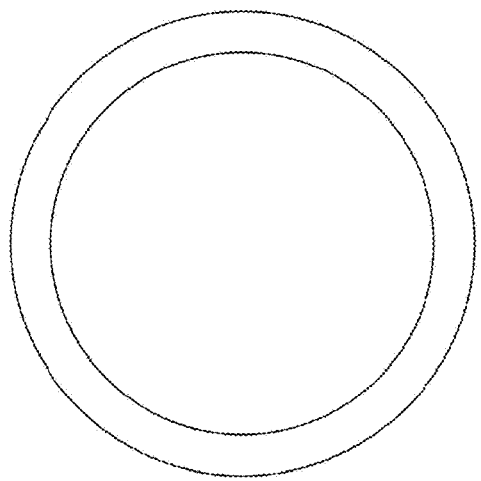
Figure 44E:
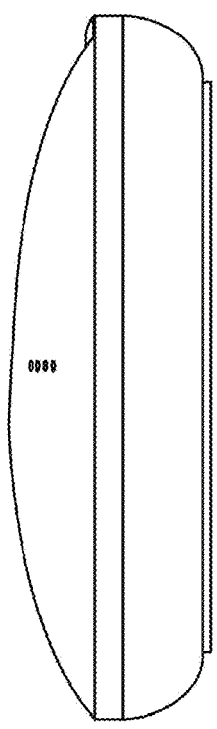
Figure 44G:
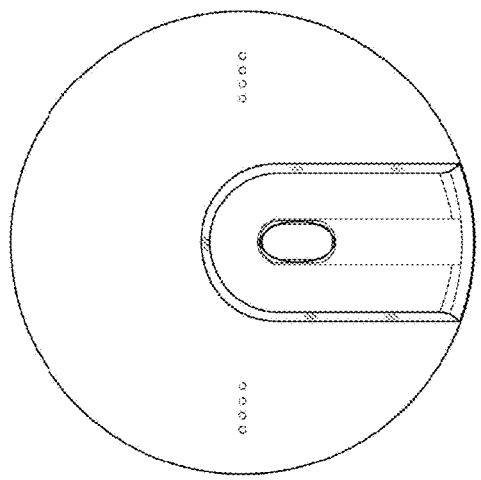
Figure 45B:
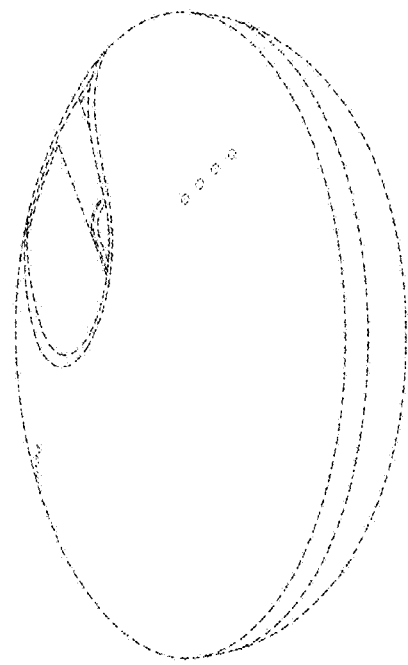
FIGS. 45A-H illustrate different views of a device for measuring vital signs of a user in broken lines, according to example embodiments.
Figure 45D:
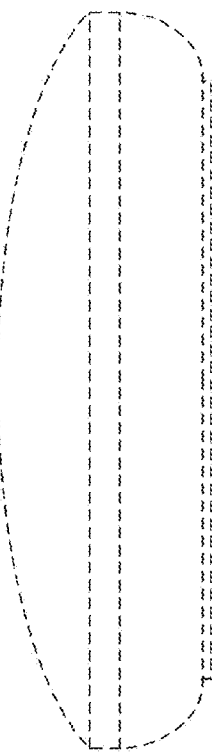
Figure 45A:
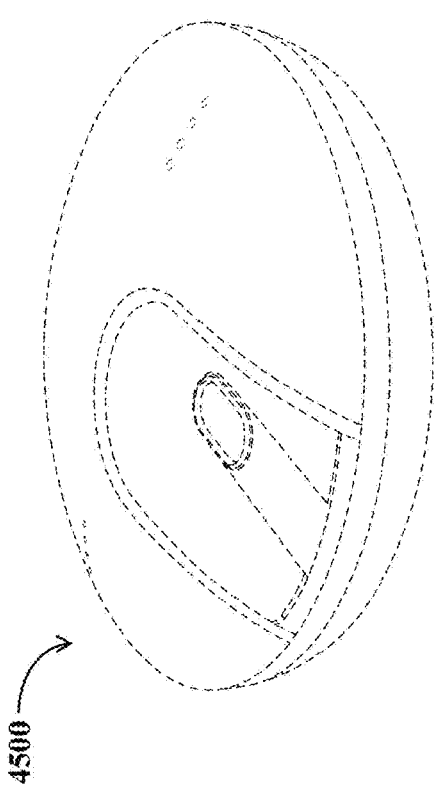
Figure 45C:
Figure 45F:
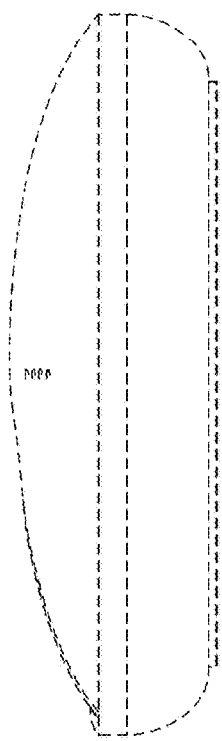
Figure 45H:
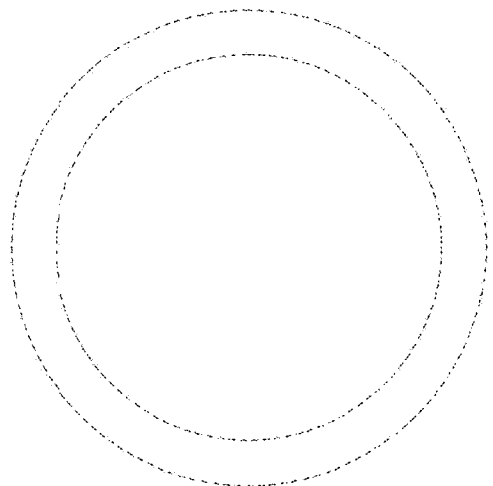
Figure 45E:
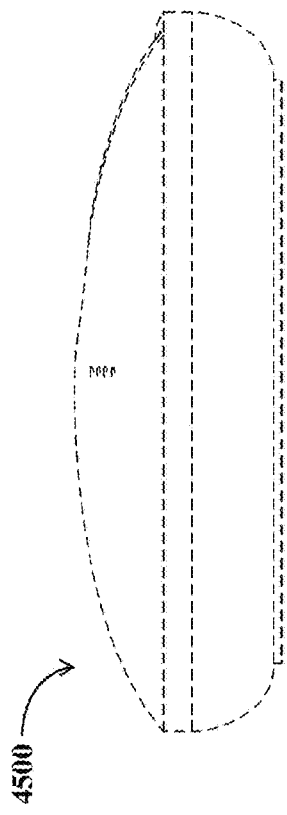
Figure 45G:
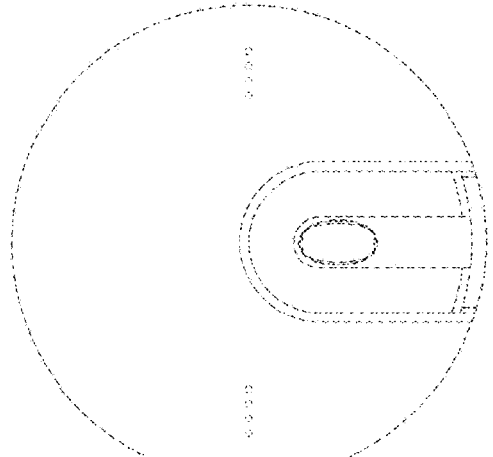
Figure 46A:
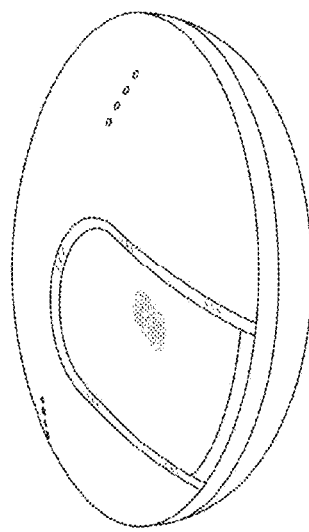
FIGS. 46A-D illustrate perspective and top views of a device with a rough surface in a groove, according to example embodiments.
Figure 46B:
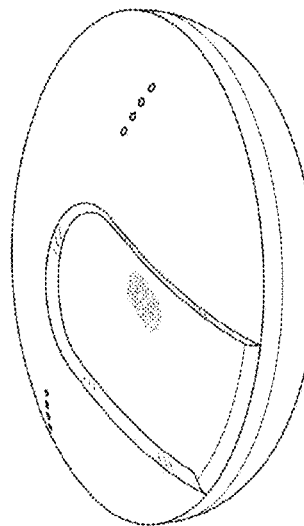
Figure 46C:
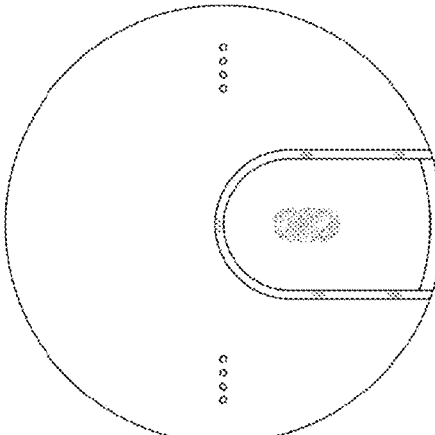
Figure 46D:
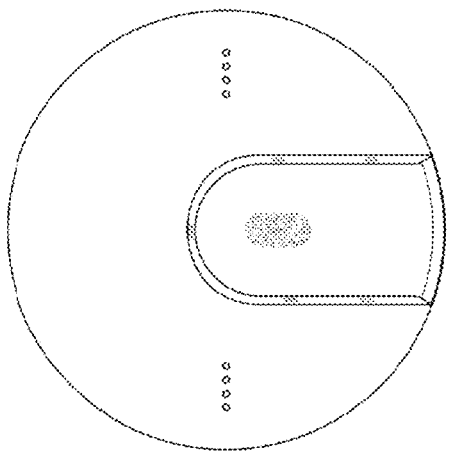

Referring to FIG. 42, a flowchart of a blood pressure classification method 4200 is shown, according to example embodiments. The method 4200 can include obtaining one or more PPG signals, each of which generated from a corresponding sequence of images obtained from a photodetector (STEP 4202). The PPG signals can be generated as discussed above with regard to FIGS. 4 and 7 above.

The method 4200 can include extracting a plurality of features of the PPG signal (STEP 4204). The computer system 100 or the feature extraction module 3704 can extract features of the PPG signal that are used by the classification model to classify the blood pressure of the subject. In general, the categories of features used by the classification model are similar to the feature categories used by the calibration free estimation model 4100. That is, the classification model can use OBPM out features for the PPG signals, global signal features of the PPG signals and pulse related features of the PPG signals. The features extraction module can extract these features from each of the recorded (or generated PPG signals).

The features can include systolic and/or diastolic blood pressure estimates generated by the OBPM module 3702 for each of the recording PPG signals and/or the logarithmic recording PPG signals. For instance, the set of features can include a systolic blood pressure estimate for each recording PPG signal, a diastolic blood pressure estimate for each recording PPG signal, a systolic blood pressure estimate for each logarithmic recording PPG signal, and a diastolic blood pressure estimate for each logarithmic recording PPG signal. In some implementations, the features can include an average of systolic blood pressure estimate for the recording PPG signals, an average of diastolic blood pressure estimate for the recording PPG signals, an average of systolic blood pressure estimate for the logarithmic recording PPG signals, and an average of diastolic blood pressure estimates for the logarithmic recording PPG signals.

The features can include global PPG signal features of the recording PPG signal or averages (over obtained PPG signals) thereof. The feature extraction module 3704 can extract global PPG signal features from the logarithmic recording PPG signals. The global PPG signal features of can include features from Table 6 above. The feature extraction module can average each global signal feature for the obtained PPG signals.

The features can include pulse related (or pulse-specific) features of pulses of the recording PPG signals or averages thereof. Pulse related features can include pulse features described above in sub-section D.3. The computer system 100 or the feature extraction module 3704 can divide a PPG signal into single pulses and compute or extract respective pulse features, as described in sub-section D.3 above. Besides the pulse features of each pulse described in sub-section D.3, the feature extraction module 3704 can determine a quality metric of the pulse based on the autocorrelation method described in Section E. The computer system 100 or the feature extraction module 3704 can determine a weighted mean and a weighted standard deviation (across various pulse segments) for each pulse feature. The computer system 100 or the feature extraction module 3704 can use the quality metric as a weight. The computer system 100 or the feature extraction module 3704 can further average each pulse feature across the obtained PPG signals.

The feature extraction module 3704 may further provide demographic features of the user of the computer system (e.g., the individual for whom blood pressure is measured) to the classification model. Example demographic features are listed above in Table 7.

The blood pressure classification model can classify the blood pressure of the user based on the features received from the feature extraction module 3704 and internal parameters (e.g., coefficients) of the classification model. The blood pressure classification can include "Normal" "High Blood Pressure" and/or "Low Blood Pressure". The number and the types of classifications can vary depending how the classification model is designed and trained. The classification model can be a machine leaning model trained using labeled data. The classification model can be trained to receive feature averages (over multiple generated PPG signals) as input.

I. Standalone Blood Pressure Measurement Device

Referring to FIGS. 43A-H, example illustrations of a device 4300 for measuring the vital signs of a user is shown in different views, according to inventive concepts of this disclosure. For example, FIGS. 43A-B can include perspective views of the device 4300, FIGS. 43C-F can include the side views of the device 4300, FIG. 43G can include the top view (sometimes referred to as a bird-eye view) of the device 4300, and FIG. 43H can include a bottom view of the device 4300.

The device 4300 can include one or more processors and at least one memory to perform the features and functionalities discussed herein. The device 4300 can be a standalone or self-contained device. The device 4300 can measure important vital signs (e.g., pulse rate, blood pressure, respiratory rate, oxygen saturation, or temperature) by analyzing a body part (e.g., a finger) of the user. The device 4300 can be referred to as other descriptive terms, such as a node, a measurement component, or a PPG analyzer, for example. The device 4300 can measure and provide the user with the result of the vital signs within a time period or duration (e.g., under 30 seconds, 20 seconds, etc.). In some cases, the time period can refer to the duration for capturing measurements of the body part to obtain the results, which can be predetermined by the administrator of the software of the device 4300 and configurable via an update. The device 4300 can perform one or more features and functionalities similarly to the computer system 100, a remote server, or a combination of remote devices to process measurements of the body part of the user, such as in conjunction with at least FIGS. 1-26. In some cases, the device 4300 can perform features or functionalities different from the computer system 100 or other remote devices. The device 4300 can perform steps of one or more methods discussed herein in conjunction with FIGS. 4, 12, 16, etc. In some cases, the device 4300 can perform a portion of the features or functionalities and delegate the remaining portions to at least one remote device (e.g., the computer system 100 or a server). The device 4300 can interface with one or more remote devices, such as a laptop, a mobile device, a desktop computer, a server device, among others.

The device 4300 can measure one or more vital signs including at least, but not limited to blood pressure ("BP") (e.g., systolic, diastolic, or mean arterial pressure ("MAP")), heart rate ("HR") (sometimes referred to as pulse rate, e.g., heart rate variability), respiratory rate (e.g., recurrent respiratory papillomatosis ("RRp") or breaths per minute), oxygen ("O2") (e.g., blood oxygen saturation), and temperature (e.g., skin temperature or body temperature). The device 4300 can be constructed using or composed of hardware, software, or a combination of hardware and software capable of measuring at least the vital signs mentioned above. The device 4300 can be constructed with other sensors or components discussed herein to perform other measurements or analyses. The device 4300 can perform error checking procedures, for example, to raise one or more error conditions to the user in order to obtain good PPG signals for computing or generating good results based on the PPG signals. The different error conditions can be based on readings of the PPG signal, the temperature of the user, acceleration data, among others.

The device 4300 can be a cuffless optical device for measuring vital signs of the user, e.g., via contact with a body part of the user. The device 4300 can capture PPG signals by the reflection of light at the fingertip. The device 4300 can convert the PPG signal into the user's vital signs (e.g., BP, HR, RRp, or O2) by using one or more formulas or algorithms. For example, a PPG is an optically obtained plethysmogram that can be used to detect blood volume changes in the microvascular bed of tissue. The device 4300 can obtain PPG signals by passing light through the tissues at a body part. By going through the tissue, light can be absorbed in some proportions by the different layers of the tissues, such as the venous blood layer, the non-pulsatile component of the artery blood, or the pulsatile component of artery blood. As an example, FIGS. 3A-D can illustrate a decomposition of the absorption caused by the incoming light. Most of the tissues are fixed in the finger, while the blood volume can vary, which can be measured by the device 4300. Therefore, the device 4300 can be used to measure the pulsatile component of the PPG signal.

The device 4300 can include a housing 4302 encapsulating one or more components. The housing 4302 can refer to a casing, a shell, a frame, or an exterior enclosure for the components. The housing 4302 can include at least one or more features, structures, elements, or appearances as discussed herein. The housing 4302 can include, but is not limited to, one or more light indicators 4304, a housing edge 4306, a center region 4308, and a contact region 4310. The contact region 4310 can include one or more components to measure or assist the user with capturing images of a body part, such as the fingertip of the user to obtain at least one PPG signal. The contact region 4310 can be referred to as or used interchangeably with other descriptive terms, such as a placement region/area, a groove region, a finger region, a measurement region, or generally as region 4310. The region 4310 can include at least a light pipe 4312, a groove 4314, a bottom region 4316 (e.g., a general bottom area or region of the groove 4314, which can be part of the groove 4314), a portion 4318 of the bottom region 4314, and an edge 4320 around the portion 4318 of the bottom region 4314.

The housing 4302 of the device 4300 can be constructed with any materials including, but not limited to, plastic, steel, carbon fiber, wood, cloth, composite materials, among others. The housing 4302 can be in any shape, such as cylindrical, cubic, spherical, or a combination of one or more shapes. As an example herein, the housing 4302 can be in a circular, cylindrical, or semi-spherical shape as shown in example illustrations of at least FIGS. 43A-B. In some cases, the housing 4302 can exhibit a dome-like structure. In some other cases, the top of the housing 4302 can be a flat surface. The housing 4302 can include an edge 4306 surrounding (or encircling) the housing 4302. The housing 4302 may include other appearance or design. The bottom of the housing 4302 can include a flat surface. In some cases, at least a portion of the bottom of the housing 4302 can include one or more indentation, footing, among other elements to assist with placing the device 4300 onto a surface.

The housing 4302 can encapsulate the internal hardware component of the device 4300. In some cases, the housing 4302 can refer to the top housing of the device 4300. In this case, the device 4300 can include a side 4324, a bottom housing 4326, and a foot 4328 of the device 4300. The housing 4302, the side 4324, the bottom housing 4326, and the foot 4328 of the device 4300 can be referred to as the casing or external enclosures of hardware components of the device 4300. The components of the external enclosures (e.g., the housing 4302, the side 4324, the bottom housing 4326, and the foot 4328 of the device 4300) can be composed of the same materials. In some cases, the external enclosures may not be composed of the same materials. For example, the top housing and the bottom housing 4326 may be composed of glass and plastic, the side 4324 may be composed of aluminum, and the foot 4328 may be composed of rubber. Other materials can be used to construct the external enclosures.

The side 4324 may be referred to as the corner or the edge of the device 4300. For example, the diameter of the device 4300 can be measured from one side to the opposite (or the other) side of the side 4324. The side 4324 can be located, positioned, or sandwiched between the top housing and the bottom housing 4326. In some cases, the side 4324 or the material of the side 4324 may be a part of the bottom region 4316 of the groove 4314. For example, one of the side 4324 positioned at the region 4310 can be extended towards the curved end 4322 of the groove 4314.

The bottom of the housing 4302 can include curvatures, flat surfaces, among other characteristics. In edge or corners of the bottom housing 4326 can be aligned with the side 4324 of the device 4300. The edge of the bottom housing 4326 may also be aligned with the edges of the top housing. In some cases, the edge of the bottom housing 4326 may not be aligned with the edges of the top housing. For example, the edge of the top housing (e.g., housing 4302) may not extend to or be flushed with all sides 4324 of the device 4300. Instead, at least an edge of the top housing may be spaced from the side 4324. In some cases, the edges of the top housing can be flushed on all sides 4324 of the device 4300. The bottom housing 4326 can include texture, pattern, or indentation to facilitate the user handling or carrying the device 4300.

The foot 4328 can be a part of the bottom housing 4326. In some cases, the foot 4328 can be a separate component for installation to the device 4300 (e.g., at the bottom housing 4326). The foot 4328 may be referred to as the bottom surface of the device 4300, bottom support, gripper, anti-slip feet, among other elements. The foot 4328 can facilitate or assist with the placement of the device 4300 onto a surface (e.g., a desk, floor, etc.). For example, the foot 4328 can be constructed with anti-slip materials, such that the device does not move when taking measurements. In another example, the foot 4328 can be constructed with a magnet to attach to metal objects. In some embodiments, the foot 4328 can be constructed with a flexible or bendable material, such as to conform with the shapes, textures, or contours of the placement surface. In some implementations, the housing 4302 can include all components of the external enclosures, such as the side 4324, the bottom housing 4326, and the foot 4328 of the device 4300.

The groove 4314 can be an area within or on the housing 4302 of the device 4300 configured for placement of the finger of a user. The groove 4314 can extend from the edge 4306 of the housing 4302 towards the center region 4308 (e.g., the center of the device 4300 from the top-view perspective). The groove 4314 can include a curved end 4322 towards the center region 4308 of the housing 4302. The groove 4314 can include one or more dimensions, such as a first dimension (e.g., length) between 20 mm and 70 mm, a second dimension (e.g., width) between 18 mm and 35 mm, and a third dimension (e.g., depth) between 3 mm and 10 mm. The dimensions of the groove 4314 can vary based on the construction, including different ranges either shorter or longer than the above-described ranges. For example, the first dimension of the groove 4314 can be between 14 mm and 80 mm, the second dimension can be between 15 mm and 45 mm, and the third dimension can be between 2 mm and 12 mm. the curved end 4322 can refer to a curved region of the groove 4314, edging or curving towards the center region 4308 of the housing 4302. The center region 4308 can refer to the center portion, the center area, the midpoint of the housing 4302, or a general area of the housing 4302 equidistant from the edge 4306 of the housing 4302. The center region 4308 can a point at the center of the housing 4302 or a general area portion around the center point, such as a span of 1 mm, 2 mm, or 3 mm from the center point.

The groove 4314 can include a bottom region 4316 which may include curvature similar to the groove 4314. In some cases, the bottom region 4316 can be or include a flat surface. The bottom region 4316 can include a portion 4318 composed with one or more sensors, e.g., for capturing images of the user's finger for conversion to PPG signal. The portion 4318 can be constructed with glass or other transparent materials which can allow light to pass and images outside of the housing 4302 to be captured. The one or more sensors within the groove 4314 can include a light source (e.g., similar to light source 108), a photodetector (e.g., optical sensor or a camera), a temperature sensor, pressure sensor, among other sensors disposed within the housing 4302 to measure the vital signs as discussed herein. The device 4300 can include other sensors, such as an accelerometer, tilt sensor, sound sensor, humidity sensor, etc.

The light source can be positioned at the bottom region 4316 of the groove 4314, such as at the portion 4318 or other portions of the bottom region 4316 or the groove 4314. The light source can be configured to emit light responsive to receiving an instruction from the one or more processors of the device 4300. For example, the light source can emit light upon an indication of a finger contacting or within the proximity of the groove 4314 or the bottom region 4316 of the groove 4314. The device 4300 (or the computer system 100) can include a RGB light source, a full light spectrum light source or a combination of a RGB light source and an infrared (IR) light source. A full light spectrum can emit light having a full light frequency spectrum. Light having full light frequency spectrum when reflected from a finger or other body part can be used to generate PPG signals as well as to detect the amount of oxygen in the finger or the other body part. Specifically, the IR component of the full light frequency spectrum can be used to detect the amount of oxygen content in the blood of the subject. In some implementations, the device 4300 can include a RGB light source to emit RGB light for use to generate PPG signals, and an IR light source to emit IR light for use to detect the amount of oxygen in the subject's blood.

The photodetector can be disposed within the housing 4302. The photodetector can be positioned at the bottom region 4316 of the groove 4314, similar to the light source. The photodetector can be adjacent to the light source, such that the finger, when placed in the groove 4314, can cover both the photodetector and the light source simultaneously. The photodetector can capture a sequence of image frames including images of the finger or other body parts. The photodetector can capture a sequence of image frames while the light is emitted by the light source or responsive to the emission of light (e.g., immediately or shortly after the light is emitted on or into the finger). Hence, the photodetector and the light source can operate in conjunction with one another to capture images of the user's finger for generating the PPG signals. In some cases, the photodetector or the light source can operate in conjunction with other sensors, such as a temperature sensor (e.g., to measure the temperature of the finger while capturing the images) or an accelerometer (e.g., to measure the acceleration of the device 4300 during capturing of the images).

The device 4300 (or the computer system 100) can include a RGB photodetector, a full light spectrum photodetector, or a combination of a RGB photodetector and an infrared (IR) photodetector. The device 4300 can include a full light spectrum photodetector capable of detecting the full frequency spectrum of light. The device 4300 can include light filters to filter RGB light and IR light from light detected by the full light spectrum photodetector. In some implementations, the device 4300 can include a separate RGB photodetector to detect RGB light and a separate IR photodetector to detect IR light. Detected RGB light can be used to generate PPG signals, and detected IR light can be used be measure the amount of blood oxygen of the subject.

The device 4300 can include one or more processors configured to generate a PPG signal of a user using the sequence of image frames to determine the blood pressure or other vital signs of the user. The device 4300 can obtain the PPG signal by the reflection of light, e.g., via capturing images of the reflection of light from the finger indicative of decomposition of the PPG signal. The features or functionalities for the device 4300 to obtain the PPG signal can be described in further detail in at least FIGS. 3A-D, for example. The device 4300 can include other components for processing the data captured by one or more sensors composed in the housing 4302, for example. The device 4300 can include at least a memory or a data storage for storing images, processed data, among other information generated by the device 4300 or received from one or more remote servers or devices. The one or more processors of the device 4300 can be in electrical communication with other components within the device 4300. The one or more processors can transmit instructions to the components. The instructions can trigger at least a feature or a function of the respective components, e.g., turning the light source on or off, dimming the light, increasing light intensity, capture an image, record a video (capturing a sequence of images), among other commands. The one or more processors can perform other features or functionalities discussed herein.

The housing 4302 can include at least one light pipe 4312. The light pipe 4312 may be referred to as a light rail, a light strip, a translucent perimeter with lights, or a luminescent thread. The light pipe 4312 can be disposed within the housing 4302. In some cases, the light pipe 4312 can be attached or coupled to the housing 4302. The light pipe 4312 can be located at the upper edge of the groove 4314 (sometimes referred to as an indented channel into the housing 4302 of the device 4300). The light pipe 4312 can extend across the upper edge of the groove 4314, such as from a first edge portion of the housing 4302, to the center region 4308, and to a second edge portion of the housing 4302. The light pipe 4312 can include curvatures or bend according to the design of the groove 4314. In some cases, the light pipe 4312 can be integrated with the groove 4314, such that the light pipe 4312 is a part of the groove 4314. In some cases, the light pipe 4312 can be inside the groove 4314, such as between the upper edge of the groove 4314 and the bottom region 4316 of the groove 4314. In some implementations, the light pipe 4312 (or an additional light pipe) can be implemented at the bottom region 4316 of the groove 4314.

The light pipe 4312 can receive instructions from the one or more processors of the device 4300 configured to turn on or off (e.g., illuminate or darken). For example, the light pipe 4312 can illuminate or emit lights to prompt the user to take the measurement of the one or more vital signs. The light pipe 4312 can illuminate indicating or guiding the placement of the finger. In this case, by illuminating around the groove 4314, the light pipe 4312 can assist the user with an indication of a general area to place the finger, even in a dark environment. Therefore, the light pipe 4312 can allow the user to better identify the groove 4314 (e.g., surrounded by the light pipe 4312) or the location of where to place the finger for measuring the vital signs.

The light pipe 4312 can be configured to prompt the user at a predetermined time to measure at least one vital sign. The predetermined time (sometimes referred to as a reminder time) can be configured by the user, such as every day, week, bi-week, or month at a certain hour, minute, or second in the day. In some cases, the reminder time can be configured to other times during the day or night. The light pipe 4312, along with other lighting components (e.g., light source or light indicator 4304), can emit any colored lights (e.g., RGB light) at any supported intensity level or lumens. Further, the light pipe 4312 and other lighting components can pulsate at one or more frequencies or intervals based on the configuration of the device 4300. In some cases, the light pipe 4312 and the light indicator 4304 can emit light synchronously. For example, the light pipe 4312 and light indicator 4304 can blick, flash, or pulsate at the same interval. Flashing the lights can indicate at least one of triggering of an error condition, an alert, or a reminder to measure vital signs. The frequency or interval of the lighting pulse can be increase or decrease based on user configuration or configuration by a remote server managing the software or firmware of the device 4300, for example.

The device 4300 can include one or more tactile surfaces as depicted in FIGS. 46A-46D. The tactile surface can include or can be at least one of a rough surface, a protrusion, an indentation, a ridge, a smooth texture, a hard texture, a soft texture, among other types of features or textures. The tactile surface can be different from the texture of between one or more portions of the bottom region 4316. For example, a portion 4318 of the bottom region 4316 can include a tactile surface (e.g., at least a type of tactile surface can occupy the portion 4318 of the bottom region 4316). The tactile surface can be a rough texture, while other portions of the bottom region 4316 can be a smooth texture. The tactile surface can assist or aid the user to position the finger such that the pulp region (e.g., fleshy mass on the palmar aspect) of the finger is positioned above at least the photodetector, e.g., by providing users with a tactile feedback when in contact with the tactile surface. For example, the user can physically sense (e.g., feel by touching) the tactile surface to determine the position of the finger with respect to at least one of the portions of the bottom region 4316.

In some cases, the tactile surface can be at least a part of the portion 4318 or at least a part of the portion 4318 can include the tactile surface. In some other cases, the tactile surface can be present at the portion 4318, which can be different from the surface features of the bottom region 4316. For example, the portion 4318 can include the tactile surface surrounding one or more translucent areas where the photodetector and the light source are positioned. In this case, if the portion 4318 is constructed with glass, the area or position above the photodetector and the light source can be composed of clear glasses while rough glasses surround the clear glasses, for example. In some cases, the tactile surface can include a protrusion 4320 at the bottom region 4316. The protrusion 4320 can form a closed loop to accommodate the pulp region of the finger of the user. The protrusion 4320 can encapsulate the portion 4318 of the bottom region 4316. In some cases, the protrusion 4320 can be a ridge, a channel, or an indent forming a closed loop at the bottom region 4316 of the housing 4302. The protrusion 4320 (or the indent) can include a thickness (or depth) of less than 1 mm. The thickness or depth can be configured during the manufacturing process. The protrusion 4320 can be constructed with other thicknesses, such as above at least 1 mm.

The photodetector can be positioned within the portion 4318 of the bottom region 4316. The photodetector can be configured to capture images of the pulp region of the finger of the user. The photodetector can be initiated to capture the images upon detecting the finger within the proximity or in contact with a portion of the groove 4316, for example. The photodetector can be an RGB photodetector to capture images with various colors.

The light source can be positioned within the portion 4318 of the bottom region 4316. For example, the portion 4318 can position the light source with the photodetector. The light source can be adjacent to or within the proximity of the photodetector. The light source can be spaced from the photodetector between, for example, 2 mm to 5 mm, among other distances where neither the photodetector nor the light source extends beyond the portion 4318 of the bottom region 4316. The light source can be spaced at a distance such that the light can penetrate through the flesh layers and to the pulp region of the finger. Accordingly, the photodetector can capture the reflection of the lights emitted from the light source into the finger.

The portion 4318 of the bottom region 4316 can include a first dimension (e.g., width) between 2 mm and 10 mm and a second dimension (e.g., length) between 5 mm and 20 mm. The length and width can be interchangeable. The portion 4318, as well as other components or features of the device 4300, can include other dimensions, e.g., the first dimension may be between 1.9 mm to 12 mm and the second dimension may be between 4 mm and 25 mm. The portion 4318 can be distanced from the center of the curved end 4322 of the groove 4314 (e.g., measured at any point of the portion 4318 to the curved end 4322). For example, the distance can be greater than 2 mm and less than 15 mm from the center of the curved end 4322. The distance can be less than or equal to 2 mm or greater than or equal to 15 mm, in some cases. The distance of the portion 4318 to the curved end 4322 can be similar to a distance from the portion 4318 to the center region 4308 of the housing 4302, in some cases.

The groove 4314 (and the light pipe 4312) can extend towards the center region 4308 of the housing 4302. In some implementations, the groove 4314 can extend to the midpoint of the center region 4308. In some implementations, the groove 4314 can extend near the midpoint of the center region 4308. In some implementations, the groove 4314 can extend beyond the midpoint of the center region 4308, based on the configuration or construction of the device 4300. The bottom region 4316 of the groove 4314 can be a leveled surface. In some implementations, the bottom region 4316 can be angled (e.g., inclined or declined) from the leveled surface.

The device 4300 can include a communication interface composed within the housing 4302. The communication interface can be Bluetooth, Wi-Fi, radio frequency ("RF") communication, LTE, among other communication ports. The communication interface can be configured to establish one or more communication channels with remote devices or remote servers. The communication interface can communicate, transmit, or receive data packets to or from other remote devices. The one or more processors of the device 4300 can cause the communication interface to transmit data to a remote device. For example, the one or more processors can cause the communication interface to transmit the PPG signal to a remote device or a remote server. In this example, the device 4300 can delegate one or more tasks to the remote device or remote server. The task can include determining a measurement of one or more vital signs of the user using the PPG signal. Further, the device 4300 can delegate the task of displaying the measurement of one or more vital signs to the remote device (e.g., for display on the display device 112 of the computer system 100). In some cases, the one or more processors of the device 4300 can perform the tasks delegated to the remote device.

In some implementations, the device 4300 can include a display device with one or more features or functionalities similar to the display device 112. The display device can be disposed within the housing 4302. The display device can be located or positioned opposite to the region 4310. For example, if the region 4310 is at the south end of the device 4300, the display device can be located at the north end of the device 4300. The display device can face the side where the region 4310 is positioned, such that characters can be upright for comprehensibility by the user. The display device can provide a graphical user interface ("GUI") to the user. The display device can display information related to the device 4300, such as the results from the measurement including one or more vital signs, the body temperature or finger temperature of the user if the device 4300 is equipped with a temperature sensor, an error condition that is raised or triggered by the one or more processors, a notification from a remote device, status of the device 4300 including update status, connection type, connection quality, battery percentage, or connected remote devices, or other measurement results. In some cases, the display device can display other information available on a remote server or within the memory or configuration of the device 4300, such as the time, the temperature of the room, weather forecast, alarm function, among others. In some cases, the display device can provide the user with hints on how to improve the quality of the PPG signal including, but not limited to, warming the finger if the user has a cold finger, readjusting the position of the finger (e.g., direction and distance to adjust the finger), maintaining stability or not to move while taking measurements, place the finger into the groove 4314 or the portion 4318 of the grove 4314, among other hints or instructions. Accordingly, using the display device, the device 4300 can display one or more vital signs (e.g., a blood pressure) for the user, determined using the PPG signal.

In some implementations, the device 4300 can include at least one of a pressure sensor, a thermometer, or an oximeter for assisting with determining one or more vital signs of the user. The sensor may be position at the portion 4318 of the bottom region 4316 with the photodetector or the light source, adjacent to the portion 4318, other portions of the bottom region 4316, or at a portion of the groove 4314. For example, the device 4300 can use the pressure sensor to measure the pressure applied by the finger to a portion 4318 of the bottom region 4316 of the groove 4314. Based on the saturation level (e.g., low saturation or high saturation), the device 4300 can notify the user to increase or decrease the pressure applied by the finger. In some embodiments, the device 4300 can use the thermometer (e.g., skin temperature probe) to measure the temperature of the finger. Based on the temperature of the finger (e.g., too cold), the device 4300 can notify the user to warm up the finger for improving the quality of the signal. In another example, the device 4300 can use the oximeter to measure the oxygen level in the blood flowing through the finger. The device 4300 can notify the user of the oxygen level, e.g., if the oxygen level is normal, too high, or too low. The device 4300 can notify the user via the display device disposed within the housing 4302.

In some implementations, the device 4300 can include a visual output device. The visual output device can be different from a display device. The visual output device can include one or more light indicators 4304. Each of the light indicators 4304 can be shaped like a dot, a square, a light strip, or other shapes of any size to fit within the housing 4302. The one or more light indicators 4304 can be disposed at any position within the housing 4302, such as offset to the left of the contact region 4310 and the center region 4308, offset to the right of the contact region 4310 and the center region 4308, adjacent to the contact region 4310, adjacent to a display device of the device 4300, or other portions of the housing 4302. The visual output device can provide an indication of the quality of the sequence of image frames to the user. For example, the device 4300 (e.g., the one or more processors) can assess the quality of the sequence of image frames captured by the photodetector. The device 4300 can assess the quality of the PPG signal generated based on the captured sequence of image frames. The device 4300 can select a light output from various light outputs based on the quality of the sequence of image frames or the quality of the PPG signal. The light outputs can include instructions for different lighting effects to be performed by the visual output device. The light outputs can include various configurations or animations for the visual output device. The device 4300 can cause the visual output device to emit at least one light output (e.g., the light output selected based on the quality of the image frames or the PPG signal). The light output can be referred to as a light signal. The light signal can be indicative of the quality of the sequence of image frames or the quality of the PPG signal. Emitting the light output can refer to instructing one or more light indicators 4304 to emit lights.

In some embodiments, the light indicators 4304 can emit lights based on the light signal. The light indicators 4304 can emit any light color, such as red, green, or blue. In view of the example illustrations of at least FIG. 43A, the device 4300 can include four light indicators 4304 on the left and another four light indicators 4304 on the right of the device 4300. The device 4300 can include other numbers of light indicators 4304, such as a total of 3, 6, 10, 12, etc. In some implementations, only one side of the device 4300 may include the light indicators 4304. As referred to in this example for simplification, the device 4304 can include a total of four light indicators 4304 disposed of in the housing 4302. An example animation and sequences of the light indicators 4304 can be as follows. When the user placed a finger in the groove 4314 or channel, one or more light indicators 4304 can pulse rapidly three times (e.g., three times within one second or half a second) indicating that the device 4300 detected the finger. After the device 4300 detects the finger, the light indicators 4304 can represent a quality meter indicating the quality of the sequence of images or the PPG signal. The light indicators 4304 can perform an animation while the signal quality is being measured. The animation can stop once the signal quality has been established. Further, the light indicators 4304 can change color (or animation) at any processing or analysis stage (e.g., during the evaluation of the signal quality, transition from evaluating the signal quality to displaying the quality of the signal, etc.).

Once the quality level or metric is available, the device 4300 can instruct the visual display device to emit at least one of various light indicators 4304 indicating the quality of the signal. For example, in the case of four light indicators 4304, emission of one light indicator 4304 can represent low quality, with increasing quality up to four-light indicators 4304 representing high quality. The light indicators 4304 may flash while displaying the quality level or when completing a task, for example. During the measurement or recording of the sequence of image frames, the device 4300 can refresh or update the number of light indicators 4304 emitting lights, based on the variation of the signal quality.

In some implementations, the device 4300 can alert or raise an error condition to the user if the quality meter or metric is below a threshold. For example, if the device 4300 includes four light indicators 4304, the threshold may be set to 3 lights. If the quality of the signal declines to 1 to 2 lights, the device 4300 can transmit an instruction to the light indicators 4304 to change from blue to orange color, thereby indicating that the signal quality is not good. In some cases, the device 4300 can change the color indicating an error condition (e.g., poor quality signal) based on the quality meter falling below the threshold for a predetermined duration. For example, if the predetermined duration is configured to 2 seconds, the device 4300 may not change the color of the light indicators 4304 falling below 3 lights until after 2 seconds.

In some embodiments, the device 4300 can be configured with a timeout threshold indicating a duration which the user should improve the quality meter before the device 4300 time out. The thresholds can be configured by the administrator of the device 4300 during manufacturing or as part of the software, which can be updated via over-the-air updates, data packets from a remote server, or a physical connection to a remote device to download the updated software, for example. Further from the previous example, the device 4300 can change the color of the light indicators 4304 from orange to red if the quality metric does not improve within the timeout threshold. The light indicators 4304 can also blink or flash rapidly for a predetermined number of times (e.g., 3, 5, or 7 times). Responsive to triggering the timeout, the device 4300 can stop capturing images and wait for the user to restart the measurement. To restart the measurement, the user can lift the finger off the groove 4314 for at least 1 second (or other pre-configured duration) and place the finger back in the groove 4314, for example. In some embodiments, the device 4300 can include a button for initiating or restarting the measurement. In some implementations, the initiate or restart a measurement, the user can use an application from a remote device to restart the measurement using the device 4300.

The device 4300 can be configured to execute any animation (e.g., light pulse, breathing effect, dimming effect, wave effect, etc.), brightness level, or color (e.g., R, G, or B) for the light indicators 4304 based on the status or stage of the one or more processors. For example, different animations, color, or brightness can be initiated during the process of detecting the finger, when taking images of the finger, generating the PPG signal based on the images, computing the quality metric or level, displaying the quality level, measuring the vital signs, or when the results of the vital signs are available, either displayed on the local display device of the device 4300 or transmitted to an application executing on a remote device of the user (e.g., application 114 executing on the computer system 100). In some implementations, if the device 4300 includes a display device, the device 4300 may not be composed of the visual output device in addition to the display device. Instead, in these implementations, the display device can perform display an animation, dotted lights, or other features similar to the light indicators 4304.

In some implementations, the device 4300 can detect if the finger of the user is positioned correctly on the photodetector and/or the light source positioned at a portion 4318 of the bottom region 4316 of the groove 4314. For example, the device 4300 can determine at least the local variation values of the pixels for each image of the sequence of images captured by the photodetector. The local variation values of the respective pixels can represent the variation magnitude (e.g., based on intensity or color values) for each of the inner pixels of the downsampled image compared to pixels orthogonally adjacent to the respective pixel. Based on the local variation values, the device 4300 can determine a respective metric for each downsampled image. Further, for each pixel of downsampled images, the device 4300 can determine a respective aggregate pixel similarity score used to determine a vector indicative of a position of the user's finger. The vector can represent the distance of the center of mass of the finger (e.g., the pulp region of the finger or other regions used to apply pressure to the portion 4318 of the bottom region 4316) from the center of the photodetector. The vector can indicate the quality of the sequence of image frames or the PPG signal, where the shorter the distance can indicate higher quality, and the longer the distance can indicate poorer quality of the images or the signal. Thus, the device 4300 can determine if the finger is present near the photodetector and the direction (e.g., based on the vector) the user should reposition the finger to be centered above the photodetector for good quality measurement. The methods and techniques to determine the adjustment of the position of the finger can be described in conjunction with at least FIGS. 16-18C, for example. Accordingly, the device 4300 can instruct the user to adjust the placement of the finger within the groove 4314, responsive to determining a poor quality of the sequence of image frames or poor quality of the PPG signal.

In some implementations, the device 4300 may perform a "preflight test" routine, sometimes referred to as an initial test or booting process. The initial test can be performed on startup (e.g., during first boot for each day or weekly). The device 4300 can determine the quality of one or more sensors (e.g., photodetector, light source, or temperature probe) or signals received by the sensors. The device 4300 may recalibrate one or more sensors based on the initial test. For example, the device 4300 can determine that the images captured by the photodetector are blurred before detecting a finger in the groove 4314. Based on this determination, the device 4300 can recalibrate or reset the settings of the photodetector to obtain clear images. The device 4300 can perform other startup processing or checks to prepare for measuring one or more vital signs of the user. In some implementations, the initial test can include or refer to a process for detecting that the finger is present in the groove 4314 and the conditions (e.g., cold finger or temperature condition, saturation condition, among others) for starting the measurements are met, prior to measuring the vital signs.

In some implementations, the device 4300 can compose of different features or components based on the model, version, or constructed components of the device 4300. For example, each model of the device 4300 can compose of different sensors, microcontroller unit ("MCU"), connectivity, or display capabilities (e.g., with or without a display unit local to the device 4300). The MCU may process raw data, including at least the PPG signal or blood pressure recording data locally on the device 4300. With a display device, the device 4300 can display at least the blood pressure value (e.g., systolic/diastolic) and heart rate locally using the embedded display device. In some cases, the MCU may process sensor data and display all vital measurements using the embedded display device to the user. Hence, based on the respective model, the device 4300 can include additional features for measuring vital signs or be limited to various features for measuring some of the subsets of vital signs, for example.

The one or more hardware components of the device 4300 can be described in further detail as follows. For example, the hardware components can include at least a core sensor, temperature sensor (e.g., temperature probe), embedded display (e.g., display device), battery, pressure sensor (e.g., a piezoelectric sensor), haptic feedback, finger groove light pipe (e.g., light pipe 4312), cloud connectivity, Bluetooth, printed circuit board ("PCB"), and sound generator (e.g., speaker). The core sensor can include a series of RGB LEDs and a photodetector (e.g., specialized or RGB) configured to capture the PPG signal. The device 4300 can use the temperature sensor to measure the body part temperature (e.g., skin temperature of the finger) for estimating the temperature of the user's body. The device 4300 can use the embedded display to display measurement information (e.g., BP or other vitals), as well as other illuminated indicators, such as alerts, hints, error conditions, finger position, etc. The embedded display can include an LED array that shines through the surface of the housing 4302, for example. The device 4300 can include a battery to power the device 4300 when not plugged in or charging. The battery can be composed of a rechargeable li-ion battery, for example. The device 4300 can include components for enabling sleep or hibernation mode, such that the device 4300 can be woken up upon a touch of the finger or having the finger near the device for conservation of energy. The device can use a photoelectric sensor, proximity sensor, or pressure sensor to determine when the user places a finger in the groove or on a portion of the device 4300. In some cases, the device 4300 may not be woken up from hibernation, unless a certain amount of force is applied to the sensor area, e.g., by the finger.

In some embodiments, the pressure sensor can be a piezoelectric sensor. The device 4300 can use the pressure sensor to measure or indicate an adjustment (e.g., via a display device either of the device 4300 or a remote device) to the amount of force that the finger is applying to the sensor area (e.g., the portion 4318 of the bottom region 4316). The device 4300 can use the haptic feedback (e.g., haptic actuator or vibration motor) to communicate different state-events with the user, such as if the measurement is starting, the measurement ended, etc. The light pipe 4312 can illuminate through the housing 4302 from the channel supporting the light pipe 4312. The light pipe 4312 can be used to guide the user to place the finger into the groove 4314. The light pipe 4312 can receive a programmable alert schedule (e.g., from an application executing on a remote device) for a time of day or week to prompt an alarm to provide a reminder to take measurements. The device 4300 can use cloud connectivity, which can be a low-powered Wi-Fi connection, to transmit data to a remote server or a cloud.

In some embodiments, the device 4300 can use Bluetooth communication, for example, to sync the BP results and user's vital information with an application executing on a remote device and/or stream (e.g., concurrently or asynchronously) the raw PPG signal or information to the application for data analysis. The one or more components of the device 4300 can be in electrical communication with the PCB, which can carry or transmit internal communication between components (e.g., battery power status, wireless communication, display data, etc.) of the device 4300. The device 4300 can use the speaker to provide a sound, such as an alarm sound or notification to the user. The generated sound can be preconfigured by the administrator of the application synced to the device 4300 or by factory default. The generated sounds can provide an audio notification for any texts or characters display on the display device of either the device 4300 or a remote device connected to the device 4300. In some cases, the speaker can notify the measurement results, among other information available to the device 4300, to the user. In some implementations, the device 4300 can include a microphone to receive voice commands, such as turn on/off the device 4300, "tell me the measurements," start measurements, among others. In some implementations, the UI displayed by the display device of the device 4300 can be replicated to the application of a remote device, or vice versa where the display from the remote device can be synced to the display of the device 4300.

In some implementations, the device 4300 may be display-less. For example, the device 4300 may not include a display device. Instead, the device 4300 can be connected to a remote device executing an application (e.g., application 114). For example, the device 4300 can transfer at least one of captured images, PPG signals, raw PPG or BP recording data, processed data, one or more error conditions, or among other data or alerts to be present to the user via a display device of a remote device. In some cases, the device 4300 can transfer the data to a web server or a portion using the communication interface. In some implementations, the results (e.g., vital signs or health condition), error conditions, or hints to reposition the finger can be displayed on a UI within an application executing on the remote device. In this case, the user can view or obtain at least the measurement values inside the application of the remote device or a portion within a web browser.

In some embodiments, the device 4300 can transmit the processed data to the connected remote device for displaying one or more vital signs or measurement results via the UI of the application to the user. In some cases, the device 4300 may be a relay device to provide data to the remote device for processing. For example, the device 4300 can collect one or more images of the finger. Responsive to capturing the images, the device 4300 can transmit the image data to the remote device for downsampling, converting the images to a PPG signal, among other processing techniques. In this case, the remote device can determine one or more vital signs of the user and display the respective vital signs on a display device of the remote device for the user. Since the device 4300 can be easily wiped or cleaned, the device 4300 can be shared across multiple users for measuring vital signs. Therefore, with a single device 4300, multiple users can measure their respective vital signs to determine their health conditions. Accordingly, the device 4300 can be used routinely to maintain the health conditions of any user.

In some implementations, the device 4300 (or the computer system 100) can include or can host one or more batteries to charge the device 4300 (or the computer system 100). The device 4300 (or the computer system 100) may include one or more coils (e.g., located at the bottom surface of the device 4300) to wirelessly charge the device 4300 (or the computer system 100). The device 4300 (or the computer system 100) may include a micro USB port that can be used to charge the device 4300 (or the computer system 100). The device 4300 (or the computer system 100) may include other means for wired or wireless charging of the device 4300 (or the computer system 100).

In some implementations, the device 4300 (or the computer system 100) can include fingerprint-based authentication means or capabilities. For instance, the photodetector 110 can capture images of a subject fingerprints, and the processor 102 can process the captured fingerprint images, and compare them to stored fingerprints of a user of the device 4300 (or the computer system 100). The device 4300 (or the computer system 100) can authenticate users based on the comparison of captured fingerprint images and maintained fingerprints of one or more registered users. In some implementations, the device 4300 (or the computer system 100) can include a separate photo sensor for receiving images of user fingerprints.

J. Design of Standalone Blood Pressure Measurement Device

FIG. 44A-H illustrate different views of a device 4400 for measuring vital signs of a user, according to example embodiments. FIG. 45A-H illustrate different views of a device 4500 for measuring vital signs of a user in broken lines, according to example embodiments. FIG. 46A-D illustrate perspective and top views of a device 4600 with a rough surface in a groove, according to example embodiments.

The ornamental design which is claimed is shown in solid lines in the drawings. The broken line showing a device, a housing, a groove, light indicators, a bottom region, or other components of the device, in the drawings are for illustrative purposes only and form no part of the claimed design. Broken lines formed by equal length dashes show unclaimed portions of the design.

While the accompanying drawings illustrate one or more exemplary embodiments, it should be understood that according to other exemplary embodiments that should be considered to be within the possession of the inventors of the present application at the time this application is being filed, it is contemplated that any illustrated solid lines (or portions thereof) may be converted to broken lines and that any illustrated broken lines (or portions thereof) may be converted to solid lines so as to claim or disclaim portions, components, or sub-components of the designs shown. It is further contemplated that shading may be added or removed to claim or disclaim the corresponding surfaces.

Each method described in this disclosure can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of assessing photoplethysmographic (PPG) signals generated based on transdermal optical data, the method comprising:
   acquiring, by a computing device, a sequence of images representing transdermal optical data of a subject;
   generating, by the computing device, a sequence of downsampled color frames corresponding to the sequence of images by downsampling a respective color frame for each image of the sequence of images;
   generating, by the computing device, a PPG signal using color intensity values corresponding to central image blocks defined across the sequence of downsampled color frames, each color intensity value generated using a corresponding central image block defined in a corresponding downsampled color frame in the sequence of downsampled color frames;
   computing, by the computing device, using a sliding window, a plurality of normalized autocorrelation signals of the PPG signal, each normalized autocorrelation signal corresponding to a portion of the PPG signal defined by a corresponding position of the sliding window;
   determining, by the computing device, using the plurality of normalized autocorrelation signals, a plurality of quality metrics indicative of a quality of the PPG signal, determining the plurality of quality metrics includes determining, for each normalized autocorrelation signal, a respective peak; and
   generating, by the computing device, based on the plurality of quality metrics, an indicator indicative of the quality of the PPG signal,
wherein determining the respective peak for each normalized autocorrelation signal includes:

penalizing correlation values of the normalized autocorrelation signal using powers of corresponding indices; and identifying an index of the respective peak as an index of a maximum of penalized correlation values.

2. The method of claim 1, further comprising:

comparing, by the computing device, for each normalized autocorrelation signal, the respective peak to a threshold value; and determining, by the computing device, the quality of the PPG signal based on comparing the respective peak to the threshold value.

3. The method of claim 1, further comprising:

determining, by the computing device, a local period of the PPG signal using respective peaks of the plurality of normalized autocorrelation signals.

4. The method of claim 2, further comprising:

aborting, by the computing device, acquisition of the sequence of images if respective peaks of a subset of the plurality of normalized autocorrelation signals corresponding to a predefined cumulative time period are below the threshold value.

5. The method of claim 1, further comprising at least one of:

displaying, by the computing device, a graph of at least a portion of the PPG signal;

displaying, by the computing device, a signal quality bar depicting the indicator indicative of the quality of the PPG signal; or displaying, by the computing device, a timer indicative of time left for completing acquisition of the sequence of images.

6. A computing device comprising:

a processor; and a memory storing computer code instructions, the computer code instructions when executed by the processor cause the computing device to:

acquire a sequence of images representing transdermal optical data of a subject;

generate a sequence of downsampled color frames corresponding to the sequence of images by downsampling a respective color frame for each image of the sequence of images;

generate a photoplethysmographic (PPG) signal using color intensity values corresponding to central image blocks defined across the sequence of downsampled color frames, each color intensity value generated using a corresponding central image block defined in a corresponding downsampled color frame in the sequence of downsampled color frames;

compute, using a sliding window, a plurality of normalized autocorrelation signals of the PPG signal, each normalized autocorrelation signal corresponding to a portion of the PPG signal defined by a corresponding position of the sliding window;

determine, using the plurality of normalized autocorrelation signals, a plurality of quality metrics indicative of a quality of the PPG signal, determining the plurality of quality metrics includes determining, for each normalized autocorrelation signal, a respective peak; and generate, based on the plurality of quality metrics, an indicator of the quality of the PPG signal, wherein in determining the respective peak for each normalized autocorrelation signal, the computing device is configured to:

penalize correlation values of the normalized autocorrelation signal using powers of corresponding indices; and identify an index of the respective peak as an index of a maximum of penalized correlation values.

7. The computing device of claim 6, further configured to:

compare, for each normalized autocorrelation signal, the respective peak to a threshold value; and determine the quality of the PPG signal based on comparing the respective peak to the threshold value.

8. The computing device of claim 6, further configured to:

determine a local period of the PPG signal using respective peaks of the plurality of normalized autocorrelation signals.

9. The computing device of claim 7, wherein the processor is further configured to:

abort acquisition of the sequence of images if respective peaks of a subset of the plurality of normalized autocorrelation signals corresponding to a predefined cumulative time period are below the threshold value.

10. The computing device of claim 6, wherein the processor is further configured to perform at least one of:

display a graph of at least a portion of the PPG signal;

display a signal quality bar depicting the indicator indicative of the quality of the PPG signal; or display a timer indicative of time left for completing acquisition of the sequence of images.

* * * * *